(12) United States Patent
Sippy

(10) Patent No.: US 12,194,046 B2
(45) Date of Patent: *Jan. 14, 2025

(54) D9-CAFFEINE COMPOSITIONS AND USES THEREOF

(71) Applicant: Lennham Pharmaceuticals, Inc., Acton, MA (US)

(72) Inventor: Bradford C. Sippy, Acton, MA (US)

(73) Assignee: Lennham Pharmaceuticals, Inc., Concord, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/535,103

(22) Filed: Nov. 24, 2021

(65) Prior Publication Data

US 2022/0288083 A1 Sep. 15, 2022

Related U.S. Application Data

(60) Provisional application No. 63/242,165, filed on Sep. 9, 2021, provisional application No. 63/211,442, filed (Continued)

(51) Int. Cl.
| | | |
|---|---|---|
| *A61K 31/522* | (2006.01) | |
| *A61K 45/06* | (2006.01) | |
| *A61P 25/00* | (2006.01) | |

(52) U.S. Cl.
CPC .......... *A61K 31/522* (2013.01); *A61K 45/06* (2013.01); *A61P 25/00* (2018.01)

(58) Field of Classification Search
CPC .. A61K 31/522; A61K 45/06; A61K 2300/00; A61P 25/00
See application file for complete search history.

(56) References Cited

U.S. PATENT DOCUMENTS

| 4,486,436 A | 12/1984 | Sunshine et al. |
| 5,700,484 A * | 12/1997 | Chauffard ............ A61K 9/5078 |
| | | 424/490 |

(Continued)

FOREIGN PATENT DOCUMENTS

| JP | 2005-145856 A | 6/2005 |
| JP | 2008-201768 A | 9/2008 |

(Continued)

OTHER PUBLICATIONS

Ioannidis (Ostracising caffeine from the pharmacological arsenal for attention-deficit hyperactivity disorder—was this a correct decision? A literature review, Journal of Psychopharmacology 2014, vol. 28(9) 830-836).*

(Continued)

*Primary Examiner* — Savitha M Rao
(74) *Attorney, Agent, or Firm* — Wolf, Greenfield & Sacks, P.C.

(57) ABSTRACT

Provided herein are compositions (e.g., pharmaceutical compositions, nutraceutical compositions, foods, beverages, cosmetic compositions, nutritional supplements) comprising d9-caffeine. The provided compositions may be useful for treating and/or preventing various diseases and conditions, such as obesity, causing weight loss, increasing metabolic rate, reducing appetite, increasing energy expenditure, decreasing daytime sleepiness, increasing urine output, increasing sodium excretion, reducing edema, a pain disorder, apnea, hypotension, an encephalopathy, a neurological or psychiatric disorder, and an inflammatory disorder.

29 Claims, 9 Drawing Sheets

Related U.S. Application Data on Jun. 16, 2021, provisional application No. 63/158,550, filed on Mar. 9, 2021.

(56) References Cited

U.S. PATENT DOCUMENTS

| | | | |
|---|---|---|---|
| 8,187,647 | B2 | 5/2012 | Bhargava |
| 8,632,834 | B2 | 1/2014 | Bhargava |
| 8,658,236 | B2 | 2/2014 | Czarnik et al. |
| 10,582,716 | B1 | 3/2020 | Sippy |
| 10,765,130 | B1 | 9/2020 | Sippy |
| 11,547,127 | B2 | 1/2023 | Sippy |
| 11,666,073 | B2 | 6/2023 | Sippy |
| 2008/0279766 | A1 | 11/2008 | Everson et al. |
| 2008/0299271 | A1 | 12/2008 | Inoue |
| 2009/0214682 | A1 | 8/2009 | Heuer et al. |
| 2009/0325984 | A1 | 12/2009 | Costentin et al. |
| 2010/0087455 | A1* | 4/2010 | Gant ................ A61P 35/00 514/263.34 |
| 2010/0112050 | A1 | 5/2010 | Ryoo et al. |
| 2010/0124578 | A1 | 5/2010 | Heuer et al. |
| 2013/0344177 | A1 | 12/2013 | Young et al. |
| 2015/0005326 | A1 | 1/2015 | Pacific |
| 2015/0119407 | A1 | 4/2015 | Tung et al. |
| 2015/0196579 | A1 | 7/2015 | Bio |
| 2015/0342899 | A1 | 12/2015 | Kulakofsky et al. |
| 2017/0275285 | A1 | 9/2017 | Hydra |
| 2017/0304309 | A1 | 10/2017 | Artero |
| 2018/0085297 | A1 | 3/2018 | Robert |
| 2018/0086751 | A1 | 3/2018 | Karanewsky |
| 2018/0116950 | A1 | 5/2018 | Pan et al. |
| 2018/0325907 | A1 | 11/2018 | Cardix |
| 2019/0070184 | A1 | 3/2019 | Wang et al. |
| 2020/0029892 | A1 | 1/2020 | Brown et al. |
| 2020/0390128 | A1* | 12/2020 | Sippy ................ A23L 2/56 |
| 2021/0068429 | A1 | 3/2021 | Sippy |
| 2021/0378266 | A9 | 12/2021 | Sippy |
| 2022/0225642 | A1 | 7/2022 | Sippy |
| 2022/0248720 | A1 | 8/2022 | Sippy |
| 2023/0355632 | A1 | 11/2023 | Sippy |
| 2023/0371555 | A1 | 11/2023 | Sippy |

FOREIGN PATENT DOCUMENTS

| | | | |
|---|---|---|---|
| WO | WO 2008/080005 A1 | 7/2008 | |
| WO | WO-2014197601 A1 * | 12/2014 | ........... A61K 31/519 |

OTHER PUBLICATIONS

Gutierrez-Sanchez (Coffee Biotechnology and quality (book), chaper 42, 2000, pp. 447-453)(hereinafter known as Sanchez).*
Ledbetter (Atomoxetine: a novel treatment for child and adult ADHD, Neuropsychiatric Disease and Treatment 2006:2(4) 455-466).*
Berg (Journal of pharmaceutical Sciences, Pharmaceutical Salts, Jan. 1977, Vo 66, No. 1).*
Nair (Management of attention-deficit hyperactivity disorder in adults: focus on methylphenidate Hydrochloride, Neuropsychiatric Disease and Treatment 2009:5 421-432).*
Kileen et al. (Neuroscience and Biobehavioral Reviews, 37 (2013) 625-657) (Year: 2013).*
International Search Report and Written Opinion for Application No. PCT/US2020/037485, mailed on Oct. 9, 2020.
International Preliminary Report on Patentability for Application No. PCT/US2020/037485, mailed on Dec. 23, 2021.
[No Author Listed], Caffeine-(trimethyl-d9). SIGMA-ALDRICH. 2 pages.
[No Author Listed], Caffeine. Dermstore.com. https://www.dermstore.com/profile_Caffeine_503552.htm [last accessed Jul. 22, 2019], 8 pages.
[No Author Listed], Cafcit (caffeine citrate) Injection and Oral Solution. RLI. Apr. 2000. https://www.accessdata.fda.gov/drugsatfda_docs/label/2000/20793s1lbl.pdf [last accessed Jul. 22, 2019], 19 pages.
[No Author Listed], Cvs Health Caffeine Tablets, 80 CT. CVS.com. https://www.cvs.com/shop/cvs-health-caffeine-tablets-80ct-prodid-984401?skuid=984401 [last accessed Jul. 22, 2019], 1 page.
[No Author Listed], Fda Approved Drug Products. U.S. Food and Drug Administration https://www.accessdata.fda.gov/scripts/cder/daf/index.cfm?event=overview.process&varApplNo=020793 [last accessed Jul. 22, 2019], 2 pages.
[No Author Listed], 5-hour Energy Shot Ingredients. Living Essentials Marketing, LLC. https://5hourenergy.com/facts/ingredients/ [last accessed Jul. 22, 2019], 3 pages.
[No Author Listed], Milk Chocolate Bars. Awake Energy USA. https://awakechocolate.com/products/awake-milk-chocolate-bars-12-pack [last accessed Jul. 22, 2019], 6 pages.
[No Author Listed], Red Bull Energy Drink Ingredients. Red Bull GmbH. https://energydrink-US.redbull.com/en/ingredients-red-bull [last accessed Jul. 22, 2019], 5 pages.
[No Author Listed], Vitamin Water-Energy Tropical Citrus. The Coca Cola Company. https://www.vitaminwater.com/products/energy/ [last accessed Jul. 22, 2019], 2 pages.
[No Author Listed], Cas Registry Caffeine. entered Aug. 21, 2019. 64 pages.
[No Author Listed] Weight-loss drugs and your heart. Harvard Health Publishing. Apr. 2015. 3 pages.
Ayala et al., Quantitative determination of caffeine and alcohol in energy drinks and the potential to produce positive transdermal alcohol concentrations in human subjects. J Anal Toxicol. Jan.-Feb. 2009;33(1):27-33.
Banks et al., Characteristics of compounds that cross the blood-brain barrier. BMC Neurol. Jun. 12, 2009;9 Suppl 1(Suppl 1):S3. doi: 10.1186/1471-2377-9-S1-S3.
Bechalany et al., Isotope Effects on the Lipophilicity of Deuterated Caffeines. Helv Chim Acta. May 3, 1989;72(3):472-476.
Benchekroun et al., Deuterium isotope effects on caffeine metabolism. Eur J Drug Metab Pharmacokinet. Apr.-Jun. 1997;22(2):127-33.
Bier et al., Collision-induced dissociation studies of caffeine in positive electrospray ionisation mass spectrometry using six deuterated isotopomers and one N1-ethylated homologue. Rapid Commun Mass Spectrom. Apr. 30, 2013;27(8):885-95. doi: 10.1002/rcm.6520.
Cherrah et al., Study of deuterium isotope effects on protein binding by gas chromatography/mass spectrometry. Caffeine and deuterated isotopomers. Biomed Environ Mass Spectrom. Nov. 1987;14(11):653-7. doi: 10.1002/bms.1200141115.
Falconnet et al., Synthesis of Seven Deuteromethyl-Caffeine Analogues Observatxon of Deuterium Xsotope Effects on Cmr Analysis. Journal of Labelled Compounds and Radiopharmaceuticals. Jul. 18, 1985; XXIII(3): 267-276.
Hewitt, Using the 'deuterium switch' to understand how receptors work. Jun. 7, 2016. www.phys.org/news/2016-06-deuterium-receptors.html. [last accessed Jun. 26, 2019], 5 pages.
Horning, Effect of Deuterium Substitution on the Rate of Caffeine Metabolism, Stable Isotopes, Proceedings of the Third International Conference, 1979:379-384.
Kot et al., Caffeine as a marker substrate for testing cytochrome P450 activity in human and rat. Pharmacol Rep. Nov.-Dec. 2008;60(6):789-97. PMID: 19211970.
Marturana, Here's How Much Caffeine is in a Cup of Coffee [Online], published Feb. 2017, [retrieved on Oct. 2, 2019]. Retrieved from the Internet: https://www.self.com/story/heres-how-much-caffeine-is-in-a-cup-of-coffee.
Nehlig, Interindividual Differences in Caffeine Metabolism and Factors Driving Caffeine Consumption. Pharmacol Rev. Apr. 2018;70(2):384-411. doi: 10.1124/pr.117.014407. Epub Mar. 7, 2018.
Timmins, Deuterated drugs; where are we now? Expert Opin Ther Pat. Oct. 2014;24(10):1067-75. doi: 10.1517/13543776.2014.943184. Epub Jul. 29, 2014.
Harbeson et al., Deuterium in Drug Discovery and Development, Annual Reports in Med. Chem., 2011;46:403-417.
Schnackenberg et al., Caffeine as a substitute for Schedule II stimulants in hyperkinetic children. American J Psychiatry. 1973;130:796-798.

(56) References Cited

OTHER PUBLICATIONS

Shao et al., Derivatives of tramadol for increased duration of effect. Bioorg Med Chem Lett. Feb. 2006;16(3):691-4. doi: 10.1016/j.bmcl.2005.10.024. Epub Oct. 27, 2005. PMID: 16257206.

Stein et al., ADHD Treatments, Sleep, and Sleep Problems: Complex Associations, Neurotherapeutics. 2012;9:509-517.

International Search Report and Written Opinion for PCT/US2022/019362, mailed on May 23, 2022.

[No Author Listed] Cofactor, Universal Protein Resource (UniProt) Website, accessed via Internet Archive The Wayback Machine as indexed on Jun. 9, 2019.

Alsabri et al., Kinetic and Dynamic Description of Caffeine. J Caffeine Adenosine Res 2018;8(1): 3-9; DOI: 10.1089/caff.2017.0011. Correction: J Caffeine Adenosine Res. Dec. 1, 2021;11(4):107. doi: 10.1089/caff.2017.0011.correx. Epub Dec. 15, 2021. Erratum for: J Caffeine Adenosine Res. 8:3. PMID: 35019904; PMCID: PMC8742265.

Aprile et al., An Unexpected Deuterium-Induced Metabolic Switch in Doxophylline. ACS Med Chem Lett. Jul. 14, 2022;13(8):1278-1285. doi: 10.1021/acsmedchemlett.2c00166.

De Bolster et al., Glossary of Terms Used in Bioinorganic Chemistry (IUPAC Recommendations 1997), Pure & Appl. Chem. 1997, 69, 1251-1303.

Declaration for Vinita Uttamsingh, filed in U.S. Appl. No. 12/102,164, filed Feb. 1, 2012. 3 pages.

Summerfield et al., Central Nervous System Drug Disposition: The Relationship between in Situ Brain Permeability and Brain Free Fraction. J Pharmacology Experimental Therapeutics Jul. 1, 2007, 322 (1) 205-213; DOI: https://doi.org/10.1124/jpet.107.121525.

Wang et al., An experimentally validated approach to calculate the blood-brain barrier permeability of small molecules. Sci Rep. 9, 6117 (2019).

Extended European Search Report for Application No. EP20821951.9, mailed Jun. 6, 2023.

Invitation to Pay Additional Fees for Application No. PCT/US2021/049755, mailed Nov. 24, 2021.

International Search Report and Written Opinion for Application No. PCT/US2021/049755, mailed Feb. 28, 2022.

International Preliminary Reports on Patentability for Application No. PCT/US2021/049755, mailed Mar. 23, 2023.

Edmondson et al., Kinetic studies on the substrate reduction of xanthine oxidase. J Biol Chem. Sep. 10, 1973;248(17):6135-44.

Russak et al., Impact of Deuterium Substitution on the Pharmacokinetics of Pharmaceuticals. Ann Pharmacother. Feb. 2019;53(2):211-216. doi: 10.1177/1060028018797110. Epub Aug. 23, 2018. (Abstract Only).

International Preliminary Reports on Patentability for Application No. PCT/US2022/019362, mailed on Sep. 21, 2023.

Wang (Ed.), Molecular Nuclear Medicine. China Union Medical University Press. Apr. 30, 2004. pp. 417-418. ISBN 7-81072-483-5.

* cited by examiner

| CYP1A2 | rs2069514 c.-3860G>A | rs2069526 c.-739T>G | rs762551 c.-163C>A | rs12720461 c.-729C>T |
|---|---|---|---|---|
| Genotype | *1C | *1E | *1F | *1K |
| *1A/*1A | WT | WT | WT | WT |
| *1A/*1C | HET | WT | WT | WT |
| *1A/*1E | WT | HET | WT | WT |
| *1A/*1F | WT | WT | HET | WT |
| *1A/*1J | WT | HET | HET | WT |
| *1A/*1K | WT | HET | HET | HET |
| *1C/*1C | MUT | WT | WT | WT |
| *1C/*1E | HET | HET | WT | WT |
| *1C/*1F | HET | WT | HET | WT |
| *1C/*1J | HET | HET | HET | WT |
| *1C/*1K | HET | HET | HET | HET |
| *1E/*1E | WT | MUT | WT | WT |
| *1E/*1F | WT | HET | HET | WT |
| *1E/*1J | WT | MUT | HET | WT |
| *1E/*1K | WT | MUT | HET | HET |
| *1F/*1F | WT | WT | MUT | WT |
| *1F/*1J | WT | HET | MUT | WT |
| *1F/*1K | WT | HET | MUT | HET |
| *1J/*1J | WT | MUT | MUT | WT |
| *1J/*1K | WT | MUT | MUT | HET |
| *1K/*1K | WT | MUT | MUT | MUT |
| *1C*1F/*1F | HET | WT | MUT | WT |
| *1C*1F/*1J | HET | HET | MUT | WT |
| *1C*1F/*1C*1F | MUT | WT | MUT | WT |

Increased Activity:
*1F

Active alleles:
*1A, *1E, *1J

Partially active alleles:
*1C, *1K

RM = R / R or R / A
NM = A / A or A / P or R / P
IM = P / P

R = Increased activity
A = active
P = partially active

FIG. 12

D9-CAFFEINE COMPOSITIONS AND USES THEREOF

RELATED APPLICATIONS

This application claims priority under 35 U.S.C. § 119 (e) to U.S. Provisional Application, U.S. Ser. No. 63/242,165, filed on Sep. 9, 2021, to U.S. Provisional Application, U.S. Ser. No. 63/211,442, filed on Jun. 16, 2021, and to U.S. Provisional Application, U.S. Ser. No. 63/158,550, filed on Mar. 9, 2021, the contents of which are incorporated by reference herein in their entirety.

BACKGROUND

Caffeine is a central nervous system (CNS) stimulant belonging to the methylxanthine chemical class. It is the world's most widely consumed psychoactive drug. Caffeine affects several biological processes. The most prominent is reversibly blocking the action of adenosine on the adenosine receptor, thus, preventing the onset of drowsiness and fatigue induced by adenosine. It is also known that caffeine stimulates portions of the autonomic nervous system. In addition to its anti-drowsiness effect, caffeine has also been shown to positively impact learning, memory, reaction time, wakefulness, concentration, and motor coordination. Caffeine is also useful in treating bronchopulmonary dysplasia in premature infants, improving weight gain during therapy, and reducing the incidence of cerebral palsy, in addition to reducing language and cognitive delays. Additionally, caffeine has demonstrated promising results in treating orthostatic hypotension, hypoxic-ischemic encephalopathy (HIE), and delaying the progression of Alzheimer's disease. Furthermore, caffeine citrate, marketed under the brand name, CAFCIT®, is approved by the FDA for the treatment of apnea of prematurity in neonates.

However, despite the positive attributes discussed above, caffeine suffers from some significant physical and psychological adverse effects that limit its use. Caffeine can increase blood pressure, affect gastrointestinal motility and gastric secretion, cause heart palpitations, cause and worsen anxiety and insomnia, and can be addictive. It is believed that some or all of the aforementioned adverse effects can be attributed to caffeine's pharmacokinetic and metabolic profile. Caffeine ingestion results in a high maximal plasma concentration (plasma $C_{max}$), a short time of maximal plasma concentration ($T_{max}$) after ingestion, short half-life ($t_{1/2}$), and rapid clearance, mainly by hepatic cytochrome P450 (CYP450) demethylation to afford paraxanthine, theobromine, and theophylline. In other words, ingestion of caffeine results in a large "spike" in caffeine plasma concentration (i.e., large $C_{max}$) shortly after caffeine ingestion (i.e., short $T_{max}$) followed by a "crash" in caffeine plasma concentration due to rapid metabolism and clearance. It is believed that the magnitude of this "spike" and the rapidity of this "crash" are at least partially responsible for the aforementioned adverse effects. Therefore, one approach to mitigate these adverse effects is to develop compounds and compositions that harness the positive attributes of caffeine without the negative effects, that is, with pharmacokinetic profiles providing for a similar or equivalent $C_{max}$, greater overall exposure, longer half-life, and/or longer $T_{max}$ values than non-isotopically enriched caffeine but without the sharp drop (or "crash") in blood or brain plasma levels after $C_{max}$ that typically results from the administration or consumption of non-isotopically enriched caffeine.

It has been surprisingly discovered that d9-caffeine is safe when administered or consumed and exhibits unexpectedly superior and previously unknown properties compared to non-isotopically enriched (natural) caffeine, including less exposure to caffeine metabolites, a significantly longer blood plasma half-life, and avoidance of the "crash" (the sharp drop in blood plasma levels) following $C_{max}$ that is typically observed following administration or consumption of non-isotopically enriched caffeine. It has been surprisingly discovered that d9-caffeine may be incorporated into a pharmaceutical composition, nutraceutical composition, food or food product, beverage, cosmetic composition, or nutritional supplement for a number of uses, including use in increasing energy or wakefulness, decreasing drowsiness or sleepiness, increasing athletic performance (including providing for sustained athletic performance), or treating or preventing a number of diseases or conditions, including but not limited to excessive daytime sleepiness arising from narcolepsy, obstructive sleep apnea, and depression. It has also been surprisingly discovered that the total exposure and half-life of d9-caffeine when measured in blood plasma are so superior to non-isotopically enriched caffeine when administered to human subjects that the pharmaceutical compositions, nutraceutical compositions, foods or food products, beverages, cosmetic compositions, or nutritional supplements described herein may be effective when administered once daily.

SUMMARY OF THE INVENTION

The present invention relates to compositions (e.g., pharmaceutical compositions, nutraceutical compositions, foods, beverages, cosmetic compositions, nutritional supplements) comprising d9-caffeine as described herein (i.e., wherein each of the three methyl groups is enriched with deuterium). In certain embodiments, the composition is suitable for oral administration. In certain embodiments, the composition is suitable for intravenous (IV) administration. In certain embodiments, the composition is suitable for topical administration. In certain embodiments, the composition is suitable for delivery to the lungs. In certain embodiments, the composition is administered using an electronic cigarette or other vaping device, a nebulizer, a pressurized metered dose inhaler (pMDI), or a dry powder inhaler (DPI). In certain embodiments, the composition is a solid dose composition (e.g., tablet, capsule, granule, powder, sachet, or chewable), solution, gel, suspension, emulsion, shampoo, conditioner, cream, foam, gel, lotion, ointment, transdermal patch, tincture, or paste. Also provided herein are kits containing the compositions and instructions for use. Further provided herein are use of the compositions described herein for treating a disease, preventing a disease, treating a condition, and/or preventing a condition.

The compositions described herein comprise d9-caffeine:

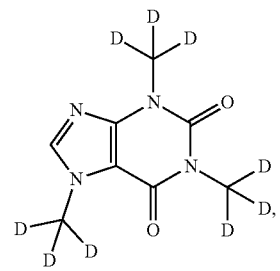

or a pharmaceutically or nutraceutically acceptable salt, hydrate, solvate, or prodrug thereof.

In certain embodiments, the composition comprises about 1 mg to about 10,000 mg of d9-caffeine, or a pharmaceutically or nutraceutically acceptable salt, hydrate, or solvate thereof. In some embodiments, the composition comprises about 1 mg to about 275 mg of d9-caffeine, or a pharmaceutically or nutraceutically acceptable salt, hydrate, or solvate thereof. In certain embodiments, the composition comprises about 30 mg to about 275 mg of d9-caffeine, or a pharmaceutically or nutraceutically acceptable, salt, hydrate, or solvate thereof. In certain embodiments, the percentage of the amount of d9-caffeine, or a pharmaceutically or nutraceutically acceptable salt, hydrate, solvate, or prodrug thereof, relative to the total amount of caffeine present in the composition ranges from about 5% to about 99%. In certain embodiments, the percentage of the amount of d9-caffeine, or a pharmaceutically or nutraceutically acceptable salt, hydrate, solvate, or prodrug thereof, relative to the total amount of caffeine present in the composition ranges from about 5% to about 100%. In another aspect, the composition is an oral composition. In another aspect, the composition is a solid dose composition (e.g., tablet, capsule, granule, powder, sachet, or chewable). In another aspect, the composition is suitable for intravenous (IV) administration. In another aspect, the composition is a topical composition. In another aspect, the composition is a shampoo, conditioner, cream, foam, gel, lotion, ointment, transdermal patch, tincture, or paste. In another aspect, the composition is suitable for inhalation. In another aspect, the composition is administered using an electronic cigarette or other vaping device, a nebulizer, a pressurized metered dose inhaler (pMDI), or a dry powder inhaler (DPI). In another aspect, the composition is suitable for buccal administration.

The disclosure further provides a food product comprising d9-caffeine.

The disclosure further provides a beverage (e.g., energy drink, vitamin water) comprising d9-caffeine.

The disclosure further provides kits comprising one or more compositions described herein and instructions for using the composition(s).

The disclosure further provides methods of delivering d9-caffeine, or a pharmaceutically or nutraceutically acceptable salt, hydrate, solvate, composition, or prodrug thereof, to a subject in need thereof comprising administering to the subject in need thereof d9-caffeine, or a pharmaceutically or nutraceutically acceptable salt, hydrate, solvate, composition, or prodrug thereof.

The disclosure further provides methods of treating a disease in a subject in need thereof comprising administering to the subject in need thereof d9-caffeine, or a pharmaceutically or nutraceutically acceptable salt, hydrate, solvate, composition, or prodrug thereof.

The disclosure further provides methods of preventing a disease in a subject in need thereof comprising administering to the subject in need thereof d9-caffeine, or a pharmaceutically or nutraceutically acceptable salt, hydrate, solvate, composition, or prodrug thereof.

The disclosure further provides methods of treating a condition in a subject in need thereof comprising administering to the subject in need thereof d9-caffeine, or a pharmaceutically or nutraceutically acceptable salt, hydrate, solvate, composition, or prodrug thereof.

The disclosure further provides methods of preventing a condition in a subject in need thereof comprising administering to the subject in need thereof d9-caffeine, or a pharmaceutically or nutraceutically acceptable salt, hydrate, solvate, composition, or prodrug thereof.

In certain embodiments, the subject is a human. In certain embodiments, the subject is an animal.

In certain embodiments, the methods described herein do not cause or increase the risk of the subject having or developing insomnia or sleep deprivation.

In another aspect, the side effects experienced after administration of d9-caffeine, or a pharmaceutically or nutraceutically acceptable salt, hydrate, solvate, composition, or prodrug thereof, are reduced relative to the administration of caffeine at an equivalent dose. In another aspect, the side effect is anxiety, insomnia, delirium, gastrointestinal issues (e.g., loose stools, diarrhea, stomach ulcers, gastroesophageal reflux, etc.), rhabdomyolysis, addiction, hypertension, rapid heart rate, atrial fibrillation, fatigue, irritability, nervousness, restlessness, nausea, or muscle tremors.

In another aspect, the reduction of side effects following administration of d9-caffeine, or a pharmaceutically or nutraceutically acceptable salt, hydrate, solvate, composition, or prodrug thereof, compared to the administration of non-isotopically enriched caffeine at an equivalent dose, is due (in whole or in part) to the reduced production and exposure of one or more metabolites of caffeine. In some embodiments, the metabolites of caffeine are paraxanthine, theophylline, or theobromine.

In another aspect, the administration of d9-caffeine, or a pharmaceutically or nutraceutically acceptable salt, hydrate, solvate, composition, or prodrug thereof, results in an increased duration of action, reduction in frequency of administration, increase in patient compliance and/or ease of use relative to the administration of caffeine at an equivalent dose.

In another aspect, the administration of d9-caffeine, or a pharmaceutically or nutraceutically acceptable salt, hydrate, solvate, composition, or prodrug thereof, results in a similar relative magnitude of exposure in plasma and the central nervous system as compared to the administration of non-isotopically enriched caffeine at an equivalent dose.

The details of one or more embodiments of the present disclosure are set forth herein. Other features, objects, and advantages of the present disclosure will be apparent from the Detailed Description, Examples, and Claims.

BRIEF DESCRIPTION OF THE DRAWINGS

The present invention is further described below with reference to the following non-limiting examples and with reference to the following figures, in which:

FIG. 8A. paraxanthine versus d6-paraxanthine, FIG. 8B. theobromine versus d6-theobromine, FIG. 8C. theophylline versus d6-theophyllline, FIG. 8D. TMU versus d9-TMU.

FIG. 9A. paraxanthine versus d6-paraxanthine, FIG. 9B. theobromine versus d6-theobromine, FIG. 9C. theophylline versus d6-theophyllline, FIG. 9D. TMU versus d9-TMU.

FIG. 11A. 0.26 mmol dose, FIG. 11B. 1.29 mmol dose.

FIG. 12. depicts human genotypes of slow, normal, and hyperinducer/fast metabolizers of caffeine.

DEFINITIONS

Figure 1:
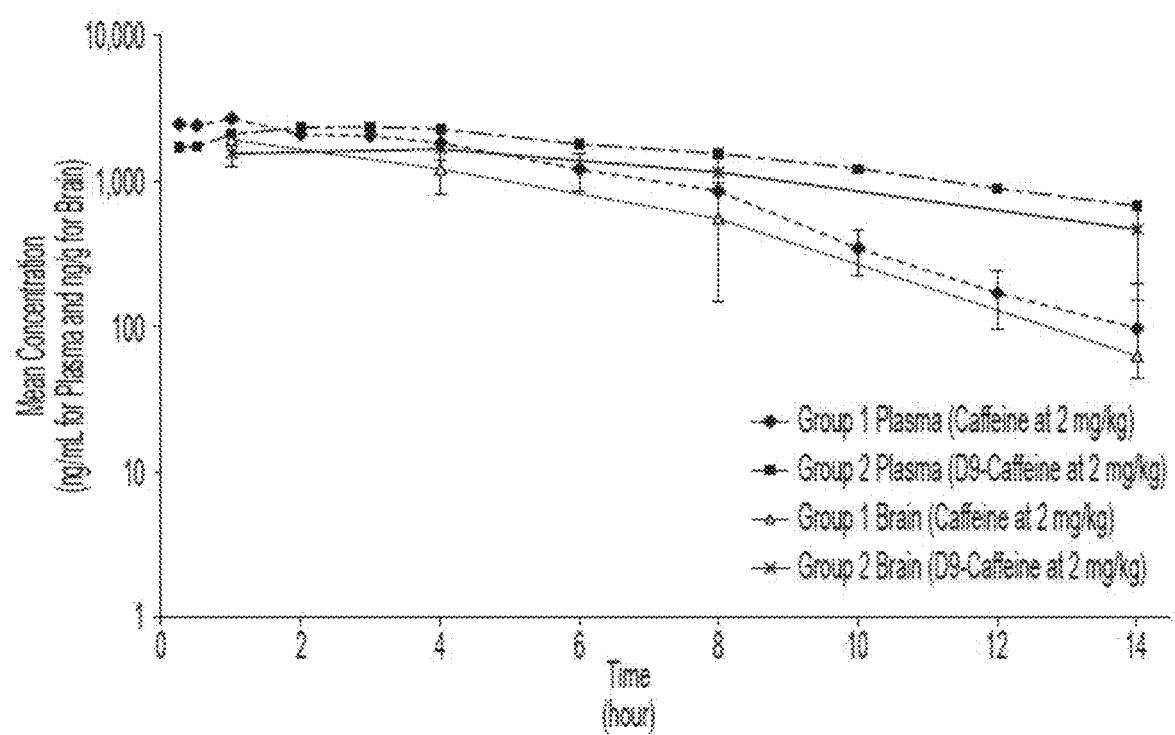
FIG. 1. depicts the mean (+SD) concentrations of caffeine and d9-caffeine in plasma and brain over 14 hours following an oral (gavage) dose of caffeine or d9-caffeine to fasted male Sprague Dawley rats at a dose of 2 mg/kg.

Before further description of the present invention, and in order that the invention may be more readily understood, certain terms are first defined and collected here for convenience.

The term "administer," "administering," or "administration" refers to any method of providing a compound, composition, food product, dietary supplement, or beverage as described herein to a subject. The terms "administer", "administering," or "administration" include implanting, absorbing, ingesting, injecting, inhaling, or otherwise introducing a compound described herein, or a composition thereof, in or on a subject. In certain embodiments, administration is oral. In certain embodiments, oral administration includes consumption, such as eating, drinking, swallowing, gavage, and the like. Administration can be continuous or intermittent. In some embodiments, "administering" and "consuming", as well as "administration" and "consumption", are used interchangeably.

The terms "composition" and "formulation" are used interchangeably.

The term "total amount of caffeine" refers to the combined total amount of d9-caffeine and non-isotopically enriched caffeine.

The term "total systemic exposure" refers to the area under the concentration-time curve (AUC) and represents the total drug exposure across time. In some embodiments, the "total systemic exposure" refers to $AUC_{inf}$ or $AUC_{inf, D}$. In some embodiments, the "total systemic exposure" refers to $AUC_{last}$. In some embodiments, the "total systemic exposure" refers to $AUC_{0-t}$ or $AUC_{0-t, D}$.

The amount of an active agent (e.g., d9-caffeine) or combination of active agents thereof included in a provided composition, food product, beverage, or nutritional supplement described herein will depend on the target population. In some embodiments, a provided composition, food product, beverage, or nutritional supplement contains an effective amount of an active agent (e.g., d9-caffeine). The term "effective amount," as used herein, refers to a sufficient amount of the active agent (e.g., d9-caffeine) to produce a desired outcome. The exact amount required will vary from subject to subject, depending on the species, age, general condition of the subject, and the indication. The term "therapeutically effective amount" as used herein refers to a sufficient amount of a pharmaceutical or nutraceutical agent (e.g., d9-caffeine) to achieve the intended purpose, such as, for example, to cause a reduction of symptoms of a condition or disease. A "prophylactically effective amount" refers to a sufficient amount of a pharmaceutical or nutraceutical agent (e.g., d9-caffeine) to achieve the intended purpose, such as prevention of a condition or disease, one or more symptoms associated with the condition or disease, and/or the recurrence thereof. In certain embodiments, an effective amount of a composition, food product, beverage, or nutritional supplement is the effective amount of the active agent (e.g., d9-caffeine) included in the composition, food product, beverage, or nutritional supplement.

The term "energy beverage" refers to a type of drink containing one or more stimulant compounds (e.g., caffeine), and optionally sugar or artificial sweeteners, which provides mental and/or physical stimulation.

The term "vitamin water" refers to water with added vitamins or minerals, and optionally natural or artificial flavors, sugar, or sweeteners.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium, and $N^+(C_{1-4} \text{ alkyl})_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate. In certain particular embodiments, a pharmaceutically acceptable salt of d9-caffeine is a citrate salt. In other particular embodiments, a pharmaceutically acceptable salt of d9-caffeine is a hydrochloride salt. In other particular embodiments, a pharmaceutically acceptable salt of d9-caffeine is a salicylate salt.

The term "athlete" refers to a human person performing exercises for training, maintaining health, general health improvement, and for rehabilitation. The term athlete includes people with beginner, intermediate, and expert levels of experience. The term "athletic performance" is used herein to generically refer to any type of athletic activity, event, exercise, training, routine, or the like. This is a complex term that relates to at least one of the following: skills, achievements, strength, endurance, speed, power, and recovery of a subject after performing a physical activity, e.g. an intense physical activity.

The terms "improving athletic performance", "enhancing athletic performance" or variations thereof as used herein should be understood to encompass improvement of at least one sport parameter. Non-limiting examples of such improvements are: testosterone elevation, cortisol reduction, fatigue reduction, faster recovery from exercise, reduced muscle soreness, improved endurance, improved muscle strength, improved muscle size, enhanced athletic performance, improved sports-related decision making, improved selective attention of sports-related stimuli, improved concentration during sports events, and improved mental resilience during sports events. According to some embodiments, improving athletic performance comprises elongating the duration of the physical activities, performing it faster and combination thereof. According to some embodiments, improving athletic performance comprises improving endurance, fatigue reduction, faster recovery and any combination thereof. The terms "improving athletic performance" refers to a change in athletic performance, where the change is defined as a difference in the performance between a subject obtaining the administration according to the invention and a subject in similar conditions or the same subject who does not. In some embodiments, the change is detected or measured on the same subject. The change is regarded as an improvement if such change is positive for said subject. In some embodiments, an improvement in athletic performance depends on the type of athletic activity. According to some embodiments, improving athletic performance comprises improving athletic achievements.

The terms "slow metabolizer," "normal metabolizer," and "hyperinducer/fast metabolizer" refer to a human according to their ability to metabolize caffeine based on the genotypes provided in FIG. 12. The genotypes listed in the left-most column reflect the results of a polymorphism test. The entries in the subsequent columns reflect whether the genotype is considered wild-type, heterozygous, or mutant for each polymorphism. If a genotype contains two alleles associated with increased activity (*1F); or one allele associated with increased activity (*1F) and one active allele (*1A, *1E, or *1J), that individual is labeled a hyperinducer/fast metabolizer. If a genotype contains two active alleles (*1A, *1E, or *1J); or an active allele (*1A, *1E, or *1J) and a partially active allele (*1C or *1K); or an allele with increased activity (*1F) and a partially active allele (*1C or *1K), that individual is labeled a normal metabolizer. If a genotype contains two partially active alleles (*1C or *1K), that individual is labeled with impaired metabolism/slow metabolizer.

DETAILED DESCRIPTION OF CERTAIN EMBODIMENTS OF THE INVENTION

The present invention relates to compositions comprising d9-caffeine. Also provided herein are kits containing the compositions and instructions for use. Further provided herein are uses of any of the compounds or compositions described herein for treating a disease, preventing a disease, treating a condition, preventing a condition, and/or causing an effect.

Compositions, Kits, and Administration

In one aspect, the invention provides a composition comprising d9-caffeine, or a pharmaceutically or nutraceutically acceptable salt, hydrate, or solvate thereof.

In some embodiments, the composition is a pharmaceutical composition. In certain embodiments, the composition is a nutraceutical composition. In some embodiments, the composition is a cosmetic composition.

In another aspect, the invention provides a beverage comprising d9-caffeine, or a nutraceutically acceptable salt, hydrate, solvate, or prodrug thereof.

In another aspect, the invention provides a food product comprising d9-caffeine, or a nutraceutically acceptable salt, hydrate, solvate, or prodrug thereof.

In another aspect, the invention provides a nutritional supplement comprising d9-caffeine, or a nutraceutically acceptable salt, hydrate, solvate, or prodrug thereof.

In another aspect is provided a salt of d9-caffeine. In another aspect, the salt is an HCl, sulfate, acetate, phosphate, diphosphate, maleate, citrate, mesylate, nitrate, tartrate, or gluconate salt. In another aspect, the salt is a citrate salt. The citrate salt may be represented by the structure:

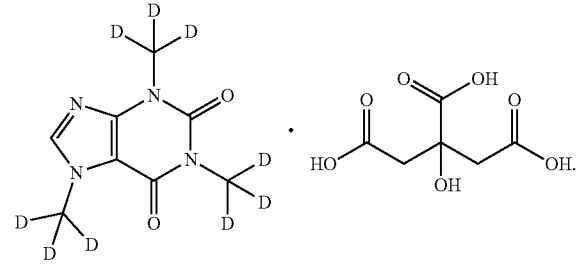 [SMILES: [2H]C([2H])([2H])n1c(=O)c2c(ncn2C([2H])([2H])[2H])n(C([2H])([2H])[2H])c1=O ; O=C(O)CC(O)(CC(=O)O)C(=O)O]

In another aspect, d9-caffeine, or a pharmaceutically or nutraceutically acceptable salt, hydrate, or solvate thereof, has an isotopic purity of at least 50.0%, 60.0%, 70.0%, 75.0%, 80.0%, 85.0%, 90.0%, 95.0%, 97.0%, 98.0%, 99.0%, 99.5%, 99.7%, 99.8%, or 99.9%. More specifically, in certain embodiments the term "d9-caffeine" indicates more than a single molecule. For example, d9-caffeine may be present in an amount measured in micrograms, milligrams, grams, or kilograms, and as such comprises a large number of individual molecules. For such isotopically-labeled molecules, isotopic enrichment may be described as a percentage indicating the percent of isotopic atoms at a particular site on the molecule. The percentage can be referred to as the "isotopic purity" of the isotopically-labeled compound. In any of the pharmaceutical compositions, nutraceutical compositions, food products, beverages, or nutritional supplements described herein, d9-caffeine, or a pharmaceutically or nutraceutically acceptable salt, hydrate, or solvate thereof, has an isotopic purity of at least 50.0%. In another aspect, d9-caffeine, or a pharmaceutically or nutraceutically acceptable salt, hydrate, or solvate thereof, has an isotopic purity of at least 60.0%. In another aspect, d9-caffeine, or a pharmaceutically or nutraceutically acceptable salt, hydrate, or solvate thereof, has an isotopic purity of at least 70.0%. In another aspect, d9-caffeine, or a pharmaceutically or nutraceutically acceptable salt, hydrate, or solvate thereof, has an isotopic purity of at least 75.0%. In another aspect, d9-caffeine, or a pharmaceutically or nutraceutically acceptable salt, hydrate, or solvate thereof, has an isotopic purity of at least 80.0%. In another aspect, d9-caffeine, or a pharmaceutically or nutraceutically acceptable salt, hydrate, or solvate thereof, has an isotopic purity of at least 85.0%. In another aspect, d9-caffeine, or a pharmaceutically or nutraceutically acceptable salt, hydrate, or solvate thereof, has an isotopic purity of at least 90.0%. In another aspect, d9-caffeine, or a pharmaceutically or nutraceutically acceptable salt, hydrate, or solvate thereof, has an isotopic purity of at least 95.0%. In another aspect, d9-caffeine, or a pharmaceutically or nutraceutically acceptable salt, hydrate, or solvate thereof, has an isotopic purity of at least 97.0%. In another aspect, d9-caffeine, or a pharmaceutically or nutraceutically acceptable salt, hydrate, or solvate thereof, has an isotopic purity of at least 98.0%. In another aspect, d9-caffeine, or a pharmaceutically or nutraceutically acceptable salt, hydrate, or solvate thereof, has an isotopic purity of at least 99.0%. In another aspect, d9-caffeine, or a pharmaceutically or nutraceutically acceptable salt, hydrate, or solvate thereof, has an isotopic purity of at least 99.5%. In another aspect, d9-caffeine, or a pharmaceutically or nutraceutically acceptable salt, hydrate, or solvate thereof, has an isotopic purity of at least 99.7%. In another aspect, d9-caffeine, or a pharmaceutically or nutraceutically acceptable salt, hydrate, or solvate thereof, has an isotopic purity of at least 99.9%. In another aspect, d9-caffeine, or a pharmaceutically or nutraceutically acceptable salt, hydrate, or solvate thereof, is suitable for administration to a human or animal. In another aspect, d9-caffeine, or a pharmaceutically or nutraceutically acceptable salt, hydrate, or solvate thereof, is produced and tested in compliance with the Good Manufacturing Practice (GMP) requirements.

In another aspect, any of the pharmaceutical compositions, nutraceutical compositions, food products, beverages, or nutritional supplements described herein comprises about 1 mg to about 10,000 mg of d9-caffeine, or a pharmaceutically or nutraceutically acceptable salt, hydrate, or solvate thereof. In another aspect, any of the pharmaceutical compositions, nutraceutical compositions, food products, beverages, or nutritional supplements described herein comprises about 1 mg to about 5,000 mg of d9-caffeine, or a pharmaceutically or nutraceutically acceptable salt, hydrate, or solvate thereof. In another aspect, any of the pharmaceutical compositions, nutraceutical compositions, food products, beverages, or nutritional supplements described herein comprises about 1 mg to about 1000 mg of d9-caffeine, or a pharmaceutically or nutraceutically acceptable salt, hydrate, or solvate thereof. In another aspect, the pharmaceutical composition, nutraceutical composition, food product, beverage, or nutritional supplement comprises about 1 mg to about 800 mg of d9-caffeine, or a pharmaceutically or nutraceutically acceptable salt, hydrate, or solvate thereof. In another aspect, the pharmaceutical composition, nutraceutical composition, food product, beverage, or nutritional supplement comprises about 1 mg to about 600 mg of d9-caffeine, or a pharmaceutically or nutraceutically acceptable salt, hydrate, or solvate thereof. In another aspect, the pharmaceutical composition, nutraceutical composition, food product, beverage, or nutritional supplement comprises about 1 mg to about 400 mg of d9-caffeine, or a pharmaceutically or nutraceutically acceptable salt, hydrate, or solvate thereof. In another aspect, the pharmaceutical composition, nutraceutical composition, food product, beverage, or nutritional supplement comprises about 1 mg to about 300 mg of d9-caffeine, or a pharmaceutically or nutraceutically acceptable salt, hydrate, or solvate thereof. In another aspect, the pharmaceutical composition, nutraceutical composition, food product, beverage, or nutritional supplement comprises about 1 mg to about 250 mg of d9-caffeine, or a pharmaceutically or nutraceutically acceptable salt, hydrate, or solvate thereof. In another aspect, the pharmaceutical composition, nutraceutical composition, food product, beverage, or nutritional supplement comprises about 1 mg to about 200 mg of d9-caffeine, or a pharmaceutically or nutraceutically acceptable salt, hydrate, or solvate thereof. In another aspect, the pharmaceutical composition, nutraceutical composition, food product, beverage, or nutritional supplement comprises about 1 mg to about 125 mg of d9-caffeine, or a pharmaceutically or nutraceutically acceptable salt, hydrate, or solvate thereof. In another aspect, the pharmaceutical composition, nutraceutical composition, food product, beverage, or nutritional supplement comprises about 5 mg to about 75 mg of the compound of d9-caffeine, or a pharmaceutically or nutraceutically acceptable salt, hydrate, or solvate thereof. In another aspect, the pharmaceutical composition, nutraceutical composition, food product, beverage, or nutritional supplement comprises about 10 mg to about 200 mg of d9-caffeine, or a pharmaceutically or nutraceutically acceptable salt, hydrate, or solvate thereof. In another aspect, the pharmaceutical composition, nutraceutical composition, food product, beverage, or nutritional supplement comprises about 10 mg to about 150 mg of d9-caffeine, or a pharmaceutically or nutraceutically acceptable salt, hydrate, or solvate thereof. In another aspect the pharmaceutical composition, nutraceutical composition, food product, beverage, or nutritional supplement comprises about 10 mg to about 100 mg of d9-caffeine, or a pharmaceutically or nutraceutically acceptable salt, hydrate, or solvate thereof. In another aspect, the pharmaceutical composition, nutraceutical composition, food product, beverage, or nutritional supplement comprises about 10 mg to about 75 mg of d9-caffeine, or a pharmaceutically or nutraceutically acceptable salt, hydrate, or solvate thereof. In another aspect, the pharmaceutical composition, nutraceutical composition, food product, beverage, or nutritional supplement comprises about 10 mg to about 50 mg of d9-caffeine, or a pharmaceutically or nutraceutically acceptable salt, hydrate, or solvate thereof. In another aspect, the pharmaceutical composition, nutraceutical composition, food product, beverage, or nutritional supplement comprises about 20 mg to about 200 mg of d9-caffeine, or a pharmaceutically or nutraceutically acceptable salt, hydrate, or solvate thereof. In another aspect, the pharmaceutical composition, nutraceutical composition, food product, beverage, or nutritional supplement comprises about 20 mg to about 150 mg of d9-caffeine, or a pharmaceutically or nutraceutically acceptable salt, hydrate, or solvate thereof. In another aspect, the pharmaceutical composition, nutraceutical composition, food product, beverage, or nutritional supplement comprises about 20 mg to about 100 mg of d9-caffeine, or a pharmaceutically or nutraceutically acceptable salt, hydrate, or solvate thereof. In another aspect, the pharmaceutical composition, nutraceutical composition, food product, beverage, or nutritional supplement comprises about 20 mg to about 75 mg of d9-caffeine, or a pharmaceutically or nutraceutically acceptable salt, hydrate, or solvate thereof. In another aspect, the pharmaceutical composition, nutraceutical composition, food product, beverage, or nutritional supplement comprises about 20 mg to about 50 mg of d9-caffeine, or a pharmaceutically or nutraceutically acceptable salt, hydrate, or solvate thereof.

In another aspect, the pharmaceutical composition, nutraceutical composition, food product, beverage, or nutritional supplement comprises about 1 mg to about 275 mg of d9-caffeine, or a pharmaceutically or nutraceutically acceptable salt, hydrate, or solvate thereof. In another aspect, the pharmaceutical composition, nutraceutical composition, food product, beverage, or nutritional supplement comprises about 10 mg to about 275 mg of d9-caffeine, or a pharmaceutically or nutraceutically acceptable, salt, hydrate, or solvate thereof. For example, the pharmaceutical composition, nutraceutical composition, food product, beverage, or nutritional supplement may comprise about 10-15 mg, 15-20 mg, 20-25 mg, 25-30 mg, 30-35 mg, 35-40 mg, 40-45 mg, 45-50 mg, 50-55 mg, 55-60 mg, 60-65 mg, 65-70 mg, 70-75 mg, 75-80 mg, 80-85 mg, 85-90 mg, 90-95 mg, 95-100 mg, 100-105 mg, 105-110 mg, 110-115 mg, 115-120 mg, 120-125 mg, 125-130 mg, 130-135 mg, 135-140 mg, 140-145 mg, 145-150 mg, 150-155 mg, 155-160 mg, 160-165 mg, 165-170 mg, 170-175 mg, 175-180 mg, 180-185 mg, 185-190 mg, 190-195 mg, 195-200 mg, 200-205 mg, 205-210 mg, 210-215 mg, 215-220 mg, 220-225 mg, 225-230 mg, 230-235 mg, 235-240 mg, 240-245 mg, 245-250 mg, 250-255 mg, 255-260 mg, 260-265 mg, 265-270 mg, or 270-275 mg of d9-caffeine, or a pharmaceutically or nutraceutically acceptable salt, hydrate, or solvate thereof. In certain embodiments, the pharmaceutical composition, nutraceutical composition, food product, beverage, or nutritional supplement comprises about 10-15 mg of d9-caffeine, or a pharmaceutically or nutraceutically acceptable salt, hydrate, or solvate thereof. In certain embodiments, the pharmaceutical composition, nutraceutical composition, food product, beverage, or nutritional supplement comprises about 15-20 mg of d9-caffeine, or a pharmaceutically or nutraceutically acceptable salt, hydrate, or solvate thereof. In certain embodiments, the pharmaceutical composition, nutraceutical composition, food product, beverage, or nutritional supplement comprises about 20-25 mg of d9-caffeine, or a pharmaceutically or nutraceutically acceptable salt, hydrate, or solvate thereof. In certain embodiments, the pharmaceutical composition, nutraceutical composition, food product, beverage, or nutritional supplement comprises about 25-30 mg of d9-caffeine, or a pharmaceutically or nutraceutically acceptable salt, hydrate, or solvate thereof. In certain embodiments, the pharmaceutical composition, nutraceutical composition, food product, beverage, or nutritional supplement comprises about 30-35 mg of d9-caffeine, or a pharmaceutically or nutraceutically acceptable salt, hydrate, or solvate thereof. In some embodiments, the pharmaceutical composition, nutraceutical composition, food product, beverage, or nutritional supplement comprises about 35-40 mg of d9-caffeine, or a pharmaceutically or nutraceutically acceptable salt, hydrate, or solvate thereof. In certain embodiments, the pharmaceutical composition, nutraceutical composition, food product, beverage, or nutritional supplement comprises about 40-45 mg of d9-caffeine, or a pharmaceutically or nutraceutically acceptable salt, hydrate, or solvate thereof. In some embodiments, the pharmaceutical composition, nutraceutical composition, food product, beverage, or nutritional supplement comprises about 45-50 mg of d9-caffeine, or a pharmaceutically or nutraceutically acceptable salt, hydrate, or solvate thereof. In certain embodiments, the pharmaceutical composition, nutraceutical composition, food product, beverage, or nutritional supplement comprises about 50-55 mg of d9-caffeine, or a pharmaceutically or nutraceutically acceptable salt, hydrate, or solvate thereof. In some embodiments, the pharmaceutical composition, nutraceutical composition, food product, beverage, or nutritional supplement comprises about 55-60 mg of d9-caffeine, or a pharmaceutically or nutraceutically acceptable salt, hydrate, or solvate thereof. In certain embodiments, the pharmaceutical composition, nutraceutical composition, food product, beverage, or nutritional supplement comprises about 60-65 mg of d9-caffeine, or a pharmaceutically or nutraceutically acceptable salt, hydrate, or solvate thereof. In some embodiments, the pharmaceutical composition, nutraceutical composition, food product, beverage, or nutritional supplement comprises about 65-70 mg of d9-caffeine, or a pharmaceutically or nutraceutically acceptable salt, hydrate, or solvate thereof. In certain embodiments, the pharmaceutical composition, nutraceutical composition, food product, beverage, or nutritional supplement comprises about 70-75 mg of d9-caffeine, or a pharmaceutically or nutraceutically acceptable salt, hydrate, or solvate thereof. In some embodiments, the pharmaceutical composition, nutraceutical composition, food product, beverage, or nutritional supplement comprises about 75-80 mg of d9-caffeine, or a pharmaceutically or nutraceutically acceptable salt, hydrate, or solvate thereof. In certain embodiments, the pharmaceutical composition, nutraceutical composition, food product, beverage, or nutritional supplement comprises about 80-85 mg of d9-caffeine, or a pharmaceutically or nutraceutically acceptable salt, hydrate, or solvate thereof. In some embodiments, the pharmaceutical composition, nutraceutical composition, food product, beverage, or nutritional supplement comprises about 85-90 mg of d9-caffeine, or a pharmaceutically or nutraceutically acceptable salt, hydrate, or solvate thereof. In certain embodiments, the pharmaceutical composition, nutraceutical composition, food product, beverage, or nutritional supplement comprises about 90-95 mg of d9-caffeine, or a pharmaceutically or nutraceutically acceptable salt, hydrate, or solvate thereof. In some embodiments, the pharmaceutical composition, nutraceutical composition, food product, beverage, or nutritional supplement comprises about 95-100 mg of d9-caffeine, or a pharmaceutically or nutraceutically acceptable salt, hydrate, or solvate thereof. In certain embodiments, the pharmaceutical composition, nutraceutical composition, food product, beverage, or nutritional supplement comprises about 100-105 mg of d9-caffeine, or a pharmaceutically or nutraceutically acceptable salt, hydrate, or solvate thereof. In some embodiments, the pharmaceutical composition, nutraceutical composition, food product, beverage, or nutritional supplement comprises about 105-110 mg of d9-caffeine, or a pharmaceutically or nutraceutically acceptable salt, hydrate, or solvate thereof. In certain embodiments, the pharmaceutical composition, nutraceutical composition, food product, beverage, or nutritional supplement comprises about 110-115 mg of d9-caffeine, or a pharmaceutically or nutraceutically acceptable salt, hydrate, or solvate thereof. In some embodiments, the pharmaceutical composition, nutraceutical composition, food product, beverage, or nutritional supplement comprises about 115-120 mg of d9-caffeine, or a pharmaceutically or nutraceutically acceptable salt, hydrate, or solvate thereof. In certain embodiments, the pharmaceutical composition, nutraceutical composition, food product, beverage, or nutritional supplement comprises about 120-125 mg of d9-caffeine, or a pharmaceutically or nutraceutically acceptable salt, hydrate, or solvate thereof. In some embodiments, the pharmaceutical composition, nutraceutical composition, food product, beverage, or nutritional supplement comprises about 125-130 mg of d9-caffeine, or a pharmaceutically or nutraceutically acceptable salt, hydrate, or solvate thereof. In certain embodiments, the pharmaceutical composition, nutraceutical composition, food product, beverage, or nutritional supplement comprises about 130-135 mg of d9-caffeine, or a pharmaceutically or nutraceutically acceptable salt, hydrate, or solvate thereof. In some embodiments, the pharmaceutical composition, nutraceutical composition, food product, beverage, or nutritional supplement comprises about 135-140 mg of d9-caffeine, or a pharmaceutically or nutraceutically acceptable salt, hydrate, or solvate thereof. In certain embodiments, the pharmaceutical composition, nutraceutical composition, food product, beverage, or nutritional supplement comprises about 140-145 mg of d9-caffeine, or a pharmaceutically or nutraceutically acceptable salt, hydrate, or solvate thereof. In some embodiments, the pharmaceutical composition, nutraceutical composition, food product, beverage, or nutritional supplement comprises about 145-150 mg of d9-caffeine, or a pharmaceutically or nutraceutically acceptable salt, hydrate, or solvate thereof. In certain embodiments, the pharmaceutical composition, nutraceutical composition, food product, beverage, or nutritional supplement comprises about 150-155 mg of d9-caffeine, or a pharmaceutically or nutraceutically acceptable salt, hydrate, or solvate thereof. In some embodiments, the pharmaceutical composition, nutraceutical composition, food product, beverage, or nutritional supplement comprises about 155-160 mg of d9-caffeine, or a pharmaceutically or nutraceutically acceptable salt, hydrate, or solvate thereof. In certain embodiments, the pharmaceutical composition, nutraceutical composition, food product, beverage, or nutritional supplement comprises about 160-165 mg of d9-caffeine, or a pharmaceutically or nutraceutically acceptable salt, hydrate, or solvate thereof. In some embodiments, the pharmaceutical composition, nutraceutical composition, food product, beverage, or nutritional supplement comprises about 165-170 mg of d9-caffeine, or a pharmaceutically or nutraceutically acceptable salt, hydrate, or solvate thereof. In certain embodiments, the pharmaceutical composition, nutraceutical composition, food product, beverage, or nutritional supplement comprises about 170-175 mg of d9-caffeine, or a pharmaceutically or nutraceutically acceptable salt, hydrate, or solvate thereof. In some embodiments, the pharmaceutical composition, nutraceutical composition, food product, beverage, or nutritional supplement comprises about 175-180 mg of d9-caffeine, or a pharmaceutically or nutraceutically acceptable salt, hydrate, or solvate thereof. In certain embodiments, the pharmaceutical composition, nutraceutical composition, food product, beverage, or nutritional supplement comprises about 180-185 mg of d9-caffeine, or a pharmaceutically or nutraceutically acceptable salt, hydrate, or solvate thereof. In some embodiments, the pharmaceutical composition, nutraceutical composition, food product, beverage, or nutritional supplement comprises about 185-190 mg of d9-caffeine, or a pharmaceutically or nutraceutically acceptable salt, hydrate, or solvate thereof. In certain embodiments, the pharmaceutical composition, nutraceutical composition, food product, beverage, or nutritional supplement comprises about 190-195 mg of d9-caffeine, or a pharmaceutically or nutraceutically acceptable salt, hydrate, or solvate thereof. In some embodiments, the pharmaceutical composition, nutraceutical composition, food product, beverage, or nutritional supplement comprises about 195-200 mg of d9-caffeine, or a pharmaceutically or nutraceutically acceptable salt, hydrate, or solvate thereof. In certain embodiments, the pharmaceutical composition, nutraceutical composition, food product, beverage, or nutritional supplement comprises about 200-205 mg of d9-caffeine, or a pharmaceutically or nutraceutically acceptable salt, hydrate, or solvate thereof. In some embodiments, the pharmaceutical composition, nutraceutical composition, food product, beverage, or nutritional supplement comprises about 205-210 mg of d9-caffeine, or a pharmaceutically or nutraceutically acceptable salt, hydrate, or solvate thereof. In certain embodiments, the pharmaceutical composition, nutraceutical composition, food product, beverage, or nutritional supplement comprises about 210-215 mg of d9-caffeine, or a pharmaceutically or nutraceutically acceptable salt, hydrate, or solvate thereof. In some embodiments, the pharmaceutical composition, nutraceutical composition, food product, beverage, or nutritional supplement comprises about 215-220 mg of d9-caffeine, or a pharmaceutically or nutraceutically acceptable salt, hydrate, or solvate thereof. In certain embodiments, the pharmaceutical composition, nutraceutical composition, food product, beverage, or nutritional supplement comprises about 220-225 mg of d9-caffeine, or a pharmaceutically or nutraceutically acceptable salt, hydrate, or solvate thereof. In some embodiments, the pharmaceutical composition, nutraceutical composition, food product, beverage, or nutritional supplement comprises about 225-230 mg of d9-caffeine, or a pharmaceutically or nutraceutically acceptable salt, hydrate, or solvate thereof. In certain embodiments, the pharmaceutical composition, nutraceutical composition, food product, beverage, or nutritional supplement comprises about 230-235 mg of d9-caffeine, or a pharmaceutically or nutraceutically acceptable salt, hydrate, or solvate thereof. In some embodiments, the pharmaceutical composition, nutraceutical composition, food product, beverage, or nutritional supplement comprises about 235-240 mg of d9-caffeine, or a pharmaceutically or nutraceutically acceptable salt, hydrate, or solvate thereof. In certain embodiments, the pharmaceutical composition, nutraceutical composition, food product, beverage, or nutritional supplement comprises about 240-245 mg of d9-caffeine, or a pharmaceutically or nutraceutically acceptable salt, hydrate, or solvate thereof. In some embodiments, the pharmaceutical composition, nutraceutical composition, food product, beverage, or nutritional supplement comprises about 245-250 mg of d9-caffeine, or a pharmaceutically or nutraceutically acceptable salt, hydrate, or solvate thereof. In certain embodiments, the pharmaceutical composition, nutraceutical composition, food product, beverage, or nutritional supplement comprises about 250-255 mg of d9-caffeine, or a pharmaceutically or nutraceutically acceptable salt, hydrate, or solvate thereof. In some embodiments, the pharmaceutical composition, nutraceutical composition, food product, beverage, or nutritional supplement comprises about 255-260 mg of d9-caffeine, or a pharmaceutically or nutraceutically acceptable salt, hydrate, or solvate thereof. In certain embodiments, the pharmaceutical composition, nutraceutical composition, food product, beverage, or nutritional supplement comprises about 260-265 mg of d9-caffeine, or a pharmaceutically or nutraceutically acceptable salt, hydrate, or solvate thereof. In some embodiments, the pharmaceutical composition, nutraceutical composition, food product, beverage, or nutritional supplement comprises about 265-270 mg of d9-caffeine, or a pharmaceutically or nutraceutically acceptable salt, hydrate, or solvate thereof. In certain embodiments, the pharmaceutical composition, nutraceutical composition, food product, beverage, or nutritional supplement comprises about 270-275 mg of d9-caffeine, or a pharmaceutically or nutraceutically acceptable salt, hydrate, or solvate thereof.

In another aspect, any of the pharmaceutical compositions, nutraceutical compositions, food products, beverages, or nutritional supplements described herein comprise an amount of d9-caffeine, or a pharmaceutically or nutraceutically acceptable salt, hydrate, or solvate thereof, wherein the d9-caffeine comprises a greater percentage of d9-caffeine than that which would occur naturally, e.g., as a result of the natural abundance of deuterium. For example, the percentage of d9-caffeine in the caffeine may be at least 0.1%, at least 0.5%, at least 1.0, at least 2.0%, at least 3.0%, at least 4.0%, at least 5.0%, at least 10.0%, at least 20.0%, at least 30.0%, at least 40.0%, at least 50.0%, at least 60.0%, at least 70.0%, at least 75.0%, at least 80.0%, at least 85.0%, at least 90.0%, at least 95.0%, at least 97.0%, at least 98.0%, at least 99.0%, at least 99.5%, at least 99.7%, at least 99.8%, at least 99.9%, or at least 100%. In certain embodiments of such a pharmaceutical composition, nutraceutical composition, food product, beverage, or nutritional supplement, the amount of caffeine, or a pharmaceutically or nutraceutically acceptable salt, hydrate, or solvate thereof, is about 1 mg to about 10,000 mg. In certain embodiments, the amount is about 1 mg to about 5,000 mg. In certain embodiments, the amount is about 1 mg to about 1000 mg. In certain embodiments, the amount is about 1 mg to about 800 mg. In certain embodiments, the amount is about 1 mg to about 600 mg. In certain embodiments, the amount is about 1 mg to about 400 mg. In certain embodiments, the amount is about 1 mg to about 300 mg. In certain embodiments, the amount is about 1 mg to about 250 mg. In certain embodiments, the amount is about 1 mg to about 200 mg. In certain embodiments, the amount is about 1 mg to about 125 mg. In certain embodiments, the amount is about 5 mg to about 75 mg. In certain embodiments, the amount is about 10 mg to about 200 mg. In certain embodiments, the amount is about 10 mg to about 150 mg. In certain embodiments, the amount is about 10 mg to about 100 mg. In certain embodiments, the amount is about 10 mg to about 75 mg. In certain embodiments, the amount is about 10 mg to about 50 mg. In certain embodiments, the amount is about 20 mg to about 200 mg. In certain embodiments, the amount is about 20 mg to about 150 mg. In certain embodiments, the amount is about 20 mg to about 100 mg. In certain embodiments, the amount is about 20 mg to about 75 mg. In certain embodiments, the amount is about 20 mg to about 50 mg. In another aspect, any of the pharmaceutical compositions, nutraceutical compositions, food products, beverages, or nutritional supplements described herein comprises about 1 mg/ml to about 100 mg/ml of d9-caffeine, or a pharmaceutically or nutraceutically acceptable salt, hydrate, or solvate thereof. In another aspect the pharmaceutical composition, nutraceutical composition, food product, beverage, or nutritional supplement comprises about 1 mg/ml to about 75 mg/ml of d9-caffeine, or a pharmaceutically or nutraceutically acceptable salt, hydrate, or solvate thereof. In another aspect, the pharmaceutical composition, nutraceutical composition, food product, beverage, or nutritional supplement comprises about 1 mg/ml to about 50 mg/ml of d9-caffeine, or a pharmaceutically or nutraceutically acceptable salt, hydrate, or solvate thereof. In another aspect, the pharmaceutical composition, nutraceutical composition, food product, beverage, or nutritional supplement comprises about 1 mg/ml to about 25 mg/ml of d9-caffeine, or a pharmaceutically or nutraceutically acceptable salt, hydrate, or solvate thereof. In another aspect, the pharmaceutical composition, nutraceutical composition, food product, beverage, or nutritional supplement comprises about 2 mg/ml to about 100 mg/ml of d9-caffeine, or a pharmaceutically or nutraceutically acceptable salt, hydrate, or solvate thereof. In another aspect, the pharmaceutical composition, nutraceutical composition, food product, beverage, or nutritional supplement comprises about 2 mg/ml to about 75 mg/ml of d9-caffeine, or a pharmaceutically or nutraceutically acceptable salt, hydrate, or solvate thereof. In another aspect, the pharmaceutical composition, nutraceutical composition, food product, beverage, or nutritional supplement comprises about 2 mg/ml to about 50 mg/ml of d9-caffeine, or a pharmaceutically or nutraceutically acceptable salt, hydrate, or solvate thereof. In another aspect, the pharmaceutical composition, nutraceutical composition, food product, beverage, or nutritional supplement comprises about 2 mg/ml to about 25 mg/ml of d9-caffeine, or a pharmaceutically or nutraceutically acceptable salt, hydrate, or solvate thereof. In another aspect the pharmaceutical composition, nutraceutical composition, food product, beverage, or nutritional supplement comprises about 2 mg/ml to about 15 mg/ml of d9-caffeine, or a pharmaceutically or nutraceutically acceptable salt, hydrate, or solvate thereof. In another aspect, the pharmaceutical composition, nutraceutical composition, food product, beverage, or nutritional supplement comprises about 5 mg/ml to about 100 mg/ml of d9-caffeine, or a pharmaceutically or nutraceutically acceptable salt, hydrate, or solvate thereof. In another aspect, the pharmaceutical composition, nutraceutical composition, food product, beverage, or nutritional supplement comprises about 5 mg/ml to about 75 mg/ml of d9-caffeine, or a pharmaceutically or nutraceutically acceptable salt, hydrate, or solvate thereof. In another aspect, the pharmaceutical composition, nutraceutical composition, food product, beverage, or nutritional supplement comprises about 5 mg/ml to about 50 mg/ml of d9-caffeine, or a pharmaceutically or nutraceutically acceptable salt, hydrate, or solvate thereof. In another aspect, the pharmaceutical composition, nutraceutical composition, food product, beverage, or nutritional supplement comprises about 5 mg/ml to about 25 mg/ml of d9-caffeine, or a pharmaceutically or nutraceutically acceptable salt, hydrate, or solvate thereof. In another aspect, the pharmaceutical composition, nutraceutical composition, food product, beverage, or nutritional supplement comprises about 5 mg/ml to about 15 mg/ml of d9-caffeine, or a pharmaceutically or nutraceutically acceptable salt, hydrate, or solvate thereof. In another aspect, the pharmaceutical or nutraceutical composition may comprise about 10 mg/ml to about 100 mg/ml of d9-caffeine, or a pharmaceutically or nutraceutically acceptable salt, hydrate, or solvate thereof. In another aspect, the pharmaceutical or nutraceutical composition may comprise about 10 mg/ml to about 75 mg/ml of d9-caffeine, or a pharmaceutically or nutraceutically acceptable salt, hydrate, or solvate thereof. In another aspect, the pharmaceutical or nutraceutical composition may comprise about 10 mg/ml to about 50 mg/ml of d9-caffeine, or a pharmaceutically or nutraceutically acceptable salt, hydrate, or solvate thereof. In another aspect, the pharmaceutical or nutraceutical composition may comprise about 10 mg/ml to about 25 mg/ml of d9-caffeine, or a pharmaceutically or nutraceutically acceptable salt, hydrate, or solvate thereof.

In another aspect, any of the pharmaceutical compositions, nutraceutical compositions, food products, beverages, or nutritional supplements described herein comprise a concentration of d9-caffeine, or a pharmaceutically or nutraceutically acceptable salt, hydrate, or solvate thereof, wherein d9-caffeine comprises a greater percentage of d9-caffeine than that which would occur naturally, e.g., as a result of the natural abundance of deuterium. For example, the percentage of d9-caffeine in the caffeine may be at least 0.1%, at least 0.5%, at least 1.0, at least 2.0%, at least 3.0%, at least 4.0%, at least 5.0%, at least 10.0%, at least 20.0%, at least 30.0%, at least 40.0%, at least 50.0%, at least 60.0%, at least 70.0%, at least 75.0%, at least 80.0%, at least 85.0%, at least 90.0%, at least 95.0%, at least 97.0%, at least 98.0%, at least 99.0%, at least 99.5%, at least 99.7%, at least 99.8%, at least 99.9%, or at least 100%. In certain embodiments of such a pharmaceutical composition, nutraceutical composition, food product, beverage, or nutritional supplement, the concentration of d9-caffeine, or a pharmaceutically or nutraceutically acceptable salt, hydrate, or solvate thereof, is about 1 mg/ml to about 100 mg/ml. In certain embodiments, the concentration is about 1 mg/ml to about 75 mg/ml. In certain embodiments, the concentration is about 1 mg/ml to about 50 mg/ml. In certain embodiments, the concentration is about 1 mg/ml to about 25 mg/ml. In certain embodiments, the concentration is about 1 mg/ml to about 75 mg/ml. In certain embodiments, the concentration is about 2 mg/ml to about 100 mg/ml. In certain embodiments, the concentration is about 2 mg/ml to about 75 mg/ml. In certain embodiments, the concentration is about 2 mg/ml to about 50 mg/ml. In certain embodiments, the concentration is about 2 mg/ml to about 25 mg/ml. In certain embodiments, the concentration is about 2 mg/ml to about 15 mg/ml. In certain embodiments, the concentration is about 5 mg/ml to about 100 mg/ml. In certain embodiments, the concentration is about 5 mg/ml to about 75 mg/ml. In certain embodiments, the concentration is about 5 mg/ml to about 50 mg/ml. In certain embodiments, the concentration is about 5 mg/ml to about 25 mg/ml. In certain embodiments, the concentration is about 5 mg/ml to about 15 mg/ml. In certain embodiments, the concentration is about 10 mg/ml to about 100 mg/ml. In certain embodiments, the concentration is about 10 mg/ml to about 75 mg/ml. In certain embodiments, the concentration is about 10 mg/ml to about 50 mg/ml. In certain embodiments, the concentration is about 10 mg/ml to about 25 mg/ml.

The following aspects of the pharmaceutical compositions, nutraceutical compositions, food products, beverages, or nutritional supplements described herein are provided. The pharmaceutical compositions, nutraceutical compositions, cosmetic compositions, food products, beverages, or nutritional supplements described herein may comprise both d9-caffeine and non-isotopically enriched caffeine (including but not limited to as a result of mixing isotopically enriched d9-caffeine and non-isotopically enriched caffeine). In any of the pharmaceutical compositions, nutraceutical compositions, food products, beverages, or nutritional supplements described herein, the percentage of the amount of d9-caffeine, or a pharmaceutically or nutraceutically acceptable salt, hydrate, or solvate thereof, relative to the total amount of caffeine present in the composition, food product, beverage, or nutritional supplement ranges from about 1% to about 99%. In any of the pharmaceutical compositions, nutraceutical compositions, food products, beverages, or nutritional supplements described herein, the percentage of the amount of d9-caffeine, or a pharmaceutically or nutraceutically acceptable salt, hydrate, or solvate thereof, relative to the total amount of caffeine present in the composition, food product, beverage, or nutritional supplement ranges from about 1% to about 99.99%. In any of the pharmaceutical compositions, nutraceutical compositions, food products, beverages, or nutritional supplements described herein, the percentage of the amount of d9-caffeine, or a pharmaceutically or nutraceutically acceptable salt, hydrate, or solvate thereof, relative to the total amount of caffeine present in the composition, food product, beverage, or nutritional supplement ranges from about 1% to about 100%. In any of the pharmaceutical compositions, nutraceutical compositions, food products, beverages, or nutritional supplements described herein, d9-caffeine, or a pharmaceutically or nutraceutically acceptable salt, hydrate, or solvate thereof, represents greater than 50%, 60%, 70%, 80%, 90%, 95%, 97%, 98%, 99%, 99.5%, 99.7%, or 99.9% of the total amount of caffeine present in the composition, food product, beverage, or nutritional supplement. In any of the pharmaceutical compositions, nutraceutical compositions, food products, beverages, or nutritional supplements described herein, d9-caffeine, or a pharmaceutically or nutraceutically acceptable salt, hydrate, or solvate thereof, represents 100% of the total amount of caffeine present in the composition. In another aspect, the percentage of the amount of d9-caffeine, or a pharmaceutically or nutraceutically acceptable salt, hydrate, or solvate thereof, relative to the total amount of caffeine present in the composition, food product, beverage, or nutritional supplement ranges from about 1% to about 100%. In another aspect, the percentage of the amount of d9-caffeine, or a pharmaceutically or nutraceutically acceptable salt, hydrate, or solvate thereof, relative to the total amount of caffeine present in the composition, food product, beverage, or nutritional supplement ranges from about 10% to about 100%. In another aspect, the percentage of the amount of d9-caffeine, or a pharmaceutically or nutraceutically acceptable salt, hydrate, or solvate thereof, relative to the total amount of caffeine present in the composition, food product, beverage, or nutritional supplement ranges from about 10% to about 99%. In another aspect, the percentage of the amount of d9-caffeine, or a pharmaceutically or nutraceutically acceptable salt, hydrate, or solvate thereof, relative to the total amount of caffeine present in the composition, food product, beverage, or nutritional supplement ranges from about 10% to about 90%. In another aspect, the percentage of the amount of d9-caffeine, or a pharmaceutically or nutraceutically acceptable salt, hydrate, or solvate thereof, relative to the total amount of caffeine present in the composition, food product, beverage, or nutritional supplement ranges from about 10% to about 80%. In another aspect, the percentage of the amount of d9-caffeine, or a pharmaceutically or nutraceutically acceptable salt, hydrate, or solvate thereof, relative to the total amount of caffeine present in the composition, food product, beverage, or nutritional supplement ranges from about 10% to about 70%. In another aspect, the percentage of the amount of d9-caffeine, or a pharmaceutically or nutraceutically acceptable salt, hydrate, or solvate thereof, relative to the total amount of caffeine present in the composition, food product, beverage, or nutritional supplement ranges from about 10% to about 60%. In another aspect, the percentage of the amount of d9-caffeine, or a pharmaceutically or nutraceutically acceptable salt, hydrate, or solvate thereof, relative to the total amount of caffeine present in the composition, food product, beverage, or nutritional supplement ranges from about 10% to about 50%. In another aspect, the percentage of the amount of d9-caffeine, or a pharmaceutically or nutraceutically acceptable salt, hydrate, or solvate thereof, relative to the total amount of caffeine present in the composition, food product, beverage, or nutritional supplement ranges from about 10% to about 40%. In another aspect, the percentage of the amount of d9-caffeine, or a pharmaceutically or nutraceutically acceptable salt, hydrate, or solvate thereof, relative to the total amount of caffeine present in the composition, food product, beverage, or nutritional supplement ranges from about 10% to about 25%. In another aspect, the percentage of the amount of d9-caffeine, or a pharmaceutically or nutraceutically acceptable salt, hydrate, or solvate thereof, relative to the total amount of caffeine present in the composition, food product, beverage, or nutritional supplement ranges from about 25% to about 100%. In another aspect, the percentage of the amount of d9-caffeine, or a pharmaceutically or nutraceutically acceptable salt, hydrate, or solvate thereof, relative to the total amount of caffeine present in the composition, food product, beverage, or nutritional supplement ranges from about 25% to about 99%. In another aspect, the percentage of the amount of d9-caffeine, or a pharmaceutically or nutraceutically acceptable salt, hydrate, or solvate thereof, relative to the total amount of caffeine present in the composition, food product, beverage, or nutritional supplement ranges from about 25% to about 90%. In another aspect, the percentage of the amount of d9-caffeine, or a pharmaceutically or nutraceutically acceptable salt, hydrate, or solvate thereof, relative to the total amount of caffeine present in the composition, food product, beverage, or nutritional supplement ranges from about 25% to about 80%. In another aspect, the percentage of the amount of d9-caffeine, or a pharmaceutically or nutraceutically acceptable salt, hydrate, or solvate thereof, relative to the total amount of caffeine present in the composition, food product, beverage, or nutritional supplement ranges from about 25% to about 70%. In another aspect, the percentage of the amount of d9-caffeine, or a pharmaceutically or nutraceutically acceptable salt, hydrate, or solvate thereof, relative to the total amount of caffeine present in the composition, food product, beverage, or nutritional supplement ranges from about 25% to about 60%. In another aspect, the percentage of the amount of d9-caffeine, or a pharmaceutically or nutraceutically acceptable salt, hydrate, or solvate thereof, relative to the total amount of caffeine present in the composition, food product, beverage, or nutritional supplement ranges from about 25% to about 50%. In another aspect, the percentage of the amount of d9-caffeine, or a pharmaceutically or nutraceutically acceptable salt, hydrate, or solvate thereof, relative to the total amount of caffeine present in the composition, food product, beverage, or nutritional supplement ranges from about 25% to about 40%. In another aspect, the percentage of the amount of d9-caffeine, or a pharmaceutically or nutraceutically acceptable salt, hydrate, or solvate thereof, relative to the total amount of caffeine present in the composition, food product, beverage, or nutritional supplement ranges from about 30% to about 100%. In another aspect, the percentage of the amount of d9-caffeine, or a pharmaceutically or nutraceutically acceptable salt, hydrate, or solvate thereof, relative to the total amount of caffeine present in the composition, food product, beverage, or nutritional supplement ranges from about 30% to about 99%. In another aspect, the percentage of the amount of d9-caffeine, or a pharmaceutically or nutraceutically acceptable salt, hydrate, or solvate thereof, relative to the total amount of caffeine present in the composition, food product, beverage, or nutritional supplement ranges from about 30% to about 90%. In another aspect, the percentage of the amount of d9-caffeine, or a pharmaceutically or nutraceutically acceptable salt, hydrate, or solvate thereof, relative to the total amount of caffeine present in the composition, food product, beverage, or nutritional supplement ranges from about 30% to about 80%. In another aspect, the percentage of the amount of d9-caffeine, or a pharmaceutically or nutraceutically acceptable salt, hydrate, or solvate thereof, relative to the total amount of caffeine present in the composition, food product, beverage, or nutritional supplement ranges from about 30% to about 70%. In another aspect, the percentage of the amount of d9-caffeine, or a pharmaceutically or nutraceutically acceptable salt, hydrate, or solvate thereof, relative to the total amount of caffeine present in the composition, food product, beverage, or nutritional supplement ranges from about 30% to about 60%. In another aspect, the percentage of the amount of d9-caffeine, or a pharmaceutically or nutraceutically acceptable salt, hydrate, or solvate thereof, relative to the total amount of caffeine present in the composition, food product, beverage, or nutritional supplement ranges from about 30% to about 50%. In another aspect, the percentage of the amount of d9-caffeine, or a pharmaceutically or nutraceutically acceptable salt, hydrate, or solvate thereof, relative to the total amount of caffeine present in the composition, food product, beverage, or nutritional supplement ranges from about 40% to about 100%. In another aspect, the percentage of the amount of d9-caffeine, or a pharmaceutically or nutraceutically acceptable salt, hydrate, or solvate thereof, relative to the total amount of caffeine present in the composition, food product, beverage, or nutritional supplement ranges from about 40% to about 99%. In another aspect, the percentage of the amount of d9-caffeine, or a pharmaceutically or nutraceutically acceptable salt, hydrate, or solvate thereof, relative to the total amount of caffeine present in the composition, food product, beverage, or nutritional supplement ranges from about 40% to about 90%. In another aspect, the percentage of the amount of d9-caffeine, or a pharmaceutically or nutraceutically acceptable salt, hydrate, or solvate thereof, relative to the total amount of caffeine present in the composition, food product, beverage, or nutritional supplement ranges from about 40% to about 80%. In another aspect, the percentage of the amount of d9-caffeine, or a pharmaceutically or nutraceutically acceptable salt, hydrate, or solvate thereof, relative to the total amount of caffeine present in the composition, food product, beverage, or nutritional supplement ranges from about 40% to about 70%. In another aspect, the percentage of the amount of d9-caffeine, or a pharmaceutically or nutraceutically acceptable salt, hydrate, or solvate thereof, relative to the total amount of caffeine present in the composition, food product, beverage, or nutritional supplement ranges from about 40% to about 60%. In another aspect, the percentage of the amount of d9-caffeine, or a pharmaceutically or nutraceutically acceptable salt, hydrate, or solvate thereof, relative to the total amount of caffeine present in the composition, food product, beverage, or nutritional supplement ranges from about 40% to about 50%. In another aspect, the percentage of the amount of d9-caffeine, or a pharmaceutically or nutraceutically acceptable salt, hydrate, or solvate thereof, relative to the total amount of caffeine present in the composition, food product, beverage, or nutritional supplement ranges from about 50% to about 100%. In another aspect, the percentage of the amount of d9-caffeine, or a pharmaceutically or nutraceutically acceptable salt, hydrate, or solvate thereof, relative to the total amount of caffeine present in the composition, food product, beverage, or nutritional supplement ranges from about 50% to about 99%. In another aspect, the percentage of the amount of d9-caffeine, or a pharmaceutically or nutraceutically acceptable salt, hydrate, or solvate thereof, relative to the total amount of caffeine present in the composition, food product, beverage, or nutritional supplement ranges from about 50% to about 90%. In another aspect, the percentage of the amount of d9-caffeine, or a pharmaceutically or nutraceutically acceptable salt, hydrate, or solvate thereof, relative to the total amount of caffeine present in the composition, food product, beverage, or nutritional supplement ranges from about 50% to about 80%. In another aspect, the percentage of the amount of d9-caffeine, or a pharmaceutically or nutraceutically acceptable salt, hydrate, or solvate thereof, relative to the total amount of caffeine present in the composition, food product, beverage, or nutritional supplement ranges from about 50% to about 70%. In another aspect, the percentage of the amount of d9-caffeine, or a pharmaceutically or nutraceutically acceptable salt, hydrate, or solvate thereof, relative to the total amount of caffeine present in the composition, food product, beverage, or nutritional supplement ranges from about 50% to about 60%.

In another aspect, d9-caffeine, or a pharmaceutically or nutraceutically acceptable salt, hydrate, or solvate thereof, is included in an amount from about 0.001% to 50% based on the weight of all the components of the composition, food product, beverage, or nutritional supplement. In certain embodiments, d9-caffeine, or a pharmaceutically or nutraceutically acceptable salt, hydrate, or solvate thereof, is included in an amount from about 0.1% to 5% (e.g., 0.1% to 1%, 1% to 5%) based on the weight of all the components of the composition, food product, beverage, or nutritional supplement. In certain embodiments, d9-caffeine, or a pharmaceutically or nutraceutically acceptable salt, hydrate, or solvate thereof, is included in an amount from about 5% to 20% based on the weight of all the components of the composition, food product, beverage, or nutritional supplement. In certain embodiments, d9-caffeine, or a pharmaceutically or nutraceutically acceptable salt, hydrate, or solvate thereof, is included in an amount from about 20% to 50% based on the weight of all the components of the composition, food product, beverage, or nutritional supplement.

It will be understood that the total daily usage of the pharmaceutical composition described herein may be decided by an attending physician within the scope of sound medical judgment, and will depend safety and toxicity profile of the components of the pharmaceutical composition. The specific therapeutically effective dose level for any particular patient or organism will depend upon a variety of factors including the disorder being treated and the severity of the disorder; the clinical studies results, the activity of the specific compound employed; the specific pharmaceutical composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts (see, for example, Goodman and Gilman's, *The Pharmacological Basis of Therapeutics*, Tenth Edition, A. Gilman, J. Hardman, and L. Limbird, eds., McGraw-Hill Press, 155-173, 2001).

In certain embodiments, a composition (e.g., pharmaceutical composition, nutraceutical composition, or cosmetic composition) or nutritional supplement as described herein is administered 1-8 times daily. In a particular embodiment, the composition is administered 1 time per day. In a particular embodiment, the composition is administered 2 times per day. In a particular embodiment, the composition is administered 3 times per day. In a particular embodiment, the composition is administered 4 times per day. In a particular embodiment, the composition is administered use 5 times per day. In a particular embodiment, the composition is administered 6 times per day. In a particular embodiment, the composition is administered 7 times per day. In a particular embodiment, the composition is administered 8 times per day. In a particular embodiment, the composition is administered every two hours. In a particular embodiment, the composition is administered every four hours. In a particular embodiment, the composition is administered every six hours. In a particular embodiment, the composition is administered every eight hours. In a particular embodiment, the composition is administered every twelve hours. In a particular embodiment, the composition is administered every sixteen hours. In a particular embodiment, the composition is administered every twenty-four hours. In a particular embodiment, the composition is administered every forty-eight hours.

In certain embodiments, a composition (e.g., pharmaceutical composition, nutraceutical composition, or cosmetic composition) or nutritional supplement as described herein is administered for a day. In some embodiments, a composition (e.g., pharmaceutical composition, nutraceutical composition, or cosmetic composition) or nutritional supplement as described herein is administered for a week. In certain embodiments, a composition (e.g., pharmaceutical composition, nutraceutical composition, or cosmetic composition) or nutritional supplement as described herein is administered for a month. In some embodiments, a composition (e.g., pharmaceutical composition, nutraceutical composition, or cosmetic composition) or nutritional supplement as described herein is administered for two months. In certain embodiments, a composition (e.g., pharmaceutical composition, nutraceutical composition, or cosmetic composition) or nutritional supplement as described herein is administered for three months. In some embodiments, a composition (e.g., pharmaceutical composition, nutraceutical composition, or cosmetic composition) or nutritional supplement as described herein is administered for four months. In certain embodiments, a composition (e.g., pharmaceutical composition, nutraceutical composition, or cosmetic composition) or nutritional supplement as described herein is administered for six months. In some embodiments, a composition (e.g., pharmaceutical composition, nutraceutical composition, or cosmetic composition) or nutritional supplement as described herein is administered for eight months. In certain embodiments, a composition (e.g., pharmaceutical composition, nutraceutical composition, or cosmetic composition) or nutritional supplement as described herein is administered for a year. In some embodiments, a composition (e.g., pharmaceutical composition, nutraceutical composition, or cosmetic composition) or nutritional supplement as described herein is administered for more than a year. In certain embodiments, a composition (e.g., pharmaceutical composition, nutraceutical composition, or cosmetic composition) or nutritional supplement as described herein is administered indefinitely.

In another aspect, any of the pharmaceutical compositions described herein may be suitable for oral administration, parenteral (e.g., intravenous (IV)) administration, topical administration, inhalation, buccal administration, or for delivery to the lungs. In another aspect, the pharmaceutical composition is suitable for oral administration. In another aspect, the pharmaceutical composition is suitable for parenteral administration. In another aspect, the pharmaceutical composition is suitable for intravenous (IV) administration. In another aspect, the pharmaceutical composition is suitable for topical administration. In another aspect, the pharmaceutical composition is suitable for delivery to the lungs.

In another aspect, any of the nutraceutical compositions described herein may be suitable for oral administration.

In another aspect, the composition is a cosmetic composition. In another aspect, the cosmetic composition is suitable for topical administration.

In another aspect, any of the pharmaceutical or nutraceutical compositions described herein suitable for oral administration may be a solid dose composition. In another aspect, the solid dose composition may be a tablet, capsule, granule, powder, sachet, or chewable. In certain embodiment, the chewable solid dose composition is chewing gum. In certain embodiments, the chewable solid dose composition is a chewable tablet. In certain embodiments, the solid dose composition is an orally dissolving tablet. In certain embodiments, the solid dose composition is an orally dissolving strip, e.g., a thin film strip.

In another aspect, any of the pharmaceutical, nutraceutical, or cosmetic compositions described herein suitable for topical administration may be a shampoo, conditioner, shampoo, conditioner, cream, foam, gel, lotion, ointment, transdermal patch, tincture, or paste.

In another aspect, any of the pharmaceutical compositions described herein suitable for delivery to the lungs may be administered using an electronic cigarette or other vaping device, a nebulizer, a pressurized metered dose inhaler (pMDI), or a dry powder inhaler (DPI).

In another aspect, any of the pharmaceutical, nutraceutical, or cosmetic compositions described herein may further comprise a pharmaceutically or nutraceutically acceptable carrier.

In another aspect, any of the pharmaceutical, nutraceutical, or cosmetic compositions described herein may further comprise an additional agent. In another aspect, the additional agent refers to natural or synthetic compound(s) capable of activity or other direct effect in the diagnosis, cure, mitigation, treatment or prevention of disease or to affect the structure and function of the body. In any of the foregoing embodiments, a provided composition may contain one or more additional active agents, including, but not limiting to pharmaceutical agent that belong to different Biopharmaceutics Classification System (BCS), for example, from BCS class I, II, III or IV, and/or peptides and/or vaccines and/or nucleic acid-based products and/or immunologic agents and/or phytopharmaceutical agents and/or nutraceutical agents and/or cosmetic agents and/or supplements. In certain embodiments, the additional active agent is a small molecule (e.g., when the molecular weight is lower than 500, 800, 1000, or 1500, g/mol). In certain embodiments, the additional active agent is a drug approved by the U.S. Food and Drug Administration and/or the European Medicines Agency.

In the present invention, each additional agent may be incorporated into the composition. Depending upon the qualitative and quantitative composition of the formulation chosen, the additional agent(s) may be released from the composition over a period of time (i.e. sustained release) or immediately. The present invention can be used in the treatment of both humans and animals.

In another aspect, the additional agent is ergotamine, an anti-inflammatory agent, a steroid, a barbiturate, an opioid analgesic, or a combination thereof. In another aspect, any of the hydrogen atoms in ergotamine, the anti-inflammatory agent, the steroid, the barbiturate, or the opioid analgesic may be replaced with deuterium. In another aspect, the anti-inflammatory agent is a cyclooxygenase-3 (COX-3) inhibitor, a non-steroidal anti-inflammatory drug (NSAID), or a cyclooxygenase-2 (COX-2) inhibitor.

In another aspect, the NSAID is ibuprofen, naproxen, sulindac, ketoprofen, tolmetin, etodolac, fenoprofen, diclofenac, flurbiprofen, piroxicam, ketorolac, indomethacin, nabumetone, oxaprozin, mefanamic acid, or diflunisal.

In another aspect, the opioid analgesic is codeine, fentanyl, hydrocodone, hydromorphone, meperidine, methadone, morphine, or oxycodone.

In another aspect, the barbiturate is secobarbital, mephobarbital, pentobarbital, butabarbital, phenobarbital, or amobarbital.

In another aspect, the COX-2 inhibitor is celecoxib, valdecoxib, rofecoxib, or etoricoxib.

In another aspect, the COX-3 inhibitor is acetaminophen, phenacetin, antipyrine, or dipyrone.

In another aspect, the percentage of deuterium (i.e., the percentage of hydrogen atoms replaced by deuterium atoms) in ergotamine, the anti-inflammatory agent, the steroid, the barbiturate, or the opioid analgesic is at least 0.1%. In another aspect, the percentage of deuterium in ergotamine, the anti-inflammatory agent, the steroid, the barbiturate, or the opioid analgesic is at least 0.5%. In another aspect, the percentage of deuterium in ergotamine, the anti-inflammatory agent, the steroid, the barbiturate, or the opioid analgesic is at least 1%. In another aspect, the percentage of deuterium in ergotamine, the anti-inflammatory agent, the steroid, the barbiturate, or the opioid analgesic is at least 5%. In another aspect, the percentage of deuterium in ergotamine, the anti-inflammatory agent, the steroid, the barbiturate, or the opioid analgesic is at least 10%. In another aspect, the percentage of deuterium in ergotamine, the anti-inflammatory agent, the steroid, the barbiturate, or the opioid analgesic is at least 15%. In another aspect, the percentage of deuterium in ergotamine, the anti-inflammatory agent, the steroid, the barbiturate, or the opioid analgesic is at least 20%. In another aspect, the percentage of deuterium in ergotamine, the anti-inflammatory agent, the steroid, the barbiturate, or the opioid analgesic is at least 25%. In another aspect, the percentage of deuterium in ergotamine, the anti-inflammatory agent, the steroid, the barbiturate, or the opioid analgesic is at least 30%. In another aspect, the percentage of deuterium in ergotamine, the anti-inflammatory agent, the steroid, the barbiturate, or the opioid analgesic is at least 40%. In another aspect, the percentage of deuterium in ergotamine, the anti-inflammatory agent, the steroid, the barbiturate, or the opioid analgesic is at least 50%. In another aspect, the percentage of deuterium in ergotamine, the anti-inflammatory agent, the steroid, the barbiturate, or the opioid analgesic is at least 60%. In another aspect, the percentage of deuterium in ergotamine, the anti-inflammatory agent, the steroid, the barbiturate, or the opioid analgesic is at least 70%. In another aspect, the percentage of deuterium in ergotamine, the anti-inflammatory agent, the steroid, the barbiturate, or the opioid analgesic is at least 80%. In another aspect, the percentage of deuterium in ergotamine, the anti-inflammatory agent, the steroid, the barbiturate, or the opioid analgesic is at least 90%. In another aspect, the percentage of deuterium in ergotamine, the anti-inflammatory agent, the steroid, the barbiturate, or the opioid analgesic is at least 95%. In another aspect, the percentage of deuterium in ergotamine, the anti-inflammatory agent, the steroid, the barbiturate, or the opioid analgesic is at least 97%. In another aspect, the percentage of deuterium in ergotamine, the anti-inflammatory agent, the steroid, the barbiturate, or the opioid analgesic is at least 98%. In another aspect, the percentage of deuterium in ergotamine, the anti-inflammatory agent, the steroid, the barbiturate, or the opioid analgesic is at least 99%. In another aspect, the percentage of deuterium in ergotamine, the anti-inflammatory agent, the steroid, the barbiturate, or the opioid analgesic is at least 99.5%. In another aspect, the percentage of deuterium in ergotamine, the anti-inflammatory agent, the steroid, the barbiturate, or the opioid analgesic is 100%.

In another aspect, the additional agent is a stimulant or therapy (i.e., therapeutic agent) for ADHD. In another aspect, the additional agent is a stimulant for ADHD. In another aspect, the additional agent is a therapy for ADHD.

In another aspect, the stimulant for ADHD is methylphenidate, dexmethylphenidate, serdexmethylphenidate, amphetamine, dextroamphetamine, lisdexamfetamine, or a pharmaceutically acceptable salt thereof; or any combination thereof. In another aspect, the pharmaceutically acceptable salt is a hydrochloride salt or a sulfate salt. In another aspect, the stimulant for ADHD is methylphenidate, methylphenidate hydrochloride, dexmethylphenidate, serdexmethylphenidate, amphetamine, amphetamine sulfate, dextroamphetamine, lisdexamfetamine, or any combination thereof.

In another aspect, the combination of a stimulant or therapy for ADHD is serdexmethylphenidate/dexmethylphenidate or amphetamine/dextroamphetamine. In another aspect, the combination of a stimulant or therapy for ADHD is a mixed salt of a single-entity amphetamine product. In another aspect, the combination of a stimulant or therapy for ADHD is a mixed salt of one or more amphetamine products.

In another aspect, the therapy for ADHD is atomoxetine, clonidine, guanfacine, bupropion, desipramine, imipramine, nortriptyline, venlafaxine, viloxazine, buspirone, or neuroleptics. In another aspect, the therapy for ADHD is atomoxetine, clonidine, guanfacine, bupropion, desipramine, imipramine, nortriptyline, venlafaxine, viloxazine, or buspirone. In another aspect, the therapy for ADHD is atomoxetine, clonidine, guanfacine, bupropion, or viloxazine. In another aspect, the therapy for ADHD is atomoxetine, clonidine, or guanfacine. In another aspect, the therapy for ADHD is atomoxetine. In another aspect, the therapy for ADHD is clonidine or guanfacine. In another aspect, the therapy for ADHD is desipramine, imipramine, or nortriptyline.

In certain embodiments, the composition further comprises a sweetener. Sweeteners can be used to improve palatability and are usually classified as natural or artificial. A sweetener may be a natural sweetener or artificial sweetener. Exemplary natural sweeteners include, but are not limited to, dextrose, fructose, glucose, liquid glucose, maltose, rebiana, glycyrrhizin, thaumatin, sorbitol, mannitol, isomalt, glycerol, maltitol, xylitol, and erythritol. Exemplary artificial sweeteners include, but are not limited to, saccharin, cyclamate, aspartame, acesulfame-K, sucralose, alitame, and neotame. In certain embodiments, sucralose is used as a sweetener. In certain embodiments, one or combination of neohespiridin dihydrochalcone, glycerol, and/or sucralose are used as sweeteners. In some embodiments, the concentration of the sweetener in the composition is between 0.01% and 5%, inclusive, by weight. In some embodiments, the concentration of the sweetener in the composition is between 0.01% and 1%, inclusive, by weight. In some embodiments, the concentration of the sweetener in the composition is between 0.5% and 1%, inclusive, by weight. In certain embodiments, the composition further comprises sucralose. In certain embodiments, the composition further comprises sucralose as about 0.01-0.25% based on the dry weight of all the components of the composition.

In certain embodiments, a composition further comprises a colorant. A colorant can be added to enhance the aesthetic appeal of the composition, especially when formulation ingredients or drugs are presented in a non-solution form. Generally, any colorant could be added, such as for example FD&C pigments (for example, blue no 1, blue no 2, red no 3, red no 40, yellow no 5, or yellow no 6). Exemplary colorants include, but are not limited to annatto extract, dehydrated beets (beet powder), canthaxanthin, caramel, β-apo-8'-carotenal, β-carotene, cochineal extract, carmine, sodium copper chlorophyllin, toasted partially defatted cooked cottonseed flour, ferrous gluconate, ferrous lactate, grape color extract, grape skin extract (enocianina), synthetic iron oxide, fruit juice, vegetable juice, carrot oil, paprika, paprika oleoresin, mica-based pearlescent pigments, riboflavin, saffron, *spirulina* extract, titanium dioxide, tomato lycopene extract; tomato lycopene concentrate, turmeric, turmeric oleoresin, alumina (dried aluminum hydroxide), calcium carbonate, potassium sodium copper chlorophyllin (chlorophyllin-copper complex), dihydroxyacetone, bismuth oxychloride, synthetic iron oxide, ferric ammonium ferrocyanide, ferric ferrocyanide, chromium hydroxide green, chromium oxide greens, guanine, pyrophyllite, mica, talc, aluminum powder, bronze powder, copper powder, zinc oxide, bismuth citrate, disodium EDTA-copper, guaiazulene, henna, lead acetate, pyrophyllite, silver, ultramarines, manganese violet, luminescent zinc sulfide, FD&C Blue No. 1, FD&C Blue No. 2, FD&C Green No. 3, Orange B, Citrus Red No. 2, FD&C Red No. 3, FD&C Red No. 40, FD&C Yellow No. 5, FD&C Yellow No. 6, D&C Blue No. 4, D&C Green No. 5, D&C Green No. 6, D&C Green No. 8, D&C Orange No. 4, D&C Orange No. 5, D&C Orange No. 10, D&C Orange No. 11, FD&C Red No. 4, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 33, D&C Red No. 34, D&C Red No. 36, D&C Red No. 39, D&C Violet No. 2, D&C Yellow No. 7, Ext. D&C Yellow No. 7, D&C Yellow No. 8, D&C Yellow No. 10, D&C Yellow No. 11, D&C Black No. 2, D&C Black No. 3, D&C Brown No. 1, and Ext. D&C Violet No. 2. In certain embodiments, a colorant represents 0.001% to about 0.5% based on the weight of all the components of the composition. In some embodiments, the concentration of the colorant in the composition is between 0.001% and 5%, inclusive, by weight. In some embodiments, the concentration of the colorant in the composition is between 0.001% and 1%, inclusive, by weight.

In certain embodiments, a provided composition further comprises a flavoring agent. In certain embodiments, the selection of a suitable flavoring agent to be added depends on the original taste sensation of the composition, including metallic, acidic, alkaline, salty, sweet, bitter and sour taste sensation. Certain flavoring agents, alone or in combination, mask specific taste sensations. For example, metallic taste could be masked with, but not limited to, flavoring agents based on berry fruits, grape, and/or peppermint. For example, acidic taste could be masked with, but not limited to, flavoring agents based on lemon, lime, grapefruit, orange, cherry, and/or strawberry. For example, alkaline taste could be masked with, but not limited to, flavoring agents based on aniseed, caramel, passion fruit, peach and/or banana. For example, salty taste could be masked with, but not limited to, flavoring agents based on butterscotch, caramel, hazelnut, spicy, maple, apricot, apple, peach, vanilla, and/or wintergreen mint. For example, bitter taste could be masked with, but not limited to, flavoring agents based on licorice, passion fruit, coffee, chocolate, peppermint, grapefruit, cherry, peach, raspberry, wild cherry, walnut, mint, and/or anise. For example, sweet taste could be masked with, but not limited to, flavoring agents based on grape, cream, caramel, banana, vanilla and/or fruit berry. For example, sour taste could be masked with, but not limited to, flavoring agents based on citrus flavors, licorice, root, bear and/or raspberry. Flavoring agents can be used alone or in combination and its selection will be dependent also upon the target population and any other substance (e.g., a pharmaceutical or nutraceutical agent) incorporated in the composition. The perception of the flavoring agent changes from individual to individual and also with age: typically, a geriatric population will prefer mint or orange flavors whereas younger populations tend to prefer flavors like fruit punch, raspberry, etc. Generally, the amount of flavoring agent needed to mask an unpleasant taste or improve taste overall will depend not only on the composition of the formulation but also on the flavor type and its strength.

In certain embodiments, a flavoring agent is a palatable flavor that has a long shelf life and which does not crystallize or precipitate out of the composition upon storage. In certain embodiments, flavoring agents may be natural flavors, derived from various parts of the plants like leaves, fruits and flowers, or synthetic flavor oils or powders. Exemplary flavor oils that may be used in or as flavoring agents include, but are not limited to, peppermint oil, cinnamon oil, spearmint oil, and oil of nutmeg. Exemplary fruity flavors that may be used in or as flavoring agents include, but are not limited to, vanilla, cocoa, coffee, chocolate and citrus. Exemplary fruit essence flavors that may be used in or as flavoring agents include, but are not limited to, apple, raspberry, cherry, and pineapple. The amount of flavoring agent added can vary with the flavor employed. In some embodiments, the concentration of the flavoring agent in the composition is between about 0% and 5%, by weight. In some embodiments, the concentration of the flavoring agent in the composition is between 0.001% and 5%, inclusive, by weight. In some embodiments, the concentration of the flavoring agent in the composition is between 0.1% and 1%, inclusive, by weight. In some embodiments, the concentration of the flavoring agent in the composition is between 0.5% and 1%, inclusive, by weight.

In certain embodiments, a provided composition further comprises taste-masking. Taste-masking agents can be added to ameliorate the general organoleptic characteristics of the compositions. In certain embodiments, taste-masking agents may be used to mask unpleasant taste of some components. The main taste sensations include metallic, acidic, alkaline, salty, sweet, bitter and sour. Exemplary of taste-masking agents include, but are not limited to, menthol, peppermint oil, L-menthol, cyclodextrins, glycerol, maltodextrins, ion-exchange resins, amino acids, gelatin, gelatinized starch, liposomes, lecithin, or lecithin-like substances and salts. The amount of taste-masking added can vary with the taste-masking employed. In certain embodiments, the taste-masking agent comprises about 0% to about 50% based on the dry weight of all the components of the composition. In certain embodiments, the taste-masking agent represents 0% to about 5% based on the dry weight of all the components of the composition.

In another aspect, a provided composition further comprises a cooling agent. Cooling agents may also be added in order to improve the aftertaste of the composition. Exemplary cooling agents include, but are not limited to, neohesperidine dihydrochalcone, menthol flavor, L-Menthol and some polyol sugars which are widely used for this purpose. Other components can also be added that should compete with sensory stimuli, such as Cremophor (which is used to coat the surface protein receptors), or saline solutions (e.g., sodium chloride, which competes within channel receptors with the bitter stimuli to reduce the overall perception of bitterness). In certain embodiments, the cooling agents in the composition is one or a combination of neohesperidine dihydrochalcone, menthol, and/or polyol sugar. In certain embodiments, the mucoadhesive composition further comprises cooling agents of about 0% to about 5% based on the weight of all the components of the composition. In certain embodiments, the mucoadhesive composition further comprises cooling agents as about 0.001% to about 2.5% based on the weight of all the components of the composition.

In certain embodiments, a provided composition further comprises one or more preservatives. The preservative employed in the invention can be any preservative, as long as does not negate other desirable properties of the composition. Example of a preservative is an antimicrobial preservative that is used to prevent or inhibit the growth of micro-organisms in the composition. Exemplary preservative agents include, but are not limited to, $C_3$-$C_8$ alcohols, phenylethyl alcohol, chlorbutanol, p-hydroxybenzoic, acid esters, benzathonium chloride and benzalkonium chloride, benzoic acid, propyl galate, methylparaben, propylparaben, sorbic acid, sodium benzoate and/or potassium sorbate. The amount of preservative agent added can vary with the preservative agent employed. In certain embodiments, a preservative agent represents about 0% to about 45% based on the weight of all the components of the composition. In certain embodiments, a preservative agent represents about 0% to about 1% (e.g., 0.025% to 0.2%) based on the weight of all the components of the composition.

In certain embodiments, a provided composition (e.g., cosmetic or pharmaceutical composition) further comprises penetration enhancement additives. Penetration enhancers effectively increase permeability of active agents and/or composition excipients. Preferably, penetration enhancement additives are compatible with the active agents and other formulation excipients, pharmacologically inert, non-toxic and inexpensive. Exemplary penetration enhancement additives include, but are not limited to, bile salts, surfactants, fatty acids and derivatives, glycerides, chelators, salicylates, polymers, or other compounds. Exemplary of bile salts that act as Penetration enhancement additives include, but are not limited to, Sodium glycocholate, sodium deoxycholate, sodium taurocholate, sodium fusidate, sodium glycodeoxycholate, sodium taurodihydrofusidate. Exemplary of surfactants that act as penetration enhancement additives include, but are not limited to, sodium lauryl sulfate, brij1-35, lysophosphatidylcholine, dioctyl sodium sulfosuccinate, laurenth-9, polysorbate-80, polyethyleneglycol-8-laurate, glyceryl monolaurate. Exemplary of fatty acids and derivatives that act as Penetration enhancement additives include, but are not limited to, sorbitan laurate, sodium caprate, sucrose palmitate, lauroyl choline, sodium myristate, palmitoyl carnitine. Exemplary of glycerides that act as penetration enhancement additives include, but are not limited to phospholipids, monohexanoin, medium chain glycerides. Exemplary of chelators that act as penetration enhancement additives include, but are not limited to ethylene diamine tetraacetate (EDTA), disodium EDTA. Exemplary of salicylates that act as penetration enhancement additives include, but are not limited to salicylic acid, sodium methoxysalicylate, acetyl salicylic acid. Exemplary of polymers that act as penetration enhancement additives include, but are not limited to chitosan, polycarbophil, sodium carboxymethylcellulose and their derivatives. Exemplary of other compounds that act as Penetration enhancement additives include, but are not limited to cyclodextrins, benzalkonium chloride, phenothiazines, nitric acid donors, menthol, zonula occluden toxin, poly-1-arginines, soybean derivative glucosides, citicholine, α-acid derivatives. The amount of penetration enhancement additives added can vary with the Penetration enhancement additives agent employed.

In one aspect, the invention provides a nutritional supplement comprising d9-caffeine.

In another aspect, the nutritional supplement further comprises one or more of flavoring agent(s), sweetener(s), taste-masking agent(s), vitamins, minerals, co-factors, proteins, lipids, peptides, and amino acids. In certain embodiments, the nutritional supplement further comprises a flavoring agent. In some embodiments, the nutritional supplement further comprises a sweetener. In certain embodiments, the nutritional supplement further comprises vitamins. In some embodiments, the nutritional supplement further comprises minerals. In certain embodiments, the nutritional supplement further comprises co-factors. In some embodiments, the nutritional supplement further comprises proteins. In certain embodiments, the nutritional supplement further comprises lipids. In some embodiments, the nutritional supplement further comprises peptides. In certain embodiments, the nutritional supplement further comprises amino acids. In some embodiments, the nutritional supplement further comprises a taste-masking agent.

In certain embodiments, the nutritional supplement is a composition that is mixed with water to form a beverage. In some embodiments, the nutritional supplement is a composition that is added to a beverage. In certain embodiments, the nutritional supplement is a composition that is added to a food product.

In certain embodiments, the nutritional supplement is a tablet, capsule, granule, powder, sachet, chewable, liquid, gel, paste, concentrate, suspension, emulsion, or ready-to-drink liquid. In some embodiments, the nutritional supplement is a tablet. In certain embodiments, the nutritional supplement is a capsule. In some embodiments, the nutritional supplement is a granule. In certain embodiments, the nutritional supplement is a powder. In some embodiments, the nutritional supplement is a sachet. In certain embodiments, the nutritional supplement is a chewable. In certain embodiment, the chewable nutritional supplement is chewing gum. In certain embodiments, the chewable nutritional supplement is a chewable tablet. In certain embodiments, the nutritional supplement is an orally dissolving tablet. In certain embodiments, the nutritional supplement is an orally dissolving strip, e.g., a thin film strip. In some embodiments, the nutritional supplement is liquid. In certain embodiments, the nutritional supplement is a gel. In some embodiments, the nutritional supplement is a paste. In certain embodiments, the nutritional supplement is a concentrate. In some embodiments, the nutritional supplement is a suspension. In certain embodiments, the nutritional supplement is an emulsion. In some embodiments, the nutritional supplement is a ready-to-drink liquid. In some embodiments, the nutritional supplement has a caloric density of 50-500 kcal. In certain embodiments, the nutritional supplement has a caloric density of about 50 kcal. In some embodiments, the nutritional supplement has a caloric density of about 100 kcal. In certain embodiments, the nutritional supplement has a caloric density of about 200 kcal. In some embodiments, the nutritional supplement has a caloric density of about 300 kcal. In certain embodiments, the nutritional supplement has a caloric density of about 400 kcal. In some embodiments, the nutritional supplement has a caloric density of about 500 kcal.

In another aspect, the nutritional supplement comprises about 1 mg to about 10,000 mg of d9-caffeine, or a pharmaceutically or nutraceutically acceptable salt, hydrate, or solvate thereof. For example, the nutritional supplement may comprise about 1 mg to about 9000 mg, about 1 mg to about 8000 mg, about 1 mg to about 7000 mg, about 1 mg to about 6000 mg, about 1 mg to about 5000 mg, about 1 mg to about 4000 mg, about 1 mg to about 3000 mg, or about 1 mg to about 2000 mg of d9-caffeine, or a pharmaceutically or nutraceutically acceptable salt, hydrate, or solvate thereof. In another aspect, the nutritional supplement comprises about 1 mg to about 1000 mg of d9-caffeine, or a pharmaceutically or nutraceutically acceptable salt, hydrate, or solvate thereof. In another aspect, the nutritional supplement comprises about 1 mg to about 800 mg of d9-caffeine, or a pharmaceutically or nutraceutically acceptable salt, hydrate, or solvate thereof. In another aspect, the nutritional supplement comprises about 1 mg to about 600 mg of d9-caffeine, or a pharmaceutically or nutraceutically acceptable salt, hydrate, or solvate thereof. In another aspect, the nutritional supplement comprises about 1 mg to about 400 mg of d9-caffeine, or a pharmaceutically or nutraceutically acceptable salt, hydrate, or solvate thereof. In another aspect, the nutritional supplement comprises about 1 mg to about 300 mg of d9-caffeine, or a pharmaceutically or nutraceutically acceptable salt, hydrate, or solvate thereof. In another aspect, the nutritional supplement comprises about 1 mg to about 250 mg of d9-caffeine, or a pharmaceutically or nutraceutically acceptable salt, hydrate, or solvate thereof. In another aspect, the nutritional supplement comprises about 1 mg to about 200 mg of d9-caffeine, or a pharmaceutically or nutraceutically acceptable salt, hydrate, or solvate thereof. In another aspect, the nutritional supplement comprises about 1 mg to about 125 mg of d9-caffeine, or a pharmaceutically or nutraceutically acceptable salt, hydrate, or solvate thereof. In another aspect, the nutritional supplement comprises about 5 mg to about 75 mg of d9-caffeine, or a pharmaceutically or nutraceutically acceptable salt, hydrate, or solvate thereof. In another aspect, the nutritional supplement comprises about 10 mg to about 200 mg of d9-caffeine, or a pharmaceutically or nutraceutically acceptable salt, hydrate, or solvate thereof. In another aspect, the nutritional supplement comprises about 10 mg to about 150 mg of d9-caffeine, or a pharmaceutically or nutraceutically acceptable salt, hydrate, or solvate thereof. In another aspect, the nutritional supplement comprises about 10 mg to about 100 mg of d9-caffeine, or a pharmaceutically or nutraceutically acceptable salt, hydrate, or solvate thereof. In another aspect, the nutritional supplement comprises about 10 mg to about 75 mg of d9-caffeine, or a pharmaceutically or nutraceutically acceptable salt, hydrate, or solvate thereof. In another aspect, the nutritional supplement comprises about 10 mg to about 50 mg of d9-caffeine, or a pharmaceutically or nutraceutically acceptable salt, hydrate, or solvate thereof. In another aspect, the nutritional supplement comprises about 20 mg to about 200 mg of d9-caffeine, or a pharmaceutically or nutraceutically acceptable salt, hydrate, or solvate thereof. In another aspect, the nutritional supplement comprises about 20 mg to about 150 mg of d9-caffeine, or a pharmaceutically or nutraceutically acceptable salt, hydrate, or solvate thereof. In another aspect, the nutritional supplement comprises about 20 mg to about 100 mg of d9-caffeine, or a pharmaceutically or nutraceutically acceptable salt, hydrate, or solvate thereof. In another aspect, the nutritional supplement comprises about 20 mg to about 75 mg of d9-caffeine, or a pharmaceutically or nutraceutically acceptable salt, hydrate, or solvate thereof. In another aspect, the nutritional supplement comprises about 20 mg to about 50 mg of d9-caffeine, or a pharmaceutically or nutraceutically acceptable salt, hydrate, or solvate thereof.

In another aspect, the nutritional supplement comprises about 1 mg to about 275 mg of d9-caffeine, or a pharmaceutically or nutraceutically acceptable salt, hydrate, or solvate thereof. In another aspect, the nutritional supplement comprises about 30 mg to about 275 mg of d9-caffeine, or a pharmaceutically or nutraceutically acceptable, salt, hydrate, or solvate thereof. For example, the nutritional supplement may comprise about 10-15 mg, 15-20 mg, 20-25 mg, 25-30 mg, 30-35 mg, 35-40 mg, 40-45 mg, 45-50 mg, 50-55 mg, 55-60 mg, 60-65 mg, 65-70 mg, 70-75 mg, 75-80 mg, 80-85 mg, 85-90 mg, 90-95 mg, 95-100 mg, 100-105 mg, 105-110 mg, 110-115 mg, 115-120 mg, 120-125 mg, 125-130 mg, 130-135 mg, 135-140 mg, 140-145 mg, 145-150 mg, 150-155 mg, 155-160 mg, 160-165 mg, 165-170 mg, 170-175 mg, 175-180 mg, 180-185 mg, 185-190 mg, 190-195 mg, 195-200 mg, 200-205 mg, 205-210 mg, 210-215 mg, 215-220 mg, 220-225 mg, 225-230 mg, 230-235 mg, 235-240 mg, 240-245 mg, 245-250 mg, 250-255 mg, 255-260 mg, 260-265 mg, 265-270 mg, or 270-275 mg of d9-caffeine, or a pharmaceutically or nutraceutically acceptable salt, hydrate, or solvate thereof. In certain embodiments, the nutritional supplement comprises about 30-35 mg of d9-caffeine, or a pharmaceutically or nutraceutically acceptable salt, hydrate, or solvate thereof. In some embodiments, the nutritional supplement comprises about 35-40 mg of d9-caffeine, or a pharmaceutically or nutraceutically acceptable salt, hydrate, or solvate thereof. In certain embodiments, the nutritional supplement comprises about 40-45 mg of d9-caffeine, or a pharmaceutically or nutraceutically acceptable salt, hydrate, or solvate thereof. In some embodiments, the nutritional supplement comprises about 45-50 mg of d9-caffeine, or a pharmaceutically or nutraceutically acceptable salt, hydrate, or solvate thereof. In certain embodiments, the nutritional supplement comprises about 50-55 mg of d9-caffeine, or a pharmaceutically or nutraceutically acceptable salt, hydrate, or solvate thereof. In some embodiments, the nutritional supplement comprises about 55-60 mg of d9-caffeine, or a pharmaceutically or nutraceutically acceptable salt, hydrate, or solvate thereof. In certain embodiments, the nutritional supplement comprises about 60-65 mg of d9-caffeine, or a pharmaceutically or nutraceutically acceptable salt, hydrate, or solvate thereof. In some embodiments, the nutritional supplement comprises about 65-70 mg of d9-caffeine, or a pharmaceutically or nutraceutically acceptable salt, hydrate, or solvate thereof. In certain embodiments, the nutritional supplement comprises about 70-75 mg of d9-caffeine, or a pharmaceutically or nutraceutically acceptable salt, hydrate, or solvate thereof. In some embodiments, the nutritional supplement comprises about 75-80 mg of d9-caffeine, or a pharmaceutically or nutraceutically acceptable salt, hydrate, or solvate thereof. In certain embodiments, the nutritional supplement comprises about 80-85 mg of d9-caffeine, or a pharmaceutically or nutraceutically acceptable salt, hydrate, or solvate thereof. In some embodiments, the nutritional supplement comprises about 85-90 mg of d9-caffeine, or a pharmaceutically or nutraceutically acceptable salt, hydrate, or solvate thereof. In certain embodiments, the nutritional supplement comprises about 90-95 mg of d9-caffeine, or a pharmaceutically or nutraceutically acceptable salt, hydrate, or solvate thereof. In some embodiments, the nutritional supplement comprises about 95-100 mg of d9-caffeine, or a pharmaceutically or nutraceutically acceptable salt, hydrate, or solvate thereof. In certain embodiments, the nutritional supplement comprises about 100-105 mg of d9-caffeine, or a pharmaceutically or nutraceutically acceptable salt, hydrate, or solvate thereof. In some embodiments, the nutritional supplement comprises about 105-110 mg of d9-caffeine, or a pharmaceutically or nutraceutically acceptable salt, hydrate, or solvate thereof. In certain embodiments, the nutritional supplement comprises about 110-115 mg of d9-caffeine, or a pharmaceutically or nutraceutically acceptable salt, hydrate, or solvate thereof. In some embodiments, the nutritional supplement comprises about 115-120 mg of d9-caffeine, or a pharmaceutically or nutraceutically acceptable salt, hydrate, or solvate thereof. In certain embodiments, the nutritional supplement comprises about 120-125 mg of d9-caffeine, or a pharmaceutically or nutraceutically acceptable salt, hydrate, or solvate thereof. In some embodiments, the nutritional supplement comprises about 125-130 mg of d9-caffeine, or a pharmaceutically or nutraceutically acceptable salt, hydrate, or solvate thereof. In certain embodiments, the nutritional supplement comprises about 130-135 mg of d9-caffeine, or a pharmaceutically or nutraceutically acceptable salt, hydrate, or solvate thereof. In some embodiments, the nutritional supplement comprises about 135-140 mg of d9-caffeine, or a pharmaceutically or nutraceutically acceptable salt, hydrate, or solvate thereof. In certain embodiments, the nutritional supplement comprises about 140-145 mg of d9-caffeine, or a pharmaceutically or nutraceutically acceptable salt, hydrate, or solvate thereof. In some embodiments, the nutritional supplement comprises about 145-150 mg of d9-caffeine, or a pharmaceutically or nutraceutically acceptable salt, hydrate, or solvate thereof. In certain embodiments, the nutritional supplement comprises about 150-155 mg of d9-caffeine, or a pharmaceutically or nutraceutically acceptable salt, hydrate, or solvate thereof. In some embodiments, the nutritional supplement comprises about 155-160 mg of d9-caffeine, or a pharmaceutically or nutraceutically acceptable salt, hydrate, or solvate thereof. In certain embodiments, the nutritional supplement comprises about 160-165 mg of d9-caffeine, or a pharmaceutically or nutraceutically acceptable salt, hydrate, or solvate thereof. In some embodiments, the nutritional supplement comprises about 165-170 mg of d9-caffeine, or a pharmaceutically or nutraceutically acceptable salt, hydrate, or solvate thereof. In certain embodiments, the nutritional supplement comprises about 170-175 mg of d9-caffeine, or a pharmaceutically or nutraceutically acceptable salt, hydrate, or solvate thereof. In some embodiments, the nutritional supplement comprises about 175-180 mg of d9-caffeine, or a pharmaceutically or nutraceutically acceptable salt, hydrate, or solvate thereof. In certain embodiments, the nutritional supplement comprises about 180-185 mg of d9-caffeine, or a pharmaceutically or nutraceutically acceptable salt, hydrate, or solvate thereof. In some embodiments, the nutritional supplement comprises about 185-190 mg of d9-caffeine, or a pharmaceutically or nutraceutically acceptable salt, hydrate, or solvate thereof. In certain embodiments, the nutritional supplement comprises about 190-195 mg of d9-caffeine, or a pharmaceutically or nutraceutically acceptable salt, hydrate, or solvate thereof. In some embodiments, the nutritional supplement comprises about 195-200 mg of d9-caffeine, or a pharmaceutically or nutraceutically acceptable salt, hydrate, or solvate thereof. In certain embodiments, the nutritional supplement comprises about 200-205 mg of d9-caffeine, or a pharmaceutically or nutraceutically acceptable salt, hydrate, or solvate thereof. In some embodiments, the nutritional supplement comprises about 205-210 mg of d9-caffeine, or a pharmaceutically or nutraceutically acceptable salt, hydrate, or solvate thereof. In certain embodiments, the nutritional supplement comprises about 210-215 mg of d9-caffeine, or a pharmaceutically or nutraceutically acceptable salt, hydrate, or solvate thereof. In some embodiments, the nutritional supplement comprises about 215-220 mg of d9-caffeine, or a pharmaceutically or nutraceutically acceptable salt, hydrate, or solvate thereof. In certain embodiments, the nutritional supplement comprises about 220-225 mg of d9-caffeine, or a pharmaceutically or nutraceutically acceptable salt, hydrate, or solvate thereof. In some embodiments, the nutritional supplement comprises about 225-230 mg of d9-caffeine, or a pharmaceutically or nutraceutically acceptable salt, hydrate, or solvate thereof. In certain embodiments, the nutritional supplement comprises about 230-235 mg of d9-caffeine, or a pharmaceutically or nutraceutically acceptable salt, hydrate, or solvate thereof. In some embodiments, the nutritional supplement comprises about 235-240 mg of d9-caffeine, or a pharmaceutically or nutraceutically acceptable salt, hydrate, or solvate thereof. In certain embodiments, the nutritional supplement comprises about 240-245 mg of d9-caffeine, or a pharmaceutically or nutraceutically acceptable salt, hydrate, or solvate thereof. In some embodiments, the nutritional supplement comprises about 245-250 mg of d9-caffeine, or a pharmaceutically or nutraceutically acceptable salt, hydrate, or solvate thereof. In certain embodiments, the nutritional supplement comprises about 250-255 mg of d9-caffeine, or a pharmaceutically or nutraceutically acceptable salt, hydrate, or solvate thereof. In some embodiments, the nutritional supplement comprises about 255-260 mg of d9-caffeine, or a pharmaceutically or nutraceutically acceptable salt, hydrate, or solvate thereof. In certain embodiments, the nutritional supplement comprises about 260-265 mg of d9-caffeine, or a pharmaceutically or nutraceutically acceptable salt, hydrate, or solvate thereof. In some embodiments, the nutritional supplement comprises about 265-270 mg of d9-caffeine, or a pharmaceutically or nutraceutically acceptable salt, hydrate, or solvate thereof. In certain embodiments, the nutritional supplement comprises about 270-275 mg of d9-caffeine, or a pharmaceutically or nutraceutically acceptable salt, hydrate, or solvate thereof.

In one aspect, the invention provides a beverage comprising d9-caffeine. In another aspect, the beverage is configured to improve athletic performance in a subject when consumed. In another aspect, the beverage comprises one or more of water, flavoring agent(s), sweetener(s), vitamins, minerals, co-factors, proteins, lipids, peptides, and amino acids.

In another aspect, the invention provides a beverage comprising water and d9-caffeine, or a pharmaceutically or nutraceutically acceptable salt, hydrate, or solvate thereof.

In another aspect, the beverage further comprises one or more of a flavoring and a sweetener.

In another aspect, the beverage further comprises one or more of vitamins, minerals, co-factors, proteins, lipids, peptides, and amino acids.

In another aspect, the beverage is an energy beverage. In another aspect, the energy beverage further comprises one or more of water, taurine, citicoline, vitamin B6, vitamin B12, folic acid, niacinamide, glucuronolactone, N-acetyl-L-tyrosine, L-phenylalanine, and malic acid.

In another aspect, the beverage is a vitamin water. In another aspect, the vitamin water further comprises one or more of water, vitamin C, vitamin B5, vitamin B6, vitamin B12, magnesium, and pantothenic acid.

In another aspect, the beverage is a coffee (decaffeinated or comprising non-isotopically enriched caffeine) that is enhanced or "spiked" with d9-caffeine, or a pharmaceutically or nutraceutically acceptable salt, hydrate, or solvate thereof.

In another aspect, the beverage is a chocolate-containing beverage (decaffeinated or comprising non-isotopically enriched caffeine) that is enhanced or "spiked" with d9-caffeine, or a pharmaceutically or nutraceutically acceptable salt, hydrate, or solvate thereof.

In another aspect, the beverage comprises about 1 mg to about 10,000 mg of d9-caffeine, or a pharmaceutically or nutraceutically acceptable salt, hydrate, or solvate thereof. For example, the beverage may comprise about 1 mg to about 9000 mg, about 1 mg to about 8000 mg, about 1 mg to about 7000 mg, about 1 mg to about 6000 mg, about 1 mg to about 5000 mg, about 1 mg to about 4000 mg, about 1 mg to about 3000 mg, or about 1 mg to about 2000 mg of d9-caffeine, or a pharmaceutically or nutraceutically acceptable salt, hydrate, or solvate thereof. In another aspect, the beverage comprises about 1 mg to about 1000 mg of d9-caffeine, or a pharmaceutically or nutraceutically acceptable salt, hydrate, or solvate thereof. In another aspect, the beverage comprises about 1 mg to about 800 mg of d9-caffeine, or a pharmaceutically or nutraceutically acceptable salt, hydrate, or solvate thereof. In another aspect, the beverage comprises about 1 mg to about 600 mg of d9-caffeine, or a pharmaceutically or nutraceutically acceptable salt, hydrate, or solvate thereof. In another aspect, the beverage comprises about 1 mg to about 400 mg of d9-caffeine, or a pharmaceutically or nutraceutically acceptable salt, hydrate, or solvate thereof. In another aspect, the beverage comprises about 1 mg to about 300 mg of d9-caffeine, or a pharmaceutically or nutraceutically acceptable salt, hydrate, or solvate thereof. In another aspect, the beverage comprises about 1 mg to about 250 mg of d9-caffeine, or a pharmaceutically or nutraceutically acceptable salt, hydrate, or solvate thereof. In another aspect, the beverage comprises about 1 mg to about 200 mg of d9-caffeine, or a pharmaceutically or nutraceutically acceptable salt, hydrate, or solvate thereof. In another aspect, the beverage comprises about 1 mg to about 125 mg of d9-caffeine, or a pharmaceutically or nutraceutically acceptable salt, hydrate, or solvate thereof. In another aspect, the beverage comprises about 5 mg to about 75 mg of d9-caffeine, or a pharmaceutically or nutraceutically acceptable salt, hydrate, or solvate thereof. In another aspect, the beverage comprises about 10 mg to about 200 mg of d9-caffeine, or a pharmaceutically or nutraceutically acceptable salt, hydrate, or solvate thereof. In another aspect, the beverage comprises about 10 mg to about 150 mg of d9-caffeine, or a pharmaceutically or nutraceutically acceptable salt, hydrate, or solvate thereof. In another aspect, the beverage comprises about 10 mg to about 100 mg of d9-caffeine, or a pharmaceutically or nutraceutically acceptable salt, hydrate, or solvate thereof. In another aspect, the beverage comprises about 10 mg to about 75 mg of d9-caffeine, or a pharmaceutically or nutraceutically acceptable salt, hydrate, or solvate thereof. In another aspect, the beverage comprises about 10 mg to about 50 mg of d9-caffeine, or a pharmaceutically or nutraceutically acceptable salt, hydrate, or solvate thereof. In another aspect, the beverage comprises about 20 mg to about 200 mg of d9-caffeine, or a pharmaceutically or nutraceutically acceptable salt, hydrate, or solvate thereof. In another aspect, the beverage comprises about 20 mg to about 150 mg of d9-caffeine, or a pharmaceutically or nutraceutically acceptable salt, hydrate, or solvate thereof. In another aspect, the beverage comprises about 20 mg to about 100 mg of d9-caffeine, or a pharmaceutically or nutraceutically acceptable salt, hydrate, or solvate thereof. In another aspect, the beverage comprises about 20 mg to about 75 mg of d9-caffeine, or a pharmaceutically or nutraceutically acceptable salt, hydrate, or solvate thereof. In another aspect, the beverage comprises about 20 mg to about 50 mg of d9-caffeine, or a pharmaceutically or nutraceutically acceptable salt, hydrate, or solvate thereof.

In another aspect, the beverage comprises about 1 mg to about 275 mg of d9-caffeine, or a pharmaceutically or nutraceutically acceptable salt, hydrate, or solvate thereof. In another aspect, the beverage comprises about 30 mg to about 275 mg of d9-caffeine, or a pharmaceutically or nutraceutically acceptable, salt, hydrate, or solvate thereof. For example, the beverage may comprise about 10-15 mg, 15-20 mg, 20-25 mg, 25-30 mg, 30-35 mg, 35-40 mg, 40-45 mg, 45-50 mg, 50-55 mg, 55-60 mg, 60-65 mg, 65-70 mg, 70-75 mg, 75-80 mg, 80-85 mg, 85-90 mg, 90-95 mg, 95-100 mg, 100-105 mg, 105-110 mg, 110-115 mg, 115-120 mg, 120-125 mg, 125-130 mg, 130-135 mg, 135-140 mg, 140-145 mg, 145-150 mg, 150-155 mg, 155-160 mg, 160-165 mg, 165-170 mg, 170-175 mg, 175-180 mg, 180-185 mg, 185-190 mg, 190-195 mg, 195-200 mg, 200-205 mg, 205-210 mg, 210-215 mg, 215-220 mg, 220-225 mg, 225-230 mg, 230-235 mg, 235-240 mg, 240-245 mg, 245-250 mg, 250-255 mg, 255-260 mg, 260-265 mg, 265-270 mg, or 270-275 mg of d9-caffeine, or a pharmaceutically or nutraceutically acceptable salt, hydrate, or solvate thereof. In certain embodiments, the beverage comprises about 30-35 mg of d9-caffeine, or a pharmaceutically or nutraceutically acceptable salt, hydrate, or solvate thereof. In some embodiments, the beverage comprises about 35-40 mg of d9-caffeine, or a pharmaceutically or nutraceutically acceptable salt, hydrate, or solvate thereof. In certain embodiments, the beverage comprises about 40-45 mg of d9-caffeine, or a pharmaceutically or nutraceutically acceptable salt, hydrate, or solvate thereof. In some embodiments, the beverage comprises about 45-50 mg of d9-caffeine, or a pharmaceutically or nutraceutically acceptable salt, hydrate, or solvate thereof. In certain embodiments, the beverage comprises about 50-55 mg of d9-caffeine, or a pharmaceutically or nutraceutically acceptable salt, hydrate, or solvate thereof. In some embodiments, the beverage comprises about 55-60 mg of d9-caffeine, or a pharmaceutically or nutraceutically acceptable salt, hydrate, or solvate thereof. In certain embodiments, the beverage comprises about 60-65 mg of d9-caffeine, or a pharmaceutically or nutraceutically acceptable salt, hydrate, or solvate thereof. In some embodiments, the beverage comprises about 65-70 mg of d9-caffeine, or a pharmaceutically or nutraceutically acceptable salt, hydrate, or solvate thereof. In certain embodiments, the beverage comprises about 70-75 mg of d9-caffeine, or a pharmaceutically or nutraceutically acceptable salt, hydrate, or solvate thereof. In some embodiments, the beverage comprises about 75-80 mg of d9-caffeine, or a pharmaceutically or nutraceutically acceptable salt, hydrate, or solvate thereof.

In certain embodiments, the beverage comprises about 80-85 mg of d9-caffeine, or a pharmaceutically or nutraceutically acceptable salt, hydrate, or solvate thereof. In some embodiments, the beverage comprises about 85-90 mg of d9-caffeine, or a pharmaceutically or nutraceutically acceptable salt, hydrate, or solvate thereof. In certain embodiments, the beverage comprises about 90-95 mg of d9-caffeine, or a pharmaceutically or nutraceutically acceptable salt, hydrate, or solvate thereof. In some embodiments, the beverage comprises about 95-100 mg of d9-caffeine, or a pharmaceutically or nutraceutically acceptable salt, hydrate, or solvate thereof. In certain embodiments, the beverage comprises about 100-105 mg of d9-caffeine, or a pharmaceutically or nutraceutically acceptable salt, hydrate, or solvate thereof. In some embodiments, the beverage comprises about 105-110 mg of d9-caffeine, or a pharmaceutically or nutraceutically acceptable salt, hydrate, or solvate thereof. In certain embodiments, the beverage comprises about 110-115 mg of d9-caffeine, or a pharmaceutically or nutraceutically acceptable salt, hydrate, or solvate thereof. In some embodiments, the beverage comprises about 115-120 mg of d9-caffeine, or a pharmaceutically or nutraceutically acceptable salt, hydrate, or solvate thereof. In certain embodiments, the beverage comprises about 120-125 mg of d9-caffeine, or a pharmaceutically or nutraceutically acceptable salt, hydrate, or solvate thereof. In some embodiments, the beverage comprises about 125-130 mg of d9-caffeine, or a pharmaceutically or nutraceutically acceptable salt, hydrate, or solvate thereof. In certain embodiments, the beverage comprises about 130-135 mg of d9-caffeine, or a pharmaceutically or nutraceutically acceptable salt, hydrate, or solvate thereof. In some embodiments, the beverage comprises about 135-140 mg of d9-caffeine, or a pharmaceutically or nutraceutically acceptable salt, hydrate, or solvate thereof. In certain embodiments, the beverage comprises about 140-145 mg of d9-caffeine, or a pharmaceutically or nutraceutically acceptable salt, hydrate, or solvate thereof. In some embodiments, the beverage comprises about 145-150 mg of d9-caffeine, or a pharmaceutically or nutraceutically acceptable salt, hydrate, or solvate thereof. In certain embodiments, the beverage comprises about 150-155 mg of d9-caffeine, or a pharmaceutically or nutraceutically acceptable salt, hydrate, or solvate thereof. In some embodiments, the beverage comprises about 155-160 mg of d9-caffeine, or a pharmaceutically or nutraceutically acceptable salt, hydrate, or solvate thereof. In certain embodiments, the beverage comprises about 160-165 mg of d9-caffeine, or a pharmaceutically or nutraceutically acceptable salt, hydrate, or solvate thereof. In some embodiments, the beverage comprises about 165-170 mg of d9-caffeine, or a pharmaceutically or nutraceutically acceptable salt, hydrate, or solvate thereof. In certain embodiments, the beverage comprises about 170-175 mg of d9-caffeine, or a pharmaceutically or nutraceutically acceptable salt, hydrate, or solvate thereof. In some embodiments, the beverage comprises about 175-180 mg of d9-caffeine, or a pharmaceutically or nutraceutically acceptable salt, hydrate, or solvate thereof. In certain embodiments, the beverage comprises about 180-185 mg of d9-caffeine, or a pharmaceutically or nutraceutically acceptable salt, hydrate, or solvate thereof. In some embodiments, the beverage comprises about 185-190 mg of d9-caffeine, or a pharmaceutically or nutraceutically acceptable salt, hydrate, or solvate thereof. In certain embodiments, the beverage comprises about 190-195 mg of d9-caffeine, or a pharmaceutically or nutraceutically acceptable salt, hydrate, or solvate thereof. In some embodiments, the beverage comprises about 195-200 mg of d9-caffeine, or a pharmaceutically or nutraceutically acceptable salt, hydrate, or solvate thereof. In certain embodiments, the beverage comprises about 200-205 mg of d9-caffeine, or a pharmaceutically or nutraceutically acceptable salt, hydrate, or solvate thereof. In some embodiments, the beverage comprises about 205-210 mg of d9-caffeine, or a pharmaceutically or nutraceutically acceptable salt, hydrate, or solvate thereof. In certain embodiments, the beverage comprises about 210-215 mg of d9-caffeine, or a pharmaceutically or nutraceutically acceptable salt, hydrate, or solvate thereof. In some embodiments, the beverage comprises about 215-220 mg of d9-caffeine, or a pharmaceutically or nutraceutically acceptable salt, hydrate, or solvate thereof. In certain embodiments, the beverage comprises about 220-225 mg of d9-caffeine, or a pharmaceutically or nutraceutically acceptable salt, hydrate, or solvate thereof. In some embodiments, the beverage comprises about 225-230 mg of d9-caffeine, or a pharmaceutically or nutraceutically acceptable salt, hydrate, or solvate thereof. In certain embodiments, the beverage comprises about 230-235 mg of d9-caffeine, or a pharmaceutically or nutraceutically acceptable salt, hydrate, or solvate thereof. In some embodiments, the beverage comprises about 235-240 mg of d9-caffeine, or a pharmaceutically or nutraceutically acceptable salt, hydrate, or solvate thereof. In certain embodiments, the beverage comprises about 240-245 mg of d9-caffeine, or a pharmaceutically or nutraceutically acceptable salt, hydrate, or solvate thereof. In some embodiments, the beverage comprises about 245-250 mg of d9-caffeine, or a pharmaceutically or nutraceutically acceptable salt, hydrate, or solvate thereof. In certain embodiments, the beverage comprises about 250-255 mg of d9-caffeine, or a pharmaceutically or nutraceutically acceptable salt, hydrate, or solvate thereof. In some embodiments, the beverage comprises about 255-260 mg of d9-caffeine, or a pharmaceutically or nutraceutically acceptable salt, hydrate, or solvate thereof. In certain embodiments, the beverage comprises about 260-265 mg of d9-caffeine, or a pharmaceutically or nutraceutically acceptable salt, hydrate, or solvate thereof. In some embodiments, the beverage comprises about 265-270 mg of d9-caffeine, or a pharmaceutically or nutraceutically acceptable salt, hydrate, or solvate thereof. In certain embodiments, the beverage comprises about 270-275 mg of d9-caffeine, or a pharmaceutically or nutraceutically acceptable salt, hydrate, or solvate thereof.

In another aspect, the beverage comprises about 0.005 mg/ml to about 100 mg/ml of d9-caffeine, or a pharmaceutically or nutraceutically acceptable salt, hydrate, or solvate thereof. In another aspect, the beverage comprises about 0.01 mg/ml to about 100 mg/ml of d9-caffeine, or a pharmaceutically or nutraceutically acceptable salt, hydrate, or solvate thereof. In another aspect, the beverage comprises about 0.05 mg/ml to about 100 mg/ml of d9-caffeine, or a pharmaceutically or nutraceutically acceptable salt, hydrate, or solvate thereof. In another aspect, the beverage comprises about 0.1 mg/ml to about 100 mg/ml of d9-caffeine, or a pharmaceutically or nutraceutically acceptable salt, hydrate, or solvate thereof. In another aspect, the beverage comprises about 0.5 mg/ml to about 100 mg/ml of d9-caffeine, or a pharmaceutically or nutraceutically acceptable salt, hydrate, or solvate thereof. In another aspect, the beverage comprises about 1 mg/ml to about 100 mg/ml of d9-caffeine, or a pharmaceutically or nutraceutically acceptable salt, hydrate, or solvate thereof.

In another aspect, the beverages comprises about 0.005 mg/ml to about 75 mg/ml of d9-caffeine, or a pharmaceutically or nutraceutically acceptable salt, hydrate, or solvate thereof. In another aspect, the beverage comprises about 0.01 mg/ml to about 75 mg/ml of d9-caffeine, or a pharmaceutically or nutraceutically acceptable salt, hydrate, or solvate thereof. In another aspect, the beverage comprises about 0.05 mg/ml to about 75 mg/ml of d9-caffeine, or a pharmaceutically or nutraceutically acceptable salt, hydrate, or solvate thereof. In another aspect, the beverage comprises about 0.1 mg/ml to about 75 mg/ml of d9-caffeine, or a pharmaceutically or nutraceutically acceptable salt, hydrate, or solvate thereof. In another aspect, the beverage comprises about 0.5 mg/ml to about 75 mg/ml of d9-caffeine, or a pharmaceutically or nutraceutically acceptable salt, hydrate, or solvate thereof. In another aspect, the beverage comprises about 1 mg/ml to about 75 mg/ml of d9-caffeine, or a pharmaceutically or nutraceutically acceptable salt, hydrate, or solvate thereof.

In another aspect, the beverage comprises about 0.005 mg/ml to about 50 mg/ml of d9-caffeine, or a pharmaceutically or nutraceutically acceptable salt, hydrate, or solvate thereof. In another aspect, the beverage comprises about 0.01 mg/ml to about 50 mg/ml of d9-caffeine, or a pharmaceutically or nutraceutically acceptable salt, hydrate, or solvate thereof. In another aspect, the beverage comprises about 0.05 mg/ml to about 50 mg/ml of d9-caffeine, or a pharmaceutically or nutraceutically acceptable salt, hydrate, or solvate thereof. In another aspect, the beverage comprises about 0.1 mg/ml to about 50 mg/ml of d9-caffeine, or a pharmaceutically or nutraceutically acceptable salt, hydrate, or solvate thereof. In another aspect, the beverage comprises about 0.5 mg/ml to about 50 mg/ml of d9-caffeine, or a pharmaceutically or nutraceutically acceptable salt, hydrate, or solvate thereof. In another aspect, the beverage comprises about 1 mg/ml to about 50 mg/ml of d9-caffeine, or a pharmaceutically or nutraceutically acceptable salt, hydrate, or solvate thereof.

In another aspect, the beverage comprises about 0.005 mg/ml to about 25 mg/ml of d9-caffeine, or a pharmaceutically or nutraceutically acceptable salt, hydrate, or solvate thereof. In another aspect, the beverage comprises about 0.01 mg/ml to about 25 mg/ml of d9-caffeine, or a pharmaceutically or nutraceutically acceptable salt, hydrate, or solvate thereof. In another aspect, the beverage comprises about 0.05 mg/ml to about 25 mg/ml of d9-caffeine, or a pharmaceutically or nutraceutically acceptable salt, hydrate, or solvate thereof. In another aspect, the beverage comprises about 0.1 mg/ml to about 25 mg/ml of d9-caffeine, or a pharmaceutically or nutraceutically acceptable salt, hydrate, or solvate thereof. In another aspect, the beverage comprises about 0.5 mg/ml to about 25 mg/ml of d9-caffeine, or a pharmaceutically or nutraceutically acceptable salt, hydrate, or solvate thereof. In another aspect, the beverage comprises about 1 mg/ml to about 25 mg/ml of d9-caffeine, or a pharmaceutically or nutraceutically acceptable salt, hydrate, or solvate thereof.

In another aspect, the beverage comprises about 2 mg/ml to about 100 mg/ml of d9-caffeine, or a pharmaceutically or nutraceutically acceptable salt, hydrate, or solvate thereof. In another aspect, the beverage comprises about 2 mg/ml to about 75 mg/ml of d9-caffeine, or a pharmaceutically or nutraceutically acceptable salt, hydrate, or solvate thereof. In another aspect, the beverage comprises about 2 mg/ml to about 50 mg/ml of d9-caffeine, or a pharmaceutically or nutraceutically acceptable salt, hydrate, or solvate thereof. In another aspect, the beverage comprises about 2 mg/ml to about 25 mg/ml of d9-caffeine, or a pharmaceutically or nutraceutically acceptable salt, hydrate, or solvate thereof. In another aspect, the beverage comprises about 2 mg/ml to about 15 mg/ml of d9-caffeine, or a pharmaceutically or nutraceutically acceptable salt, hydrate, or solvate thereof. In another aspect, the beverage comprises about 5 mg/ml to about 100 mg/ml of d9-caffeine, or a pharmaceutically or nutraceutically acceptable salt, hydrate, or solvate thereof. In another aspect, the beverage comprises about 5 mg/ml to about 75 mg/ml of d9-caffeine, or a pharmaceutically or nutraceutically acceptable salt, hydrate, or solvate thereof. In another aspect, the beverage comprises about 5 mg/ml to about 50 mg/ml of d9-caffeine, or a pharmaceutically or nutraceutically acceptable salt, hydrate, or solvate thereof. In another aspect, the beverage comprises about 5 mg/ml to about 25 mg/ml of d9-caffeine, or a pharmaceutically or nutraceutically acceptable salt, hydrate, or solvate thereof. In another aspect, the beverage comprises about 5 mg/ml to about 15 mg/ml of d9-caffeine, or a pharmaceutically or nutraceutically acceptable salt, hydrate, or solvate thereof. In another aspect, the beverage comprises about 10 mg/ml to about 100 mg/ml of d9-caffeine, or a pharmaceutically or nutraceutically acceptable salt, hydrate, or solvate thereof. In another aspect, the beverage comprises about 10 mg/ml to about 75 mg/ml of d9-caffeine, or a pharmaceutically or nutraceutically acceptable salt, hydrate, or solvate thereof. In another aspect, the beverage comprises about 10 mg/ml to about 50 mg/ml of d9-caffeine, or a pharmaceutically or nutraceutically acceptable salt, hydrate, or solvate thereof. In another aspect, the beverage comprises about 10 mg/ml to about 25 mg/ml of d9-caffeine, or a pharmaceutically or nutraceutically acceptable salt, hydrate, or solvate thereof.

In another aspect, the beverage comprises about 0.005 mg/ml to about 0.1 mg/ml of d9-caffeine, or a pharmaceutically or nutraceutically acceptable salt, hydrate, or solvate thereof. In another aspect, the beverage comprises about 0.01 mg/ml to about 0.1 mg/ml of d9-caffeine, or a pharmaceutically or nutraceutically acceptable salt, hydrate, or solvate thereof. In another aspect, the beverage comprises about 0.05 mg/ml to about 0.1 mg/ml of d9-caffeine, or a pharmaceutically or nutraceutically acceptable salt, hydrate, or solvate thereof.

In another aspect, the beverage comprises about 0.005 mg/ml to about 15 mg/ml of d9-caffeine, or a pharmaceutically or nutraceutically acceptable salt, hydrate, or solvate thereof. In another aspect, the beverage comprises about 0.01 mg/ml to about 15 mg/ml of d9-caffeine, or a pharmaceutically or nutraceutically acceptable salt, hydrate, or solvate thereof. In another aspect, the beverage comprises about 0.05 mg/ml to about 15 mg/ml of d9-caffeine, or a pharmaceutically or nutraceutically acceptable salt, hydrate, or solvate thereof. In another aspect, the beverage comprises about 0.1 mg/ml to about 15 mg/ml of d9-caffeine, or a pharmaceutically or nutraceutically acceptable salt, hydrate, or solvate thereof. In another aspect, the beverage comprises about 0.5 mg/ml to about 15 mg/ml of d9-caffeine, or a pharmaceutically or nutraceutically acceptable salt, hydrate, or solvate thereof. In another aspect, the beverage comprises about 1 mg/ml to about 15 mg/ml of d9-caffeine, or a pharmaceutically or nutraceutically acceptable salt, hydrate, or solvate thereof.

In another aspect, the beverages comprise about 0.005 mg/ml to about 10 mg/ml of d9-caffeine, or a pharmaceutically or nutraceutically acceptable salt, hydrate, or solvate thereof. In another aspect, the beverage comprises about 0.01 mg/ml to about 10 mg/ml of d9-caffeine, or a pharmaceutically or nutraceutically acceptable salt, hydrate, or solvate thereof. In another aspect, the beverage comprises about 0.05 mg/ml to about 10 mg/ml of d9-caffeine, or a pharmaceutically or nutraceutically acceptable salt, hydrate, or solvate thereof. In another aspect, the beverage comprises about 0.1 mg/ml to about 10 mg/ml of d9-caffeine, or a pharmaceutically or nutraceutically acceptable salt, hydrate, or solvate thereof. In another aspect, the beverage comprises about 0.5 mg/ml to about 10 mg/ml of d9-caffeine, or a pharmaceutically or nutraceutically acceptable salt, hydrate, or solvate thereof. In another aspect, the beverage comprises about 1 mg/ml to about 10 mg/ml of d9-caffeine, or a pharmaceutically or nutraceutically acceptable salt, hydrate, or solvate thereof.

In another aspect, the beverage comprises about 0.005 mg/ml to about 5 mg/ml of d9-caffeine, or a pharmaceutically or nutraceutically acceptable salt, hydrate, or solvate thereof. In another aspect, the beverage comprises about 0.01 mg/ml to about 5 mg/ml of d9-caffeine, or a pharmaceutically or nutraceutically acceptable salt, hydrate, or solvate thereof. In another aspect, the beverage comprises about 0.05 mg/ml to about 5 mg/ml of d9-caffeine, or a pharmaceutically or nutraceutically acceptable salt, hydrate, or solvate thereof. In another aspect, the beverage comprises about 0.1 mg/ml to about 5 mg/ml of d9-caffeine, or a pharmaceutically or nutraceutically acceptable salt, hydrate, or solvate thereof. In another aspect, the beverage comprises about 0.5 mg/ml to about 5 mg/ml of d9-caffeine, or a pharmaceutically or nutraceutically acceptable salt, hydrate, or solvate thereof. In another aspect, the beverage comprises about 1 mg/ml to about 5 mg/ml of d9-caffeine, or a pharmaceutically or nutraceutically acceptable salt, hydrate, or solvate thereof.

In another aspect, the beverage comprises about 0.005 mg/ml to about 2 mg/ml of d9-caffeine, or a pharmaceutically or nutraceutically acceptable salt, hydrate, or solvate thereof. In another aspect, the beverage comprises about 0.01 mg/ml to about 2 mg/ml of d9-caffeine, or a pharmaceutically or nutraceutically acceptable salt, hydrate, or solvate thereof. In another aspect, the beverage comprises about 0.05 mg/ml to about 2 mg/ml of d9-caffeine, or a pharmaceutically or nutraceutically acceptable salt, hydrate, or solvate thereof. In another aspect, the beverage comprises about 0.1 mg/ml to about 2 mg/ml of d9-caffeine, or a pharmaceutically or nutraceutically acceptable salt, hydrate, or solvate thereof. In another aspect, the beverage comprises about 0.5 mg/ml to about 2 mg/ml of d9-caffeine, or a pharmaceutically or nutraceutically acceptable salt, hydrate, or solvate thereof. In another aspect, the beverage comprises about 1 mg/ml to about 2 mg/ml of d9-caffeine, or a pharmaceutically or nutraceutically acceptable salt, hydrate, or solvate thereof.

In another aspect, the beverage comprises about 1 mg/ml to about 15 mg/ml of d9-caffeine, or a pharmaceutically or nutraceutically acceptable salt, hydrate, or solvate thereof. In another aspect, the beverage comprises about 1 mg/ml to about 10 mg/ml of d9-caffeine, or a pharmaceutically or nutraceutically acceptable salt, hydrate, or solvate thereof. In another aspect, the beverage comprises about 1 mg/ml to about 5 mg/ml of d9-caffeine, or a pharmaceutically or nutraceutically acceptable salt, hydrate, or solvate thereof. In another aspect, the beverage comprises about 1 mg/ml to about 2 mg/ml of d9-caffeine, or a pharmaceutically or nutraceutically acceptable salt, hydrate, or solvate thereof. In another aspect, the beverage comprises about 5 mg/ml to about 15 mg/ml of d9-caffeine, or a pharmaceutically or nutraceutically acceptable salt, hydrate, or solvate thereof. In another aspect, the beverage comprises about 5 mg/ml to about 10 mg/ml of d9-caffeine, or a pharmaceutically or nutraceutically acceptable salt, hydrate, or solvate thereof.

In another aspect, the beverage comprises about 0.005 mg/ml to about 0.25 mg/ml of d9-caffeine, or a pharmaceutically or nutraceutically acceptable salt, hydrate, or solvate thereof. In another aspect, the beverage comprises about 0.01 mg/ml to about 0.25 mg/ml of d9-caffeine, or a pharmaceutically or nutraceutically acceptable salt, hydrate, or solvate thereof. In another aspect, the beverage comprises about 0.05 mg/ml to about 0.25 mg/ml of d9-caffeine, or a pharmaceutically or nutraceutically acceptable salt, hydrate, or solvate thereof. In another aspect, the beverage comprises about 0.1 mg/ml to about 0.25 mg/ml of d9-caffeine, or a pharmaceutically or nutraceutically acceptable salt, hydrate, or solvate thereof.

In another aspect, the beverage comprises about 0.005 mg/ml to about 0.5 mg/ml of d9-caffeine, or a pharmaceutically or nutraceutically acceptable salt, hydrate, or solvate thereof. In another aspect, the beverage comprises about 0.01 mg/ml to about 0.5 mg/ml of d9-caffeine, or a pharmaceutically or nutraceutically acceptable salt, hydrate, or solvate thereof. In another aspect, the beverage comprises about 0.05 mg/ml to about 0.5 mg/ml of d9-caffeine, or a pharmaceutically or nutraceutically acceptable salt, hydrate, or solvate thereof. In another aspect, the beverage comprises about 0.1 mg/ml to about 0.5 mg/ml of d9-caffeine, or a pharmaceutically or nutraceutically acceptable salt, hydrate, or solvate thereof. In another aspect, the beverage comprises about 0.25 mg/ml to about 0.5 mg/ml of d9-caffeine, or a pharmaceutically or nutraceutically acceptable salt, hydrate, or solvate thereof.

In another aspect, the beverage comprises about 0.005 mg/ml to about 1.0 mg/ml of d9-caffeine, or a pharmaceutically or nutraceutically acceptable salt, hydrate, or solvate thereof. In another aspect, the beverage comprises about 0.01 mg/ml to about 1.0 mg/ml of d9-caffeine, or a pharmaceutically or nutraceutically acceptable salt, hydrate, or solvate thereof. In another aspect, the beverage comprises about 0.05 mg/ml to about 1.0 mg/ml of d9-caffeine, or a pharmaceutically or nutraceutically acceptable salt, hydrate, or solvate thereof. In another aspect, the beverage comprises about 0.1 mg/ml to about 1.0 mg/ml of d9-caffeine, or a pharmaceutically or nutraceutically acceptable salt, hydrate, or solvate thereof. In another aspect, the beverage comprises about 0.5 mg/ml to about 1.0 mg/ml of d9-caffeine, or a pharmaceutically or nutraceutically acceptable salt, hydrate, or solvate thereof.

In one aspect, the percentage (i.e., weight percentage) of the amount of d9-caffeine, or a pharmaceutically or nutraceutically acceptable salt, hydrate, or solvate thereof, relative to the total amount of caffeine present in the beverage ranges from about 1% to about 100%. In another aspect, the percentage of the amount of d9-caffeine, or a pharmaceutically or nutraceutically acceptable salt, hydrate, or solvate thereof, relative to the total amount of caffeine present in the beverage ranges from about 1% to about 99%. In another aspect, the percentage of the amount of d9-caffeine, or a pharmaceutically or nutraceutically acceptable salt, hydrate, or solvate thereof, relative to the total amount of caffeine present in the beverage ranges from about 10% to about 100%. In another aspect, the percentage of the amount of d9-caffeine, or a pharmaceutically or nutraceutically acceptable salt, hydrate, or solvate thereof, relative to the total amount of caffeine present in the beverage ranges from about 10% to about 99%. In another aspect, the percentage of the amount of d9-caffeine, or a pharmaceutically or nutraceutically acceptable salt, hydrate, or solvate thereof, relative to the total amount of caffeine present in the beverage ranges from about 10% to about 90%. In another aspect, the percentage of the amount of d9-caffeine, or a pharmaceutically or nutraceutically acceptable salt, hydrate, or solvate thereof, relative to the total amount of caffeine present in the beverage ranges from about 10% to about 80%. In another aspect, the percentage of the amount of d9-caffeine, or a pharmaceutically or nutraceutically acceptable salt, hydrate, or solvate thereof, relative to the total amount of caffeine present in the beverage ranges from about 10% to about 70%. In another aspect, the percentage of the amount of d9-caffeine, or a pharmaceutically or nutraceutically acceptable salt, hydrate, or solvate thereof, relative to the total amount of caffeine present in the beverage ranges from about 10% to about 60%. In another aspect, the percentage of the amount of d9-caffeine, or a pharmaceutically or nutraceutically acceptable salt, hydrate, or solvate thereof, relative to the total amount of caffeine present in the beverage ranges from about 10% to about 50%. In another aspect, the percentage of the amount of d9-caffeine, or a pharmaceutically or nutraceutically acceptable salt, hydrate, or solvate thereof, relative to the total amount of caffeine present in the beverage ranges from about 10% to about 40%. In another aspect, the percentage of the amount of d9-caffeine, or a pharmaceutically or nutraceutically acceptable salt, hydrate, or solvate thereof, relative to the total amount of caffeine present in the beverage ranges from about 10% to about 25%. In another aspect, the percentage of the amount of d9-caffeine, or a pharmaceutically or nutraceutically acceptable salt, hydrate, or solvate thereof, relative to the total amount of caffeine present in the beverage ranges from about 25% to about 100%. In another aspect, the percentage of the amount of d9-caffeine, or a pharmaceutically or nutraceutically acceptable salt, hydrate, or solvate thereof, relative to the total amount of caffeine present in the beverage ranges from about 25% to about 99%. In another aspect, the percentage of the amount of d9-caffeine, or a pharmaceutically or nutraceutically acceptable salt, hydrate, or solvate thereof, relative to the total amount of caffeine present in the beverage ranges from about 25% to about 90%. In another aspect, the percentage of the amount of d9-caffeine, or a pharmaceutically or nutraceutically acceptable salt, hydrate, or solvate thereof, relative to the total amount of caffeine present in the beverage ranges from about 25% to about 80%. In another aspect, the percentage of the amount of d9-caffeine, or a pharmaceutically or nutraceutically acceptable salt, hydrate, or solvate thereof, relative to the total amount of caffeine present in the beverage ranges from about 25% to about 70%. In another aspect, the percentage of the amount of d9-caffeine, or a pharmaceutically or nutraceutically acceptable salt, hydrate, or solvate thereof, relative to the total amount of caffeine present in the beverage ranges from about 25% to about 60%. In another aspect, the percentage of the amount of d9-caffeine, or a pharmaceutically or nutraceutically acceptable salt, hydrate, or solvate thereof, relative to the total amount of caffeine present in the beverage ranges from about 25% to about 50%. In another aspect, the percentage of the amount of d9-caffeine, or a pharmaceutically or nutraceutically acceptable salt, hydrate, or solvate thereof, relative to the total amount of caffeine present in the beverage ranges from about 25% to about 40%. In another aspect, the percentage of the amount of d9-caffeine, or a pharmaceutically or nutraceutically acceptable salt, hydrate, or solvate thereof, relative to the total amount of caffeine present in the beverage ranges from about 30% to about 100%. In another aspect, the percentage of the amount of d9-caffeine, or a pharmaceutically or nutraceutically acceptable salt, hydrate, or solvate thereof, relative to the total amount of caffeine present in the beverage ranges from about 30% to about 99%. In another aspect, the percentage of the amount of d9-caffeine, or a pharmaceutically or nutraceutically acceptable salt, hydrate, or solvate thereof, relative to the total amount of caffeine present in the beverage ranges from about 30% to about 90%. In another aspect, the percentage of the amount of d9-caffeine, or a pharmaceutically or nutraceutically acceptable salt, hydrate, or solvate thereof, relative to the total amount of caffeine present in the beverage ranges from about 30% to about 80%. In another aspect, the percentage of the amount of d9-caffeine, or a pharmaceutically or nutraceutically acceptable salt, hydrate, or solvate thereof, relative to the total amount of caffeine present in the beverage ranges from about 30% to about 70%. In another aspect, the percentage of the amount of d9-caffeine, or a pharmaceutically or nutraceutically acceptable salt, hydrate, or solvate thereof, relative to the total amount of caffeine present in the beverage ranges from about 30% to about 60%. In another aspect, the percentage of the amount of d9-caffeine, or a pharmaceutically or nutraceutically acceptable salt, hydrate, or solvate thereof, relative to the total amount of caffeine present in the beverage ranges from about 30% to about 50%. In another aspect, the percentage of the amount of d9-caffeine, or a pharmaceutically or nutraceutically acceptable salt, hydrate, or solvate thereof, relative to the total amount of caffeine present in the beverage ranges from about 40% to about 100%. In another aspect, the percentage of the amount of d9-caffeine, or a pharmaceutically or nutraceutically acceptable salt, hydrate, or solvate thereof, relative to the total amount of caffeine present in the beverage ranges from about 40% to about 99%. In another aspect, the percentage of the amount of d9-caffeine, or a pharmaceutically or nutraceutically acceptable salt, hydrate, or solvate thereof, relative to the total amount of caffeine present in the beverage ranges from about 40% to about 90%. In another aspect, the percentage of the amount of d9-caffeine, or a pharmaceutically or nutraceutically acceptable salt, hydrate, or solvate thereof, relative to the total amount of caffeine present in the beverage ranges from about 40% to about 80%. In another aspect, the percentage of the amount of d9-caffeine, or a pharmaceutically or nutraceutically acceptable salt, hydrate, or solvate thereof, relative to the total amount of caffeine present in the beverage ranges from about 40% to about 70%. In another aspect, the percentage of the amount of d9-caffeine, or a pharmaceutically or nutraceutically acceptable salt, hydrate, or solvate thereof, relative to the total amount of caffeine present in the beverage ranges from about 40% to about 60%. In another aspect, the percentage of the amount of d9-caffeine, or a pharmaceutically or nutraceutically acceptable salt, hydrate, or solvate thereof, relative to the total amount of caffeine present in the beverage ranges from about 40% to about 50%. In another aspect, the percentage of the amount of d9-caffeine, or a pharmaceutically or nutraceutically acceptable salt, hydrate, or solvate thereof, relative to the total amount of caffeine present in the beverage ranges from about 50% to about 100%. In another aspect, the percentage of the amount of d9-caffeine, or a pharmaceutically or nutraceutically acceptable salt, hydrate, or solvate thereof, relative to the total amount of caffeine present in the beverage ranges from about 50% to about 99%. In another aspect, the percentage of the amount of d9-caffeine, or a pharmaceutically or nutraceutically acceptable salt, hydrate, or solvate thereof, relative to the total amount of caffeine present in the beverage ranges from about 50% to about 90%. In another aspect, the percentage of the amount of d9-caffeine, or a pharmaceutically or nutraceutically acceptable salt, hydrate, or solvate thereof, relative to the total amount of caffeine present in the beverage ranges from about 50% to about 80%. In another aspect, the percentage of the amount of d9-caffeine, or a pharmaceutically or nutraceutically acceptable salt, hydrate, or solvate thereof, relative to the total amount of caffeine present in the beverage ranges from about 50% to about 70%. In another aspect, the percentage of the amount of d9-caffeine, or a pharmaceutically or nutraceutically acceptable salt, hydrate, or solvate thereof, relative to the total amount of caffeine present in the beverage ranges from about 50% to about 60%.

In another aspect, a beverage product is provided in a container having a volume of about 1 ounce, 2 ounces, 4 ounces, 6 ounces, 8 ounces, 10 ounces, 12 ounces, 14 ounces, 16 ounces, 18 ounces, 20 ounces, 22 ounces, 24 ounces, 26 ounces, 28 ounces, 30 ounces, 32 ounces, ½ liter, 1 liter, ½ gallon, 1 gallon, 2 gallons, 3 gallons, 4 gallons, 5 gallons, or 6 gallons or more of the beverage described herein. In another aspect, a beverage product is provided in a container having a volume of between 1-4 ounces, 4-12 ounces, 12-20 ounces, 20-32 ounces, ½ liter-1 liter, 1 liter-½ gallon, or ½ gallon-6 gallons of the beverage described herein. In another aspect, the container is a can (e.g., aluminum can), plastic or glass bottle, plastic or glass jug, or tank (e.g., stainless steel tank).

Numerous processes, methods, and instruments for the manufacture of beverages are known to those skilled in the art. See, for example, *Production and Management of Beverages*, Eds. Grumezescu and Holban, Woodhead Publishing, December 2018, which is herein incorporated by reference. In certain aspects, methods are provided for manufacturing a beverage comprising d9-caffeine, or a pharmaceutically or nutraceutically acceptable salt, hydrate, or solvate thereof. In one aspect, the method comprises adding d9-caffeine, or a pharmaceutically or nutraceutically acceptable salt, hydrate, or solvate thereof to a liquid comprising water to produce a beverage. In one aspect, the liquid comprises carbonated water. In one aspect, the method comprises adding 1 mg to 10,000 mg of d9-caffeine, or a pharmaceutically or nutraceutically acceptable salt, hydrate, or solvate thereof, to the liquid. In one aspect, the method comprises adding 1 mg to 1,000 mg of d9-caffeine, or a pharmaceutically or nutraceutically acceptable salt, hydrate, or solvate thereof, to the liquid. In one aspect, the method comprises adding 1 mg to 8,000 mg of d9-caffeine, or a pharmaceutically or nutraceutically acceptable salt, hydrate, or solvate thereof, to the liquid. In one aspect, the method comprises adding 1 mg to 600 mg of d9-caffeine, or a pharmaceutically or nutraceutically acceptable salt, hydrate, or solvate thereof, to the liquid. In one aspect, the method comprises adding 1 mg to 400 mg of d9-caffeine, or a pharmaceutically or nutraceutically acceptable salt, hydrate, or solvate thereof, to the liquid. In one aspect, the method comprises adding 1 mg to 300 mg of d9-caffeine, or a pharmaceutically or nutraceutically acceptable salt, hydrate, or solvate thereof, to the liquid. In one aspect, the method comprises adding 1 mg to 275 mg of d9-caffeine, or a pharmaceutically or nutraceutically acceptable salt, hydrate, or solvate thereof, to the liquid. In one aspect, the method comprises adding 1 mg to 250 mg of d9-caffeine, or a pharmaceutically or nutraceutically acceptable salt, hydrate, or solvate thereof, to the liquid. In one aspect, the method comprises adding 1 mg to 200 mg of d9-caffeine, or a pharmaceutically or nutraceutically acceptable salt, hydrate, or solvate thereof, to the liquid. In one aspect, the method comprises adding 1 mg to 150 mg of d9-caffeine, or a pharmaceutically or nutraceutically acceptable salt, hydrate, or solvate thereof, to the liquid. In one aspect, the method comprises adding 1 mg to 100 mg of d9-caffeine, or a pharmaceutically or nutraceutically acceptable salt, hydrate, or solvate thereof, to the liquid. In one aspect, the method comprises adding 1 mg to 75 mg of d9-caffeine, or a pharmaceutically or nutraceutically acceptable salt, hydrate, or solvate thereof, to the liquid. In one aspect, the method comprises adding 1 mg to 50 mg of d9-caffeine, or a pharmaceutically or nutraceutically acceptable salt, hydrate, or solvate thereof, to the liquid. In one aspect, the method comprises adding 1 mg to 25 mg of d9-caffeine, or a pharmaceutically or nutraceutically acceptable salt, hydrate, or solvate thereof, to the liquid. In one aspect, the method comprises adding 1 mg to 20 mg of d9-caffeine, or a pharmaceutically or nutraceutically acceptable salt, hydrate, or solvate thereof, to the liquid. In one aspect, the method comprises adding 1 mg to 10 mg of d9-caffeine, or a pharmaceutically or nutraceutically acceptable salt, hydrate, or solvate thereof, to the liquid. In one aspect, the method comprises adding 1 mg to 5 mg of d9-caffeine, or a pharmaceutically or nutraceutically acceptable salt, hydrate, or solvate thereof, to the liquid. In one aspect, the method comprises adding 30 mg to 275 mg of d9-caffeine, or a pharmaceutically or nutraceutically acceptable salt, hydrate, or solvate thereof, to the liquid. In one aspect, the method comprises adding 240 mg to 275 mg of d9-caffeine, or a pharmaceutically or nutraceutically acceptable salt, hydrate, or solvate thereof, to the liquid. In one aspect, the method comprises adding 245 mg to 265 mg of d9-caffeine, or a pharmaceutically or nutraceutically acceptable salt, hydrate, or solvate thereof, to the liquid. In one aspect, the method comprises adding 250 mg to 265 mg of d9-caffeine, or a pharmaceutically or nutraceutically acceptable salt, hydrate, or solvate thereof, to the liquid. In one aspect, the method comprises adding 30 mg to 100 mg of d9-caffeine, or a pharmaceutically or nutraceutically acceptable salt, hydrate, or solvate thereof, to the liquid. In one aspect, the method comprises adding 30 mg to 75 mg of d9-caffeine, or a pharmaceutically or nutraceutically acceptable salt, hydrate, or solvate thereof, to the liquid. In one aspect, the method comprises adding 45 mg to 55 mg of d9-caffeine, or a pharmaceutically or nutraceutically acceptable salt, hydrate, or solvate thereof, to the liquid. In one aspect, the method comprises adding 50 mg to 55 mg of d9-caffeine, or a pharmaceutically or nutraceutically acceptable salt, hydrate, or solvate thereof, to the liquid.

In another aspect, a method is provided for manufacturing a beverage comprising d9-caffeine, or a pharmaceutically or nutraceutically acceptable salt, hydrate, or solvate thereof. In one aspect, the method comprises mixing a composition comprising d9-caffeine, or a pharmaceutically or nutraceutically acceptable salt, hydrate, or solvate thereof, with a liquid comprising water to produce a beverage. In one aspect, the composition comprises a syrup comprising a natural or artificial sweetener. In one aspect, the composition comprises a powder or tablet. In one aspect, the liquid comprises carbonated water. In one aspect, the method comprises mixing 1 mg to 10,000 mg of the composition comprising d9-caffeine, or a pharmaceutically or nutraceutically acceptable salt, hydrate, or solvate thereof, with the liquid. In one aspect, the method comprises mixing 1 mg to 1,000 mg of the composition comprising d9-caffeine, or a pharmaceutically or nutraceutically acceptable salt, hydrate, or solvate thereof, with the liquid. In one aspect, the method comprises mixing 1 mg to 8,000 mg of the composition comprising d9-caffeine, or a pharmaceutically or nutraceutically acceptable salt, hydrate, or solvate thereof, with the liquid. In one aspect, the method comprises mixing 1 mg to 600 mg of the composition comprising d9-caffeine, or a pharmaceutically or nutraceutically acceptable salt, hydrate, or solvate thereof, with the liquid. In one aspect, the method comprises mixing 1 mg to 400 mg of the composition comprising d9-caffeine, or a pharmaceutically or nutraceutically acceptable salt, hydrate, or solvate thereof, with the liquid. In one aspect, the method comprises mixing 1 mg to 300 mg of the composition comprising d9-caffeine, or a pharmaceutically or nutraceutically acceptable salt, hydrate, or solvate thereof, with the liquid. In one aspect, the method comprises mixing 1 mg to 275 mg of the composition comprising d9-caffeine, or a pharmaceutically or nutraceutically acceptable salt, hydrate, or solvate thereof, with the liquid. In one aspect, the method comprises mixing 1 mg to 250 mg of the composition comprising d9-caffeine, or a pharmaceutically or nutraceutically acceptable salt, hydrate, or solvate thereof, with the liquid. In one aspect, the method comprises mixing 1 mg to 200 mg of the composition comprising d9-caffeine, or a pharmaceutically or nutraceutically acceptable salt, hydrate, or solvate thereof, with the liquid. In one aspect, the method comprises mixing 1 mg to 150 mg of the composition comprising d9-caffeine, or a pharmaceutically or nutraceutically acceptable salt, hydrate, or solvate thereof, with the liquid. In one aspect, the method comprises mixing 1 mg to 100 mg of the composition comprising d9-caffeine, or a pharmaceutically or nutraceutically acceptable salt, hydrate, or solvate thereof, with the liquid. In one aspect, the method comprises mixing 1 mg to 75 mg of the composition comprising d9-caffeine, or a pharmaceutically or nutraceutically acceptable salt, hydrate, or solvate thereof, with the liquid. In one aspect, the method comprises mixing 1 mg to 50 mg of the composition comprising d9-caffeine, or a pharmaceutically or nutraceutically acceptable salt, hydrate, or solvate thereof, with the liquid. In one aspect, the method comprises mixing 1 mg to 25 mg of the composition comprising d9-caffeine, or a pharmaceutically or nutraceutically acceptable salt, hydrate, or solvate thereof, with the liquid. In one aspect, the method comprises mixing 1 mg to 20 mg of the composition comprising d9-caffeine, or a pharmaceutically or nutraceutically acceptable salt, hydrate, or solvate thereof, with the liquid. In one aspect, the method comprises mixing 1 mg to 10 mg of the composition comprising d9-caffeine, or a pharmaceutically or nutraceutically acceptable salt, hydrate, or solvate thereof, with the liquid. In one aspect, the method comprises mixing 1 mg to 5 mg of the composition comprising d9-caffeine, or a pharmaceutically or nutraceutically acceptable salt, hydrate, or solvate thereof, with the liquid. In one aspect, the method comprises mixing 30 mg to 275 mg of the composition comprising d9-caffeine, or a pharmaceutically or nutraceutically acceptable salt, hydrate, or solvate thereof, with the liquid. In one aspect, the method comprises mixing 240 mg to 275 mg of the composition comprising d9-caffeine, or a pharmaceutically or nutraceutically acceptable salt, hydrate, or solvate thereof, with the liquid. In one aspect, the method comprises mixing 245 mg to 265 mg of the composition comprising d9-caffeine, or a pharmaceutically or nutraceutically acceptable salt, hydrate, or solvate thereof, with the liquid. In one aspect, the method comprises mixing 250 mg to 265 mg of the composition comprising d9-caffeine, or a pharmaceutically or nutraceutically acceptable salt, hydrate, or solvate thereof, with the liquid. In one aspect, the method comprises mixing 30 mg to 100 mg of the composition comprising d9-caffeine, or a pharmaceutically or nutraceutically acceptable salt, hydrate, or solvate thereof, with the liquid. In one aspect, the method comprises mixing 30 mg to 75 mg of the composition comprising d9-caffeine, or a pharmaceutically or nutraceutically acceptable salt, hydrate, or solvate thereof, with the liquid. In one aspect, the method comprises mixing 45 mg to 55 mg of the composition comprising d9-caffeine, or a pharmaceutically or nutraceutically acceptable salt, hydrate, or solvate thereof, with the liquid. In one aspect, the method comprises mixing 50 mg to 55 mg of the composition comprising d9-caffeine, or a pharmaceutically or nutraceutically acceptable salt, hydrate, or solvate thereof, with the liquid.

In another aspect, the invention provides a food product comprising d9-caffeine, or a pharmaceutically or nutraceutically acceptable salt, hydrate, or solvate thereof.

In another aspect, the food product is any item that is to be processed, partially processed, or unprocessed for consumption. In another aspect, the food product is an energy bar, energy gel, pre-work out supplement, or other performance enhancing supplements. In another aspect, the food product is configured to improve athletic performance when consumed by a subject. In certain embodiments, a performance enhancing supplement is an energy gel or gummy. In certain embodiments, a performance enhancing supplement is a pre-work out supplement. In another aspect, the food product is a food additive. In another aspect, the food product is a dietary supplement. In another aspect, the food product is an energy bar. In another aspect, the energy bar further comprises one or more of sugar, cocoa butter, chocolate liquor, whole milk powder, soy lecithin, vanilla extract, caramel, peanuts, peanut butter, almonds, oats, molasses, cinnamon, salt, and soybean oil. In another aspect, the food product is a powder for combination with a liquid to form a beverage. In another aspect, the food product is a tablet, e.g. an effervescent tablet or drink tablet, to be dissolved with a liquid (e.g. water) to form a beverage. In another aspect, the food product is a chewable tablet. In another aspect, the food product is chewing gum. In another aspect, the food product is an orally dissolving tablet. In another aspect, the food product is an orally dissolving strip, e.g., a thin film strip.

In another aspect, the food product may comprise about 1 mg to about 10,000 mg of d9-caffeine, or a pharmaceutically or nutraceutically acceptable salt, hydrate, or solvate thereof. In another aspect, the food product may comprise about 1 mg to about 5,000 mg of d9-caffeine, or a pharmaceutically or nutraceutically acceptable salt, hydrate, or solvate thereof. In another aspect, the food product may comprise about 1 mg to about 2,000 mg of d9-caffeine, or a pharmaceutically or nutraceutically acceptable salt, hydrate, or solvate thereof. In another aspect, the food product may comprise about 1 mg to about 1,000 mg of d9-caffeine, or a pharmaceutically or nutraceutically acceptable salt, hydrate, or solvate thereof. In another aspect, the food product may comprise about 1 mg to about 800 mg of d9-caffeine, or a pharmaceutically or nutraceutically acceptable salt, hydrate, or solvate thereof. In another aspect, the food product may comprise about 1 mg to about 600 mg of d9-caffeine, or a pharmaceutically or nutraceutically acceptable salt, hydrate, or solvate thereof. In another aspect, the food product may comprise about 1 mg to about 400 mg of d9-caffeine, or a pharmaceutically or nutraceutically acceptable salt, hydrate, or solvate thereof. In another aspect, the food product may comprise about 1 mg to about 300 mg of d9-caffeine, or a pharmaceutically or nutraceutically acceptable salt, hydrate, or solvate thereof. In another aspect, the food product may comprise about 1 mg to about 250 mg of d9-caffeine, or a pharmaceutically or nutraceutically acceptable salt, hydrate, or solvate thereof. In another aspect, the food product may comprise about 1 mg to about 200 mg of d9-caffeine, or a pharmaceutically or nutraceutically acceptable salt, hydrate, or solvate thereof. In another aspect, the food product may comprise about 1 mg to about 125 mg of d9-caffeine, or a pharmaceutically or nutraceutically acceptable salt, hydrate, or solvate thereof. In another aspect, the food product may comprise about 5 mg to about 75 mg of d9-caffeine, or a pharmaceutically or nutraceutically acceptable salt, hydrate, or solvate thereof. In another aspect, the food product may comprise about 10 mg to about 200 mg of d9-caffeine, or a pharmaceutically or nutraceutically acceptable salt, hydrate, or solvate thereof. In another aspect, the food product may comprise about 10 mg to about 150 mg of d9-caffeine, or a pharmaceutically or nutraceutically acceptable salt, hydrate, or solvate thereof. In another aspect, the food product may comprise about 10 mg to about 100 mg of d9-caffeine, or a pharmaceutically or nutraceutically acceptable salt, hydrate, or solvate thereof. In another aspect, the food product may comprise about 10 mg to about 75 mg of d9-caffeine, or a pharmaceutically or nutraceutically acceptable salt, hydrate, or solvate thereof. In another aspect, the food product may comprise about 10 mg to about 50 mg of d9-caffeine, or a pharmaceutically or nutraceutically acceptable salt, hydrate, or solvate thereof. In another aspect, the food product may comprise about 20 mg to about 200 mg of d9-caffeine, or a pharmaceutically or nutraceutically acceptable salt, hydrate, or solvate thereof. In another aspect, the food product may comprise about 20 mg to about 150 mg of d9-caffeine, or a pharmaceutically or nutraceutically acceptable salt, hydrate, or solvate thereof. In another aspect, the food product may comprise about 20 mg to about 100 mg of d9-caffeine, or a pharmaceutically or nutraceutically acceptable salt, hydrate, or solvate thereof. In another aspect, the food product may comprise about 20 mg to about 75 mg of d9-caffeine, or a pharmaceutically or nutraceutically acceptable salt, hydrate, or solvate thereof. In another aspect, the food product may comprise about 20 mg to about 50 mg of d9-caffeine, or a pharmaceutically or nutraceutically acceptable salt, hydrate, or solvate thereof.

In another aspect, the food product may comprise about 1 mg to about 275 mg of d9-caffeine, or a pharmaceutically or nutraceutically acceptable salt, hydrate, or solvate thereof. In another aspect, the food product may comprise about 30 mg to about 275 mg of d9-caffeine, or a pharmaceutically or nutraceutically acceptable, salt, hydrate, or solvate thereof. For example, the beverage may comprise about 30-35 mg, 35-40 mg, 40-45 mg, 45-50 mg, 50-55 mg, 55-60 mg, 60-65 mg, 65-70 mg, 70-75 mg, 75-80 mg, 80-85 mg, 85-90 mg, 90-95 mg, 95-100 mg, 100-105 mg, 105-110 mg, 110-115 mg, 115-120 mg, 120-125 mg, 125-130 mg, 130-135 mg, 135-140 mg, 140-145 mg, 145-150 mg, 150-155 mg, 155-160 mg, 160-165 mg, 165-170 mg, 170-175 mg, 175-180 mg, 180-185 mg, 185-190 mg, 190-195 mg, 195-200 mg, 200-205 mg, 205-210 mg, 210-215 mg, 215-220 mg, 220-225 mg, 225-230 mg, 230-235 mg, 235-240 mg, 240-245 mg, 245-250 mg, 250-255 mg, 255-260 mg, 260-265 mg, 265-270 mg, or 270-275 mg of d9-caffeine, or a pharmaceutically or nutraceutically acceptable salt, hydrate, or solvate thereof. In certain embodiments, the food product may comprise about 30-35 mg of d9-caffeine, or a pharmaceutically or nutraceutically acceptable salt, hydrate, or solvate thereof. In some embodiments, the food product may comprise about 35-40 mg of d9-caffeine, or a pharmaceutically or nutraceutically acceptable salt, hydrate, or solvate thereof. In certain embodiments, the food product may comprise about 40-45 mg of d9-caffeine, or a pharmaceutically or nutraceutically acceptable salt, hydrate, or solvate thereof. In some embodiments, the food product may comprise about 45-50 mg of d9-caffeine, or a pharmaceutically or nutraceutically acceptable salt, hydrate, or solvate thereof. In certain embodiments, the food product may comprise about 50-55 mg of d9-caffeine, or a pharmaceutically or nutraceutically acceptable salt, hydrate, or solvate thereof. In some embodiments, the food product may comprise about 55-60 mg of d9-caffeine, or a pharmaceutically or nutraceutically acceptable salt, hydrate, or solvate thereof. In certain embodiments, the food product may comprise about 60-65 mg of d9-caffeine, or a pharmaceutically or nutraceutically acceptable salt, hydrate, or solvate thereof. In some embodiments, the food product may comprise about 65-70 mg of d9-caffeine, or a pharmaceutically or nutraceutically acceptable salt, hydrate, or solvate thereof. In certain embodiments, the food product may comprise about 70-75 mg of d9-caffeine, or a pharmaceutically or nutraceutically acceptable salt, hydrate, or solvate thereof. In some embodiments, the food product may comprise about 75-80 mg of d9-caffeine, or a pharmaceutically or nutraceutically acceptable salt, hydrate, or solvate thereof. In certain embodiments, the food product may comprise about 80-85 mg of d9-caffeine, or a pharmaceutically or nutraceutically acceptable salt, hydrate, or solvate thereof. In some embodiments, the food product may comprise about 85-90 mg of d9-caffeine, or a pharmaceutically or nutraceutically acceptable salt, hydrate, or solvate thereof. In certain embodiments, the food product may comprise about 90-95 mg of d9-caffeine, or a pharmaceutically or nutraceutically acceptable salt, hydrate, or solvate thereof. In some embodiments, the food product may comprise about 95-100 mg of d9-caffeine, or a pharmaceutically or nutraceutically acceptable salt, hydrate, or solvate thereof. In certain embodiments, the food product may comprise about 100-105 mg of d9-caffeine, or a pharmaceutically or nutraceutically acceptable salt, hydrate, or solvate thereof. In some embodiments, the food product may comprise about 105-110 mg of d9-caffeine, or a pharmaceutically or nutraceutically acceptable salt, hydrate, or solvate thereof. In certain embodiments, the food product may comprise about 110-115 mg of d9-caffeine, or a pharmaceutically or nutraceutically acceptable salt, hydrate, or solvate thereof. In some embodiments, the food product may comprise about 115-120 mg of d9-caffeine, or a pharmaceutically or nutraceutically acceptable salt, hydrate, or solvate thereof. In certain embodiments, the food product may comprise about 120-125 mg of d9-caffeine, or a pharmaceutically or nutraceutically acceptable salt, hydrate, or solvate thereof. In some embodiments, the food product may comprise about 125-130 mg of d9-caffeine, or a pharmaceutically or nutraceutically acceptable salt, hydrate, or solvate thereof. In certain embodiments, the food product may comprise about 130-135 mg of d9-caffeine, or a pharmaceutically or nutraceutically acceptable salt, hydrate, or solvate thereof. In some embodiments, the food product may comprise about 135-140 mg of d9-caffeine, or a pharmaceutically or nutraceutically acceptable salt, hydrate, or solvate thereof. In certain embodiments, the food product may comprise about 140-145 mg of d9-caffeine, or a pharmaceutically or nutraceutically acceptable salt, hydrate, or solvate thereof. In some embodiments, the food product may comprise about 145-150 mg of d9-caffeine, or a pharmaceutically or nutraceutically acceptable salt, hydrate, or solvate thereof. In certain embodiments, the food product may comprise about 150-155 mg of d9-caffeine, or a pharmaceutically or nutraceutically acceptable salt, hydrate, or solvate thereof. In some embodiments, the food product may comprise about 155-160 mg of d9-caffeine, or a pharmaceutically or nutraceutically acceptable salt, hydrate, or solvate thereof. In certain embodiments, the food product may comprise about 160-165 mg of d9-caffeine, or a pharmaceutically or nutraceutically acceptable salt, hydrate, or solvate thereof. In some embodiments, the food product may comprise about 165-170 mg of d9-caffeine, or a pharmaceutically or nutraceutically acceptable salt, hydrate, or solvate thereof. In certain embodiments, the food product may comprise about 170-175 mg of d9-caffeine, or a pharmaceutically or nutraceutically acceptable salt, hydrate, or solvate thereof. In some embodiments, the food product may comprise about 175-180 mg of d9-caffeine, or a pharmaceutically or nutraceutically acceptable salt, hydrate, or solvate thereof. In certain embodiments, the food product may comprise about 180-185 mg of d9-caffeine, or a pharmaceutically or nutraceutically acceptable salt, hydrate, or solvate thereof. In some embodiments, the food product may comprise about 185-190 mg of d9-caffeine, or a pharmaceutically or nutraceutically acceptable salt, hydrate, or solvate thereof. In certain embodiments, the food product may comprise about 190-195 mg of d9-caffeine, or a pharmaceutically or nutraceutically acceptable salt, hydrate, or solvate thereof. In some embodiments, the food product may comprise about 195-200 mg of d9-caffeine, or a pharmaceutically or nutraceutically acceptable salt, hydrate, or solvate thereof. In certain embodiments, the food product may comprise about 200-205 mg of d9-caffeine, or a pharmaceutically or nutraceutically acceptable salt, hydrate, or solvate thereof. In some embodiments, the food product may comprise about 205-210 mg of d9-caffeine, or a pharmaceutically or nutraceutically acceptable salt, hydrate, or solvate thereof. In certain embodiments, the food product may comprise about 210-215 mg of d9-caffeine, or a pharmaceutically or nutraceutically acceptable salt, hydrate, or solvate thereof. In some embodiments, the food product may comprise about 215-220 mg of d9-caffeine, or a pharmaceutically or nutraceutically acceptable salt, hydrate, or solvate thereof. In certain embodiments, the food product may comprise about 220-225 mg of d9-caffeine, or a pharmaceutically or nutraceutically acceptable salt, hydrate, or solvate thereof. In some embodiments, the food product may comprise about 225-230 mg of d9-caffeine, or a pharmaceutically or nutraceutically acceptable salt, hydrate, or solvate thereof. In certain embodiments, the food product may comprise about 230-235 mg of d9-caffeine, or a pharmaceutically or nutraceutically acceptable salt, hydrate, or solvate thereof. In some embodiments, the food product may comprise about 235-240 mg of d9-caffeine, or a pharmaceutically or nutraceutically acceptable salt, hydrate, or solvate thereof. In certain embodiments, the food product may comprise about 240-245 mg of d9-caffeine, or a pharmaceutically or nutraceutically acceptable salt, hydrate, or solvate thereof. In some embodiments, the food product may comprise about 245-250 mg of d9-caffeine, or a pharmaceutically or nutraceutically acceptable salt, hydrate, or solvate thereof. In certain embodiments, the food product may comprise about 250-255 mg of d9-caffeine, or a pharmaceutically or nutraceutically acceptable salt, hydrate, or solvate thereof. In some embodiments, the food product may comprise about 255-260 mg of d9-caffeine, or a pharmaceutically or nutraceutically acceptable salt, hydrate, or solvate thereof. In certain embodiments, the food product may comprise about 260-265 mg of d9-caffeine, or a pharmaceutically or nutraceutically acceptable salt, hydrate, or solvate thereof. In some embodiments, the food product may comprise about 265-270 mg of d9-caffeine, or a pharmaceutically or nutraceutically acceptable salt, hydrate, or solvate thereof. In certain embodiments, the food product may comprise about 270-275 mg of d9-caffeine, or a pharmaceutically or nutraceutically acceptable salt, hydrate, or solvate thereof.

In another aspect, the percentage of the amount of d9-caffeine, or a pharmaceutically or nutraceutically acceptable salt, hydrate, or solvate thereof, relative to the total amount of caffeine present in the food product ranges from about 1% to about 100%. In another aspect, the percentage of the amount of d9-caffeine, or a pharmaceutically or nutraceutically acceptable salt, hydrate, or solvate thereof, relative to the total amount of caffeine present in the food product ranges from about 1% to about 99%. In another aspect, the percentage of the amount of d9-caffeine, or a pharmaceutically or nutraceutically acceptable salt, hydrate, or solvate thereof, relative to the total amount of caffeine present in the food product ranges from about 10% to about 100%. In another aspect, the percentage of the amount of d9-caffeine, or a pharmaceutically or nutraceutically acceptable salt, hydrate, or solvate thereof, relative to the total amount of caffeine present in the food product ranges from about 10% to about 99%. In another aspect, the percentage of the amount of d9-caffeine, or a pharmaceutically or nutraceutically acceptable salt, hydrate, or solvate thereof, relative to the total amount of caffeine present in the food product ranges from about 10% to about 90%. In another aspect, the percentage of the amount of d9-caffeine, or a pharmaceutically or nutraceutically acceptable salt, hydrate, or solvate thereof, relative to the total amount of caffeine present in the food product ranges from about 10% to about 80%. In another aspect, the percentage of the amount of d9-caffeine, or a pharmaceutically or nutraceutically acceptable salt, hydrate, or solvate thereof, relative to the total amount of caffeine present in the food product ranges from about 10% to about 70%. In another aspect, the percentage of the amount of d9-caffeine, or a pharmaceutically or nutraceutically acceptable salt, hydrate, or solvate thereof, relative to the total amount of caffeine present in the food product ranges from about 10% to about 60%. In another aspect, the percentage of the amount of d9-caffeine, or a pharmaceutically or nutraceutically acceptable salt, hydrate, or solvate thereof, relative to the total amount of caffeine present in the food product ranges from about 10% to about 50%. In another aspect, the percentage of the amount of d9-caffeine, or a pharmaceutically or nutraceutically acceptable salt, hydrate, or solvate thereof, relative to the total amount of caffeine present in the food product ranges from about 10% to about 40%. In another aspect, the percentage of the amount of d9-caffeine, or a pharmaceutically or nutraceutically acceptable salt, hydrate, or solvate thereof, relative to the total amount of caffeine present in the food product ranges from about 10% to about 25%. In another aspect, the percentage of the amount of d9-caffeine, or a pharmaceutically or nutraceutically acceptable salt, hydrate, or solvate thereof, relative to the total amount of caffeine present in the food product ranges from about 25% to about 100%. In another aspect, the percentage of the amount of d9-caffeine, or a pharmaceutically or nutraceutically acceptable salt, hydrate, or solvate thereof, relative to the total amount of caffeine present in the food product ranges from about 25% to about 99%. In another aspect, the percentage of the amount of d9-caffeine, or a pharmaceutically or nutraceutically acceptable salt, hydrate, or solvate thereof, relative to the total amount of caffeine present in the food product ranges from about 25% to about 90%. In another aspect, the percentage of the amount of d9-caffeine, or a pharmaceutically or nutraceutically acceptable salt, hydrate, or solvate thereof, relative to the total amount of caffeine present in the food product ranges from about 25% to about 80%. In another aspect, the percentage of the amount of d9-caffeine, or a pharmaceutically or nutraceutically acceptable salt, hydrate, or solvate thereof, relative to the total amount of caffeine present in the food product ranges from about 25% to about 70%. In another aspect, the percentage of the amount of d9-caffeine, or a pharmaceutically or nutraceutically acceptable salt, hydrate, or solvate thereof, relative to the total amount of caffeine present in the food product ranges from about 25% to about 60%. In another aspect, the percentage of the amount of d9-caffeine, or a pharmaceutically or nutraceutically acceptable salt, hydrate, or solvate thereof, relative to the total amount of caffeine present in the food product ranges from about 25% to about 50%. In another aspect, the percentage of the amount of d9-caffeine, or a pharmaceutically or nutraceutically acceptable salt, hydrate, or solvate thereof, relative to the total amount of caffeine present in the food product ranges from about 25% to about 40%. In another aspect, the percentage of the amount of d9-caffeine, or a pharmaceutically or nutraceutically acceptable salt, hydrate, or solvate thereof, relative to the total amount of caffeine present in the food product ranges from about 30% to about 100%. In another aspect, the percentage of the amount of d9-caffeine, or a pharmaceutically or nutraceutically acceptable salt, hydrate, or solvate thereof, relative to the total amount of caffeine present in the food product ranges from about 30% to about 99%. In another aspect, the percentage of the amount of d9-caffeine, or a pharmaceutically or nutraceutically acceptable salt, hydrate, or solvate thereof, relative to the total amount of caffeine present in the food product ranges from about 30% to about 90%. In another aspect, the percentage of the amount of d9-caffeine, or a pharmaceutically or nutraceutically acceptable salt, hydrate, or solvate thereof, relative to the total amount of caffeine present in the food product ranges from about 30% to about 80%. In another aspect, the percentage of the amount of d9-caffeine, or a pharmaceutically or nutraceutically acceptable salt, hydrate, or solvate thereof, relative to the total amount of caffeine present in the food product ranges from about 30% to about 70%. In another aspect, the percentage of the amount of d9-caffeine, or a pharmaceutically or nutraceutically acceptable salt, hydrate, or solvate thereof, relative to the total amount of caffeine present in the food product ranges from about 30% to about 60%. In another aspect, the percentage of the amount of d9-caffeine, or a pharmaceutically or nutraceutically acceptable salt, hydrate, or solvate thereof, relative to the total amount of caffeine present in the food product ranges from about 30% to about 50%. In another aspect, the percentage of the amount of d9-caffeine, or a pharmaceutically or nutraceutically acceptable salt, hydrate, or solvate thereof, relative to the total amount of caffeine present in the food product ranges from about 40% to about 100%. In another aspect, the percentage of the amount of d9-caffeine, or a pharmaceutically or nutraceutically acceptable salt, hydrate, or solvate thereof, relative to the total amount of caffeine present in the food product ranges from about 40% to about 99%. In another aspect, the percentage of the amount of d9-caffeine, or a pharmaceutically or nutraceutically acceptable salt, hydrate, or solvate thereof, relative to the total amount of caffeine present in the food product ranges from about 40% to about 90%. In another aspect, the percentage of the amount of d9-caffeine, or a pharmaceutically or nutraceutically acceptable salt, hydrate, or solvate thereof, relative to the total amount of caffeine present in the food product ranges from about 40% to about 80%. In another aspect, the percentage of the amount of d9-caffeine, or a pharmaceutically or nutraceutically acceptable salt, hydrate, or solvate thereof, relative to the total amount of caffeine present in the food product ranges from about 40% to about 70%. In another aspect, the percentage of the amount of d9-caffeine, or a pharmaceutically or nutraceutically acceptable salt, hydrate, or solvate thereof, relative to the total amount of caffeine present in the food product ranges from about 40% to about 60%. In another aspect, the percentage of the amount of d9-caffeine, or a pharmaceutically or nutraceutically acceptable salt, hydrate, or solvate thereof, relative to the total amount of caffeine present in the food product ranges from about 40% to about 50%. In another aspect, the percentage of the amount of d9-caffeine, or a pharmaceutically or nutraceutically acceptable salt, hydrate, or solvate thereof, relative to the total amount of caffeine present in the food product ranges from about 50% to about 100%. In another aspect, the percentage of the amount of d9-caffeine, or a pharmaceutically or nutraceutically acceptable salt, hydrate, or solvate thereof, relative to the total amount of caffeine present in the food product ranges from about 50% to about 99%. In another aspect, the percentage of the amount of d9-caffeine, or a pharmaceutically or nutraceutically acceptable salt, hydrate, or solvate thereof, relative to the total amount of caffeine present in the food product ranges from about 50% to about 90%. In another aspect, the percentage of the amount of d9-caffeine, or a pharmaceutically or nutraceutically acceptable salt, hydrate, or solvate thereof, relative to the total amount of caffeine present in the food product ranges from about 50% to about 80%. In another aspect, the percentage of the amount of d9-caffeine, or a pharmaceutically or nutraceutically acceptable salt, hydrate, or solvate thereof, relative to the total amount of caffeine present in the food product ranges from about 50% to about 70%. In another aspect, the percentage of the amount of d9-caffeine, or a pharmaceutically or nutraceutically acceptable salt, hydrate, or solvate thereof, relative to the total amount of caffeine present in the food product ranges from about 50% to about 60%.

It will be understood that when a range is recited in the application, the ends of the range are specifically disclosed as if specifically recited. For example, a range of about 19% to about 99% specifically include a disclosure separately of 19% and separately of 99%.

Also encompassed by the present disclosure are kits (e.g., pharmaceutical or nutraceutical packs). In certain embodiments, the kit comprises a pharmaceutical or nutraceutical composition described herein, and instructions for using the pharmaceutical or nutraceutical composition. In certain embodiments, the kit comprises a first container, wherein the first container includes the pharmaceutical or nutraceutical composition. In some embodiments, the kit further comprises a second container. In certain embodiments, the second container includes an excipient (e.g., an excipient for dilution or suspension of the pharmaceutical or nutraceutical composition). In certain embodiments, the second container includes an additional agent. In some embodiments, the kit further comprises a third container. In certain embodiments, the third container includes an additional agent. In some embodiments, the pharmaceutical or nutraceutical composition included in the first container and the excipient or additional agent(s) included in the second container are combined to form one-unit dosage form. In some embodiments, the pharmaceutical or nutraceutical composition included in the first container, the excipient included in the second container, and the additional agent included in the third container are combined to form one-unit dosage form. In certain embodiments, each of the first, second, and third containers is independently a vial, ampule, bottle, syringe, dispenser package, tube, sprayer, or inhaler. In certain embodiments, at least one of the first, second, and third containers is a sprayer.

In certain embodiments, the instructions are for administering the pharmaceutical or nutraceutical composition to a subject in need thereof. In certain embodiments, the instructions comprise information required by a regulatory agency, such as the U.S. Food and Drug Administration (FDA) or the European Agency for the Evaluation of Medicinal Products (EMA). In certain embodiments, the instructions comprise prescribing information. In certain embodiments, the instructions comprise information on how to administer or consume the compounds or compositions described herein. In certain embodiments, a nutraceutical composition or food product is provided with instructions for administering or consuming the composition or food product. In certain embodiments, the instructions describe mixing the nutraceutical composition or food product with a liquid (e.g., water) to form a beverage for consumption. In certain embodiments, the instructions may warn a healthcare provider, patient, or consumer to: administer or consume the compounds or compositions described herein only once daily, or avoid administering or consuming non-isotopically enriched caffeine products (e.g., coffee or soda) with the compounds or compositions described herein (whether at the same time, or across the same day).

In certain embodiments, a composition (e.g., cosmetic composition, pharmaceutical composition, or nutraceutical composition), food product, beverage, or nutritional supplement as described herein is safe for human use (e.g., consumption) 1-8 times per day. In a particular embodiment, the composition, food product, beverage, or nutritional supplement is safe for human use 1 time per day. In a particular embodiment, the composition, food product, beverage, or nutritional supplement is safe for human use 2 times per day. In a particular embodiment, the composition, food product, beverage, or nutritional supplement is safe for human use 3 times per day. In a particular embodiment, the composition, food product, beverage, or nutritional supplement is safe for human use 4 times per day. In a particular embodiment, the composition, food product, beverage, or nutritional supplement is safe for human use 5 times per day. In a particular embodiment, the composition, food product, beverage, or nutritional supplement is safe for human use 6 times per day. In a particular embodiment, the composition, food product, beverage, or nutritional supplement is safe for human use 7 times per day. In a particular embodiment, the composition, food product, beverage, or nutritional supplement is safe for human use 8 times per day. In a particular embodiment, the composition, food product, beverage, or nutritional supplement is safe for human use every two hours. In a particular embodiment, the composition, food product, beverage, or nutritional supplement is safe for human use every four hours. In a particular embodiment, the composition, food product, beverage, or nutritional supplement is safe for human use every six hours. In a particular embodiment, the composition, food product, beverage, or nutritional supplement is safe for human use every eight hours. In a particular embodiment, the composition, food product, beverage, or nutritional supplement is safe for human use every twelve hours. In a particular embodiment, the composition, food product, beverage, or nutritional supplement is safe for human use every sixteen hours. In a particular embodiment, the composition, food product, beverage, or nutritional supplement is safe for human use every twenty-four hours. In a particular embodiment, the composition, food product, beverage, or nutritional supplement is safe for human use every forty-eight hours.

In certain embodiments, a composition (e.g., cosmetic composition, pharmaceutical composition, or nutraceutical composition), food product, beverage, or nutritional supplement as described herein is safe for human use (e.g., consumption) 1-5 times per week. In a particular embodiment, the composition, food product, beverage, or nutritional supplement is safe for human use 1 time per week. In a particular embodiment, the composition, food product, beverage, or nutritional supplement is safe for human use 2 times per week. In a particular embodiment, the composition, food product, beverage, or nutritional supplement is safe for human use 3 times per week. In a particular embodiment, the composition, food product, beverage, or nutritional supplement is safe for human use 4 times per week. In a particular embodiment, the composition, food product, beverage, or nutritional supplement is safe for human use 5 times per week.

In certain embodiments, a composition (e.g., cosmetic composition, pharmaceutical composition, or nutraceutical composition), food product, beverage, or nutritional supplement as described herein is safe for human use (e.g., consumption) 1-5 times per month. In a particular embodiment, the composition, food product, beverage, or nutritional supplement is safe for human use 1 time per month. In a particular embodiment, the composition, food product, beverage, or nutritional supplement is safe for human use 2 times per month. In a particular embodiment, the composition, food product, beverage, or nutritional supplement is safe for human use 3 times per month. In a particular embodiment, the composition, food product, beverage, or nutritional supplement is safe for human use 4 times per month. In a particular embodiment, the composition, food product, beverage, or nutritional supplement is safe for human use 5 times per month.

Methods of Use and Uses

Various factors contribute to the utility or efficacy of the disclosed compounds, compositions, beverages, and food products in the methods described herein. Such factors include the pharmacokinetics of non-deuterated caffeine and the previously unknown pharmacokinetics of d9-caffeine, and the associated formation of their four key metabolites: paraxanthine (1,7 dimethylxanthine), theobromine (3,7-dimethylxanthine), theophylline 1,3 dimethylxanthine) and TMU (1,3,7-trimethyluric acid). The pharmacokinetics of deuterated and non-deuterated caffeine may be affected by the route of administration, or the means of consumption, and manifest in physiological effects including blood pressure, heart rate, heart rhythm and respiratory rate. Pharmacokinetics in a particular subject may also be affected by such factors as age, weight, body mass index, characterization as either a slow or a fast metabolizer of caffeine, previous or concurrent injection or use of other pharmacologically-active substances, including certain foods, beverages, alcohol, and nicotine, as well as the physical fitness of the subject, and the frequency/duration of exercise or other strenuous activities engaged in by the subject.

Accordingly, in certain embodiments, the d9-caffeine compounds, compositions, beverages, and food products described herein have favorable or advantageous pharmacokinetic properties. Such properties include a favorable metabolic profile, e.g., a favorable ratio of metabolite formation upon administration or consumption. In certain embodiments, the favorable metabolic profile results in a reduction of undesirable effects on the respiratory or cardiovascular system of the subject, such as blood pressure, heart rate, heart rhythm and respiratory rate. In certain embodiments, the methods described herein can result in reduced exposure to one or more primary or secondary metabolites of caffeine compared to an equivalent dose of non-isotopically enriched caffeine. In certain embodiments, administration or consumption of d9-caffeine compounds or compositions, beverages, and food products results in about a 5%, 10%, 20%, 30%, 40%, 50%, 60%, 70%, 80%, or 90% or greater reduction in a parent to metabolite ratio, as determined by a pharmacokinetic measure (e.g., mean $C_{max}$ or mean AUC), compared to non-isotopically enriched caffeine. In certain embodiments, the metabolites are paraxanthine (1,7-dimethylxanthine), theobromine (3,7-dimethylxanthine), theophylline 1,3-dimethylxanthine) and TMU (1,3,7-trimethyluric acid). In certain embodiments, the metabolite is paraxanthin. In certain embodiments, the metabolite is theobromine. In certain embodiments, the metabolite is theophylline. In certain embodiments, the metabolite is TMU or 1,3,7-trimethyluric acid.

In certain embodiments, the subject is a slow metabolizer of caffeine and/or d9-caffeine described herein. In certain embodiments, the subject is a fast metabolizer of caffeine and/or d9-caffeine described herein. In certain embodiments, the metabolic profile of d9-caffeine compound is affected by the metabolic classification of the subject, i.e., slow metabolizer or fast metabolizer. In certain embodiments, the metabolic profile of d9-caffeine compound is affected by the health, physical fitness, sleep quality, dietary habits, and pharmacological habits of the subject.

Other factors that contribute to the utility or efficacy of the disclosed compounds, compositions, beverages, and food products relate to the cognitive or emotional health of the subject. Such factors include clinical conditions such as psychiatric or neurological disorders.

In certain particular embodiments, the aforementioned favorable metabolic profile and or properties are associated with d9-caffeine.

The present disclosure also provides methods of using the compounds, compositions, beverages, and food products of the present disclosure. In another aspect, the present disclosure provides methods of delivering to a subject in need thereof a composition (e.g., an effective amount of the composition) (e.g., pharmaceutical composition, nutraceutical composition, cosmetic composition, nutritional supplement) of the present disclosure.

In another aspect, the present disclosure provides methods of treating a disease or condition in a subject in need thereof comprising administering to the subject in need thereof an effective amount (e.g., therapeutically effective amount) of a compound or composition (e.g., pharmaceutical or nutraceutical composition) of the present disclosure.

In another aspect, the present disclosure provides methods of preventing a disease or condition in a subject in need thereof comprising administering to the subject in need thereof an effective amount (e.g., therapeutically effective amount) of a compound or composition (e.g., pharmaceutical or nutraceutical composition) of the present disclosure.

In another aspect, provided herein are uses of the compounds or compositions of the present disclosure in the manufacture of a medicament for use in a method (e.g., method of delivering an active agent to a subject in need thereof, method of treating a disease or condition in a subject in need thereof, method of preventing a disease in a subject in need thereof) of the present disclosure.

In another aspect, provided herein are uses of the compounds or compositions of the present disclosure in a method (e.g., method of delivering an active agent to a subject in need thereof, method of treating a disease or condition in a subject in need thereof, method of preventing a disease in a subject in need thereof) of the present disclosure. In some embodiments, the method provides for administering a composition comprising d9-caffeine while reducing exposure to a primary or secondary metabolite of caffeine.

In certain embodiments, the subject is an animal. The animal may be of either sex and may be at any stage of development. In certain embodiments, the subject described herein is a human. The human may be a child or an adult. In some embodiments, the subject is an adult. In certain embodiments, the subject is a healthy adult. In some embodiments, the subject is a healthy adult of 18-55 years of age. In certain embodiments, the subject is an amateur or professional athlete. In certain embodiments, the subject is an active child or adult (e.g., a child or adult regularly engaged in sports or exercise, including active non-athletes). In certain embodiments, the subject is a non-human animal. In certain embodiments, the subject is a mammal. In certain embodiments, the subject is a non-human mammal. In certain embodiments, the subject is a domesticated animal, such as a dog, cat, cow, pig, horse, sheep, or goat. In certain embodiments, the subject is a dog. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal, such as a rodent (e.g., mouse, rat), dog, pig, or non-human primate. In certain embodiments, the animal is a genetically engineered animal. In certain embodiments, the animal is a transgenic animal (e.g., transgenic mice, transgenic pigs). In certain embodiments, a subject in need thereof is a subject in need of delivery of an active agent or a composition, a subject in need of treatment of a disease, or a subject in need of prevention of a disease.

In certain embodiments, the effective amount is effective in treating the disease. In certain embodiments, the effective amount is effective in preventing the disease.

In certain embodiments, the compounds or compositions of the present disclosure are effective at treating or preventing a disease or condition when administered once daily (q.d.) due to the surprising and unexpectedly high exposure (AUC) and long plasma half-life $T_{1/2}$ of d9-caffeine following administration of d9-caffeine to a subject. In some embodiments, the methods comprise administering a compound s or compositions of the present invention twice daily, once daily, every two days, or every three days. In some embodiments, the method comprises administering to the subject a loading dose of a compound or composition of the present invention. In some embodiments, the method comprises administering a maintenance dose of a compound or composition of the present invention. In some embodiments, the loading dose comprises a greater amount of d9-caffeine than the maintenance dose.

In certain aspects, the disease is an inflammatory disease. The term "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis. An ocular inflammatory disease includes post-surgical inflammation.

In certain aspects, the disease is a neurological disease. In certain embodiments, the disease is a neurological disease. The term "neurological disease" refers to any disease of the nervous system, including diseases that involve the central nervous system (brain, brainstem and cerebellum), the peripheral nervous system (including cranial nerves), and the autonomic nervous system (parts of which are located in both central and peripheral nervous system). Neurodegenerative diseases refer to a type of neurological disease marked by the loss of nerve cells, including Alzheimer's disease, Parkinson's disease, amyotrophic lateral sclerosis, tauopathies (including frontotemporal dementia), and Huntington's disease. Examples of neurological diseases include headache, stupor and coma, dementia, seizure, sleep disorders, trauma, infections, neoplasms, neuro-ophthalmology, movement disorders, demyelinating diseases, spinal cord disorders, and disorders of peripheral nerves, muscle and neuromuscular junctions. Addiction and mental illness, include bipolar disorder and schizophrenia, are also included in the definition of neurological diseases. Further examples of neurological diseases include acquired epileptiform aphasia; acute disseminated encephalomyelitis; adrenoleukodystrophy; agenesis of the corpus callosum; agnosia; Aicardi syndrome; Alexander disease; Alpers' disease; alternating hemiplegia; Alzheimer's disease; amyotrophic lateral sclerosis; anencephaly; Angelman syndrome; angiomatosis; anoxia; aphasia; apraxia; arachnoid cysts; arachnoiditis; Arnold-Chiari malformation; arteriovenous malformation; Asperger syndrome; ataxia telangiectasia; attention deficit hyperactivity disorder; autism; autonomic dysfunction; back pain; Batten disease; Behcet's disease; Bell's palsy; benign essential blepharospasm; benign focal; amyotrophy; benign intracranial hypertension; Binswanger's disease; blepharospasm; Bloch Sulzberger syndrome; brachial plexus injury; brain abscess; bbrain injury; brain tumors (including glioblastoma multiforme); spinal tumor; Brown-Sequard syndrome; Canavan disease; carpal tunnel syndrome (CTS); causalgia; central pain syndrome; central pontine myelinolysis; cephalic disorder; cerebral aneurysm; cerebral arteriosclerosis; cerebral atrophy; cerebral gigantism; cerebral palsy; Charcot-Marie-Tooth disease; chemotherapy-induced neuropathy and neuropathic pain; Chiari malformation; chorea; chronic inflammatory demyelinating polyneuropathy (CIDP); chronic pain; chronic regional pain syndrome; Coffin Lowry syndrome; coma, including persistent vegetative state; congenital facial diplegia; corticobasal degeneration; cranial arteritis; craniosynostosis; Creutzfeldt-Jakob disease; cumulative trauma disorders; Cushing's syndrome; cytomegalic inclusion body disease (CIBD); cytomegalovirus infection; dancing eyes-dancing feet syndrome; Dandy-Walker syndrome; Dawson disease; De Morsier's syndrome; Dejerine-Klumpke palsy; dementia; dermatomyositis; diabetic neuropathy; diffuse sclerosis; dysautonomia; dysgraphia; dyslexia; dystonias; early infantile epileptic encephalopathy; empty sella syndrome; encephalitis; encephaloceles; encephalotrigeminal angiomatosis; epilepsy; Erb's palsy; essential tremor; Fabry's disease; Fahr's syndrome; fainting; familial spastic paralysis; febrile seizures; Fisher syndrome; Friedreich's ataxia; frontotemporal dementia and other "tauopathies"; Gaucher's disease; Gerstmann's syndrome; giant cell arteritis; giant cell inclusion disease; globoid cell leukodystrophy; Guillain-Barre syndrome; HTLV-1 associated myelopathy; Hallervorden-Spatz disease; head injury; headache; hemifacial spasm; hereditary spastic paraplegia; heredopathia atactica polyneuritiformis; herpes zoster oticus; herpes zoster; Hirayama syndrome; HIV-associated dementia and neuropathy (see also neurological manifestations of AIDS); holoprosencephaly; Huntington's disease and other polyglutamine repeat diseases; hydranencephaly; hydrocephalus; hypercortisolism; hypoxia; immune-mediated encephalomyelitis; inclusion body myositis; incontinentia pigmenti; infantile; phytanic acid storage disease; Infantile Refsum disease; infantile spasms; inflammatory myopathy; intracranial cyst; intracranial hypertension; Joubert syndrome; Kearns-Sayre syndrome; Kennedy disease; Kinsbourne syndrome; Klippel Feil syndrome; Krabbe disease; Kugelberg-Welander disease; kuru; Lafora disease; Lambert-Eaton myasthenic syndrome; Landau-Kleffner syndrome; lateral medullary (Wallenberg) syndrome; learning disabilities; Leigh's disease; Lennox-Gastaut syndrome; Lesch-Nyhan syndrome; leukodystrophy; Lewy body dementia; lissencephaly; locked-in syndrome; Lou Gehrig's disease (aka motor neuron disease or amyotrophic lateral sclerosis); lumbar disc disease; lyme disease-neurological sequelae; Machado-Joseph disease; macrencephaly; megalencephaly; Melkersson-Rosenthal syndrome; Menieres disease; meningitis; Menkes disease; metachromatic leukodystrophy; microcephaly; migraine; Miller Fisher syndrome; mini-strokes; mitochondrial myopathies; Mobius syndrome; monomelic amyotrophy; motor neurone disease; moyamoya disease; mucopolysaccharidoses; multi-infarct dementia; multifocal motor neuropathy; multiple sclerosis and other demyelinating disorders; multiple system atrophy with postural hypotension; muscular dystrophy; myasthenia gravis; myelinoclastic diffuse sclerosis; myoclonic encephalopathy of infants; myoclonus; myopathy; myotonia congenital; narcolepsy; neurofibromatosis; neuroleptic malignant syndrome; neurological manifestations of AIDS; neurological sequelae of lupus; neuromyotonia; neuronal ceroid lipofuscinosis; neuronal migration disorders; Niemann-Pick disease; O'Sullivan-McLeod syndrome; occipital neuralgia; occult spinal dysraphism sequence; Ohtahara syndrome; olivopontocerebellar atrophy; opsoclonus myoclonus; optic neuritis; orthostatic hypotension; overuse syndrome; paresthesia; Parkinson's disease; paramyotonia congenita; paraneoplastic diseases; paroxysmal attacks; Parry Romberg syndrome; Pelizaeus-Merzbacher disease; periodic paralyses; peripheral neuropathy; painful neuropathy and neuropathic pain; persistent vegetative state; pervasive developmental disorders; photic sneeze reflex; phytanic acid storage disease; Pick's disease; pinched nerve; pituitary tumors; polymyositis; porencephaly; Post-Polio syndrome; postherpetic neuralgia (PHN); postinfectious encephalomyelitis; postural hypotension; Prader-Willi syndrome; primary lateral sclerosis; prion diseases; progressive; hemifacial atrophy; progressive multifocal leukoencephalopathy; progressive sclerosing poliodystrophy; progressive supranuclear palsy; pseudotumor cerebri; Ramsay-Hunt syndrome (Type I and Type II); Rasmussen's Encephalitis; reflex sympathetic dystrophy syndrome; Refsum disease; repetitive motion disorders; repetitive stress injuries; restless legs syndrome; retrovirus-associated myelopathy; Rett syndrome; Reye's syndrome; Saint Vitus Dance; Sandhoff disease; Schilder's disease; schizencephaly; septo-optic dysplasia; shaken baby syndrome; shingles; Shy-Drager syndrome; Sjogren's syndrome; sleep apnea; Soto's syndrome; spasticity; spina bifida; spinal cord injury; spinal cord tumors; spinal muscular atrophy; stiff-person syndrome; stroke; Sturge-Weber syndrome; subacute sclerosing panencephalitis; subarachnoid hemorrhage; subcortical arteriosclerotic encephalopathy; sydenham chorea; syncope; syringomyelia; tardive dyskinesia; Tay-Sachs disease; temporal arteritis; tethered spinal cord syndrome; Thomsen disease; thoracic outlet syndrome; tic douloureux; Todd's paralysis; Tourette syndrome; transient ischemic attack; transmissible spongiform encephalopathies; transverse myelitis; traumatic brain injury; tremor; trigeminal neuralgia; tropical spastic paraparesis; tuberous sclerosis; vascular dementia (multi-infarct dementia); vasculitis including temporal arteritis; Von Hippel-Lindau Disease (VHL); Wallenberg's syndrome; Werdnig-Hoffman disease; West syndrome; whiplash; Williams syndrome; Wilson's disease; and Zellweger syndrome.

In certain embodiments, the disease is a painful condition. A "painful condition" includes neuropathic pain (e.g., peripheral neuropathic pain), central pain, deafferentation pain, chronic pain (e.g., chronic nociceptive pain, and other forms of chronic pain such as post-operative pain, e.g., pain arising after hip, knee, or other replacement surgery), preoperative pain, stimulus of nociceptive receptors (nociceptive pain), acute pain (e.g., phantom and transient acute pain), noninflammatory pain, inflammatory pain, pain associated with cancer, wound pain, burn pain, postoperative pain, pain associated with medical procedures, pain resulting from pruritus, painful bladder syndrome, pain associated with premenstrual dysphoric disorder and/or premenstrual syndrome, pain associated with chronic fatigue syndrome, pain associated with pre-term labor, pain associated with withdrawl symptoms from drug addiction, joint pain, arthritic pain (e.g., pain associated with crystalline arthritis, osteoarthritis, psoriatic arthritis, gouty arthritis, reactive arthritis, rheumatoid arthritis or Reiter's arthritis), lumbosacral pain, musculo-skeletal pain, headache, migraine, muscle ache, lower back pain, neck pain, toothache, dental/maxillofacial pain, visceral pain and the like. One or more of the painful conditions contemplated herein can comprise mixtures of various types of pain provided above and herein (e.g. nociceptive pain, inflammatory pain, neuropathic pain, etc.). In some embodiments, a particular pain can dominate. In other embodiments, the painful condition comprises two or more types of pains without one dominating. A skilled clinician can determine the dosage to achieve a therapeutically effective amount for a particular subject based on the painful condition.

In certain embodiments, the disease is a psychiatric disorder. The term "psychiatric disorder" refers to a disease of the mind and includes diseases and disorders listed in the Diagnostic and Statistical Manual of Mental Disorders-Fourth Edition (DSM-IV), published by the American Psychiatric Association, Washington D.C. (1994). Psychiatric disorders include anxiety disorders (e.g., acute stress disorder agoraphobia, generalized anxiety disorder, obsessive-compulsive disorder, panic disorder, posttraumatic stress disorder, separation anxiety disorder, social phobia, and specific phobia), childhood disorders, (e.g., attention-deficit/hyperactivity disorder, conduct disorder, and oppositional defiant disorder), eating disorders (e.g., anorexia nervosa and bulimia nervosa), mood disorders (e.g., depression, bipolar disorder, cyclothymic disorder, dysthymic disorder, and major depressive disorder), personality disorders (e.g., antisocial personality disorder, avoidant personality disorder, borderline personality disorder, dependent personality disorder, histrionic personality disorder, narcissistic personality disorder, obsessive-compulsive personality disorder, paranoid personality disorder, schizoid personality disorder, and schizotypal personality disorder), psychotic disorders (e.g., brief psychotic disorder, delusional disorder, schizoaffective disorder, schizophreniform disorder, schizophrenia, and shared psychotic disorder), substance-related disorders (e.g., alcohol dependence, amphetamine dependence, cannabis dependence, cocaine dependence, hallucinogen dependence, inhalant dependence, nicotine dependence, opioid dependence, phencyclidine dependence, and sedative dependence), adjustment disorder, autism, delirium, dementia, multi-infarct dementia, learning and memory disorders (e.g., amnesia and age-related memory loss), and Tourette's disorder.

In certain embodiments, the disease is a metabolic disorder. The term "metabolic disorder" refers to any disorder that involves an alteration in the normal metabolism of carbohydrates, lipids, proteins, nucleic acids, or a combination thereof. A metabolic disorder is associated with either a deficiency or excess in a metabolic pathway resulting in an imbalance in metabolism of nucleic acids, proteins, lipids, and/or carbohydrates. Factors affecting metabolism include the endocrine (hormonal) control system (e.g., the insulin pathway, the enteroendocrine hormones including GLP-1, PYY or the like), the neural control system (e.g., GLP-1 in the brain), or the like. Examples of metabolic disorders include diabetes (e.g., Type I diabetes, Type II diabetes, gestational diabetes), hyperglycemia, hyperinsulinemia, insulin resistance, and obesity.

In certain embodiments, the disease is a cardiovascular disease. In certain embodiments, the disease is a cardiovascular disease. In certain embodiments, the disease is atherogenesis or atherosclerosis. In certain embodiments, the disease is arterial stent occlusion, heart failure (e.g., congestive heart failure), a coronary arterial disease, myocarditis, pericarditis, a cardiac valvular disease, stenosis, restenosis, in-stent-stenosis, angina pectoris, myocardial infarction, acute coronary syndromes, coronary artery bypass grafting, a cardio-pulmonary bypass procedure, endotoxemia, ischemia-reperfusion injury, cerebrovascular ischemia (stroke), renal reperfusion injury, embolism (e.g., pulmonary, renal, hepatic, gastro-intestinal, or peripheral limb embolism), or myocardial ischemia.

In certain embodiments, the method further comprises administering to the subject in need thereof an additional therapy. In certain embodiments, the additional therapy is an additional pharmaceutical agent. In certain embodiments, the additional therapy is an additional nutraceutical agent. The pharmaceutical and nutraceutical compositions of the present disclosure and the additional therapy may show synergy in the methods and uses of the present disclosure.

In another aspect, the invention is directed to a method for increasing energy levels of a subject, for reducing fatigue or drowsiness in a subject, or for increasing alertness in a subject, the method comprising administering to the subject any composition described herein; or d9-caffeine, or a pharmaceutically or nutraceutically acceptable salt, hydrate, or solvate thereof.

In another aspect, the invention is directed to a method for increasing the athletic performance of a subject, the method comprising administering to the subject any composition described herein; or d9-caffeine, or a pharmaceutically or nutraceutically acceptable salt, hydrate, or solvate thereof. In another aspect, the invention provides a method for increasing athletic performance of a subject, the method comprising consuming any composition described herein; or d9-caffeine, or a pharmaceutically or nutraceutically acceptable salt, hydrate, or solvate thereof. In one aspect, the method provides for greater improvement in an athletic performance measure when compared to the administration or consumption of non-isotopically enriched caffeine at an equivalent dose.

In another aspect, the invention is directed to a method of promoting wakefulness or alertness. In one aspect, a method is provided for treating a disorder or condition selected from a wakefulness disorder, hypersomnia, sleep apnea, sleep disorder of central origin, fatigue, excessive daytime sleepiness associated with narcolepsy, obstructive sleep apnea, or fatigue and excessive sleepiness associated with a major depressive disorder or with antidepressant therapy.

In another aspect, the invention is directed to hypersomnia, a condition that is characterized by reoccurring episodes of excessive daytime sleepiness (EDS) or prolonged nighttime sleep. Different from feeling tired due to lack of or interrupted sleep at night, persons with hypersomnia are compelled to nap repeatedly during the day, often at inappropriate times such as at work, during a meal, or in conversation. These daytime naps usually provide no relief from symptoms. Patients often have difficulty waking from a long sleep and may feel disoriented. Other symptoms may include anxiety, increased irritation, decreased energy, restlessness, slow thinking, slow speech, loss of appetite, hallucinations, and memory difficulty. Some patients lose the ability to function in family, social, occupational, or other settings. In certain embodiments, a method is provided for the treatment of hypersomnia in a subject in need thereof, which comprises administering to the subject any composition described herein; or d9-caffeine, or a pharmaceutically or nutraceutically acceptable salt, hydrate, or solvate thereof as a wake promoting agent. In another aspect, a method is provided for the treatment of hypersomnia, which comprises administering or providing to a subject any composition described herein; or d9-caffeine, or a pharmaceutically or nutraceutically acceptable salt, hydrate, or solvate thereof. In another aspect, a method is provided for promoting wakefulness, wherein the wakefulness disorder or condition is selected from circadian rhythm disorder and fatigue associated with multiple sclerosis.

In another aspect, the invention is directed to a method for decreasing daytime drowsiness or sleepiness, the method comprising administering to the subject any composition described herein; or d9-caffeine, or a pharmaceutically or nutraceutically acceptable salt, hydrate, or solvate thereof. In some embodiments, the daytime sleepiness is excessive daytime sleepiness (EDS). In some embodiments, the subject is a patient with a diagnosis of narcolepsy, obstructive sleep apnea, or depression. In some embodiments, the depression is major depressive disorder.

In some embodiments, the daytime sleepiness is due to narcolepsy, obstructive sleep apnea (OSA), or major depressive disorder (MDD). In certain embodiments, the daytime sleepiness is due to narcolepsy. In some embodiments, the daytime sleepiness is due to obstructive sleep apnea (OSA). In certain embodiments, the daytime sleepiness is due to major depressive disorder (MDD).

In certain embodiments, daytime sleepiness is measured using the Maintenance of Wakefulness Test (MWT) or the Epworth Sleepiness Scale (ESS). In certain embodiments, daytime sleepiness is measured using the Maintenance of Wakefulness Test (MWT). In certain embodiments, daytime sleepiness is measured using the Epworth Sleepiness Scale (ESS). The MWT measures an individual's ability to remain awake during the daytime in a darkened, quiet environment. Patients are instructed to remain awake for as long as possible during 40-minute test sessions, and sleep latency may be determined as the mean number of minutes patients could remain awake in the test sessions. The ESS is an 8-item questionnaire by which patients rate their perceived likelihood of falling asleep during usual daily life activities.

In certain embodiments, the method for decreasing daytime sleepiness improves the subject's score on the Maintenance of Wakefulness Test. In some embodiments, the method provides about a 2 minute, 3 minute, 4 minute, 5 minute, 6 minute, 7 minute, 8 minute, 9 minute, 10 minute, 11 minute, 12 minute, 13 minute, 14 minute, 15 minute, 16 minute, 17 minute, 18 minute, 19 minute, or 20 minute or more improvement on the MWT.

In certain embodiments, the method for decreasing daytime sleepiness improves the subject's score on the Epworth Sleepiness Scale. In some embodiments, the method for decreasing daytime sleepiness decreases the subject's score on the Epworth Sleepiness Scale by one point. In certain embodiments, the method for decreasing daytime sleepiness decreases the subject's score on the Epworth Sleepiness Scale by two points, three points, four points, or five points. In some embodiments, the method for decreasing daytime drowsiness decreases the subject's score on the Epworth Sleepiness Scale by five or more points.

In certain embodiments, the method for decreasing daytime drowsiness decreases the subject's score on the Stanford Sleepiness Scale. In some embodiments, the method for decreasing daytime drowsiness decreases the subject's score on the Stanford Sleepiness Scale by one point. In certain embodiments, the method for decreasing daytime drowsiness decreases the subject's score on the Stanford Sleepiness Scale by two points. In some embodiments, the method for decreasing daytime drowsiness decreases the subject's score on the Stanford Sleepiness Scale by three or more points. In some embodiments, the method for decreasing daytime drowsiness achieves a degree of sleepiness in the subject of score 1 on the Stanford Sleepiness Scale. In certain embodiments, the method for decreasing daytime drowsiness achieves a degree of sleepiness in the subject of score 2 on the Stanford Sleepiness Scale. In some embodiments, the method for decreasing daytime drowsiness achieves a degree of sleepiness in the subject of score 3 on the Stanford Sleepiness Scale. In certain embodiments, the method for decreasing daytime drowsiness achieves a degree of sleepiness in the subject of score 4 on the Stanford Sleepiness Scale.

In certain embodiments, the method for decreasing daytime drowsiness decreases response time in the Stroop Color and Word Test. In some embodiments, embodiments, the method for decreasing daytime drowsiness decreases response time in the Stroop Color and Word Test by more than 2, 5, 10, 15, 20, or 25%. In certain embodiments, the method for decreasing daytime drowsiness decreases response time in the Stroop Color and Word Test by more than 2%. In some embodiments, the method for decreasing daytime drowsiness decreases response time in the Stroop Color and Word Test by more than 5%. In certain embodiments, the method for decreasing daytime drowsiness decreases response time in the Stroop Color and Word Test by more than 10%. In some embodiments, the method for decreasing daytime drowsiness decreases response time in the Stroop Color and Word Test by more than 15%. In some embodiments, the method for decreasing daytime drowsiness decreases response time in the Stroop Color and Word Test by more than 20%. In certain embodiments, the method for decreasing daytime drowsiness decreases response time in the Stroop Color and Word Test by more than 25%. In some embodiments, the method for decreasing daytime drowsiness decreases response time in the Stroop Color and Word Test by more than 25%.

In certain embodiments, the method for decreasing daytime drowsiness decreases errors in the Stroop Color and Word Test by more than 2, 5, 10, 15, 20, or 25%. In some embodiments, the method for decreasing daytime drowsiness decreases errors in the Stroop Color and Word Test by more than 2%. In certain embodiments, the method for decreasing daytime drowsiness decreases errors in the Stroop Color and Word Test by more than 5%. In some embodiments, the method for decreasing daytime drowsiness decreases errors in the Stroop Color and Word Test by more than 10%. In certain embodiments, the method for decreasing daytime drowsiness decreases errors in the Stroop Color and Word Test by more than 15%. In some embodiments, the method for decreasing daytime drowsiness decreases errors in the Stroop Color and Word Test by more than 20%. In certain embodiments, the method for decreasing daytime drowsiness decreases errors in the Stroop Color and Word Test by more than 25%.

In certain embodiments, the method for decreasing daytime drowsiness increases the subject's T score on the Comprehensive Trail Making Test. In some embodiments, the method for decreasing daytime drowsiness increases the subject's T score on the Comprehensive Trail Making Test to greater than 29. In certain embodiments, the method for decreasing daytime drowsiness increases the subject's T score on the Comprehensive Trail Making Test to greater than 35. In some embodiments, the method for decreasing daytime drowsiness increases the subject's T score on the Comprehensive Trail Making Test to greater than 42. In certain embodiments, the method for decreasing daytime drowsiness increases the subject's T score on the Comprehensive Trail Making Test to greater than 57. In some embodiments, the method for decreasing daytime drowsiness increases the subject's T score on the Comprehensive Trail Making Test to greater than 64. In certain embodiments, the method for decreasing daytime drowsiness increases the subject's T score on the Comprehensive Trail Making Test to greater than 70.

In another aspect, the invention is directed to a method for treating obesity in a subject, for causing weight loss in a subject, for increasing metabolic rate in a subject, for reducing appetite in a subject, or for increasing energy expenditure in a subject, the method comprising administering to the subject d9-caffeine, or a pharmaceutically or nutraceutically acceptable salt, hydrate, or solvate thereof.

In another aspect, the invention is directed to a method for increasing urine output in a subject, for increasing sodium excretion in a subject, or for reducing edema in a subject, the method comprising administering to the subject d9-caffeine, or a pharmaceutically or nutraceutically acceptable salt, hydrate, or solvate thereof.

In another aspect, the invention is directed to a method for treating a pain disorder in a subject, the method comprising administering to the subject d9-caffeine, or a pharmaceutically or nutraceutically acceptable salt, hydrate, or solvate thereof.

In another aspect, the pain disorder is migraine, arthritis, headache, back pain, bursitis, chronic pain, acute pain, musculoskeletal pain, osteoarthritis, psoriatic arthritis, rheumatoid arthritis, or sciatica. In another aspect, the pain disorder is migraine. In another aspect, the pain disorder is arthritis. In another aspect, the pain disorder is headache. In another aspect, the pain disorder is back pain. In another aspect, the pain disorder is bursitis. In another aspect, the pain disorder is chronic pain. In another aspect, the pain disorder is acute pain. In another aspect, the pain disorder is musculoskeletal pain. In another aspect, the pain disorder is osteoarthritis. In another aspect, the pain disorder is psoriatic arthritis. In another aspect, the pain disorder is rheumatoid arthritis. In another aspect, the pain disorder is sciatica. In another aspect, the pain disorder is migraine or headache.

In another aspect, the invention is directed to a method for treating apnea in a subject, the method comprising administering to the subject d9-caffeine, or a pharmaceutically or nutraceutically acceptable salt, hydrate, or solvate thereof.

In another aspect, the apnea is sleep apnea. In another aspect, the sleep apnea is obstructive sleep apnea, central sleep apnea, apnea of prematurity, or complex sleep apnea syndrome. In another aspect, the apnea is apnea of prematurity. In another aspect, the subject is a neonate, preterm infant, premature infant, or low birthweight infant. In another aspect, the subject is an adult.

In another aspect, the invention is directed to a method for treating hypotension in a subject, the method comprising administering to the subject d9-caffeine, or a pharmaceutically or nutraceutically acceptable salt, hydrate, or solvate thereof.

In another aspect, the hypotension is orthostatic hypotension, postprandial hypotension, or multiple system atrophy with orthostatic hypotension. In another aspect, the hypotension is orthostatic hypotension. In another aspect, the hypotension is multiple system atrophy with orthostatic hypotension.

In another aspect, the invention is directed to a method for treating an encephalopathy in a subject, the method comprising administering to the subject d9-caffeine, or a pharmaceutically or nutraceutically acceptable salt, hydrate, or solvate thereof.

In another aspect, the encephalopathy is chronic traumatic encephalopathy, glycine encephalopathy, Hashimoto's encephalopathy, hepatic encephalopathy, hypertensive encephalopathy, hypoxic ischemic encephalopathy, toxic metabolic encephalopathy, infectious encephalopathy, uremic encephalopathy, or Wernicke encephalopathy. In another aspect, the encephalopathy is chronic traumatic encephalopathy. In another aspect, the encephalopathy is glycine encephalopathy. In another aspect, the encephalopathy is Hashimoto's encephalopathy. In another aspect, the encephalopathy is hepatic encephalopathy. In another aspect, the encephalopathy is hypertensive encephalopathy. In another aspect, the encephalopathy is hypoxic ischemic encephalopathy. In another aspect, the encephalopathy is toxic metabolic encephalopathy. In another aspect, the encephalopathy is infectious encephalopathy. In another aspect, the encephalopathy is uremic encephalopathy. In another aspect, the encephalopathy is Wernicke encephalopathy.

In another aspect, the invention is directed to a method for treating a neurological or psychiatric disorder in a subject, the method comprising administering to the subject d9-caffeine, or a pharmaceutically or nutraceutically acceptable salt, hydrate, or solvate thereof. In another aspect, the neurological or psychiatric disorder is narcolepsy, Alzheimer's disease, attention deficit hyperactivity disorder (ADHD), schizophrenia, Parkinson's disease, or depression. In another aspect, the neurological or psychiatric disorder is narcolepsy. In another aspect, the neurological or psychiatric disorder is Alzheimer's disease. In another aspect, the neurological or psychiatric disorder is attention deficit hyperactivity disorder (ADHD. In another aspect, the neurological or psychiatric disorder is schizophrenia. In another aspect, the neurological or psychiatric disorder is Parkinson's disease. In another aspect, the neurological or psychiatric disorder depression.

In certain embodiments, the neurological or psychiatric disorder is ADHD.

In another aspect, the invention is directed to a method for treating an inflammatory disorder in a subject, the method comprising administering to the subject d9-caffeine, or a pharmaceutically or nutraceutically acceptable salt, hydrate, or solvate thereof.

In another aspect, the inflammatory disorder is a pulmonary inflammatory disorder. In another aspect, the inflammatory disorder is asthma, chronic obstructive pulmonary disorder (COPD), pulmonary fibrosis, or interstitial lung disease. In another aspect, the inflammatory disorder is asthma. In another aspect, the inflammatory disorder is chronic obstructive pulmonary disorder (COPD). In another aspect, the inflammatory disorder is pulmonary fibrosis. In another aspect, the inflammatory disorder is interstitial lung disease.

In any of the methods described herein, the maximum plasma concentration ($C_{max}$) of d9-caffeine after administration or consumption of d9-caffeine, or a pharmaceutically or nutraceutically acceptable salt, hydrate, or solvate, thereof, is substantially similar to that of non-isotopically enriched caffeine at an equivalent dose.

In another aspect, the maximum plasma concentration ($C_{max}$) of d9-caffeine after administration or consumption of d9-caffeine, or a pharmaceutically or nutraceutically acceptable salt, hydrate, or solvate thereof, is higher than that of non-isotopically enriched caffeine at an equivalent dose. In another aspect, the maximum plasma concentration ($C_{max}$) of d9-caffeine after administration of d9-caffeine, or a pharmaceutically or nutraceutically acceptable salt, hydrate, or solvate thereof, is at least 5%, 10%, 15%, 20%, 25%, 30%, 35%, 40%, or 45% higher than of non-isotopically enriched caffeine at an equivalent dose. In some embodiments, the maximum plasma concentration ($C_{max}$) of d9-caffeine after administration of d9-caffeine, or a pharmaceutically or nutraceutically acceptable salt, hydrate, or solvate thereof, is at least 5% higher than of non-isotopically enriched caffeine at an equivalent dose. In certain embodiments, the maximum plasma concentration ($C_{max}$) of d9-caffeine after administration of d9-caffeine, or a pharmaceutically or nutraceutically acceptable salt, hydrate, or solvate thereof, is at least 10% higher than of non-isotopically enriched caffeine at an equivalent dose. In some embodiments, the maximum plasma concentration ($C_{max}$) of d9-caffeine after administration of d9-caffeine, or a pharmaceutically or nutraceutically acceptable salt, hydrate, or solvate thereof, is at least 15% higher than of non-isotopically enriched caffeine at an equivalent dose. In certain embodiments, the maximum plasma concentration ($C_{max}$) of d9-caffeine after administration of d9-caffeine, or a pharmaceutically or nutraceutically acceptable salt, hydrate, or solvate thereof, is at least 20% higher than of non-isotopically enriched caffeine at an equivalent dose. In some embodiments, the maximum plasma concentration ($C_{max}$) of d9-caffeine after administration of d9-caffeine, or a pharmaceutically or nutraceutically acceptable salt, hydrate, or solvate thereof, is at least 25% higher than of non-isotopically enriched caffeine at an equivalent dose. In certain embodiments, the maximum plasma concentration ($C_{max}$) of d9-caffeine after administration of d9-caffeine, or a pharmaceutically or nutraceutically acceptable salt, hydrate, or solvate thereof, is at least 30% higher than of non-isotopically enriched caffeine at an equivalent dose. In some embodiments, the maximum plasma concentration ($C_{max}$) of d9-caffeine after administration of d9-caffeine, or a pharmaceutically or nutraceutically acceptable salt, hydrate, or solvate thereof, is at least 35% higher than of non-isotopically enriched caffeine at an equivalent dose. In certain embodiments, the maximum plasma concentration ($C_{max}$) of d9-caffeine after administration of d9-caffeine, or a pharmaceutically or nutraceutically acceptable salt, hydrate, or solvate thereof, is at least 40% higher than of non-isotopically enriched caffeine at an equivalent dose. In some embodiments, the maximum plasma concentration ($C_{max}$) of d9-caffeine after administration of d9-caffeine, or a pharmaceutically or nutraceutically acceptable salt, hydrate, or solvate thereof, is at least 45% higher than of non-isotopically enriched caffeine at an equivalent dose.

In any of the methods described herein, the maximum plasma concentration ($C_{max}$) of a metabolite of d9-caffeine (e.g., d6-paraxanthine, d6-theobromine, or d6-theophylline) after administration or consumption of d9-caffeine, or a pharmaceutically or nutraceutically acceptable salt, hydrate, or solvate, thereof, is lower than that of the same metabolite of non-isotopically enriched caffeine at an equivalent dose. In another aspect, the maximum plasma concentration ($C_{max}$) of a metabolite of d9-caffeine (e.g., d6-paraxanthine, d6-theobromine, or d6-theophylline) after administration of d9-caffeine, or a pharmaceutically or nutraceutically acceptable salt, hydrate, or solvate thereof, is at least 40%, 50%, 60%, 65%, or 70%, lower than that of the same metabolite of non-isotopically enriched caffeine at an equivalent dose. In some embodiments, the maximum plasma concentration ($C_{max}$) of a metabolite of d9-caffeine (e.g., d6-paraxanthine, d6-theobromine, or d6-theophylline) after administration of d9-caffeine, or a pharmaceutically or nutraceutically acceptable salt, hydrate, or solvate thereof, is at least 40% lower than that of the same metabolite of non-isotopically enriched caffeine at an equivalent dose. In certain embodiments, the maximum plasma concentration ($C_{max}$) of a metabolite of d9-caffeine (e.g., d6-paraxanthine, d6-theobromine, or d6-theophylline) after administration of d9-caffeine, or a pharmaceutically or nutraceutically acceptable salt, hydrate, or solvate thereof, is at least 50% lower than that of the same metabolite of non-isotopically enriched caffeine at an equivalent dose. In some embodiments, the maximum plasma concentration ($C_{max}$) of a metabolite of d9-caffeine (e.g., d6-paraxanthine, d6-theobromine, or d6-theophylline) after administration of d9-caffeine, or a pharmaceutically or nutraceutically acceptable salt, hydrate, or solvate thereof, is at least 60% lower than that of the same metabolite of non-isotopically enriched caffeine at an equivalent dose. In certain embodiments, the maximum plasma concentration ($C_{max}$) of a metabolite of d9-caffeine (e.g., d6-paraxanthine, d6-theobromine, or d6-theophylline) after administration of d9-caffeine, or a pharmaceutically or nutraceutically acceptable salt, hydrate, or solvate thereof, is at least 65% lower than that of the same metabolite of non-isotopically enriched caffeine at an equivalent dose. In some embodiments, the maximum plasma concentration ($C_{max}$) of a metabolite of d9-caffeine (e.g., d6-paraxanthine, d6-theobromine, or d6-theophylline) after administration of d9-caffeine, or a pharmaceutically or nutraceutically acceptable salt, hydrate, or solvate thereof, is at least 70% lower than that of the same metabolite of non-isotopically enriched caffeine at an equivalent dose.

In any of the methods described herein, the time of maximum plasma concentration ($T_{max}$) of d9-caffeine after administration or consumption of d9-caffeine, or a pharmaceutically or nutraceutically acceptable salt, hydrate, or solvate thereof, is longer than that of non-isotopically enriched caffeine at an equivalent dose.

In another aspect, the time of maximum plasma concentration ($T_{max}$) of d9-caffeine after administration or consumption of d9-caffeine, or a pharmaceutically or nutraceutically acceptable salt, hydrate, or solvate thereof, is at least 5%, 10%, 25%, 50%, 100%, 200%, 300%, or 400% longer than that of non-isotopically enriched caffeine at an equivalent dose.

In another aspect, the time of last measurable plasma concentration ($T_{last}$) of d9-caffeine after administration or consumption of d9-caffeine, or a pharmaceutically or nutraceutically acceptable salt, hydrate, or solvate thereof, is longer than that of non-isotopically enriched caffeine at an equivalent dose. In certain embodiments, the time of last measurable plasma concentration ($T_{last}$) of d9-caffeine after administration of d9-caffeine, or a pharmaceutically or nutraceutically acceptable salt, hydrate, or solvate thereof, is at least 36 hours. In some embodiments, the time of last measurable plasma concentration ($T_{last}$) of d9-caffeine after administration of d9-caffeine, or a pharmaceutically or nutraceutically acceptable salt, hydrate, or solvate thereof, is at least 40 hours. In certain embodiments, the time of last measurable plasma concentration ($T_{last}$) of d9-caffeine after administration of d9-caffeine, or a pharmaceutically or nutraceutically acceptable salt, hydrate, or solvate thereof, is at least 42 hours. In some embodiments, the time of last measurable plasma concentration ($T_{last}$) of d9-caffeine after administration of d9-caffeine, or a pharmaceutically or nutraceutically acceptable salt, hydrate, or solvate thereof, is at least 44 hours. In certain embodiments, the time of last measurable plasma concentration ($T_{last}$) of d9-caffeine after administration of d9-caffeine, or a pharmaceutically or nutraceutically acceptable salt, hydrate, or solvate thereof, is at least 46 hours. In some embodiments, the time of last measurable plasma concentration ($T_{last}$) of d9-caffeine after administration of d9-caffeine, or a pharmaceutically or nutraceutically acceptable salt, hydrate, or solvate thereof, is at least 48 hours. In certain embodiments, the time of last measurable plasma concentration ($T_{last}$) of d9-caffeine after administration of d9-caffeine, or a pharmaceutically or nutraceutically acceptable salt, hydrate, or solvate thereof, is between 36 and 52 hours. In some embodiments, the time of last measurable plasma concentration ($T_{last}$) of d9-caffeine after administration of d9-caffeine, or a pharmaceutically or nutraceutically acceptable salt, hydrate, or solvate thereof, is between 40 and 52 hours. In certain embodiments, the time of last measurable plasma concentration ($T_{last}$) of d9-caffeine after administration of d9-caffeine, or a pharmaceutically or nutraceutically acceptable salt, hydrate, or solvate thereof, is between 44 and 52 hours. In some embodiments, the time of last measurable plasma concentration ($T_{last}$) of d9-caffeine after administration of d9-caffeine, or a pharmaceutically or nutraceutically acceptable salt, hydrate, or solvate thereof, is between 46 and 50 hours.

In another aspect, the time of last measurable plasma concentration ($T_{last}$) of d9-caffeine after administration or consumption of d9-caffeine, or a pharmaceutically or nutraceutically acceptable salt, hydrate, or solvate thereof, is at least 5%, 10%, 25%, 50%, 100%, 200%, 300%, or 400% longer than that of non-isotopically enriched caffeine at an equivalent dose. In certain embodiments, the time of last measurable plasma concentration ($T_{last}$) of d9-caffeine after administration of d9-caffeine, or a pharmaceutically or nutraceutically acceptable salt, hydrate, or solvate thereof, is at least 5% longer than that of non-isotopically enriched caffeine at an equivalent dose. In some embodiments, the time of last measurable plasma concentration ($T_{last}$) of d9-caffeine after administration of d9-caffeine, or a pharmaceutically or nutraceutically acceptable salt, hydrate, or solvate thereof, is at least 10% longer than that of non-isotopically enriched caffeine at an equivalent dose. In certain embodiments, the time of last measurable plasma concentration ($T_{last}$) of d9-caffeine after administration of d9-caffeine, or a pharmaceutically or nutraceutically acceptable salt, hydrate, or solvate thereof, is at least 25% longer than that of non-isotopically enriched caffeine at an equivalent dose. In some embodiments, the time of last measurable plasma concentration ($T_{last}$) of d9-caffeine after administration of d9-caffeine, or a pharmaceutically or nutraceutically acceptable salt, hydrate, or solvate thereof, is at least 40% longer than that of non-isotopically enriched caffeine at an equivalent dose. In certain embodiments, the time of last measurable plasma concentration ($T_{last}$) of d9-caffeine after administration of d9-caffeine, or a pharmaceutically or nutraceutically acceptable salt, hydrate, or solvate thereof, is 5-100% longer than that of non-isotopically enriched caffeine at an equivalent dose. In some embodiments, the time of last measurable plasma concentration ($T_{last}$) of d9-caffeine after administration of d9-caffeine, or a pharmaceutically or nutraceutically acceptable salt, hydrate, or solvate thereof, is 10-100% longer than that of non-isotopically enriched caffeine at an equivalent dose. In certain embodiments, the time of last measurable plasma concentration ($T_{last}$) of d9-caffeine after administration of d9-caffeine, or a pharmaceutically or nutraceutically acceptable salt, hydrate, or solvate thereof, is 25-100% longer than that of non-isotopically enriched caffeine at an equivalent dose. In some embodiments, the time of last measurable plasma concentration ($T_{last}$) of d9-caffeine after administration of d9-caffeine, or a pharmaceutically or nutraceutically acceptable salt, hydrate, or solvate thereof, is 40-100% longer than that of non-isotopically enriched caffeine at an equivalent dose. In certain embodiments, the time of last measurable plasma concentration ($T_{last}$) of d9-caffeine after administration of d9-caffeine, or a pharmaceutically or nutraceutically acceptable salt, hydrate, or solvate thereof, is 40-60% longer than that of non-isotopically enriched caffeine at an equivalent dose.

In another aspect, the plasma half-life ($t_{1/2}$) of d9-caffeine after administration or consumption of d9-caffeine, or a pharmaceutically or nutraceutically acceptable salt, hydrate, or solvate thereof, is longer than that of non-isotopically enriched caffeine at an equivalent dose.

In any of the methods described herein, the plasma half-life ($t_{1/2}$) of d9-caffeine after administration or consumption of d9-caffeine, or a pharmaceutically or nutraceutically acceptable salt, hydrate, or solvate thereof, is at least 5%, 10%, 25%, 50%, 100%, 200%, 300%, 400%, 500%, or 600% longer than that of non-isotopically enriched caffeine at an equivalent dose. In some embodiments, the plasma half-life ($t_{1/2}$) of d9-caffeine after administration of d9-caffeine, or a pharmaceutically or nutraceutically acceptable salt, hydrate, or solvate thereof, is at least 300% longer than that of non-isotopically enriched caffeine at an equivalent dose. In certain embodiments, the plasma half-life ($t_{1/2}$) of d9-caffeine after administration of d9-caffeine, or a pharmaceutically or nutraceutically acceptable salt, hydrate, or solvate thereof, is at least 400% longer than that of non-isotopically enriched caffeine at an equivalent dose. In some embodiments, the plasma half-life ($t_{1/2}$) of d9-caffeine after administration of d9-caffeine, or a pharmaceutically or nutraceutically acceptable salt, hydrate, or solvate thereof, is at least 500% longer than that of non-isotopically enriched caffeine at an equivalent dose. In certain embodiments, the plasma half-life ($t_{1/2}$) of d9-caffeine after administration of d9-caffeine, or a pharmaceutically or nutraceutically acceptable salt, hydrate, or solvate thereof, is at least 550% longer than that of non-isotopically enriched caffeine at an equivalent dose. In some embodiments, the plasma half-life ($t_{1/2}$) of d9-caffeine after administration of d9-caffeine, or a pharmaceutically or nutraceutically acceptable salt, hydrate, or solvate thereof, is at least 575% longer than that of non-isotopically enriched caffeine at an equivalent dose. In certain embodiments, the plasma half-life ($t_{1/2}$) of d9-caffeine after administration of d9-caffeine, or a pharmaceutically or nutraceutically acceptable salt, hydrate, or solvate thereof, is at least 600% longer than that of non-isotopically enriched caffeine at an equivalent dose. In some embodiments, the plasma half-life ($t_{1/2}$) of d9-caffeine after administration of d9-caffeine, or a pharmaceutically or nutraceutically acceptable salt, hydrate, or solvate thereof, is 300-400% longer than non-isotopically enriched caffeine at an equivalent dose. In certain embodiments, the plasma half-life ($t_{1/2}$) of d9-caffeine after administration of d9-caffeine, or a pharmaceutically or nutraceutically acceptable salt, hydrate, or solvate thereof, is 350-450% longer than non-isotopically enriched caffeine at an equivalent dose. In some embodiments, the plasma half-life ($t_{1/2}$) of d9-caffeine after administration of d9-caffeine, or a pharmaceutically or nutraceutically acceptable salt, hydrate, or solvate thereof, is 400-500% longer than non-isotopically enriched caffeine at an equivalent dose. In certain embodiments, the plasma half-life ($t_{1/2}$) of d9-caffeine after administration of d9-caffeine, or a pharmaceutically or nutraceutically acceptable salt, hydrate, or solvate thereof, is 450-550% longer than non-isotopically enriched caffeine at an equivalent dose. In some embodiments, the plasma half-life ($t_{1/2}$) of d9-caffeine after administration of d9-caffeine, or a pharmaceutically or nutraceutically acceptable salt, hydrate, or solvate thereof, is 500-600% longer than non-isotopically enriched caffeine at an equivalent dose. In certain embodiments, the plasma half-life ($t_{1/2}$) of d9-caffeine after administration of d9-caffeine, or a pharmaceutically or nutraceutically acceptable salt, hydrate, or solvate thereof, is 300-600% longer than non-isotopically enriched caffeine at an equivalent dose.

In some embodiments, the plasma half-life ($t_{1/2}$) of d9-caffeine after administration of d9-caffeine, or a pharmaceutically or nutraceutically acceptable salt, hydrate, or solvate thereof, is longer than 5.5 hours. In certain embodiments, the plasma half-life ($t_{1/2}$) of d9-caffeine after administration of d9-caffeine, or a pharmaceutically or nutraceutically acceptable salt, hydrate, or solvate thereof, is longer than 6 hours. In some embodiments, the plasma half-life ($t_{1/2}$) of d9-caffeine after administration of d9-caffeine, or a pharmaceutically or nutraceutically acceptable salt, hydrate, or solvate thereof, is longer than 7 hours. In certain embodiments, the plasma half-life ($t_{1/2}$) of d9-caffeine after administration of d9-caffeine, or a pharmaceutically or nutraceutically acceptable salt, hydrate, or solvate thereof, is longer than 8 hours. In some embodiments, the plasma half-life ($t_{1/2}$) of d9-caffeine after administration of d9-caffeine, or a pharmaceutically or nutraceutically acceptable salt, hydrate, or solvate thereof, is longer than 10 hours. In certain embodiments, the plasma half-life ($t_{1/2}$) of d9-caffeine after administration of d9-caffeine, or a pharmaceutically or nutraceutically acceptable salt, hydrate, or solvate thereof, is longer than 12 hours. In some embodiments, the plasma half-life ($t_{1/2}$) of d9-caffeine after administration of d9-caffeine, or a pharmaceutically or nutraceutically acceptable salt, hydrate, or solvate thereof, is longer than 16 hours. In certain embodiments, the plasma half-life ($t_{1/2}$) of d9-caffeine after administration of d9-caffeine, or a pharmaceutically or nutraceutically acceptable salt, hydrate, or solvate thereof, is longer than 20 hours. In some embodiments, the plasma half-life ($t_{1/2}$) of d9-caffeine after administration of d9-caffeine, or a pharmaceutically or nutraceutically acceptable salt, hydrate, or solvate thereof, is longer than 24 hours. In certain embodiments, the plasma half-life ($t_{1/2}$) of d9-caffeine after administration of d9-caffeine, or a pharmaceutically or nutraceutically acceptable salt, hydrate, or solvate thereof, is 6-48 hours. In some embodiments, the plasma half-life ($t_{1/2}$) of d9-caffeine after administration of d9-caffeine, or a pharmaceutically or nutraceutically acceptable salt, hydrate, or solvate thereof, is 6-36 hours. In certain embodiments, the plasma half-life ($t_{1/2}$) of d9-caffeine after administration of d9-caffeine, or a pharmaceutically or nutraceutically acceptable salt, hydrate, or solvate thereof, is 12-48 hours. In some embodiments, the plasma half-life ($t_{1/2}$) of d9-caffeine after administration of d9-caffeine, or a pharmaceutically or nutraceutically acceptable salt, hydrate, or solvate thereof, is 12-36 hours. In certain embodiments, the plasma half-life ($t_{1/2}$) of d9-caffeine after administration of d9-caffeine, or a pharmaceutically or nutraceutically acceptable salt, hydrate, or solvate thereof, is 18-48 hours. In some embodiments, the plasma half-life ($t_{1/2}$) of d9-caffeine after administration of d9-caffeine, or a pharmaceutically or nutraceutically acceptable salt, hydrate, or solvate thereof, is 18-36 hours. In certain embodiments, the plasma half-life ($t_{1/2}$) of d9-caffeine after administration of d9-caffeine, or a pharmaceutically or nutraceutically acceptable salt, hydrate, or solvate thereof, is 24-36 hours.

In certain embodiments, the d9-caffeine compounds, compositions, beverages, and food products described herein have favorable or advantageous pharmacokinetic properties due to the previously unknown pharmacokinetic properties of d9-caffeine. For example, the unexpectedly long plasma half-life ($t_{1/2}$) of d9-caffeine when administered to a subject allows for the compounds, compositions, beverages, and food products described herein that incorporate d9-caffeine to be effective at treating or preventing a disease or condition when administered once daily. In certain embodiments, the d9-caffeine compounds, compositions, beverages, and food products described herein are effective at treating or preventing a disease or condition when administered twice daily, once daily, every two days, or every three days.

In any of the methods described herein, the maximum concentration ($C_{max}$) of d9-caffeine in the central nervous system (CNS) of the subject after administration or consumption of d9-caffeine, or a pharmaceutically or nutraceutically acceptable salt, hydrate, or solvate thereof, is substantially similar to that of non-isotopically enriched caffeine at an equivalent dose.

In another aspect, the maximum concentration ($C_{max}$) of d9-caffeine in the central nervous system (CNS) of the subject after administration or consumption of d9-caffeine, or a pharmaceutically or nutraceutically acceptable salt, hydrate, or solvate thereof, is at least 5%, 10%, 25%, or 50% lower than that of non-isotopically enriched caffeine at an equivalent dose.

In any of the methods described herein, the time of maximum concentration ($T_{max}$) of d9-caffeine in the central nervous system (CNS) of the subject after administration or consumption of d9-caffeine, or a pharmaceutically or nutraceutically acceptable salt, hydrate, or solvate thereof, is longer than that of non-isotopically enriched caffeine at an equivalent dose.

In another aspect, the time of maximum concentration ($T_{max}$) of d9-caffeine in the central nervous system (CNS) of the subject after administration or consumption of d9-caffeine, or a pharmaceutically or nutraceutically acceptable salt, hydrate, or solvate thereof, is at least 5%, 10%, 25%, 50%, 100%, 200%, 300%, or 400% longer than that of non-isotopically enriched caffeine at an equivalent dose.

In another aspect, the time of last measurable concentration ($T_{last}$) of d9-caffeine in the central nervous system (CNS) of the subject after administration or consumption of d9-caffeine, or a pharmaceutically or nutraceutically acceptable salt, hydrate, or solvate thereof, is longer than that of non-isotopically enriched caffeine at an equivalent dose.

In another aspect, the time of last measurable concentration ($T_{last}$) of d9-caffeine in the central nervous system (CNS) of the subject after administration or consumption of d9-caffeine, or a pharmaceutically or nutraceutically acceptable salt, hydrate, or solvate thereof, is at least 5%, 10%, 25%, 50%, 100%, 200%, 300%, or 400% longer than that of non-isotopically enriched caffeine at an equivalent dose.

In any of the methods described herein, the total systemic exposure (AUC) in plasma of d9-caffeine after administration or consumption of d9-caffeine, or a pharmaceutically or nutraceutically acceptable salt, hydrate, or solvate thereof, is at least 5%, 10%, 25%, 50%, 100%, 200%, 300%, 400%, 450%, 500%, or 600% greater than that of non-isotopically enriched caffeine at an equivalent dose. In some embodiments, the total systemic exposure in plasma of d9-caffeine after administration of d9-caffeine, or a pharmaceutically or nutraceutically acceptable salt, hydrate, or solvate thereof, is at least 5% greater than that of non-isotopically enriched caffeine at an equivalent dose. In certain embodiments, the total systemic exposure in plasma of d9-caffeine after administration of d9-caffeine, or a pharmaceutically or nutraceutically acceptable salt, hydrate, or solvate thereof, is at least 10% greater than that of non-isotopically enriched caffeine at an equivalent dose. In some embodiments, the total systemic exposure in plasma of d9-caffeine after administration of d9-caffeine, or a pharmaceutically or nutraceutically acceptable salt, hydrate, or solvate thereof, is at least 25% greater than that of non-isotopically enriched caffeine at an equivalent dose. In certain embodiments, the total systemic exposure in plasma of d9-caffeine after administration of d9-caffeine, or a pharmaceutically or nutraceutically acceptable salt, hydrate, or solvate thereof, is at least 50% greater than that of non-isotopically enriched caffeine at an equivalent dose. In some embodiments, the total systemic exposure in plasma of d9-caffeine after administration of d9-caffeine, or a pharmaceutically or nutraceutically acceptable salt, hydrate, or solvate thereof, is at least 100% greater than that of non-isotopically enriched caffeine at an equivalent dose. In certain embodiments, the total systemic exposure in plasma of d9-caffeine after administration of d9-caffeine, or a pharmaceutically or nutraceutically acceptable salt, hydrate, or solvate thereof, is at least 200% greater than that of non-isotopically enriched caffeine at an equivalent dose. In some embodiments, the total systemic exposure in plasma of d9-caffeine after administration of d9-caffeine, or a pharmaceutically or nutraceutically acceptable salt, hydrate, or solvate thereof, is at least 300% greater than that of non-isotopically enriched caffeine at an equivalent dose. In certain embodiments, the total systemic exposure in plasma of d9-caffeine after administration of d9-caffeine, or a pharmaceutically or nutraceutically acceptable salt, hydrate, or solvate thereof, is at least 400% greater than that of non-isotopically enriched caffeine at an equivalent dose. In some embodiments, the total systemic exposure in plasma of d9-caffeine after administration of d9-caffeine, or a pharmaceutically or nutraceutically acceptable salt, hydrate, or solvate thereof, is at least 450% greater than that of non-isotopically enriched caffeine at an equivalent dose. In some embodiments, the total systemic exposure in plasma of d9-caffeine after administration of d9-caffeine, or a pharmaceutically or nutraceutically acceptable salt, hydrate, or solvate thereof, is at least 500% greater than that of non-isotopically enriched caffeine at an equivalent dose. In certain embodiments, the total systemic exposure in plasma of d9-caffeine after administration of d9-caffeine, or a pharmaceutically or nutraceutically acceptable salt, hydrate, or solvate thereof, is at least 600% greater than that of non-isotopically enriched caffeine at an equivalent dose. In some embodiments, the total systemic exposure in plasma of d9-caffeine after administration of d9-caffeine, or a pharmaceutically or nutraceutically acceptable salt, hydrate, or solvate thereof, is 400-500% greater than that of non-isotopically enriched caffeine at an equivalent dose. In certain embodiments, the total systemic exposure in plasma of d9-caffeine after administration of d9-caffeine, or a pharmaceutically or nutraceutically acceptable salt, hydrate, or solvate thereof, is 400-450% greater than that of non-isotopically enriched caffeine at an equivalent dose. In some embodiments, the total systemic exposure in plasma of d9-caffeine after administration of d9-caffeine, or a pharmaceutically or nutraceutically acceptable salt, hydrate, or solvate thereof, is 425-475% greater than that of non-isotopically enriched caffeine at an equivalent dose. In some embodiments, the total systemic exposure in plasma of d9-caffeine after administration of d9-caffeine, or a pharmaceutically or nutraceutically acceptable salt, hydrate, or solvate thereof, is 450-500% greater than that of non-isotopically enriched caffeine at an equivalent dose. In certain embodiments, the total systemic exposure in plasma of d9-caffeine after administration of d9-caffeine, or a pharmaceutically or nutraceutically acceptable salt, hydrate, or solvate thereof, is 450-550% greater than that of non-isotopically enriched caffeine at an equivalent dose. In some embodiments, the total systemic exposure in plasma of d9-caffeine after administration of d9-caffeine, or a pharmaceutically or nutraceutically acceptable salt, hydrate, or solvate thereof, is 500-600% greater than that of non-isotopically enriched caffeine at an equivalent dose. In certain embodiments, the total systemic exposure in plasma of d9-caffeine after administration of d9-caffeine, or a pharmaceutically or nutraceutically acceptable salt, hydrate, or solvate thereof, is 550-650% greater than that of non-isotopically enriched caffeine at an equivalent dose.

In another aspect, the total systemic exposure (AUC) in plasma of d9-caffeine after administration or consumption of d9-caffeine, or a pharmaceutically or nutraceutically acceptable salt, hydrate, or solvate thereof, is greater than that of non-isotopically enriched caffeine at an equivalent dose.

In some embodiments, the mean dose normalized plasma $AUC_{inf,D}$ of d9-caffeine after administration or consumption of d9-caffeine, or a pharmaceutically or nutraceutically acceptable salt, hydrate, or solvate thereof, is more than 275 h*ng/mL/mg. In certain embodiments, the mean dose normalized plasma $AUC_{inf,D}$ of d9-caffeine after administration of d9-caffeine, or a pharmaceutically or nutraceutically acceptable salt, hydrate, or solvate thereof, is more than 300 h*ng/mL/mg. In some embodiments, the mean dose normalized plasma $AUC_{inf,D}$ of d9-caffeine after administration of d9-caffeine, or a pharmaceutically or nutraceutically acceptable salt, hydrate, or solvate thereof, is more than 400 h*ng/mL/mg. In certain embodiments, the mean dose normalized plasma $AUC_{inf,D}$ of d9-caffeine after administration of d9-caffeine, or a pharmaceutically or nutraceutically acceptable salt, hydrate, or solvate thereof, is more than 500 h*ng/mL/mg. In some embodiments, the mean dose normalized plasma $AUC_{inf,D}$ of d9-caffeine after administration of d9-caffeine, or a pharmaceutically or nutraceutically acceptable salt, hydrate, or solvate thereof, is more than 600 h*ng/mL/mg. In certain embodiments, the mean dose normalized plasma $AUC_{inf,D}$ of d9-caffeine after administration of d9-caffeine, or a pharmaceutically or nutraceutically acceptable salt, hydrate, or solvate thereof, is more than 700 h*ng/mL/mg. In some embodiments, the mean dose normalized plasma $AUC_{inf,D}$ of d9-caffeine after administration of d9-caffeine, or a pharmaceutically or nutraceutically acceptable salt, hydrate, or solvate thereof, is more than 800 h*ng/mL/mg. In certain embodiments, the mean dose normalized plasma $AUC_{inf,D}$ of d9-caffeine after administration of d9-caffeine, or a pharmaceutically or nutraceutically acceptable salt, hydrate, or solvate thereof, is more than 900 h*ng/mL/mg.

In any of the methods described herein, the total systemic exposure (AUC) of a metabolite of d9-caffeine (e.g., d6-paraxanthine, d6-theobromine, or d6-theophylline) after administration of d9-caffeine, or a pharmaceutically or nutraceutically acceptable salt, hydrate, or solvate, thereof, is lower than that of the same metabolite of non-isotopically enriched caffeine at an equivalent dose. In another aspect, the total systemic exposure of a metabolite of d9-caffeine (e.g., d6-paraxanthine, d6-theobromine, or d6-theophylline) after administration of d9-caffeine, or a pharmaceutically or nutraceutically acceptable salt, hydrate, or solvate thereof, is at least 5%, 10%, 15%, 20%, 30%, 40%, 50%, 60%, or 70% lower than that of the same metabolite of non-isotopically enriched caffeine at an equivalent dose.

In certain embodiments, the total systemic exposure (AUC) of d6-paraxanthine after administration or consumption of d9-caffeine, or a pharmaceutically or nutraceutically acceptable salt, hydrate, or solvate thereof, is at least 5%, 10%, 15%, or 20% lower than that of the same metabolite of non-isotopically enriched caffeine at an equivalent dose. In some embodiments, the total systemic exposure of d6-paraxanthine after administration of d9-caffeine, or a pharmaceutically or nutraceutically acceptable salt, hydrate, or solvate thereof, is at least 5% lower than that of the same metabolite of non-isotopically enriched caffeine at an equivalent dose. In certain embodiments, the total systemic exposure of d6-paraxanthine after administration of d9-caffeine, or a pharmaceutically or nutraceutically acceptable salt, hydrate, or solvate thereof, is at least 10% lower than that of the same metabolite of non-isotopically enriched caffeine at an equivalent dose. In some embodiments, the total systemic exposure of d6-paraxanthine after administration of d9-caffeine, or a pharmaceutically or nutraceutically acceptable salt, hydrate, or solvate thereof, is at least 15% lower than that of the same metabolite of non-isotopically enriched caffeine at an equivalent dose. In certain embodiments, the total systemic exposure of d6-paraxanthine after administration of d9-caffeine, or a pharmaceutically or nutraceutically acceptable salt, hydrate, or solvate thereof, is at least 20% lower than that of the same metabolite of non-isotopically enriched caffeine at an equivalent dose. In some embodiments, the total systemic exposure of d6-paraxanthine after administration of d9-caffeine, or a pharmaceutically or nutraceutically acceptable salt, hydrate, or solvate thereof, is 10-20% lower than that of the same metabolite of non-isotopically enriched caffeine at an equivalent dose.

In certain embodiments, the total systemic exposure (AUC) of d6-theobromine after administration or consumption of d9-caffeine, or a pharmaceutically or nutraceutically acceptable salt, hydrate, or solvate thereof, is at least 15%, 20%, 30%, 40%, or 50% lower than that of the same metabolite of non-isotopically enriched caffeine at an equivalent dose. In some embodiments, the total systemic exposure of d6-theobromine after administration of d9-caffeine, or a pharmaceutically or nutraceutically acceptable salt, hydrate, or solvate thereof, is at least 15% lower than that of the same metabolite of non-isotopically enriched caffeine at an equivalent dose. In certain embodiments, the total systemic exposure of d6-theobromine after administration of d9-caffeine, or a pharmaceutically or nutraceutically acceptable salt, hydrate, or solvate thereof, is at least 20% lower than that of the same metabolite of non-isotopically enriched caffeine at an equivalent dose. In some embodiments, the total systemic exposure of d6-theobromine after administration of d9-caffeine, or a pharmaceutically or nutraceutically acceptable salt, hydrate, or solvate thereof, is at least 30% lower than that of the same metabolite of non-isotopically enriched caffeine at an equivalent dose. In certain embodiments, the total systemic exposure of d6-theobromine after administration of d9-caffeine, or a pharmaceutically or nutraceutically acceptable salt, hydrate, or solvate thereof, is at least 40% lower than that of the same metabolite of non-isotopically enriched caffeine at an equivalent dose. In some embodiments, the total systemic exposure of d6-theobromine after administration of d9-caffeine, or a pharmaceutically or nutraceutically acceptable salt, hydrate, or solvate thereof, is at least 50% lower than that of the same metabolite of non-isotopically enriched caffeine at an equivalent dose. In certain embodiments, the total systemic exposure of d6-theobromine after administration of d9-caffeine, or a pharmaceutically or nutraceutically acceptable salt, hydrate, or solvate thereof, is 20-55% lower than that of the same metabolite of non-isotopically enriched caffeine at an equivalent dose.

In certain embodiments, the total systemic exposure (AUC) of d6-theobromine after administration or consumption of d9-caffeine, or a pharmaceutically or nutraceutically acceptable salt, hydrate, or solvate thereof, is at least 30%, 40%, 50%, or 60% lower than that of the same metabolite of non-isotopically enriched caffeine at an equivalent dose. In some embodiments, the total systemic exposure of d6-theobromine after administration of d9-caffeine, or a pharmaceutically or nutraceutically acceptable salt, hydrate, or solvate thereof, is at least 30% lower than that of the same metabolite of non-isotopically enriched caffeine at an equivalent dose. In certain embodiments, the total systemic exposure of d6-theobromine after administration of d9-caffeine, or a pharmaceutically or nutraceutically acceptable salt, hydrate, or solvate thereof, is at least 40% lower than that of the same metabolite of non-isotopically enriched caffeine at an equivalent dose. In some embodiments, the total systemic exposure of d6-theobromine after administration of d9-caffeine, or a pharmaceutically or nutraceutically acceptable salt, hydrate, or solvate thereof, is at least 50% lower than that of the same metabolite of non-isotopically enriched caffeine at an equivalent dose. In certain embodiments, the total systemic exposure of d6-theobromine after administration of d9-caffeine, or a pharmaceutically or nutraceutically acceptable salt, hydrate, or solvate thereof, is at least 60% lower than that of the same metabolite of non-isotopically enriched caffeine at an equivalent dose. In some embodiments, the total systemic exposure of d6-theobromine after administration of d9-caffeine, or a pharmaceutically or nutraceutically acceptable salt, hydrate, or solvate thereof, is 50-65% lower than that of the same metabolite of non-isotopically enriched caffeine at an equivalent dose.

In any of the methods described herein, the total systemic exposure (AUC) in the central nervous system of d9-caffeine after administration or consumption of d9-caffeine, or a pharmaceutically or nutraceutically acceptable salt, hydrate, or solvate thereof, is at least 5%, 10%, 25%, 50%, 100%, or 200% greater than that of non-isotopically enriched caffeine at an equivalent dose.

In another aspect, the total systemic exposure (AUC) in the central nervous system of d9-caffeine after administration or consumption of d9-caffeine, or a pharmaceutically or nutraceutically acceptable salt, hydrate, or solvate thereof, is greater than that of non-isotopically enriched caffeine at an equivalent dose.

In any of the methods described herein, the ratio of the total systemic exposure (AUC) in plasma of d9-caffeine after administration of d9-caffeine, or a pharmaceutically or nutraceutically acceptable salt, hydrate, or solvate thereof, to the total systemic exposure (AUC) in the central nervous system of the compound, is substantially similar to that of non-isotopically enriched caffeine at an equivalent dose.

In another aspect, the ratio of the total systemic exposure (AUC) in plasma of d9-caffeine after administration or consumption of d9-caffeine, or a pharmaceutically or nutraceutically acceptable salt, hydrate, or solvate thereof, to the total systemic exposure (AUC) in the central nervous system of the compound, is within 20%, 15%, 10%, 5%, 2%, or 1% of that of non-isotopically enriched caffeine at an equivalent dose.

In any of the methods described herein, the side effects are reduced relative to the administration or consumption of non-isotopically enriched caffeine at an equivalent dose. In another aspect, the side effect is anxiety, insomnia, delirium, gastrointestinal issues (e.g., loose stools, diarrhea, stomach ulcers, gastroesophageal reflux, etc.), rhabdomyolysis, addiction, hypertension, rapid heart rate, atrial fibrillation, fatigue, irritability, nervousness, restlessness, nausea, or muscle tremors. In some embodiments, the side effect is insomnia.

In another aspect, the rate or frequency of consumption of a beverage comprising water and d9-caffeine, or a pharmaceutically or nutraceutically acceptable salt, hydrate, solvate, composition, or prodrug thereof, is reduced compared to the rate of consumption of a beverage comprising non-isotopically enriched caffeine at an equivalent dose. In certain embodiments, the rate or frequency of consumption of a beverage is reduced by about 10% to about 80% per unit time (e.g., day, week, or month) compared to the rate of consumption of a beverage comprising non-isotopically enriched caffeine at an equivalent dose. In particular embodiment, the rate or frequency of consumption of a beverage is reduced by about 10% per unit time. In a particular embodiment, the rate or frequency of consumption of a beverage is reduced by about 20% per unit time. In a particular embodiment, the rate or frequency of consumption of a beverage is reduced by about 30% per unit time. In a particular embodiment, the rate or frequency of consumption of a beverage is reduced by about 40% per unit time. In a particular embodiment, the rate or frequency of consumption of a beverage is reduced by about 50% per unit time. In a particular embodiment, the rate or frequency of consumption of a beverage is reduced by about 60% per unit time. In a particular embodiment, the rate or frequency of consumption of a beverage is reduced by about 70% per unit time. In a particular embodiment, the rate or frequency of consumption of a beverage is reduced by about 80% per unit time. In certain embodiments, the unit time is a day. In certain embodiments, the unit time is a week. In certain embodiments, the unit time is a month. The representative examples, which follow, are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that, unless otherwise indicated, the entire contents of each of the references cited herein are incorporated herein by reference to help illustrate the state of the art. The following examples contain important additional information, exemplification and guidance, which can be adapted to the practice of this invention in its various embodiments and the equivalents thereof.

These and other aspects of the present invention will be further appreciated upon consideration of the following Examples, which are intended to illustrate certain particular embodiments of the invention but are not intended to limit its scope, as defined by the claims.

EXAMPLES

In order that the disclosure described herein may be more fully understood, the following examples are set forth. The synthetic and biological examples described in this application are offered to illustrate the compounds, compositions, food products, beverages, and methods provided herein and are not to be construed in any way as limiting their scope.

Abbreviations $AUC_{0-t}$ Area under the concentration-time curve from time zero to time t
$AUC_{0-t, D}$ Dose normalized area under the concentration-time curve from time zero to time t
$AUC_{inf}$ Area under the concentration-time curve from time zero extrapolated to infinity
$AUC_{inf, D}$ Dose normalized area under the concentration-time curve from time zero extrapolated to infinity
$AUC_{last}$ Area under the concentration-time curve from time zero to the last quantifiable concentration
BQL Below quantitation limit
$C_{last}$ Last observed concentration
$C_{max}$ Maximum concentration observed
$C_{max, D}$ Dose normalized maximum concentration observed
CV Coefficient of variation
Hr Hour(s)
LC-MS/MS Liquid Chromatography Tandem Mass Spectrometry
LLOQ Lower limit of quantitation
Min Minute(s)
MRT Mean residence time
n Number of samples
NA Not applicable
No. Number
NR Not reported
QC Quality control
rpm Revolutions per minute
SD Standard deviation
Sec Second(s)
Std Standard
$T_{1/2}$ Terminal half-life
$T_{last}$ Time of last measurable concentration
$T_{max}$ Time of observed maximum concentration
ULOQ Upper limit of quantitation
v Volume Compounds Compounds delineated herein include salt, hydrate and solvates thereof. They include all compounds delineated in schemes herein, whether intermediate or final compounds in a process.

Compounds of the invention can be obtained from natural sources or made or modified made by means known in the art of organic synthesis. For example, 1,3,7-tri-trideuteromethylxanthine (d9-caffeine) may be synthesized from xanthine by the following general procedure. To a stirred solution of 100 mg of xanthine in 5 mL of acetone:water (1:1) is added 5 mL of 0.5 N sodium hydroxide and 50 µL of trideuteromethyl iodide. An additional 50 µL of trideuteromethyl iodide is added after 1 and 2 hrs. The solution is allowed to stand at room temperature for 4-6 hours. The acetone is then removed (nitrogen stream) and 10 mL of water added. The product is extracted from the aqueous solution with ethyl acetate and recrystallized three times from ethanol. See, M. G. Horning, J. Nowlin, J-P. Thenot, and O. J. Bouwsma, "Effect of Deuterium Substitution on the Rate of Caffeine Metabolism," *Stable Isotopes, Proceedings of the Third International Conference*, 1979, 379. See, also, J. B. Falconnet, J. L. Brazier and M. Desage, *J Label Compd Radiopharm*, 1986, 23, 267.

Methods for optimizing reaction conditions and, if necessary, minimizing competing by-products, are known in the art. Reaction optimization and scale-up may advantageously utilize high-speed parallel synthesis equipment and computer-controlled microreactors (e.g., *Design And Optimization in Organic Synthesis, 2nd Edition*, Carlson R, Ed, 2005; Elsevier Science Ltd.; Jähnisch, K et al., *Angew. Chem. Int. Ed. Engl.* 2004 43:406; and references therein). Additional reaction schemes and protocols may be determined by the skilled artisan by use of commercially available structure-searchable database software, for instance, SciFinder® (CAS division of the American Chemical Society) and CrossFire Beilstein® (Elsevier MDL), or by appropriate keyword searching using an internet search engine such as Google® or keyword databases, such as the US Patent and Trademark Office text database.

Example 1

Pharmacokinetic (PK) Study Design

Two groups of fasted male Sprague-Dawley rats (12 animals per group) were administered an oral single dose of caffeine in deionized water (Group 1) or d9-caffeine in deionized water (Group 2) at a target dose level of 2 mg/kg.

Serial blood samples were collected from three animals per group per timepoint prior to dosing and at 0.25, 0.5, 1, 2, 3 4, 6, 8, 10, 12, and 14-hours post dose. No more than three blood samples were collected from individual animals with the last sample being a terminal blood draw. Terminal brain samples were collected from three animals per group at 1, 4, 8, and 14-hours post dose. Blood samples were collected into tubes containing sodium heparin, and then processed for plasma and stored frozen until bioanalysis. Brain samples were collected following the terminal blood collection, rinsed with saline, and stored frozen until bioanalysis.

Plasma and brain samples were analyzed for caffeine and d9-caffeine concentration using a liquid chromatography-tandem mass spectrometry (LC-MS/MS) method. Non-compartmental pharmacokinetic parameter estimates were calculated from the mean plasma concentration-time data.

The results demonstrate that d9-caffeine provides a higher systemic exposure (as measured by AUC) and a longer half-life than a corresponding dose of caffeine in vivo.

Extraction Procedure, LC and MS Conditions, and Data Analysis

Table 1 captures the extraction procedures, liquid chromatography (LC) and mass spectrometry (MS) conditions, and the data analysis methods employed.

TABLE 1

| | |
|---|---|
| Sample Extraction | Aliquot 10 µL of sample (calibration standards, quality control samples, blanks and study samples) into a 96-well plate |
| | Add 60 µL of internal standard spiking solution (100 ng/mL $^{13}C_3$-Caffeine in acetonitrile) to each well, except for double blanks to which 60 µL of acetonitrile was added per well |
| | Vortex-mix |
| | Centrifuge at >3000 rpm for 5 minutes |
| | Transfer supernatant (50 µL) into a clean 96-well plate containing 50 µL of water per well |
| | Vortex-mix |
| LC Conditions | |
| Column | Waters Atlantis T3; 3 um, 30 × 2.1 mm |
| Temperature | 45° C. |
| Mobile Phase A | 0.1% formic acid in 95:5 (v:v) water:acetonitrile |
| Mobile Phase B | 0.1% formic acid in 50:50 (v:v) acetonitrile:methanol |

| Gradient | Time (sec) | % Mobile Phase B | Flow (mL/min) |
|---|---|---|---|
| | 15 | 5 | 0.500 |
| | 60 | 95 | 0.500 |
| | 5 | 95 | 0.500 |
| | 30 | 95 | 0.500 |
| | 40 | 5 | 0.500 |

| | |
|---|---|
| MS Conditions | |
| MS/MS | API-5500 |
| Ionization Method | Electrospray, positive ion |
| Resolution | Unit/Unit |
| Source Temperature | 550° C. |
| Transitions (m/z) | |
| Caffeine: | 195.1/138.1 |
| d9-Caffeine: | 204.1/144.1 |
| $^{13}C_3$-Caffeine | 198.1/140.1 |

TABLE 1-continued (IS):
Data
Analysis

| | |
|---|---|
| Acquisition and Processing | Analyst ® (Applied Biosystems Sciex) |
| Regression Type | Linear, $1/x^2$ |
| Acceptance Criteria | |
| Calibration Standards | At least 75% of the total number of calibration standards are within ±15.0% of their nominal concentrations (±20.0% at LLOQ).<br>At least one calibration standard at the LLOQ and at the ULOQ must be acceptable.<br>Accuracy (bias) of the mean values are within ±15.0% from nominal concentration (±20.0% at LLOQ), and precision (CV) is ≤15.0% (≤20.0% at LLOQ) |
| Quality Controls | At least two-thirds of replicates are within ±15.0% of their nominal concentrations (±20.0% at LLOQ).<br>Accuracy (bias) of the mean values are within ±15.0% from nominal concentration (±20.0% at LLOQ), and precision (CV) is ≤15.0% (≤20.0% at LLOQ) |

Preparation of Dose Formulations

Dose formulations were prepared on the day of dosing.

For Group 1, the dosing formulation was prepared at a target concentration of 0.2 mg/mL by adding caffeine (10.00 mg) to deionized water (49.778 g), vortex-mixing and sonicating.

For Group 2, the dosing formulation was prepared at a target concentration of 0.2 mg/mL by adding d9-caffeine (10.04 mg) to deionized water (49.792 g), vortex-mixing and sonicating.

After dosing, the formulations were stored in a −80° C. freezer.

Rat Acclimation and Housing

Male Sprague-Dawley rats were received from Envigo RMS on 18 Mar. 2019. After an acclimation period of three days, 24 males were assigned to the study based on acceptable health. Animals assigned to the study were uniquely identified by tail marking (indelible ink) and cage cards.

Animals were housed in Innovive® disposable micro-isolator cages (1 to 3 animals per cage). Teklad Global Diets™ (Envigo) 18% Protein Rodent Diet 2018 and tap water were provided ad libitum until the evening prior to dosing. Animals were fasted overnight prior to dose administration.

Animal quarters were maintained at a temperature between 20° C. to 26° C. (68° F. to 79° F.), a relative humidity of 30% to 70%, and with an air flow of at least 10 changes per hour. The light/dark cycle was set for 12-hour intervals, but the cycle was interrupted for the performance of study procedures.

After collection of the final blood samples, the study animals were euthanized by carbon dioxide asphyxiation in accordance with the American Veterinary Medical Association Guidelines on Euthanasia (current version).

Dose Administration

Animals were fasted overnight prior to dose administration. Water was provided ad libitum. Food was returned after the collection of the 4-hour samples. Two groups of male Sprague-Dawley rats (12 animals per group) were administered a single dose of caffeine in deionized water (Group 1) or d9-caffeine in deionized water (Group 2) at a target dose level of 2 mg/kg.

Prior to dosing, the body weight of each animal was recorded. Doses (rounded to the nearest 0.001 mL) were calculated based on the pretreatment body weight (kg) and a dose volume of 10 mL/kg. Oral doses were administered using a ball tipped feeding needle. Dosing syringes were weighed immediately prior to and immediately after dosing each animal, and the quantity of formulation administered to each animal was determined from the difference in syringe weights.

Sample Collection and Processing

Serial blood samples (~300 μL) were collected from three animals per group per timepoint into tubes containing sodium heparin prior to dosing and at 0.25, 0.5, 1, 2, 3, 4, 6, 8, 10, 12, and 14-hours post dose. Blood was collected from each animal on three occasions with the last blood draw coinciding with the sacrifice of the animal. Blood samples were stored on wet ice until being processed for plasma via centrifugation (3500 g for 10 minutes at 5° C.) within 30 minutes of collection. Plasma samples were transferred into matrix tubes and stored in a freezer set to maintain a temperature of −80° C. until analysis.

Immediately after the 1, 4, 8 and 14-hour blood collections, three animals/group were euthanized and the brain was dissected out of each rat. The brains were rinsed with saline and dried, placed in pre-weighed conical tubes, and flash frozen in liquid nitrogen. Brain weights were calculated for each sample. Brains were stored in a freezer set to maintain a temperature of −80° C.

Bioanalysis

Rat plasma and brain samples were analyzed for concentrations of caffeine and d9-caffeine using a qualified LC-MS/MS method. The extraction procedure and analytical method are detailed in Table 1.

Pharmacokinetic Analysis

Pharmacokinetic parameter estimates were calculated from the caffeine and d9-caffeine plasma concentration-time data generated from combined animal plasma data using nominal sampling times and non-compartmental methods. The concentration-time data were analyzed to fit an extravascular (oral gavage) dosing plasma analysis model (200) using the software WinNonlin Phoenix version 6.3 (Pharsight). The pharmacokinetic parameters assessed include, as appropriate: $T_{1/2}$ (terminal half-life); $T_{max}$ (time of peak concentration); $C_{max}$ (peak or maximum concentration); $AUC_{last}$ (computed from time zero to the time of the last positive Y value), and $AUC_{inf}$ (area under a concentration of analyte vs. time calculated using zero to infinity).

Areas-under-the-plasma concentration-time curves (AUC) were estimated using the linear trapezoidal rule. The area through the time ($T_{last}$) of the last observable concentration ($C_{last}$) is reported as $AUC_{last}$. AUC extrapolated to infinity, ($AUC_{inf}$) was estimated by adding $AUC_{last}$ and the ratio of $C_{last}/\lambda_z$, where $\lambda_z$ is the terminal rate constant. Apparent $T_{1/2}$ was calculated using the slope of the log-linear terminal phase of the concentration-time curve, defined by a minimum of three plasma concentration-time points. Half-lives are reported if the correlation for the regression line, as measured by r squared, is ≥0.9, when rounded.

Results

Dose Administration

Two groups of male Sprague-Dawley rats (12 animals per group) were administered a single dose of caffeine in deionized water (Group 1) or d9-caffeine in deionized water (Group 2) at a target dose level of 2 mg/kg.

In rats treated with caffeine (Group 1), the dose administered, determined gravimetrically and based on nominal concentration, ranged from 1.970 to 2.023 mg/kg (−1.48% to 1.21% dosing variance). In rats treated with d9-caffeine (Group 2), the dose administered, determined gravimetrically and based on nominal concentration, ranged from 1.971 to 2.017 mg/kg (−1.43% to 0.85% dosing variance). Dose administration data are reported in Table 2.

Sample Collection and Processing

Samples were obtained within 5% of the scheduled time with the following exceptions: the 0.5-hour blood sample from Animal No. 1 (11.61%) and the 1-hour brain samples from Animal No. 1 (8.19%), No. 2 (7.47%), No. 3 (7.06%), No. 4 (7.39%), No. 5 (8.00%), and No. 6 (6.72%).

Concentrations in Plasma

Mean caffeine concentrations in plasma following an oral (gavage) dose of caffeine to male Sprague-Dawley rats are summarized in Table 3 and data for individual animals are reported in Table 4. Mean d9-caffeine concentrations in plasma following an oral (gavage) dose of d9-caffeine to male Sprague-Dawley rats are summarized in Table 5. Data for individual animals are reported in Table 6. Mean caffeine and d9-caffeine plasma concentration-time profiles are plotted in FIG. 1.

Following administration of 2 mg/kg of caffeine or d9-caffeine, measurable plasma concentrations of caffeine or d9-caffeine were detected in all animals evaluated at each time point through 14 hours post dose.

TABLE 3

Group 1: Mean (n = 3/time point) Caffeine Concentrations in Plasma Following an Oral (Gavage) Dose of Caffeine to Fasted Male Sprague-Dawley Rats at a Target Dose Level of 2 mg/kg

| Time | Concentration (ng/mL) | | |
|---|---|---|---|
| (hour) | Mean | SD | % CV |
| Pre | BQL | NA | NA |
| 0.25 | 2423 | 219 | 9.1 |
| 0.5 | 2407 | 92.4 | 3.8 |

TABLE 2

| Group Number | Test Article | Animal Number | Animal Weight (kg) | Formulation Administered (g) | Nominal Concentration[a] (mg/mL) | Dose Administered (mg) | Dose Administered (mg/kg) | Protocol-Specified Dose (mg/kg) | Dosing Variance (%) |
|---|---|---|---|---|---|---|---|---|---|
| 1 | Caffeine | 1 | 0.339 | 3.388 | 0.2 | 0.678 | 1.999 | 2 | −0.06 |
| | | 2 | 0.333 | 3.331 | 0.2 | 0.666 | 2.001 | 2 | 0.03 |
| | | 3 | 0.338 | 3.338 | 0.2 | 0.668 | 1.975 | 2 | −1.24 |
| | | 4 | 0.380 | 3.771 | 0.2 | 0.754 | 1.985 | 2 | −0.76 |
| | | 5 | 0.341 | 3.450 | 0.2 | 0.690 | 2.023 | 2 | 1.17 |
| | | 6 | 0.328 | 3.305 | 0.2 | 0.661 | 2.015 | 2 | 0.76 |
| | | 7 | 0.351 | 3.527 | 0.2 | 0.705 | 2.010 | 2 | 0.48 |
| | | 8 | 0.348 | 3.522 | 0.2 | 0.704 | 2.024 | 2 | 1.21 |
| | | 9 | 0.331 | 3.334 | 0.2 | 0.667 | 2.015 | 2 | 0.73 |
| | | 10 | 0.332 | 3.324 | 0.2 | 0.665 | 2.002 | 2 | 0.12 |
| | | 11 | 0.332 | 3.346 | 0.2 | 0.669 | 2.016 | 2 | 0.78 |
| | | 12 | 0.317 | 3.123 | 0.2 | 0.625 | 1.970 | 2 | −1.48 |
| 2 | d9-Caffeine | 13 | 0.345 | 3.476 | 0.2 | 0.695 | 2.015 | 2 | 0.75 |
| | | 14 | 0.346 | 3.479 | 0.2 | 0.696 | 2.011 | 2 | 0.55 |
| | | 15 | 0.341 | 3.439 | 0.2 | 0.688 | 2.017 | 2 | 0.85 |
| | | 16 | 0.343 | 3.455 | 0.2 | 0.691 | 2.015 | 2 | 0.73 |
| | | 17 | 0.345 | 3.473 | 0.2 | 0.695 | 2.013 | 2 | 0.67 |
| | | 18 | 0.360 | 3.592 | 0.2 | 0.718 | 1.996 | 2 | −0.22 |
| | | 19 | 0.378 | 3.726 | 0.2 | 0.745 | 1.971 | 2 | −1.43 |
| | | 20 | 0.330 | 3.304 | 0.2 | 0.661 | 2.002 | 2 | 0.12 |
| | | 21 | 0.361 | 3.628 | 0.2 | 0.726 | 2.010 | 2 | 0.50 |
| | | 22 | 0.326 | 3.258 | 0.2 | 0.652 | 1.999 | 2 | −0.06 |
| | | 23 | 0.351 | 3.500 | 0.2 | 0.700 | 1.994 | 2 | −0.28 |
| | | 24 | 0.370 | 3.680 | 0.2 | 0.736 | 1.989 | 2 | −0.54 |

[a]Assumes a density of 1.0 g/mL.

TABLE 3-continued

Group 1: Mean (n = 3/time point) Caffeine Concentrations in Plasma Following an Oral (Gavage) Dose of Caffeine to Fasted Male Sprague-Dawley Rats at a Target Dose Level of 2 mg/kg

| Time (hour) | Concentration (ng/mL) | | |
|---|---|---|---|
| | Mean | SD | % CV |
| 1 | 2643 | 123 | 4.7 |
| 2 | 2067 | 32.1 | 1.6 |
| 3 | 2030 | 65.6 | 3.2 |
| 4 | 1820 | 121 | 6.7 |
| 6 | 1199 | 341 | 28.4 |
| 8 | 849 | 340 | 40.1 |
| 10 | 344 | 118 | 34.3 |
| 12 | 171 | 74.4 | 43.5 |
| 14 | 97.1 | 51.9 | 53.4 |

TABLE 4

Group 1: Caffeine Concentrations in Plasma Following an Oral (Gavage) Dose of Caffeine to Fasted Male Sprague Dawley Rats at a Target Dose Level of 2 mg/kg

| Time Point | Concentration (ng/mL) Animal No. | | | | | | | | | | | |
|---|---|---|---|---|---|---|---|---|---|---|---|---|
| (hr) | 1 | 2 | 3 | 4 | 5 | 6 | 7 | 8 | 9 | 10 | 11 | 12 |
| Pre | BQL | BQL | BQL | BQL | BQL | BQL | BQL | BQL | BQL | BQL | BQL | BQL |
| 0.25 | 2250 | 2670 | 2350 | — | — | — | — | — | — | — | — | — |
| 0.5 | 2460 | 2300 | 2460 | — | — | — | — | — | — | — | — | — |
| 1 | 2540 | 2610 | 2780 | — | — | — | — | — | — | — | — | — |
| 2 | — | — | — | 2080 | 2030 | 2090 | — | — | — | — | — | — |
| 3 | — | — | — | 2100 | 1970 | 2020 | — | — | — | — | — | — |
| 4 | — | — | — | 1710 | 1800 | 1950 | — | — | — | — | — | — |
| 6 | — | — | — | — | — | — | 1470 | 1310 | 816 | — | — | — |
| 8 | — | — | — | — | — | — | 1150 | 916 | 480 | — | — | — |
| 10 | — | — | — | — | — | — | — | — | — | 439 | 382 | 212 |
| 12 | — | — | — | — | — | — | — | — | — | 231 | 194 | 87.7 |
| 14 | — | — | — | — | — | — | — | — | — | 136 | 117 | 38.2 |

— Not a scheduled time point.
BQL: Below quantitation limit (<3.00 ng/mL)

TABLE 5

Group 2: Mean (n = 3/time point) d9-Caffeine Concentrations in Plasma Following an Oral (Gavage) Dose of d9-Caffeine to Fasted Male Sprague-Dawley Rats at a Target Dose Level of 2 mg/kg

| Time (hour) | Concentration (ng/mL) | | |
|---|---|---|---|
| | Mean | SD | % CV |
| Pre | BQL | NA | NA |
| 0.25 | 1717 | 230 | 13.4 |
| 0.5 | 1743 | 261 | 15.0 |
| 1 | 2093 | 145 | 6.9 |
| 2 | 2340 | 72.1 | 3.1 |
| 3 | 2357 | 73.7 | 3.1 |
| 4 | 2267 | 76.4 | 3.4 |
| 6 | 1793 | 55.1 | 3.1 |
| 8 | 1550 | 108 | 7.0 |
| 10 | 1210 | 78.1 | 6.5 |
| 12 | 897 | 70.0 | 7.8 |
| 14 | 682 | 76.4 | 11.2 |

TABLE 6

Group 2: d9-Caffeine Concentrations in Plasma Following an Oral (Gavage) Dose of d9-Caffeine to Fasted Male Sprague Dawley Rats at a Target Dose Level of 2 mg/kg

| Time Point | Concentration (ng/mL) Animal No. | | | | | | | | | | | |
|---|---|---|---|---|---|---|---|---|---|---|---|---|
| (hour) | 13 | 14 | 15 | 16 | 17 | 18 | 19 | 20 | 21 | 22 | 23 | 24 |
| Pre | BQL | BQL | BQL | BQL | BQL | BQL | BQL | BQL | BQL | BQL | BQL | BQL |
| 0.25 | 1730 | 1480 | 1940 | — | — | — | — | — | — | — | — | — |

TABLE 6-continued

Group 2: d9-Caffeine Concentrations in Plasma Following an Oral (Gavage) Dose of d9-Caffeine to Fasted Male Sprague Dawley Rats at a Target Dose Level of 2 mg/kg

| Time Point | Concentration (ng/mL) Animal No. | | | | | | | | | | | |
|---|---|---|---|---|---|---|---|---|---|---|---|---|
| (hour) | 13 | 14 | 15 | 16 | 17 | 18 | 19 | 20 | 21 | 22 | 23 | 24 |
| 0.5 | 1680 | 1520 | 2030 | — | — | — | — | — | — | — | — | — |
| 1 | 2020 | 2000 | 2260 | — | — | — | — | — | — | — | — | — |
| 2 | — | — | — | 2400 | 2360 | 2260 | — | — | — | — | — | — |
| 3 | — | — | — | 2330 | 2440 | 2300 | — | — | — | — | — | — |
| 4 | — | — | — | 2350 | 2250 | 2200 | — | — | — | — | — | — |
| 6 | — | — | — | — | — | — | 1850 | 1740 | 1790 | — | — | — |
| 8 | — | — | — | — | — | — | 1670 | 1460 | 1520 | — | — | — |
| 10 | — | — | — | — | — | — | — | — | — | 1160 | 1170 | 1300 |
| 12 | — | — | — | — | — | — | — | — | — | 910 | 821 | 959 |
| 14 | — | — | — | — | — | — | — | — | — | 633 | 643 | 770 |

— Not a scheduled time point.
BQL: Below quantitation limit (<3.00 ng/mL)

Concentrations in Brain

Mean caffeine concentrations in brain following an oral (gavage) dose of caffeine to male Sprague-Dawley rats are summarized in Table 7. Data for individual animals are reported in Table 8. Mean d9-caffeine concentrations in brain following an oral (gavage) dose of d9-caffeine to male Sprague-Dawley rats are summarized in Table 9. Data for individual animals are reported in Table 10. Mean caffeine and d9-caffeine brain concentration-time profiles are shown in FIG. 1.

Following administration of 2 mg/kg of caffeine or d9-caffeine, measurable brain concentrations of caffeine or d9-caffeine were detected in all animals evaluated at each time point through 14 hours post dose.

TABLE 7

Group 1: Mean (n = 3/time point) Caffeine Concentrations in Brain Following an Oral (Gavage) Dose of Caffeine to Fasted Male Sprague-Dawley Rats at a Target Dose Level of 2 mg/kg

| Time | Concentration (ng/g) | | |
|---|---|---|---|
| (hour) | Mean | SD | % CV |
| 1 | 1910 | 118 | 6.2 |
| 4 | 1210 | 75 | 6.2 |
| 8 | 553 | 245 | 44.3 |
| 14 | 62.6 | 33.7 | 53.8 |

TABLE 8

Group 1: Caffeine Concentrations in Brain Following an Oral (Gavage) Dose of Caffeine to Fasted Male Sprague Dawley Rats at a Target Dose Level of 2 mg/kg

| Time Point | Concentration (ng/g) Animal No. | | | | | | | | | | | |
|---|---|---|---|---|---|---|---|---|---|---|---|---|
| (hour) | 1 | 2 | 3 | 4 | 5 | 6 | 7 | 8 | 9 | 10 | 11 | 12 |
| 1 | 2010 | 1940 | 1780 | — | — | — | — | — | — | — | — | — |
| 4 | — | — | — | 1140 | 1200 | 1290 | — | — | — | — | — | — |
| 8 | — | — | — | — | — | — | 715 | 672 | 271 | — | — | — |
| 14 | — | — | — | — | — | — | — | — | — | 84 | 80 | 23.8 |

— Not a scheduled time point.

TABLE 9

Group 2: Mean (n = 3/time point) D9-Caffeine Concentrations in Brain Following an Oral (Gavage) Dose of d9-Caffeine to Fasted Male Sprague-Dawley Rats at a Target Dose Level of 2 mg/kg

| Time | Concentration (ng/g) | | |
|---|---|---|---|
| (hour) | Mean | SD | % CV |
| 1 | 1537 | 153 | 9.9 |
| 4 | 1643 | 80.8 | 4.9 |
| 8 | 1153 | 112 | 9.7 |
| 14 | 463 | 47.5 | 10.3 |

TABLE 10

Group 2: d9-Caffeine Concentrations in Brain Following an Oral (Gavage) Dose of d9-Caffeine to Fasted Male Sprague Dawley Rats at a Target Dose Level of 2 mg/kg

| Time Point | Concentration (ng/g) Animal No. | | | | | | | | | | | |
|---|---|---|---|---|---|---|---|---|---|---|---|---|
| (hour) | 13 | 14 | 15 | 16 | 17 | 18 | 19 | 20 | 21 | 22 | 23 | 24 |
| 1 | 1570 | 1370 | 1670 | — | — | — | — | — | — | — | — | — |
| 4 | — | — | — | 1570 | 1730 | 1630 | — | — | — | — | — | — |
| 8 | — | — | — | — | — | — | 1280 | 1070 | 1110 | — | — | — |
| 14 | — | — | — | — | — | — | — | — | — | 465 | 414 | 509 |

— Not a scheduled time point.

Pharmacokinetics

Mean pharmacokinetic parameter estimates for caffeine and d9-caffeine following an oral dose of caffeine or d9-caffeine to male Sprague-Dawley rats are reported in Table 11 for plasma and Table 12 for brain.

Following oral dose administration of caffeine at 2 mg/kg, the $T_{1/2}$, $C_{max}$ and $AUC_{last}$ in plasma were 1.9 hr, 2600 ng/mL and 16000 hr*ng/mL, respectively. Following oral dose administration of d9-caffeine at 2 mg/kg, the $T_{1/2}$, $C_{max}$ and $AUC_{last}$ in plasma were 5 hr, 2400 ng/mL and 22000 hr*ng/mL, respectively. d9-Caffeine provided a higher AUC exposure and a longer half-life than a corresponding dose of caffeine in plasma.

Due to differences in the molecular weights of caffeine (MW=195.1) and D9-caffeine (MW=204.1), fewer molecules of d9-caffeine were administered at a 2 mg/kg dose level than caffeine. Molecular weight corrected $C_{max}$, $AUC_{last}$, and $AUC_{inf}$ values in plasma are presented in Table 13 to enable comparison between caffeine and d9-caffeine. While plasma $C_{max}$ values were similar between d9-caffeine and caffeine ($C_{max,corr}$ ratio of 0.97), total systemic exposure ($AUC_{inf}$) to d9-caffeine was approximately 77% higher ($AUC_{inf,corr}$ ratio of 1.77).

Following oral dose administration of caffeine at 2 mg/kg, the $C_{max}$ and $AUC_{last}$ in brain were 1900 ng/mL and 11000 hr*ng/mL, respectively. Following oral dose administration of d9-caffeine at 2 mg/kg, the $C_{max}$ and $AUC_{last}$ in brain were 1600 ng/mL and 16000 hr*ng/mL, respectively. As in plasma, d9-caffeine provided a higher AUC exposure than a corresponding dose of caffeine in brain. The brain/plasma $AUC_{last}$ ratios were similar and were 0.69 and 0.73 for caffeine and d9-caffeine, respectively.

Molecular weight corrected $C_{max}$ and $AUC_{last}$ values in brain are presented in Table 14. Brain $C_{max}$ values were slightly lower for d9-caffeine than caffeine ($C_{max,corr}$ ratio of 0.88) although these differences may have been related to the low number of time points evaluated and differences in $T_{max}$. However, total brain exposure ($AUC_{last,corr}$) to d9-caffeine was approximately 52% higher than caffeine ($AUC_{last,corr}$ ratio of 1.52).

TABLE 11

Plasma Pharmacokinetic Parameters for Caffeine and D9-Caffeine Following Oral (Gavage) Administration of Caffeine or D9-Caffeine to Fasted Male Sprague Dawley Rats at a Target Dose Level of 2 mg/kg

| Group No. | Test Article | Pharmacokinetic Parameter | | | | |
|---|---|---|---|---|---|---|
| | | $T_{1/2}$ (hour) | $T_{max}$ (hour) | $C_{max}$ (ng/mL) | $AUC_{last}$ (hr · ng/mL) | $AUC_{inf}$ (hr*ng/mL) |
| 1 | Caffeine | 1.9 | 1 | 2600 | 16000 | 16000 |
| 2 | D9-Caffeine | 5 | 3 | 2400 | 22000 | 27000 |

$T_{1/2}$ Terminal half life
$T_{max}$ The time of peak concentration
$C_{max}$ The peak or maximum concentration
$AUC_{last}$ Computed from time zero to the time of the last positive Y value
$AUC_{inf}$ Area under a concentration of analyte vs time calculated using zero to infinity

TABLE 12

Brain Pharmacokinetic Parameters for Caffeine and d9-Caffeine Following Oral (Gavage) Administration of Caffeine or d9-Caffeine to Fasted Male Sprague Dawley Rats at a Target Dose Level of 2 mg/kg

| Group No. | Test Article | Pharmacokinetic Parameter | | | | | |
|---|---|---|---|---|---|---|---|
| | | $T_{max}$ (hour) | $C_{max}$ (ng/mL) | $AUC_{last}$ (hr · ng/mL) | $AUC_{inf}$ (hr*ng/mL) | Ratio Brain/Plasma Cmax | Ratio Brain/Plasma $AUC_{last}$ |
| 1 | Caffeine | 1 | 1900 | 11000 | 11000 | 0.73 | 0.69 |
| 2 | d9-Caffeine | 4 | 1600 | 16000 | NR | 0.67 | 0.73 |

NR Not reported due to insufficient characterization of the terminal phase of the plasma-concentration profile
$T_{max}$ The time of peak concentration
$C_{max}$ The peak or maximum concentration
$AUC_{last}$ Computed from time zero to the time of the last positive Y value
$AUC_{inf}$ Area under a concentration of analyte vs time calculated using zero to infinity

TABLE 13

Molecular Weight Corrected Plasma Pharmacokinetic Parameters for Caffeine and d9-Caffeine Following Oral (Gavage) Administration of Caffeine or d9-Caffeine to Fasted Male Sprague Dawley Rats at a Target Dose Level of 2 mg/kg

| | | Pharmacokinetic Parameter | | | | | |
|---|---|---|---|---|---|---|---|
| Group No. | Test Article | $C_{max,\ corr}$ (ng/mL) | $C_{max}$ Ratio | $AUC_{last,\ corr}$ (hr · ng/mL) | $AUC_{last}$ Ratio | $AUC_{inf,\ corr}$ (hr*ng/mL) | $AUC_{inf}$ Ratio |
| 1 | Caffeine | 2486 | | 15296 | | 15296 | |
| 2 | d9-Caffeine | 2400 | 0.97 | 22000 | 1.44 | 27000 | 1.77 |

$C_{max,\ corr}$ The peak or maximum concentration corrected for the molecular weight differences between the molecules (caffeine values multiplied by 0.956)
Ratio Ratio of d9-caffeine/molecular weight corrected caffeine value
$AUC_{last,\ corr}$ Computed from time zero to the time of the last positive Y value corrected for the molecular weight differences between the molecules (caffeine values multiplied by 0.956)
$AUC_{inf,\ corr}$ Area under a concentration of analyte vs time calculated using zero to infinity corrected for the molecular weight differences between the molecules (caffeine values multiplied by 0.956)

TABLE 14

Molecular Weight Corrected Brain Pharmacokinetic Parameters for Caffeine and d9-Caffeine Following Oral (Gavage) Administration of Caffeine or d9-Caffeine to Fasted Male Sprague Dawley Rats at a Target Dose Level of 2 mg/kg

| | | Pharmacokinetic Parameter | | | |
|---|---|---|---|---|---|
| Group No. | Test Article | $C_{max,\ corr}$ (ng/mL) | $C_{max}$ Ratio | $AUC_{last,\ corr}$ (hr · ng/mL) | $AUC_{last}$ Ratio |
| 1 | Caffeine | 1816 | | 10516 | |
| 2 | d9-Caffeine | 1600 | 0.88 | 16000 | 1.52 |

$C_{max,\ corr}$ The peak or maximum concentration corrected for the molecular weight differences between the molecules (caffeine values multiplied by 0.956)
Ratio Ratio of d9-caffeine/molecular weight corrected caffeine value
$AUC_{last,\ corr}$ Computed from time zero to the time of the last positive Y value corrected for the molecular weight differences between the molecules (caffeine values multiplied by 0.956)

Example 2

The following study evaluated the CNS-like activity of d9-caffeine in naïve C57/Bl6 mice using acute oral administration followed by the SmartCube® test.

Experiment Design

Male C57/Bl6 mice from Taconic Laboratories (Germantown, N.Y.) were used. Upon receipt, mice were group-housed in OPTI mouse ventilated cages with 4 mice per cage. Mice were acclimated to the colony room for at least one week prior to test, and subsequently tested at approximately 8 weeks of age. All animals were examined, handled, and weighed prior to initiation of the study to assure adequate health and suitability and to minimize nonspecific stress associated with manipulation. During the course of the study, 12/12 light/dark cycles were maintained. The room temperature was 20-23° C. with a relative humidity maintained between 30-70%. Chow and water were provided ad libitum for the duration of the study.

d9-Caffeine was tested at 0.3, 1, 3, 10, 20 and 30 mg/kg. The compound was formulated in deionized water and administered orally at a dose volume of 10 mL/kg 60 minutes prior to test. Each treatment group contained 12 animals per group. The SmartCube® test session lasted for 45 minutes.

The SmartCube® system is designed to, and can successfully, measure numerous spontaneous behaviors and response to challenges in the same testing environment. The hardware includes force sensors and a number of aversive stimuli to elicit behavior. Three high-resolution video cameras provide constant 3D view of the mouse in the SmartCube® apparatus (SC) throughout the entire testing period. During the 45 minute test session the mice are exposed to a sequence of challenges. The cubes cleaned between each run.

To build the reference data set, drugs were injected 15 min before the test and multiple challenges were presented over the course of the test session. Digital videos of the subjects were processed through computer segmentation algorithms to fit geometrical models to each mouse frame image. The resulting fitted parameters were then analyzed using behavioral classifier algorithms to extract behavioral states, such as rearing, locomotion, and immobility. The data obtained in this way was used to define a drug signature for known reference compounds and establish a therapeutic class signature against which a test sample can be compared. The data mining effort utilizes several analytical methods including Bayesian probabilistic density models and Decision trees. The algorithms consider ~2,600 measures including frequency and duration of behavioral states such as grooming, rearing, etc., and many other features obtained during the test session.

For class and subclass analyses, a reference data set has been built from hundreds of drug doses in multiple drug classes plus a control group that was given different types of vehicles alone. Drug classes are divided into subclasses. Each reference drug was tested at multiple doses appropriate for that drug in mice. The best performing classifiers were chosen from our evaluation tests and two separate types of classifiers were built that make independent predictions thus at drug class and subclass levels. The behavioral signatures of the test drugs were evaluated using these classifiers to predict potential therapeutic utility. The results of the classifications are presented as bar charts for class and subclass.

Results

Figure 2:
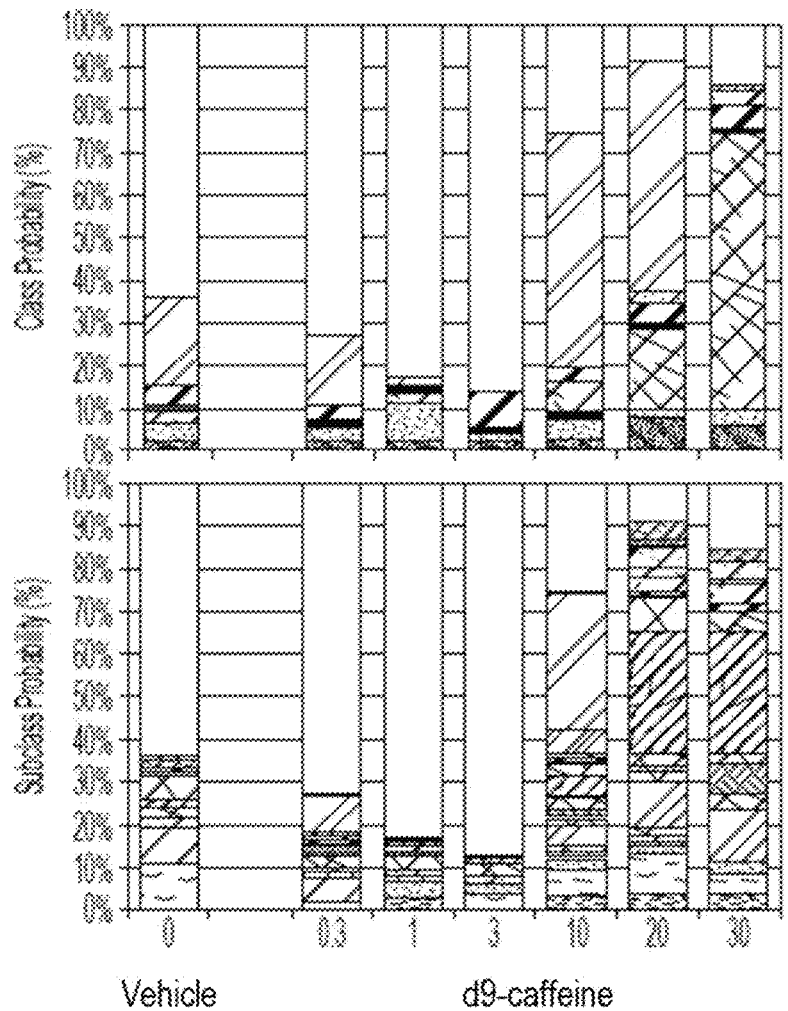
FIG. 2. depicts the class and subclass analysis of d9-caffeine. Reported doses are in mg/kg.
Figure 3A:
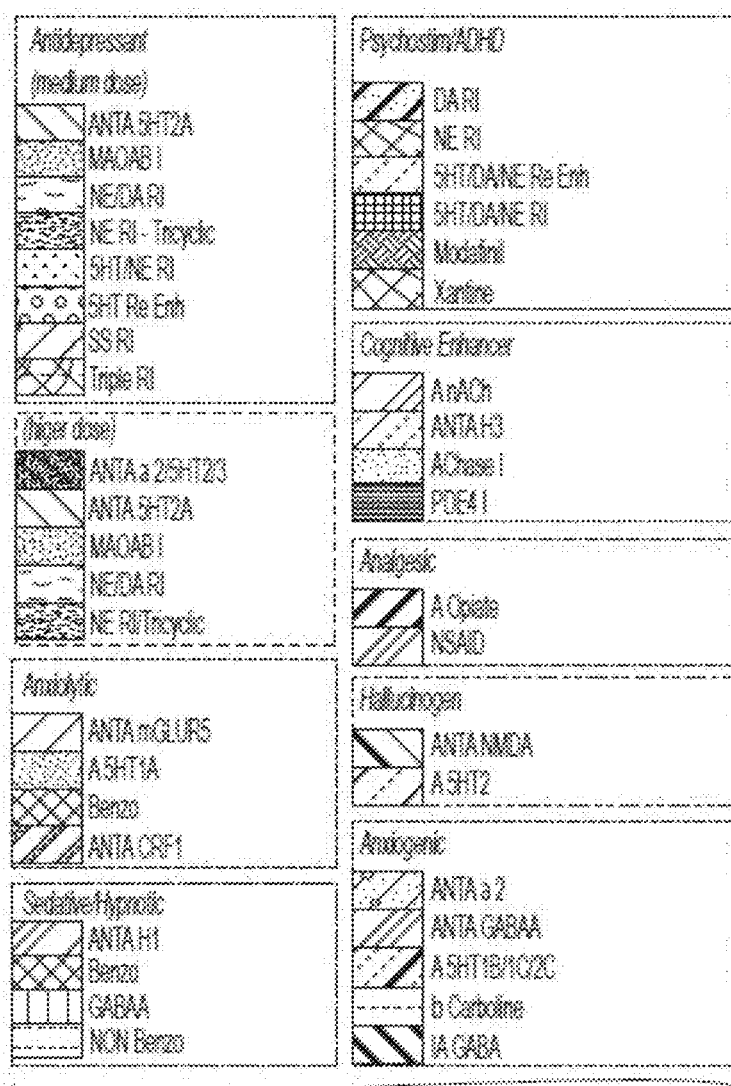
FIGS. 3A-3B. depict the class and subclass legend.
Figure 3B:
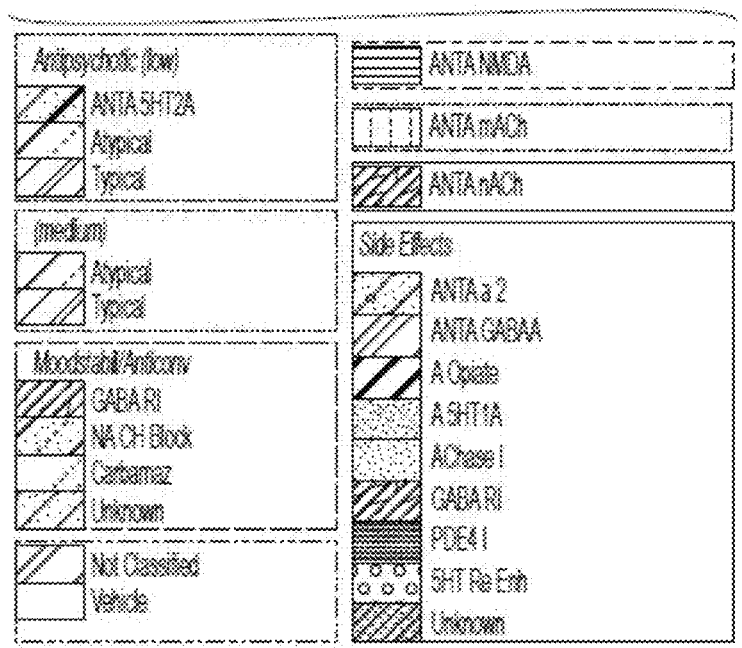
Figure 4:
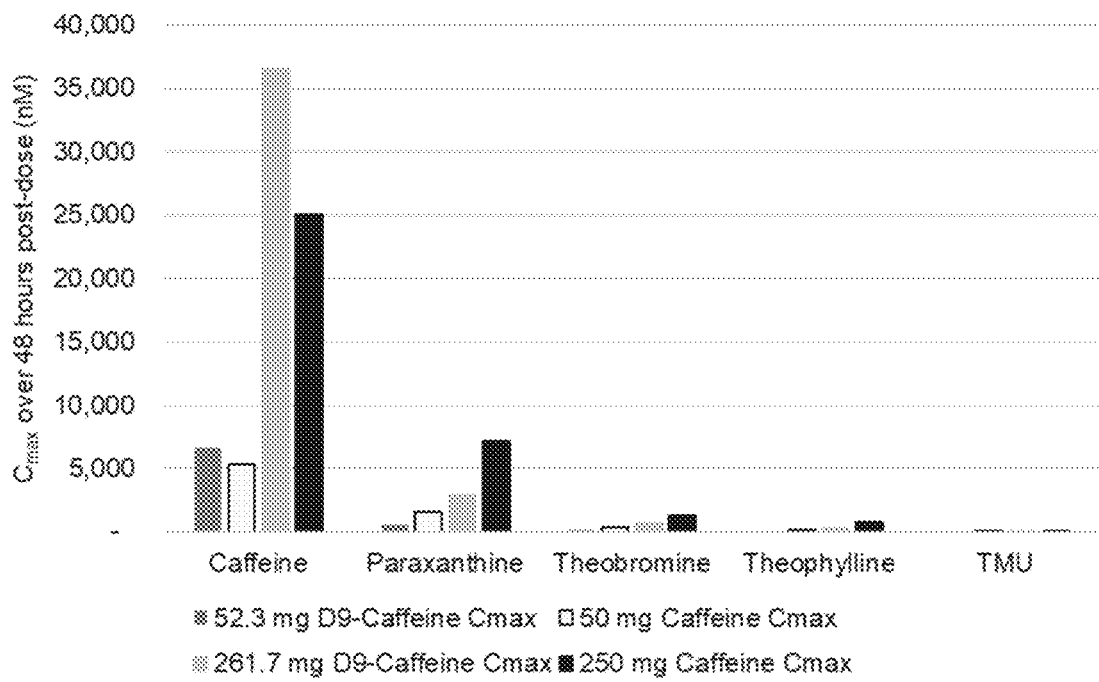
FIG. 4. depicts the plasma $C_{max}$ for d9-caffeine, caffeine, and metabolites thereof over 48 hours following an oral dose of caffeine or d9-caffeine to healthy human subjects. Caffeine was administered at doses of 50 mg and 250 mg, and d9-caffeine was administered at doses of 52.3 mg and 261.7 mg.
Figure 5:
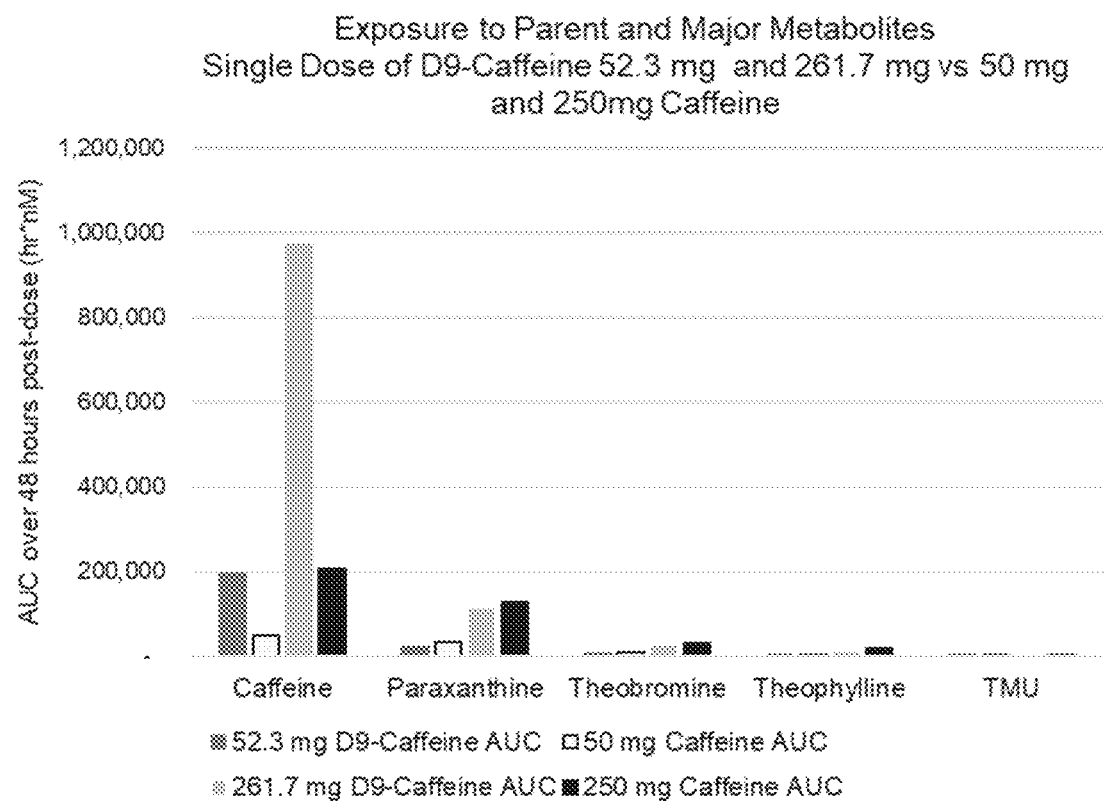
FIG. 5. depicts the exposure (plasma AUC) to d9-caffeine, caffeine, and metabolites thereof over 48 hours following an oral dose of caffeine or d9-caffeine of healthy human subjects. Caffeine was administered at doses of 50 mg and 250 mg, and d9-caffeine was administered at doses of 52.3 mg and 261.7 mg.
Figure 6:
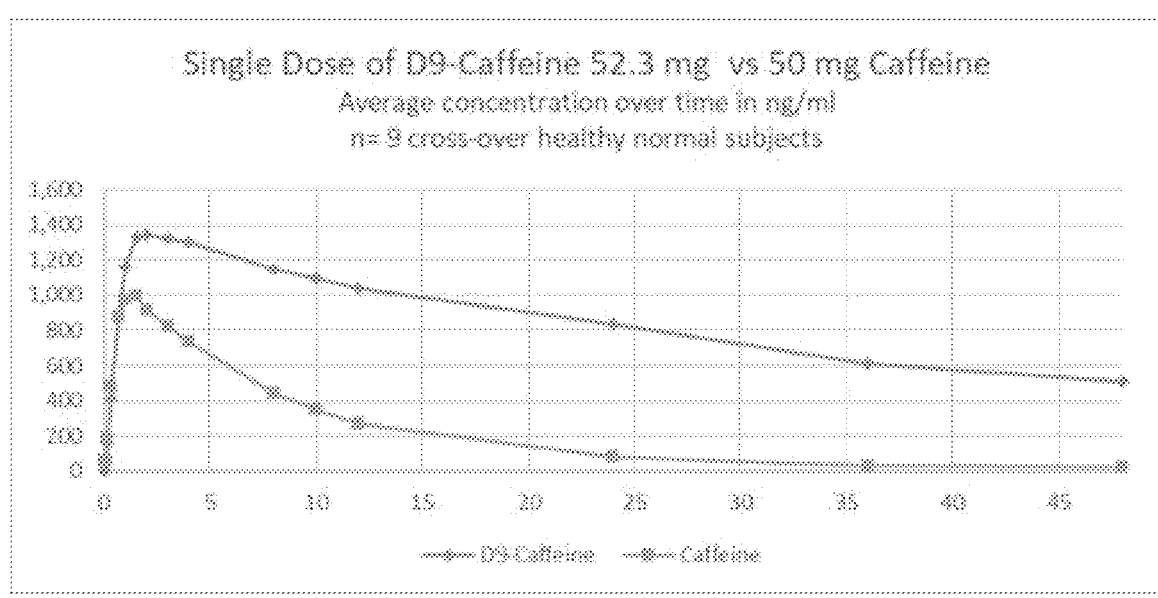
FIG. 6. depicts the average concentrations (ng/ml) of caffeine and d9-caffeine in plasma over 48 hours following an oral dose of caffeine (50 mg) or d9-caffeine (52.3 mg) to healthy human subjects.
Figure 7:
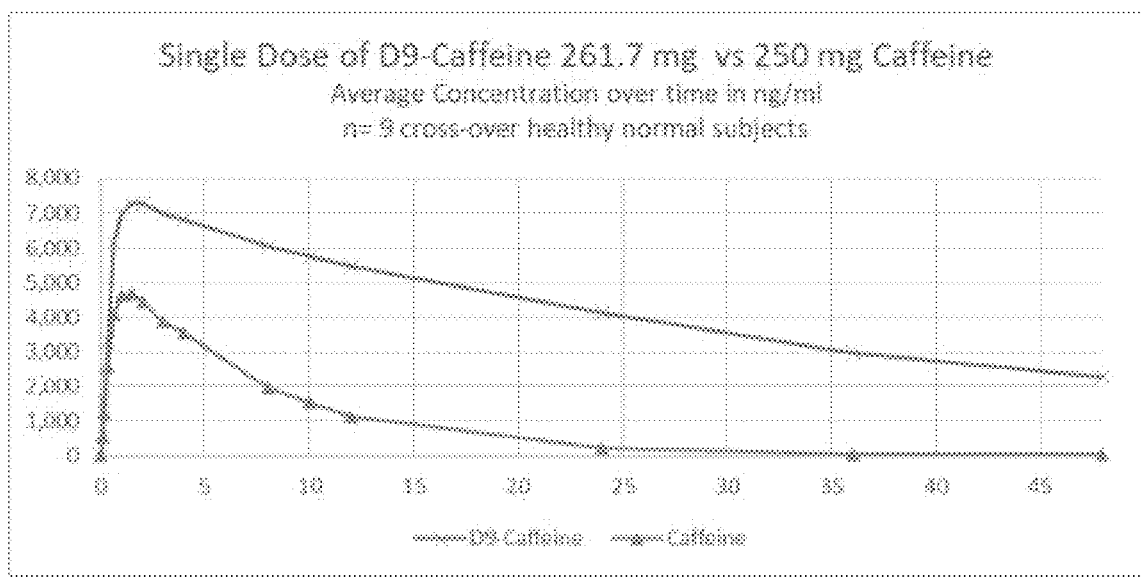
FIG. 7. depicts the average concentrations (ng/ml) of caffeine and d9-caffeine in plasma over 48 hours following an oral dose of caffeine (250 mg) or d9-caffeine (261.6 mg) to healthy human subjects.
Figure 8A:
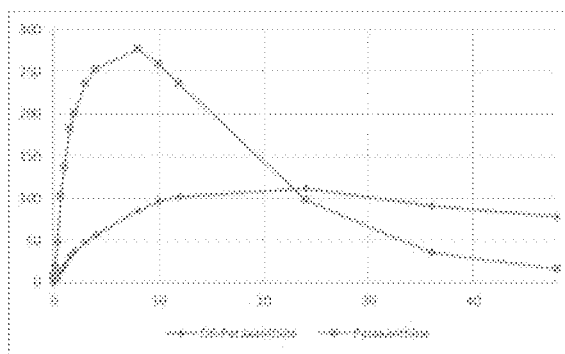
FIGS. 8A-8D. depict the average concentrations (ng/ml) of metabolites of caffeine and d9-caffeine in plasma over 48 hours following an oral dose of caffeine (50 mg) or d9-caffeine (52.3 mg) to healthy human subjects.
Figure 8B:
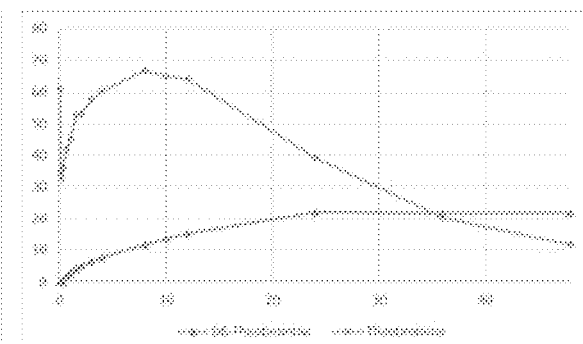
Figure 8C:
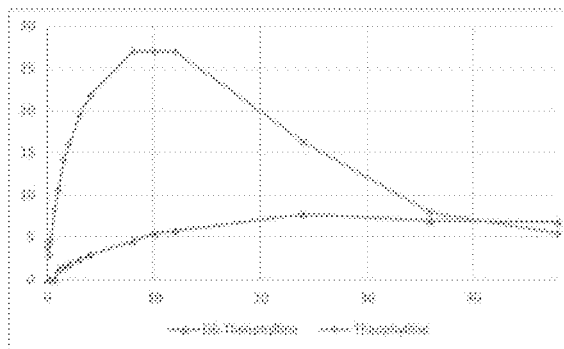
Figure 8D:
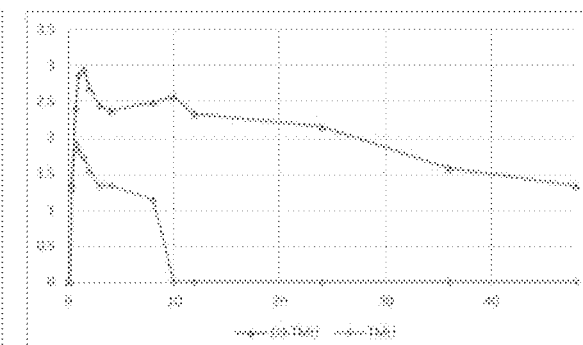
Figure 9A:
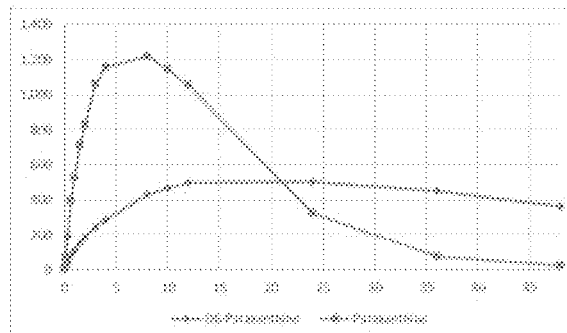
FIGS. 9A-9D. depict the average concentrations (ng/ml) of metabolites of caffeine and d9-caffeine in plasma over 48 hours following an oral dose of caffeine (250 mg) or d9-caffeine (261.7 mg) to healthy human subjects.
Figure 9B:
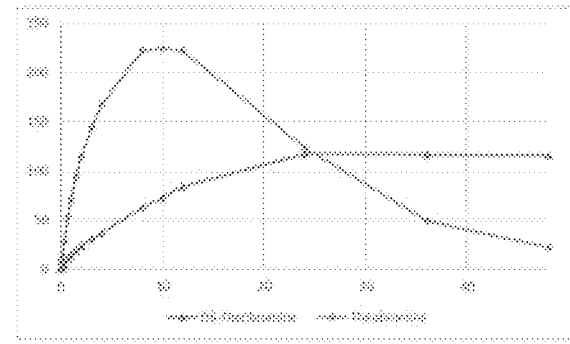
Figure 9C:
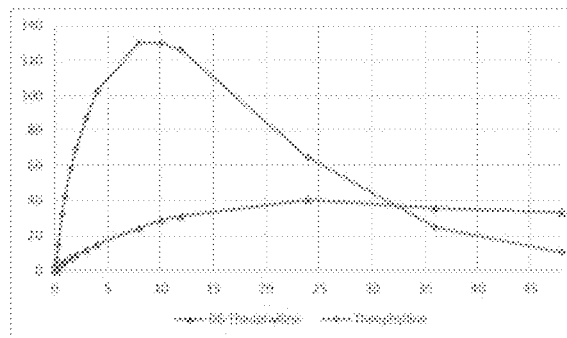
Figure 9D:
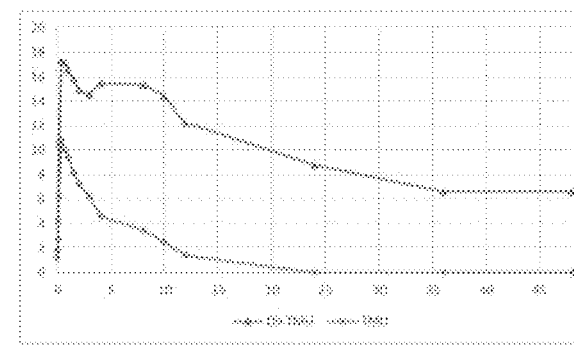
Figure 10:
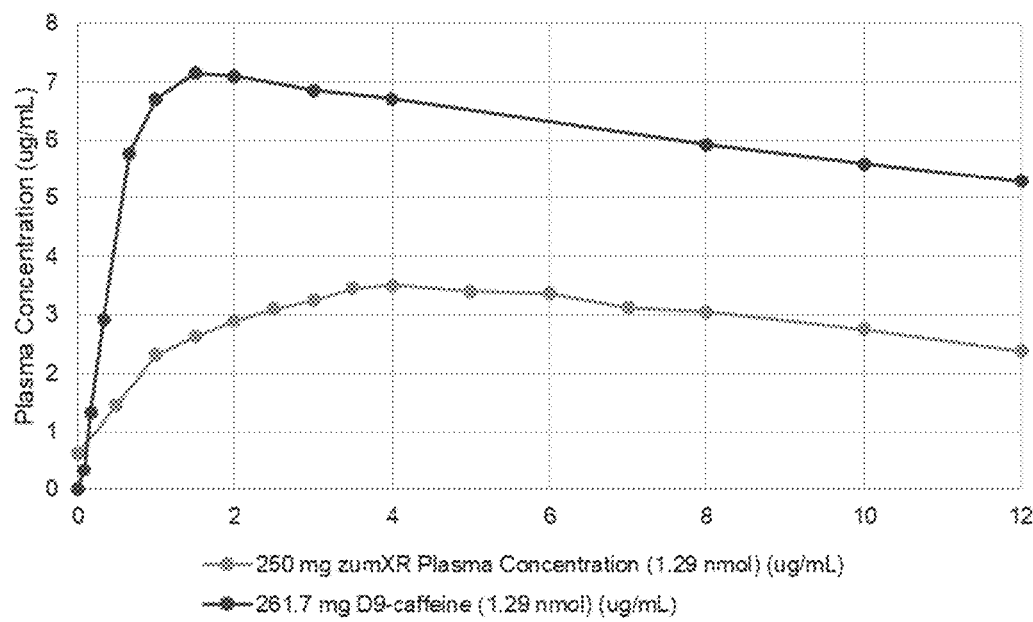
FIG. 10. depicts the average concentrations (µg/ml) in plasma of caffeine provided in an extended-release product, ZumXR, and d9-caffeine over 12 hours following an oral dose of ZumXR (250 mg) or d9-caffeine (261.7 mg).

The class and subclass analyses for the vehicle and all compounds are shown in FIG. 2. Refer to FIG. 3 for the full class and subclass legend. d9-Caffeine was behaviorally inactive at the 0.3, 1, and 3 mg/kg doses. The predominant class and subclass signature with these doses was vehicle-like as seen in the white bar. The 10 mg/kg dose showed a mixed but predominantly "unknown" class and subclass signature. This unknown portion of the signature indicates that the compound is active but the classification system could not reliably assign certain features or patterns (which may be either novel or just insufficiently strong changes exhibited at lower doses) to any CNS class, although it detected the difference from vehicle. At 20 mg/kg, while the class analysis still showed a predominant "unknown" signature mixed with a psychostimulant/ADHD-like signature, the subclass showed a predominant psychostimulant/ADHD signature. A clear psychostimulant/ADHD signature was seen at 30 mg/kg in both class and subclass. This psychostimulant/ADHD-like signature seen at 20 and 30 mg/kg resembled that of dopamine reuptake inhibitors as well as modafinil.

Example 3

The following study evaluated metabolic stability and metabolite formation for caffeine and d9-caffeine in human hepatocytes.

Cryopreserved human hepatocytes were thawed and suspended into 50 ml of InVitro GRO HT-medium. The cells were centrifuged (50 g, 5 min) and resuspended into InVitro GRO KHB-medium (protein free). The cell density and viability were determined by trypan blue exclusion method. Stock solutions of study compounds (caffeine, d9-caffeine, theophylline, theobromine, paraxanthine, d6-theophylline, and d6-theobromine) were prepared in DMSO, and were diluted to incubation medium before spiking to incubation. Instrumentation: Waters Acquity UPLC+Waters TQ-S triple quadrupole MS; Column: Phenomenex Kinetex Biphenyl (2.1×100 mm, 1.8 μm) column with guard filter; Software: MassLynx 4.2.

The samples were analysed at 0, 30, 60, 90, and 120 minutes (with and without hepatocytes) by LC/MS/MS to monitor substrate depletion and formation of metabolites theophylline, theobromine and paraxanthine. No clear disappearance was observed for caffeine or d9-caffeine in human hepatocytes or in buffer, and the observed metabolite levels were low. The most abundant metabolite was paraxanthine, as its concentration at 120 min time point was 26.6 nM with unlabeled caffeine and 6.3 nM (d6-paraxanthine) with d9-caffeine. Similarly at 120 min time point, theophylline had about 1.1 nM concentration and d6-theophylline about 0.4 nM. Theobromine was not detected in any of the incubations. Based on this, deuterium-labeling is seen to decrease the metabolic reaction rates of caffeine, but appears to have no impact on the ratios of metabolites formed.

Example 4

A Double-Blind, Randomized, Two-Part, Two-Period Crossover Study to Evaluate and Compare the Pharmacokinetics of Caffeine and its Metabolites vs. $d_9$-Caffeine and its Metabolites in Healthy Male and Female Subjects The study objectives include (i) evaluating the pharmacokinetic relationship between caffeine and $d_9$-caffeine plasma pharmacokinetics (PK) and their four key metabolites: paraxanthine (1,7-dimethylxanthine), theobromine (3,7-dimethylxanthine), theophylline 1,3-dimethylxanthine) and TMU (1,3,7-trimethyluric acid); (ii) characterizing the PK of caffeine and its metabolites in plasma following oral administration; (iii) characterizing the PK of $d_9$-caffeine and its metabolites in plasma following oral administration; and (iv) evaluating the pharmacological effect of caffeine and $d_9$-caffeine on blood pressure, heart rate, heart rhythm and respiratory rate.

Exploratory objectives of the study include evaluating the relationship between caffeine and $d_9$-caffeine on wakefulness as a measure of pharmacological effects. Exploratory objectives will include various behavioral measurements, including (i) The Comprehensive Trail Making Test $2^{nd}$ Edition (see, e.g., Bowie, C.R.C.R; P.D.P.D Harvey (2006) "Administration and interpretation of the trail making test" *Nature Protocols*. 1 (5): 2277-2281); (ii) The Stroop Color and Word Test (see, e.g., Scarpina F. and Tagini S. (2017) "The Stroop Color and Word Test" *Front. Psychol.* 8:557); and (iii) The Stanford Sleepiness Scale (see, e.g., Hoddes E. (1972). "The development and use of the Stanford sleepiness scale (SSS)" *Psychophysiology*. 9 (150)).

This study is a randomized, double-blind, 2-part, 2-period cross-over study in which subjects are randomized to the following treatment sequences. Twenty (20) subjects will be treated in two groups of equal number for each part. Subject groups include a reasonable distribution of male and female subjects, and may include between 2-3 slow metabolizers per group. As this is a crossover study, each subject will serve as their own control. Four treatments will be assessed in this study: Part One: Treatment A: caffeine, 50 mg oral, and Treatment B: $d_9$-caffeine 50 mg, oral (52.3 mg as molar equivalent); and Part Two: Treatment C: caffeine 250 mg, oral, and Treatment D: $d_9$-caffeine 250 mg, oral (261.7 mg as molar equivalent). Part One and Part Two can run simultaneously. Within each part, there will be a 7-day washout between Period 1 and Period 2 dosing. In each period, subjects will be confined to the study unit from the morning of Day −3 until the morning of Day 3. This study will be conducted at one site in conformance with GCP.

For each study period, the study drug should be administered after an overnight fast of at least 10 hours. All study drugs will be administered by delegated study personnel according to the randomization schedule. The Investigational Product and a Crystal Light packet will be mixed with six (6) oz. of room temperature bottled water in a 20 oz. blender bottle with mixing ball. The contents of the blender bottle will be vigorously shaken for at least 30 seconds to ensure dissolution, the subject will consume the dose within approximately 2 minutes. Two (2) additional ounces of water and another packet of Crystal Light will be added to the blender bottle, shaken vigorously for at least 10 seconds, and immediately consumed by the subject, ensuring all residual study product has been consumed.

No food should be allowed for at least 4 hours post-dose. Subjects will receive standardized meals approximately 4, 10, and 14 hours after study drug administration. Meal times on non-dosing days are according to the procedures of the site. Drinking fluids is restricted from 1 hour prior to through 1 hour after dosing, except fluids that are part of the study drug administration and the rinse aid following administration.

Blood samples for plasma preparation and bioanalysis of caffeine and $d_9$-caffeine and their corresponding metabolites will be collected at the following time points in each period: pre-dose (within 1.0 hour), 5, 10, 20, and 40 minutes, and 1, 1.5, 2, 3, 4, 8, 10, 12, 24, 36, and 48 hours post-dose. A total of 32 (16 per period) blood samples (96 mL) will be collected from each subject during the study for analysis of caffeine, d9-caffeine and their metabolites. Females will have blood collected for serum pregnancy testing at screening (with chemistry). In addition, for all subjects, 18 mL of blood will be collected at screening and approximately 9 mL of blood will be collected at both check in and at EOS/ET for clinical laboratory testing. The total volume of blood collected during the study is expected to be approximately 141 mL for all subjects.

Inclusion criteria:
1. The subject is male or female and is between 18 and 55 years of age (inclusive) at Screening.
2. The subject has a body weight 50.0 to 85.0 kg and body mass index (BMI) between 18.0 and 32.0 kg/m$^2$ (inclusive) at Screening.
3. The subject consents to participation in the study.

4. The subject is screened to test "fast" vs "slow" metabolizers of caffeine; that is, of the CYP1A2*1A vs CYP1A2*1F polymorphism.
5. The subject is a non-smoker or ex-smoker who has not used nicotine containing products in any form, including nicotine patches or e-cigarettes, for at least 3 months prior to Period 1 Day 1 dosing and has a negative cotinine test at Screening and Day −3 check-in of each period.
6. The subject is medically healthy with no clinically significant medical history, physical examination, laboratory profiles, vital signs, as deemed by the Principal Investigator (PI). The examination must include, but is not limited to: blood pressure, heart rate, heart rhythm and respiratory rate.
7. All female subjects must have a negative pregnancy test at Screening and check-in for each period. Female subjects of childbearing potential must agree to use effective contraceptive methods (i.e., abstinence, condoms and spermicide, diaphragm and spermicide, oral or implanted hormonal contraceptive, patches, or injections, or intra-uterine device) from at least 14 days prior to the first dose until 2 weeks after the final study treatment. Female subjects who are postmenopausal (i.e., no menses for 12 months without an alternative medical cause) or are surgically sterile (i.e., documented hysterectomy, bilateral tubal ligation, or bilateral oophorectomy) are exempt from the adequate contraception requirement.

Exclusion Criteria:
1. Subject is mentally or legally incapacitated or has significant emotional problems at the time of the Screening Visit or expected during the conduct of the study.
2. History or presence of clinically significant medical or psychiatric condition or disease in the opinion of the PI.
3. History of any illness that, in the opinion of the PI, might confound the results of the study or poses an additional risk to the subject by their participation in the study.
4. Known hypersensitivity to the investigational drug.
5. Regular daily consumption of more than 14 drinks/week (males) or 7 drink/week (females) of alcohol in any form (1 drink=5 ounces (150 mL) of wine or 12 ounces (360 mL) of beer or 1.5 ounces (45 mL) of hard liquor); History of active alcohol or substance abuse within 1 year prior to Screening.
6. A history of high caffeine consumption, eg, drinking >5 cups of coffee/day in the four months prior to first dose. Subjects will be required to provide their average daily caffeine consumption as part of the intake form. Subjects will be required to abstain from caffeine consumption for 48 hours prior to dose administration, during which time they will be in the clinic. Caffeine consumption includes, but is not limited to: coffee, tea, Coca Cola, Mountain Dew, etc), chocolate candy consumers, asthmatics taking theophylline, No-Doz; ADHD patients (taking methylphenidate, amphetamine); decongestant users.
7. Intake of any known CYP1A2 inhibitor substances (Artemisinin, atazanavir, cimetidine, ciprofloxacin, enoxacin, ethinyl estradiol, etc) or any known CYP1A2 inducers (barbiturates, cruciferous vegetables, grilled meat, carbamazepine, primidone, rifampin) for at least 48 hours prior to Period 1 Day 1 dosing.
   a. CYP 1A2 Inhibitors: α-Naphthoflavone, Furafylline* (TDI), Fluvoxamine (strong inhibitor), Ciprofloxacin (strong inhibitor), Enoxacin (strong inhibitor), Methoxsalen (moderate inhibitor), mexiletine (moderate inhibitor), acyclovir (weak inhibitor), allopurinol (weak inhibitor), Cimetidine (weak inhibitor), Peginterferon (weak inhibitor), Piperine (weak inhibitor), Zileuton (weak inhibitor)
   b. CYP 1A2 Inducers: Omeprazole, Lansoprazole, phenytoin, rifampin(b), ritonavir, teriflunomide
8. Recent (within 28 days prior to Period 1 Day 1 dosing) of any known drug that interferes with caffeine (e.g., ephedrine, adenosine, quinolone antibiotics, cimetidine, clozapine, dipyridamole, disulfiram, fluvoxamine, lithium, monoamine oxidase inhibitors, pentobarbital. Phenylpropanolamine, riluzole, theophylline, verapamil, diethylpropion, epinephrine, phentermine, pseudoephedrine, anticoagulant and antiplatelet drug).
9. Intake of nutritional supplements, juice, and herbal preparations or other foods or beverages that may affect the various drug metabolizing enzymes and transporters (e.g., alcohol, grapefruit, grapefruit juice, grapefruit-containing beverages, apple or orange juice, vegetables from the mustard green family [e.g., kale, broccoli, watercress, collard greens, kohlrabi, brussel sprouts, mustard], and charbroiled meats) within 48 hours before dosing, during which time they will be in the clinic.
10. Intake of herbal preparations containing St. John's Wort within 4 weeks before Period 1 Day 1 dosing
11. Intake of prescription, with the exception of oral contraceptives, or over-the-counter (OTC) medications within 2 weeks before Period 1 Day 1 dosing
12. Engagement in strenuous exercise within 1 week before Period 1 Day 1 dosing (eg, marathon runners, long distance cyclists, weight lifters)
13. History of any bleeding disorders, deep vein thrombosis, or thromboembolic disease.
14. Clinically significant and abnormal Screening hematology laboratory results or recurring infections, or if any of the following are observed (regardless of the PI's assessment of clinical significance):
   a. Hemoglobin <11 g/dL for females or <13 g/dL for males (<100 g/L)
   b. Absolute neutrophil count <2000 k/μL
   c. Platelets <135,000 K/μL
   d. AST 3× the ULN of the laboratory's reference values
   e. ALT 3× the ULN of the laboratory's reference values
15. Women who are pregnant, breast feeding, lactating, plan to become pregnant during the course of the study, or have a positive pregnancy test at Screening or either period check-in.
16. Positive urine drug or alcohol (breath) results at Screening or either study period check-in.
17. Positive urine cotinine at Screening, or either study period check-in.
18. Positive results at Screening for human immunodeficiency virus (HIV), hepatitis B surface antigen (HBsAg), hepatitis C antibody (HCVAb).
19. Positive result at either study period check-in for COVID-19.
20. Seated diastolic blood pressure is <40 mmHg or >90 mmHg and/or systolic blood pressure is <90 mmHg or >140 mmHg at Screening.
21. Donation of blood or significant blood loss within 30 days prior to Period 1 Day 1 dosing.
22. Plasma donation within 7 days prior to Period 1 Day 1 dosing.

23. Participation in another clinical trial within 28 days prior to Period 1 Day 1 dosing, or 10 times the plasma half-life of prior investigational agents, whichever is later. The 28-day window will be derived from the date of the last study procedure in the previous study to Period 1 Day 1 of the current study.

24. Estimated glomerular filtration rate (eGFR)<60 mL/min.

25. The PI determines, for any reason, that the participant is unsuitable for inclusion in the study.

Withdrawal criteria: Subjects will be advised that they are free to withdraw from the study at any time. Over the course of the study (from the time of informed consent to the end of the study [Period 2, Day 3]), the Sponsor and the Investigator(s) or a delegate may withdraw any subject from the study for non-compliance with protocol requirements or significant protocol deviation, in accordance with QPS Bio-Kinetic Clinical Applications, LLCs Standard Operating Procedures (SOP). Subjects may also be withdrawn by the Investigator(s) or a delegate for: safety reason, positive alcohol breath test, positive urine drug screen (including cotinine detection), positive pregnancy test, positive COVID-19/SARS-CoV-2 test, or blind is broken. Subjects will be withdrawn from the study if the PI or Sub-Investigator judges subject safety to be at risk. Any subject using a chronic medication which is assessed to interfere with the PK or assay of caffeine or $d_9$-caffeine will be withdrawn from the study. Subjects excluded from dosing as per criteria listed above, may not be invited to participate in subsequent parts of the study. Subjects withdrawn for safety reasons will be asked to remain at the clinic until the Sponsor, PI, Sub-Investigators, or a delegate agrees that the subject can be discharged. As soon as subject withdrawal is confirmed, blood sampling will be stopped. Subjects who withdraw or are withdrawn from the study after dosing will not be replaced except upon prior agreement by the Sponsor and when sufficient analysis population is at risk.

Study Restrictions:

Caffeine: Products containing caffeine should be limited to 190 mg per day (equivalent of 2 cups of coffee) during the 2 weeks prior to dosing and during washout when the subject is not confined to the clinic. Caffeine will not be permitted during study confinement, or prior to check-in on Day −3 of each period.

Alcohol: No regular alcohol consumption exceeding 7 drinks/week for female subjects or 14 drinks/week for male subjects (1 drink=5 ounces (150 mL) of wine or 12 ounces (360 mL) of beer or 1.5 ounces (45 mL) of hard liquor) and no alcohol at all within 48 hours of check in through EOS.

Smoking and tobacco use is prohibited within 3 months prior to first study drug administration and throughout the study.

Participants will abstain from any type exercise during confinement. Participants may participate in light recreational activities during the study (eg, watching television, reading). After discharge, mild physical activity can be resumed, but subjects should be counseled to avoid strenuous physical activity until the last end-of-study assessment. Subjects are requested not to do strenuous physical exercises 1 week prior to Period 1 Day 1 dosing.

The Test and Reference Products will be supplied by the Sponsor as shown in Table 15 below.

TABLE 15

Investigational Products
Investigational Products

| | Treatment A | Treatment B | Treatment C | Treatment D |
|---|---|---|---|---|
| Product Name: | 50 mg caffeine | 50 mg $d_9$-caffeine (52.3 mg as molar equivalent) | 250 mg caffeine | 250 mg $d_9$-caffeine (261.7 mg as molar equivalent) |
| Dosage Form: | Powder for solution | Powder for solution | Powder for solution | Powder for solution |
| Unit Dose | 50 mg | 50 mg | 250 mg | 250 mg |
| Route of Administration | Oral | Oral | Oral | Oral |

Blinding Procedures:

Subjects will be randomized into one of four treatment sequences (AB or BA [Part 1], CD or DC [Part 2]), in a double-blind manner on Day 1 prior to dosing. The randomization schedule will be prepared by a statistician at QPS-Qualitix, who is not involved in the daily clinical operation of the study.

The unblinded QPS-Qualitix statistician will provide the randomization codes to the delegated unblinded site pharmacy staff. The randomization code will be kept strictly confidential and will be accessible only to the delegated pharmacy staff on site.

The investigator and study staff (including lab personnel), the subjects, the monitors and the Sponsor's staff will remain blinded to the treatment assignment until study closure. Measures will be taken to ensure the taste and appearance of the IPs are indistinguishable.

The blind of the study should not be broken except in a medical emergency (where knowledge of the study product received would affect the treatment of the emergency) or regulatory requirement. If a breaking of the blind is required, the PI or delegated medical site staff will instruct the site unblinded team to proceed. If the blind has to be broken, the date, time, and reason will be recorded in the subject's case report form (CRF) and any associated serious adverse event (SAE) report, if applicable. The PI will notify the Sponsor's contact/Sponsor immediately, and if time permits, the blind should only be broken following discussion with the Sponsor's contact/Sponsor on a case-by-case basis, however, always at the discretion of the PI. If the PI, sub-investigator, site personnel performing assessments, or subject, is unblinded, the subject must be withdrawn from the study.

Meals and Fluids: In each period, subjects check-in to the unit the morning of Day −3. Throughout their confinement they will be provided breakfast, lunch, dinner and snacks according to the site SOP. In the evening of Day −1, subjects will begin an overnight fast of at least 10 hours prior to dosing. No food should be allowed for at least 4 hours post-dose. Drinking fluids is restricted from 1 hour prior to through 1 hour after dosing, except fluids that are part of the study drug administration and the rinse aid following administration. Subjects will receive standardized meals approximately 4, 10 and 14 hours after study drug administration. Meal times on non-dosing days are according to the procedures of the site. The composition of the all meals is according to the procedures of the site.

Investigational Drug Product Preparation: All study drugs will be prepared within 24 hour prior to dosing, by delegated study personnel, following the preparation instructions: (i) open 10 blender bottles (one per subject dosed); (ii) add one dose of Investigational Product (Treatment A, B, C, D), according to study part and randomization; (iii) add one Crystal Light packet to each blender bottle; (iv) gently mix the contents by swirling the bottle; (v) replace cap and ensure it and the pouring spout are tightly closed; (vi) label as needed; and (vii) store upright.

Investigational Drug Product Administration: All study drugs will be administered by delegated study personnel according to the randomization schedule and the administration instructions: (i) the Investigational Product and Crystal Light packet will be mixed with six (6) oz. of room temperature bottled water in a 20 oz. blender bottle with mixing ball; (ii) the contents of the blender bottle will be vigorously shaken for at least 30 seconds to ensure dissolution; the subject will consume the dose within approximately 2 minutes; (iii) two (2) additional ounces of water and another packet of Crystal Light will be added to the blender bottle, shaken vigorously for at least 10 seconds, and immediately consumed by the subject, ensuring all residual study product has been consumed. Treatments may be mixed with slightly warm water for dissolution and allowed to cool to room temperature prior to dose administration.

Three tests evaluating wakefulness; The CTMT2, The SCWT, and The SSS, will be given on Day 1 of each period at pre-dose (−2.5 hours±30 minutes), and at 1, 5 and 10 hours post-dose (±30 minutes).

Pharmacokinetic Assessments:

Time for Sampling: Blood samples for the determination of plasma caffeine, $d_9$-caffeine, and their corresponding metabolites will be collected at the following time points in each period: pre-dose (within 1.0 hour), 5, 10, 20, and 40 minutes, and 1, 1.5, 2, 3, 4, 8, 10, 12, 24, 36, and 48 hours.

Allowed Time Window for PK: The pre-dose sample will be collected within one hour prior to dosing. The time deviations that will be allowed for PK sample collection are tabulated below. Any blood samples drawn beyond the specified window period will be noted as early or late draws and will be recorded appropriately as a protocol deviation. A comment and explanation should be provided in the eCRF.

TABLE 16

Sample collection schedule

| Scheduled time for blood sample collection for PK | Allowed time deviation |
|---|---|
| ≤30 minutes after study drug administration | Must be on time |
| >30 minutes and ≤2 hour after study drug administration | ±1 min |
| >2 hour and ≤12 hours after study drug administration | ±2 min |
| ≥24 hours and ≤48 hours after study drug administration | ±5 min |

Procedures for sampling and processing: About 3 mL of blood for the PK samples will be collected into a Vacutainers® containing K2EDTA BD No. 367856 (1×3 mL) via venipuncture or via an intravenous (i.v.) catheter placed in an antecubital vein in the arm following site procedures. Immediately after blood collection, the collection tubes will be inverted gently for complete mix. Each blood sample should be centrifuged within 30 minutes of collection to separate the plasma. The centrifugation settings should be ~1600 g for 10 minutes. Approximately 1 mL of the resultant plasma will be transferred into a 2-4 mL cryovial with lip seal design and external threads bearing unique labels. The sample will be designated as the primary sample (Aliquot 1). The remaining portion of the plasma will be transferred into another 2-4 mL cryovial of the same type and designated as the back-up sample (Aliquot 2). The plasma samples will be transferred for storage in an upright position in a non-self-defrosting freezer with the temperature set to maintain −70° C. or lower. Plasma samples should be placed in the freezer within 2 hours of blood collection.

Bioanalysis: The concentrations of caffeine and d9-caffeine and their four key metabolites in addition to their deuterated counterparts in plasma will be determined by the QPS LLC Bioanalytical Laboratory using a validated Liquid Chromatography-Tandem Mass Spectrometry (LC/MS/MS) assay. Concentrations will be calculated by interpolation from a calibration curve. Quality control samples will be analyzed throughout the study. Their measured concentrations will be used to determine between-run, overall precision, and accuracy of the analyses. The "molar-equivalent" concentrations should be reported by bioanalytical labs.

Laboratory Tests:

Hematology: The following will be evaluated at Screening, Day −3 check-in of each period, and at EOS/ET: hemoglobin, hematocrit, total and differential leukocyte count, RBC and platelet count.

Serum Chemistry: The following will be evaluated at Screening, Day −3 check-in of each period, and at EOS/ET: BUN, creatinine, total bilirubin, alkaline phosphatase, aspartate transaminase (AST), alanine transaminase (ALT), electrolytes (Na, K, Cl), creatine kinase total, calcium, phosphate, magnesium, albumin, total cholesterol, and glucose.

Urinalysis: The following will be collected at Screening, Day −3 check-in of each period, and at EOS/ET, and evaluated by dipstick: pH, specific gravity, protein, glucose, ketones, bilirubin, blood, nitrite, and microscopic examination, if indicated.

Serology: At Screening, subjects' blood will be tested for HIV, hepatitis B and hepatitis C.

SARS-CoV-2 Test: At each study period Day −3 check-in, a SARS-CoV-2 viral RNA test will be performed to check for COVID-19 infection. Participants will be separated from one another and will have limited contact with study center staff until results are available.

CYP1A2*1A vs CYP1A2*1F Polymorphism Test: At Screening, subjects will be screened to determine if they are a "fast" or "slow" metabolizer of caffeine. Between 1.5 and 4 mL of blood will be collected into a lavender-top $K_2$EDTA Vacutainer® (1×6 mL).

Breath alcohol and urine drug screen: At Screening and at each study period check-in, subjects will be tested for drugs of abuse and alcohol. The drugs of abuse screen will include cotinine, cocaine, amphetamines, cannabinoids and opiates.

Pregnancy test: For female subjects, a serum pregnancy test will be performed at Screening, a urine pregnancy test will be performed at Day −3 check-in of each period and at EOS/ET.

Order of assessments: When several study procedures are scheduled near the same time point post-dose, the PK sample collection takes precedence over VS, ECG, Wakefulness tests, and clinical labs.

Adverse events will be recorded and evaluated for their seriousness, intensity, and relationship to the study medication. Adverse events will be collected and documented during the course of the study (from the time of informed consent to the end of the study on Day 3 of Period 2). Adverse events will be followed-up until complete resolution, or until the PI or Sub-Investigator judges safe to discontinue follow-up. The relationship to the study medication will be classified according to Bio-Kinetic Clinical Applications, LLC SOPs. An adverse event (AE) is defined as any untoward medical occurrence in a subject administered a medicinal product and which does not necessarily have to have a causal relationship with this treatment. An AE can therefore be any unfavorable and unintended sign (for example, an abnormal laboratory finding), symptom, or disease temporally associated with the use of a medicinal product, whether or not considered related to this medicinal product. A treatment emergent adverse event (TEAE) is defined as an undesirable event not present prior to medical treatment, or an already present event that worsens either in intensity or frequency following treatment. A serious adverse event (SAE)/TESAE is an AE that results in any of the following outcomes: (i) death; (ii) Life-threatening event (ie, the subject was, in the opinion of the investigator, at immediate risk of death from the event as it occurred. It does not include an event that, had it occurred in a more severe form, might have caused death); (iii) Requires in-subject hospitalization or prolongs hospitalization; (iv) A persistent or significant disability/incapacity or substantial disruption of the ability to conduct normal life functions; (v) congenital anomaly/birth defect; or (vi) Other adverse events that may be considered serious when, based upon appropriate medical judgment, they may jeopardize the patient or subject or may require medical or surgical intervention to prevent one of the previously listed outcomes. An unexpected event is any adverse drug experience, the specificity or severity of which is not consistent with the current approved product labeling (package insert) for the study medication, the Investigator's Brochure, or as described in the clinical protocol and consent materials.

The maximum intensity of an AE during a day should be recorded on the CRF. If the intensity of an AE changes over a number of days, then separate entries should be made having distinct onset dates for the changes in severity. Mild—AEs are usually transient, requiring no special treatment, and do not interfere with subject's daily activities. Moderate—AEs typically introduce a low level of inconvenience or concern to the subject and may interfere with daily activities but are usually ameliorated by simple therapeutic measures. Severe—AEs interrupt a subject's usual daily activity and traditionally require systemic drug therapy or other treatment.

The following criteria should be used in assessing the apparent causal relationship of an AE to study medication: Definitely—The AE (i) follows a reasonable temporal sequence from study medication administration; (ii) abates upon discontinuation of the study medication (dechallenge); (iii) is confirmed by reappearance of the reaction on repeat exposure. Probably—The AE: (i) follows a reasonable temporal sequence from study medication administration; (ii) abates upon discontinuation of the study medication (dechallenge); (iii) cannot be reasonably explained by the known characteristics of the subject's state. Possible—The AE: (i) follows a reasonable temporal sequence from study medication administration; (ii) but that could readily be produced by a number of other factors. Unlikely—The AE: (i) follows a reasonable temporal sequence from study medication administration; (ii) could have been produced by either the subject's clinical state or by study medication administration. Not related—The AE: (i) does not have a reasonable temporal association with the administration of study medication; (ii) has some other obvious explanation for the event The statistical analysis of the pharmacology, safety/tolerability data obtained from this study will be the responsibility of the Biostatistics department at QPS-Qualitix. The PK endpoints and PK-related statistical analysis of the PK data will be the responsibility of QPS Global PK teams. Under the subheadings below general principles of the statistical analyses are described. More details on the statistical analyses and presentation of results will be discussed in the Statistical Analysis Plan (SAP) and Pharmacokinetic Analysis Plan (PKAP), which will be finalized prior to database lock. If, after database lock, changes are made to the SAP or PKAP, then these deviations to the plan will be listed, along with an explanation as to why they occurred, in the Clinical Study Report. The data from the tests used to evaluate the exploratory endpoint of the relationship between caffeine and $d_9$-caffeine on wakefulness, will be summarized but not analyzed.

Analysis Sets: Three different analysis sets are defined. Subjects who withdraw from the study, or who have missing data, will be included in the statistical analyses provided that they are eligible for inclusion in the analysis population. All-treated set: This analysis set includes all subjects who received study drug (at least one dose). Safety set: This analysis set includes subjects from the all-treated set who had at least one safety assessment post-baseline. The safety set will be employed in the analysis of tolerability and safety variables. Per-protocol set: This analysis set comprises all subjects included in the all-treated set who did not violate the protocol in a way that might affect the evaluation of the effect of the study drug(s) on the primary endpoint, i.e., without major protocol violations or deviations. The Per-protocol set will be employed in the analysis of PK variables and pharmacology effects. All analyses will be performed on data available at the time point considered. In summary tables, the number of subjects with missing data will be presented unless otherwise specified. In calculation of percentages, subjects with missing data will not be considered in numerator or denominator unless otherwise specified.

Analysis of Pharmacokinetic Parameters: Characterizing the PK of caffeine, in addition to d9-caffeine. The plasma pharmacokinetic parameters will be evaluated using standard noncompartmental methods, and will include, if appropriate: $AUC_{0-t}$, $AUC_{0-inf}$, $C_{max}$, $t_{max}$, $k_{el}$, $t_{1/2}$, CL/F, and Vz/F for all analytes. The pharmacokinetic parameters of the non-deuterated analytes will be compared with the pharmacokinetic parameters of the deuterated analytes (Tables 17-22).

d9-Caffeine and caffeine were both rapidly absorbed. Over a period of 48 hours, at both dose levels, d9-caffeine produced a 24-46% higher $C_{max}$ and a 4-5-fold greater AUC of its parent molecule than a similar dose of caffeine. The three active metabolites of d9-caffeine demonstrated a lower $C_{max}$ and lower AUC relative to their un-deuterated counterparts: paraxanthine versus d6-paraxanthine ($C_{max}$ 60-63% lower, AUC 13-30% lower), theobromine versus d6-theobromine ($C_{max}$ 48-66% lower, AUC 20-52% lower), theophylline versus d6-theophylline ($C_{max}$ 71-74% lower, AUC 51-62% lower). The reverse was true for the metabolite TMU, where TMU-d9 exhibited a higher $C_{max}$ and $AUC_{last}$ than its un-deuterated counterpart. TMU remained a very minor metabolite however, as the relative percentage of metabolite to parent for TMU-d9 (0.02%) following administration of d9-caffeine was only slightly higher than the relative percentage for TMU (0.01%) following administration of caffeine.

Figure 11A:
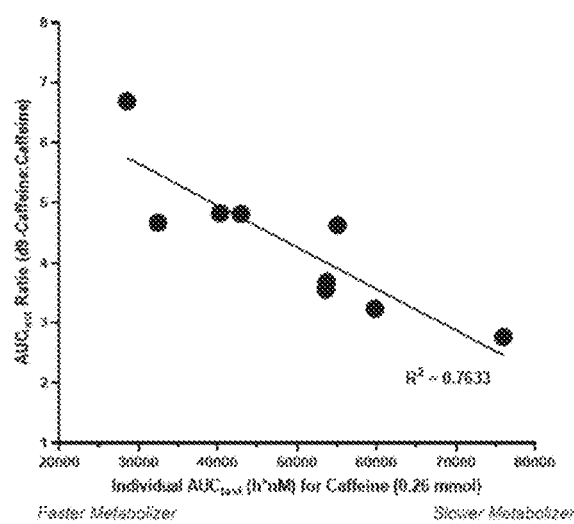
FIGS. 11A-11B. depicts the relative increase in exposure ($AUC_{last}$ ratio) of d9-caffeine relative to caffeine by individual subject exposure level to caffeine from a single dose.
Figure 11B:
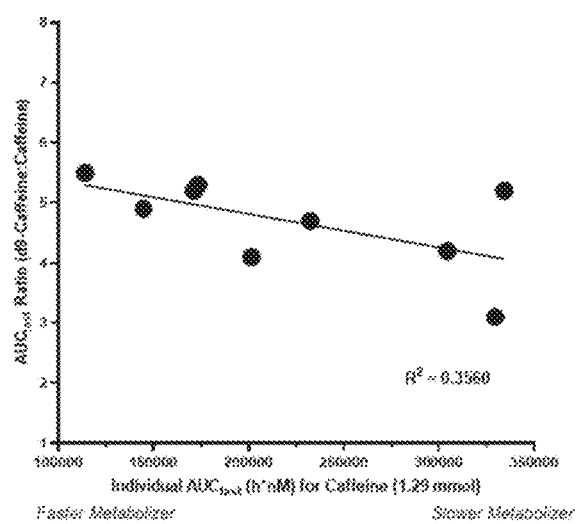

The pharmacokinetic differences between d9-caffeine and caffeine were consistent in slow and rapid metabolizers of caffeine within the study. At the lower dose (0.26 mmol) a 3-fold variance in exposure to caffeine was observed within the study, which generally correlated to the CYP1A2 genotype. The higher dose (1.29 mmol) was generally consistent with this observation, but the trend was not as strong; most likely as a result of saturation of the metabolic pathway at the higher dose (FIG. 11). Accordingly, slow metabolizers do not appear to have a greater safety risk/exposure to d9-caffeine than fast metabolizers.

Both products were well tolerated. No adverse events for insomnia were reported during the study.

Over a period of 48 hours, d9-caffeine exhibits a higher $C_{max}$ and substantial higher AUC than caffeine, and lower $C_{max}$ and AUC for the active metabolites paraxanthine, theobromine, and theophylline. d9-Caffeine may provide comparable $C_{max}$ and substantially higher exposure, or conversely substantial lower $C_{max}$ and comparable exposure, than caffeine, while reducing the exposure to the active metabolites paraxanthine, theobromine, and theophylline.

TABLE 17

Pharmacokinetic parameters of caffeine and d9-caffeine

| | Analyte: | | | |
|---|---|---|---|---|
| | caffeine | | d9-caffeine | |
| | | | Dose | |
| | 50 mg | 250 mg | 50 mg molar equivalent | 250 mg molar equivalent |
| $T_{last}$ (hr) | 30 | 34 | 48 | 48 |
| t½ (hr) | 5.41 | 4.25 | 32.2 | 25.6 |

TABLE 18

Pharmacokinetic parameters of caffeine and d9-caffeine (geometric mean)

| Source | Nominal Dose (mg) | Dose (mmol) | $C_{max}$ (nM) | $AUC_{last}$ (h*nM) | MRT (hr) | $C_{max}$ to AUC (%) |
|---|---|---|---|---|---|---|
| d9-caffeine | 52.3 | 0.26 | 6,619 | 192,192 | 19.7 | 3.4 |
| | 261.7 | 1.29 | 36,501 | 972,287 | 18.9 | 3.8 |
| caffeine | 50 | 0.26 | 5,322 | 47,151 | 7.3 | 11.3 |
| | 250 | 1.29 | 25,078 | 205,543 | 4.3 | 12.2 |

| | $C_{max}$ ratio | $AUC_{last}$ ratio | MRT ratio |
|---|---|---|---|
| d9-Caffeine:caffeine 50 mg ratio | 1.24 | 4.08 | 2.70 |
| d9-Caffeine:caffeine 250 mg ratio | 1.46 | 4.73 | 4.40 |
| Average d9-caffeine:caffeine ratio | 1.35 | 4.40 | 3.55 |

TABLE 19

Parent-metabolite ratio of caffeine and d9-caffeine to paraxanthine and d6-paraxanthine

| Source | Nominal Dose (mg) | Dose (mmol) | $C_{max}$ (nM) | $AUC_{last}$ (h*nM) | MRT (hr) | $C_{max}$ to AUC (%) |
|---|---|---|---|---|---|---|
| d9-caffeine | 52.3 | 0.26 | 592 | 22,447 | 24.2 | 2.6% |
| Ratio or percent to parent: | | | 8.9% | 11.7% | 1.23 | |
| | 261.7 | 1.29 | 2,851 | 110,420 | 24.7 | 2.6% |
| Ratio or percent to parent: | | | 7.8% | 11.4% | 1.31 | |
| caffeine | 50 | 0.26 | 1,598 | 32,050 | 13.1 | 5.0% |
| Ratio or percent to parent: | | | 30.0% | 68.0% | 1.79 | |
| | 250 | 1.29 | 7,106 | 126,657 | 11.8 | 5.6% |
| Ratio or percent to parent: | | | 28.3% | 61.6% | 2.74 | |

| | $C_{max}$ ratio | $AUC_{last}$ ratio | MRT ratio |
|---|---|---|---|
| d9-Caffeine:caffeine ratio (50 mg) | 0.37 | 0.70 | 1.85 |
| d9-Caffeine:caffeine ratio (250 mg) | 0.40 | 0.87 | 2.09 |
| Average d9-caffeine:caffeine ratio | 0.39 | 0.79 | 1.97 |

TABLE 20

Parent-metabolite ratio of caffeine and d9-caffeine to theobromine and d6-theobromine

| Source | Nominal Dose (mg) | Dose (mmol) | $C_{max}$ (nM) | $AUC_{last}$ (h*nM) | MRT (hr) | $C_{max}$ to AUC (%) |
|---|---|---|---|---|---|---|
| d9-caffeine | 52.3 | 0.26 | 121 | 4,340 | 28 | 2.8% |
| Ratio or percent to parent: | | | 1.8% | 2.3% | 1.42 | |
| | 261.7 | 1.29 | 666 | 24,228 | 27.9 | 2.8% |
| Ratio or percent to parent: | | | 1.8% | 2.5% | 1.48 | |

TABLE 20-continued

Parent-metabolite ratio of caffeine and d9-caffeine to theobromine and d6-theobromine

| | | | | | | |
|---|---|---|---|---|---|---|
| caffeine | 50 | 0.26 | 360 | 9,135 | 16.9 | 3.9% |
| | Ratio or percent to parent: | | 6.8% | 19.4% | 2.32 | |
| | 250 | 1.29 | 1,275 | 30,471 | 16.2 | 4.2% |
| | Ratio or percent to parent: | | 5.1% | 14.8% | 3.77 | |

| | $C_{max}$ ratio | $AUC_{last}$ ratio | MRT ratio |
|---|---|---|---|
| d9-Caffeine:caffeine ratio (50 mg) | 0.34 | 0.48 | 1.66 |
| d9-Caffeine: caffeine ratio (250 mg) | 0.52 | 0.80 | 1.72 |
| Average d9-caffeine: caffeine ratio | 0.43 | 0.64 | 1.69 |

TABLE 21

Parent-metabolite ratio of caffeine and d9-caffeine to theophylline and d6-theophylline

| Source | Nominal Dose (mg) | Dose (mmol) | $C_{max}$ (nM) | $AUC_{last}$ (h*nM) | MRT (hr) | $C_{max}$ to AUC (%) |
|---|---|---|---|---|---|---|
| d9-caffeine | 52.3 | 0.26 | 41 | 1,532 | 26.8 | 2.7% |
| | Ratio or percent to parent: | | 0.6% | 0.8% | 1.36 | |
| | 261.7 | 1.29 | 218 | 8,075 | 26.4 | 2.7% |
| | Ratio or percent to parent: | | 0.6% | 0.8% | 1.40 | |
| caffeine | 50 | 0.26 | 160 | 3,986 | 16.7 | 4.0% |
| | Ratio or percent to parent: | | 3.0% | 8.5% | 2.29 | |
| | 250 | 1.29 | 755 | 16,609 | 15.2 | 4.5% |
| | Ratio or percent to parent: | | 3.0% | 8.1% | 3.53 | |

| | $C_{max}$ ratio | $AUC_{last}$ ratio | MRT ratio |
|---|---|---|---|
| d9-Caffeine:caffeine ratio (50 mg) | 0.26 | 0.38 | 1.60 |
| d9-Caffeine:caffeine ratio (250 mg) | 0.29 | 0.49 | 1.74 |
| Average d9-caffeine: caffeine ratio | 0.27 | 0.44 | 1.67 |

TABLE 22

Parent-metabolite ratio of caffeine and d9-caffeine to trimethyluric acid and d9-trimethyluric acid

| Source | Nominal Dose (mg) | Dose (mmol) | $C_{max}$ (nM) | $AUC_{last}$ (h*nM) | MRT (hr) | $C_{max}$ to AUC (%) |
|---|---|---|---|---|---|---|
| d9-caffeine | 52.3 | 0.26 | 15 | 408.9 | 19.1 | 3.5% |
| | Ratio or percent to parent: | | 0.2% | 0.2% | 0.97 | |
| | 261.7 | 1.29 | 82 | 2,522 | 20.3 | 3.2% |
| | Ratio or percent to parent: | | 0.2% | 0.3% | 1.07 | |
| caffeine | 50 | 0.26 | 10 | 25.8 | 1.96 | 37.6% |
| | Ratio or percent to parent: | | 0.2% | 0.1% | 0.27 | |
| | 250 | 1.29 | 54 | 322.2 | 4.95 | 16.6% |
| | Ratio or percent to parent: | | 0.2% | 0.2% | 1.15 | |

| | $C_{max}$ ratio | $AUC_{last}$ ratio | MRT ratio |
|---|---|---|---|
| d9-Caffeine:caffeine ratio (50 mg) | 1.50 | 15.85 | 9.74 |
| d9-Caffeine:caffeine ratio (250 mg) | 1.53 | 7.83 | 4.10 |
| Average d9-caffeine:caffeine ratio | 1.51 | 11.84 | 6.92 |

Pharmacokinetic Statistical Analysis: The per-protocol analysis set will be used for all PK analyses. Individual subject listings will be provided. Mean and individual plasma concentration-time profiles for caffeine and its four key metabolites will be presented graphically for each treatment group. Plasma concentrations and PK parameters of caffeine and its four key metabolites and their deuterated counterparts will be listed by treatment for each subject. Plasma concentrations and PK parameters will be summarized including n, arithmetic mean, standard deviation (SD), coefficient of variation (CV %), median, minimum, maximum. In addition, geometric mean will be calculated for PK parameters. For each part, a mixed effects model with fixed effects for treatment, period, sequence, and with random effect for subject nested-within-sequence will be performed on the log-transformed PK exposure parameters of $C_{max}$, $AUC_{0-t}$, and $AUC_{0-inf}$. The 90% confidence interval (CI) for the ratio of the geometric least square mean ratios (deuterated analytes/non-deuterated analytes) of $C_{max}$, $AUC_{0-t}$, and $AUC_{0-inf}$ will be calculated for the Treatment B relative to the Treatment A in Part 1 and the Treatment D relative to the Treatment C in Part 2.

Demographics, Baseline Characteristic, and Safety Analysis: All subjects who received at least one dose of study drug and had at least one safety assessment post-baseline in safety set will be included in the population for demographics, baseline characteristics, and safety analysis, regardless of other considerations. Baseline is defined as the last observation prior to dosing. Baseline for VS will be pre-dose on Day 1 of each period. Baseline for PE will be Screening. Baseline for 12-lead ECGs will be pre-dose on Day 1 of each period. Baseline demographic data will be tabulated including an arithmetic mean, SD, median and range (for continuous variables). Variables to be summarized include age, sex, race, ethnicity, weight, height, and BMI. Demographic data will also be listed. Medical history data will be included in the CRFs. Analyses of demographics, baseline characteristics, and safety parameters will be based on Safety populations. Baseline for PE will be the screening evaluation. Baseline for safety clinical laboratory results will be Day−3 of each period. Baseline for vital signs and ECG, will be pre-dose on Day 1 of each period. Summary statistics and change from baseline will be computed and provided, as deemed clinically appropriate. Baseline demographic data will be tabulated, including arithmetic mean, standard deviation, median, range (for continuous variables), n, and % (for categorical variables). Variables to be summarized include age, race, ethnicity, height, weight and BMI. Demographic data will also be listed. Medical history data will be included in the CRFs. Safety data, including AEs, vital signs, ECG, PE, and clinical laboratory test results, will be summarized from the CRFs or lab data. Clinical laboratory data will be presented in the listing. Any abnormal laboratory values will be listed for each subject. A by-subject AE data listing will include verbatim term, treatment group, severity, and relationship to treatment for all AEs. Descriptive statistics tables will summarize the nature and frequency of TEAEs only, as defined in Section 12.2. A by-subject TEAE data listing will include verbatim term, treatment group, severity, and relationship to treatment. Subjects with serious adverse events and subjects who discontinue due to AE will be listed. Adverse events will be coded by the Medical Dictionary for Regulatory Activities (MedDRA) and summarized by System Organ Class and Preferred Term. Concomitant medications will be coded by World Health Organization Drug and summarized by drug class and Anatomical Therapeutic Chemical classification.

Pharmacological Effect: The exploratory endpoint of this study is to evaluate the impact of caffeine and d9-caffeine on wakefulness as a measure of pharmacological effects. The impact of caffeine and d9-caffeine on wakefulness will be measured at 4 time points on Day 1 of each period, using the following tests: The Comprehensive Trail Making Test (CTMT2), A and C, Trails 1 and 5 (see, e.g., Bowie, C.R.C.R; P.D.P.D Harvey (2006) "Administration and interpretation of the trail making test" Nature Protocols. 1 (5): 2277-2281); The Stroop Color and Word Test (SCWT) (see, e.g., Scarpina F. and Tagini S. (2017) "The Stroop Color and Word Test" Front. Psychol. 8:557); The Stanford Sleepiness Scale (SSS) (see, e.g., Hoddes E. (1972). "The development and use of the Stanford sleepiness scale (SSS)" Psychophysiology. 9 (150)). The data from the wakefulness tests will be summarized but not analyzed.

EMBODIMENTS

Embodiment 1. A composition comprising d9-caffeine, or a pharmaceutically or nutraceutically acceptable salt thereof.

Embodiment 2. The composition of Embodiment 1, wherein the composition is a pharmaceutical composition.

Embodiment 3. The composition of Embodiment 1, wherein the composition is a nutraceutical composition.

Embodiment 4. The composition of Embodiment 1, wherein the composition is a cosmetic composition.

Embodiment 5. The composition of any one of Embodiments 1-4, wherein the composition comprises 10-15 mg, 15-20 mg, 20-25 mg, 25-30 mg, 30-35 mg, 35-40 mg, 40-45 mg, 45-50 mg, 50-55 mg, 55-60 mg, 60-65 mg, 65-70 mg, 70-75 mg, 75-80 mg, 80-85 mg, 85-90 mg, 90-95 mg, 95-100 mg, 100-105 mg, 105-110 mg, 110-115 mg, 115-120 mg, 120-125 mg, 125-130 mg, 130-135 mg, 135-140 mg, 140-145 mg, 145-150 mg, 150-155 mg, 155-160 mg, 160-165 mg, 165-170 mg, 170-175 mg, 175-180 mg, 180-185 mg, 185-190 mg, 190-195 mg, 195-200 mg, 200-205 mg, 205-210 mg, 210-215 mg, 215-220 mg, 220-225 mg, 225-230 mg, 230-235 mg, 235-240 mg, 240-245 mg, 245-250 mg, 250-255 mg, 255-260 mg, 260-265 mg, 265-270 mg, or 270-275 mg of d9-caffeine, or a salt thereof.

Embodiment 6. The composition of Embodiment 2 or 3, wherein the composition is suitable for oral administration.

Embodiment 7. The composition of Embodiment 2, wherein the composition is suitable for intravenous (IV) administration.

Embodiment 8. The composition of Embodiment 2 or 4, wherein the composition is suitable for topical administration.

Embodiment 9. The composition of Embodiment 2, wherein the composition is suitable for delivery to the lungs.

Embodiment 10. The composition of Embodiment 2 or 3, wherein the composition is a solid dose composition.

Embodiment 11. The composition of any one of Embodiments 1-10, further comprising a pharmaceutically or nutraceutically acceptable carrier.

Embodiment 12. The composition of Embodiment 10, wherein the solid dose composition is a tablet, capsule, granule, powder, sachet, or chewable.

Embodiment 13. The composition of Embodiment 8, wherein the topical composition is a shampoo, conditioner, cream, foam, gel, lotion, ointment, transdermal patch, tincture, or paste.

Embodiment 14. The composition of Embodiment 9, wherein the composition is administered using a nebulizer, pressurized metered dose inhaler (pMDI), or dry powder inhaler (DPI).

Embodiment 15. The composition of any one of Embodiments 1-14 further comprising an additional agent.

Embodiment 16. The composition of Embodiment 15, wherein the additional agent is ergotamine, an anti-inflammatory agent, a steroid, a barbiturate, an opioid analgesic, or a combination thereof.

Embodiment 17. The composition of Embodiment 16, wherein the anti-inflammatory agent is a cyclooxygenase-3 (COX-3) inhibitor, a non-steroidal anti-inflammatory drug (NSAID), or a cyclooxygenase-2 (COX-2) inhibitor.

Embodiment 18. The composition of Embodiment 16, wherein any of the hydrogen atoms in ergotamine, the anti-inflammatory agent, the steroid, the barbiturate, or the opioid analgesic is replaced with deuterium.

Embodiment 19. The composition of Embodiment 18, wherein the percentage of deuterium in ergotamine, the anti-inflammatory agent, the steroid, the barbiturate, or the opioid analgesic is at least 5%.

Embodiment 20. The composition of Embodiment 18, wherein the NSAID is ibuprofen, naproxen, sulindac, ketoprofen, tolmetin, etodolac, fenoprofen, diclofenac, flurbiprofen, piroxicam, ketorolac, indomethacin, nabumetone, oxaprozin, mefanamic acid, or diflunisal.

Embodiment 21. The composition of Embodiment 18, wherein the opioid analgesic is codeine, fentanyl, hydrocodone, hydromorphone, meperidine, methadone, morphine, or oxycodone.

Embodiment 22. The composition of Embodiment 18, wherein the barbiturate is secobarbital, mephobarbital, pentobarbital, butabarbital, phenobarbital, or amobarbital.

Embodiment 23. The composition of Embodiment 18, wherein the COX-2 inhibitor is celecoxib, valdecoxib, rofecoxib, or etoricoxib.

Embodiment 24. The composition of Embodiment 18, wherein the COX-3 inhibitor is acetaminophen, phenacetin, antipyrine, or dipyrone.

The composition of claim 2 or 7, wherein the composition comprises about 1 mg/ml to about 15 mg/ml of d9-caffeine, or a pharmaceutically or nutraceutically acceptable salt thereof.

Embodiment 26. The composition of Embodiment 25, wherein the composition comprises about 2 mg/ml to about 15 mg/ml of d9-caffeine, or a pharmaceutically or nutraceutically acceptable salt thereof.

Embodiment 27. The composition of Embodiment 25, wherein the composition comprises about 5 mg/ml to about 15 mg/ml of d9-caffeine, or a pharmaceutically or nutraceutically acceptable salt thereof.

Embodiment 28. The composition of any one of Embodiments 1-25, wherein the percentage of the amount of d9-caffeine, or a pharmaceutically or nutraceutically acceptable salt thereof, relative to the amount of caffeine present in the composition ranges from about 10% to about 99%.

Embodiment 29. The composition of Embodiment 28, wherein the percentage of the amount of d9-caffeine, or a pharmaceutically or nutraceutically acceptable salt thereof, relative to the total amount of caffeine present in the composition ranges from about 10% to about 25%.

Embodiment 30. The composition of Embodiment 28, wherein the percentage of the amount of d9-caffeine, or a pharmaceutically or nutraceutically acceptable salt thereof, relative to the total amount of caffeine present in the composition ranges from about 25% to about 100%.

Embodiment 31. The composition of Embodiment 28, wherein the percentage of the amount of d9-caffeine, or a pharmaceutically or nutraceutically acceptable salt thereof, relative to the total amount of caffeine present in the composition ranges from about 25% to about 75%.

Embodiment 32. The composition of Embodiment 28, wherein the percentage of the amount of d9-caffeine, or a pharmaceutically or nutraceutically acceptable salt thereof, relative to the total amount of caffeine present in the composition ranges from about 30% to about 70%.

Embodiment 33. The composition of Embodiment 28, wherein the percentage of the amount of d9-caffeine, or a pharmaceutically or nutraceutically acceptable salt thereof, relative to the total amount of caffeine present in the composition ranges from about 25% to about 50%.

Embodiment 34. The composition of Embodiment 28, wherein the percentage of the amount of d9-caffeine, or a pharmaceutically or nutraceutically acceptable salt thereof, relative to the total amount of caffeine present in the composition ranges from about 40% to about 60%.

Embodiment 35. The composition of Embodiment 28, wherein the percentage of the amount of d9-caffeine, or a pharmaceutically or nutraceutically acceptable salt thereof, relative to the total amount of caffeine present in the composition ranges from about 50% to about 100%.

Embodiment 36. A method for increasing energy levels of a subject, for increasing athletic performance, for reducing fatigue or drowsiness in a subject, for increasing wakefulness or alertness in a subject, or for treating hyperinsomnia, the method comprising administering to the subject a composition of any one of Embodiments 1-35; or d9-caffeine, or a pharmaceutically or nutraceutically acceptable salt thereof.

Embodiment 37. A method for treating obesity in a subject, for causing weight loss in a subject, for increasing metabolic rate in a subject, for reducing appetite in a subject, or for increasing energy expenditure in a subject, the method comprising administering to the subject a composition of any one of Embodiments 1-35; or d9-caffeine, or a pharmaceutically or nutraceutically acceptable salt thereof.

Embodiment 38. A method for increasing urine output in a subject, for increasing sodium excretion in a subject, or for reducing edema in a subject, the method comprising administering to the subject a composition of any one of Embodiments 1-35; or d9-caffeine, or a pharmaceutically or nutraceutically acceptable salt thereof.

Embodiment 39. A method for treating a pain disorder in a subject, the method comprising administering to the subject a composition of any one of Embodiments 1-35; or d9-caffeine, or a pharmaceutically or nutraceutically acceptable salt thereof.

Embodiment 40. The method of Embodiment 39, wherein the pain disorder is migraine, arthritis, headache, back pain, bursitis, chronic pain, acute pain, musculoskeletal pain, osteoarthritis, psoriatic arthritis, rheumatoid arthritis, or sciatica.

Embodiment 41. The method of Embodiment 39 or 40, wherein the pain disorder is migraine or headache.

Embodiment 42. A method for treating apnea in a subject, the method comprising administering to the subject a composition of any one of Embodiments 1-35; or d9-caffeine, or a pharmaceutically or nutraceutically acceptable salt thereof.

Embodiment 43. The method of Embodiment 42, wherein the apnea is sleep apnea.

Embodiment 44. The method of Embodiment 43, wherein the sleep apnea is obstructive sleep apnea, central sleep apnea, apnea of prematurity, or complex sleep apnea syndrome.

Embodiment 45. The method of any one of Embodiments 42-44, wherein the subject is a neonate, preterm infant, premature infant, or low birthweight infant.

Embodiment 46. The method of any one of Embodiments 42-44, wherein the subject is an adult.

Embodiment 47. A method for treating hypotension in a subject, the method comprising administering to the subject a composition of any one of Embodiments 1-35; or d9-caffeine, or a pharmaceutically or nutraceutically acceptable salt thereof.

Embodiment 48. The method of Embodiment 47, wherein the hypotension is orthostatic hypotension, postprandial hypotension, or multiple system atrophy with orthostatic hypotension.

Embodiment 49. The method of Embodiment 47, wherein the hypotension is postprandial hypotension.

Embodiment 50. A method for treating an encephalopathy in a subject, the method comprising administering to the subject a composition of any one of Embodiments 1-35; or d9-caffeine, or a pharmaceutically or nutraceutically acceptable salt thereof.

Embodiment 51. The method of Embodiment 50, wherein the encephalopathy is chronic traumatic encephalopathy, glycine encephalopathy, Hashimoto's encephalopathy, hepatic encephalopathy, hypertensive encephalopathy, hypoxic ischemic encephalopathy, toxic metabolic encephalopathy, infectious encephalopathy, uremic encephalopathy, or Wernicke encephalopathy.

Embodiment 52. The method of Embodiment 50, wherein the encephalopathy is hypoxic ischemic encephalopathy.

Embodiment 53. A method for treating a neurological or psychiatric disorder in a subject, the method comprising administering to the subject a composition of any one of Embodiments 1-35; or d9-caffeine, or a pharmaceutically or nutraceutically acceptable salt thereof.

Embodiment 54. The method of Embodiment 53, wherein the neurological or psychiatric disorder is narcolepsy, Alzheimer's disease, attention deficit hyperactivity disorder (ADHD), schizophrenia, Parkinson's disease, or depression.

Embodiment 55. A method for treating an inflammatory disorder in a subject, the method comprising administering to the subject a composition of any one of Embodiments 1-35; or d9-caffeine, or a pharmaceutically or nutraceutically acceptable salt thereof.

Embodiment 56. The method of Embodiment 55, wherein the inflammatory disorder is a pulmonary inflammatory disorder.

Embodiment 57. The method of Embodiment 56, wherein the inflammatory disorder is asthma, chronic obstructive pulmonary disorder (COPD), pulmonary fibrosis, or interstitial lung disease.

Embodiment 58. A method for treating daytime sleepiness in a subject, the method comprising administering to the subject a composition of any one of Embodiments 1-35; or d9-caffeine, or a pharmaceutically or nutraceutically acceptable salt thereof.

Embodiment 59. The method of Embodiment 58, wherein the daytime sleepiness is excessive daytime sleepiness due to narcolepsy, obstructive sleep apnea (OSA), or major depressive disorder (MDD), or due to the use of a depression or anxiety therapy.

Embodiment 60. The method of any one of Embodiments 36-59, wherein the composition or d9-caffeine, or a pharmaceutically or nutraceutically acceptable salt thereof, is administered once daily.

Embodiment 61. The method of any one of Embodiments 36-60, wherein the composition achieves a mean dose normalized plasma $AUC_{0-\infty}$ of more than 300 h*ng/mL/mg following oral administration of a single dose of the formulation to a population of healthy adults of 18-55 years of age.

Embodiment 62. The method of any one of Embodiments 36-60, wherein the composition achieves a mean plasma half-life of longer than 6 hours following oral administration of a single dose of the formulation to a population of healthy adults of 18-55 years of age.

Embodiment 63. The method of any one of Embodiments 36-60, wherein the composition achieves a mean time of last measurable concentration of longer than 36 hours following oral administration of a single dose of the formulation to a population of healthy adults of 18-55 years of age.

Embodiment 64. The method of any one of Embodiments 36-60, such that the time of maximum plasma concentration ($T_{max}$) of d9-caffeine after administration of the composition of any one of Embodiments 1-48; or d9-caffeine, or a pharmaceutically or nutraceutically acceptable salt thereof, is at least 5%, 10%, 25%, 50%, 100%, 200%, 300%, or 400% longer than that of non-isotopically enriched caffeine at an equivalent dose.

Embodiment 65. The method of any one of Embodiments 36-60, such that the time of maximum plasma concentration ($T_{max}$) of d9-caffeine after administration of the composition of any one of Embodiments 1-48; or d9-caffeine, or a pharmaceutically or nutraceutically acceptable salt thereof, is longer than that of non-isotopically enriched caffeine at an equivalent dose.

Embodiment 66. The method of any one of Embodiments 36-60, such that the plasma half-life ($t_{1/2}$) of d9-caffeine after administration of the composition of any one of Embodiments 1-48; or d9-caffeine, or a pharmaceutically or nutraceutically acceptable salt thereof, is at least 400% longer than that of non-isotopically enriched caffeine at an equivalent dose.

Embodiment 67. The method of any one of Embodiments 36-60, such that the plasma half-life ($t_{1/2}$) of d9-caffeine after administration of the composition of any one of Embodiments 1-48; or d9-caffeine, or a pharmaceutically or nutraceutically acceptable salt thereof, is longer than that of non-isotopically enriched caffeine at an equivalent dose.

Embodiment 68. The method of any one of Embodiments 36-60, such that the time of maximum concentration ($T_{max}$) of d9-caffeine in the central nervous system (CNS) of the subject after administration of the composition of any one of Embodiments 1-48; d9-caffeine, or a pharmaceutically or nutraceutically acceptable salt thereof, is at least 5%, 10%, 25%, 50%, 100%, 200%, 300%, or 400% longer than that of non-isotopically enriched caffeine at an equivalent dose.

Embodiment 69. The method of any one of Embodiments 36-60, such that the time of maximum concentration ($T_{max}$) of d9-caffeine in the central nervous system (CNS) of the subject after administration of the composition of any one of Embodiments 1-48; or d9-caffeine, or a pharmaceutically or nutraceutically acceptable salt thereof, is longer than that of non-isotopically enriched caffeine at an equivalent dose.

Embodiment 70. The method of any one of Embodiments 36-60, such that the side effects are reduced relative to the administration of non-isotopically enriched caffeine at an equivalent dose.

Embodiment 71. The method of Embodiment 70, wherein the side effect is anxiety, insomnia, delirium, gastrointestinal issues, rhabdomyolysis, addiction, hypertension, rapid heart rate, atrial fibrillation, fatigue, irritability, nervousness, restlessness, nausea, or muscle tremors.

Embodiment 72. The method of Embodiment 70, wherein the side effect is insomnia.

Embodiment 73. The composition of any one of Embodiments 1-35, such that the time of maximum plasma concentration ($T_{max}$) of d9-caffeine after administration of the composition is at least 5%, 10%, 25%, 50%, 100%, 200%, 300%, or 400% longer than that of non-isotopically enriched caffeine at an equivalent dose.

Embodiment 74. The composition of any one of Embodiments 1-35, such that the time of maximum plasma concentration ($T_{max}$) of d9-caffeine after administration of the composition is longer than that of non-isotopically enriched caffeine at an equivalent dose.

Embodiment 75. The composition of any one of Embodiments 1-35, such that the plasma half-life ($t_{1/2}$) of d9-caffeine after administration of the composition is at least 400% longer than that of non-isotopically enriched caffeine at an equivalent dose.

Embodiment 76. The composition of any one of Embodiments 1-35, such that the plasma half-life ($t_{1/2}$) of d9-caffeine after administration of the composition is longer than that of non-isotopically enriched caffeine at an equivalent dose.

Embodiment 77. The composition of any one of Embodiments 1-35, such that the time of maximum concentration ($T_{max}$) of d9-caffeine in the central nervous system (CNS) of the subject after administration of the composition is at least 5%, 10%, 25%, 50%, 100%, 200%, 300%, or 400% longer than that of non-isotopically enriched caffeine at an equivalent dose.

Embodiment 78. The composition of any one of Embodiments 1-35, such that the time of maximum concentration ($T_{max}$) of d9-caffeine in the central nervous system (CNS) of the subject after administration of the composition is longer than that of non-isotopically enriched caffeine at an equivalent dose.

Embodiment 79. A beverage comprising water and d9-caffeine.

Embodiment 80. A beverage comprising water and a composition of any one of Embodiments 1-35.

Embodiment 81. The beverage of Embodiment 79 or 80, wherein the beverage comprises 10-15 mg, 15-20 mg, 20-25 mg, 25-30 mg, 30-35 mg, 35-40 mg, 40-45 mg, 45-50 mg, 50-55 mg, 55-60 mg, 60-65 mg, 65-70 mg, 70-75 mg, 75-80 mg, 80-85 mg, 85-90 mg, 90-95 mg, 95-100 mg, 100-105 mg, 105-110 mg, 110-115 mg, 115-120 mg, 120-125 mg, 125-130 mg, 130-135 mg, 135-140 mg, 140-145 mg, 145-150 mg, 150-155 mg, 155-160 mg, 160-165 mg, 165-170 mg, 170-175 mg, 175-180 mg, 180-185 mg, 185-190 mg, 190-195 mg, 195-200 mg, 200-205 mg, 205-210 mg, 210-215 mg, 215-220 mg, 220-225 mg, 225-230 mg, 230-235 mg, 235-240 mg, 240-245 mg, 245-250 mg, 250-255 mg, 255-260 mg, 260-265 mg, 265-270 mg, or 270-275 mg of d9-caffeine, or a salt thereof.

Embodiment 82. The beverage of any one of Embodiments 79-81, wherein the beverage further comprises one or more of a flavoring and a sweetener.

Embodiment 83. The beverage of any one of Embodiments 79-82, wherein the beverage further comprises one or more of vitamins, minerals, co-factors, proteins, lipids, peptides, and amino acids.

Embodiment 84. The beverage of Embodiment 83, wherein the beverage is an energy beverage.

Embodiment 85. The beverage of Embodiment 83, wherein the beverage is a vitamin water.

Embodiment 86. The beverage of Embodiment 84, wherein the energy beverage further comprises one or more of water, taurine, citicoline, vitamin B6, vitamin B12, folic acid, niacinamide, glucuronolactone, N-acetyl-L-tyrosine, L-phenylalanine, and malic acid.

Embodiment 87. The beverage of Embodiment 85, wherein the vitamin water further comprises one or more of water, vitamin C, vitamin B5, vitamin B6, vitamin B12, magnesium, and pantothenic acid.

Embodiment 88. The beverage of any one of Embodiments 79-87, wherein the percentage of the amount of d9-caffeine, or a pharmaceutically or nutraceutically acceptable salt thereof, relative to the total amount of caffeine present in the beverage ranges from about 10% to about 99%.

Embodiment 89. The beverage of any one of Embodiments 79-87, wherein the percentage of the amount of d9-caffeine, or a pharmaceutically or nutraceutically acceptable salt thereof, relative to the total amount of caffeine present in the beverage ranges from about 10% to about 25%.

Embodiment 90. The beverage of any one of Embodiments 79-87, wherein the percentage of the amount of d9-caffeine, or a pharmaceutically or nutraceutically acceptable salt thereof, relative to the total amount of caffeine present in the beverage ranges from about 25% to about 99%.

Embodiment 91. The beverage of any one of Embodiments 79-87, wherein the percentage of the amount of d9-caffeine, or a pharmaceutically or nutraceutically acceptable salt thereof, relative to the total amount of caffeine present in the beverage ranges from about 25% to about 75%.

Embodiment 92. The beverage of any one of Embodiments 79-87, wherein the percentage of the amount of d9-caffeine, or a pharmaceutically or nutraceutically acceptable salt thereof, relative to the total amount of caffeine present in the beverage ranges from about 30% to about 70%.

Embodiment 93. The beverage of any one of Embodiments 79-87, wherein the percentage of the amount of d9-caffeine, or a pharmaceutically or nutraceutically acceptable salt thereof, relative to the total amount of caffeine present in the beverage ranges from about 25% to about 50%.

Embodiment 94. The beverage of any one of Embodiments 79-87, wherein the percentage of the amount of d9-caffeine, or a pharmaceutically or nutraceutically acceptable salt thereof, relative to the total amount of caffeine present in the beverage ranges from about 40% to about 60%.

Embodiment 95. The beverage of any one of Embodiments 79-87, wherein the percentage of the amount of d9-caffeine, or a pharmaceutically or nutraceutically acceptable salt thereof, relative to the total amount of caffeine present in the beverage ranges from about 50% to about 99%.

Embodiment 96. A food product comprising d9-caffeine.

Embodiment 97. The food product of Embodiment 96, wherein the food product comprises 10-15 mg, 15-20 mg, 20-25 mg, 25-30 mg, 30-35 mg, 35-40 mg, 40-45 mg, 45-50 mg, 50-55 mg, 55-60 mg, 60-65 mg, 65-70 mg, 70-75 mg, 75-80 mg, 80-85 mg, 85-90 mg, 90-95 mg, 95-100 mg, 100-105 mg, 105-110 mg, 110-115 mg, 115-120 mg, 120-125 mg, 125-130 mg, 130-135 mg, 135-140 mg, 140-145 mg, 145-150 mg, 150-155 mg, 155-160 mg, 160-165 mg, 165-170 mg, 170-175 mg, 175-180 mg, 180-185 mg, 185-190 mg, 190-195 mg, 195-200 mg, 200-205 mg, 205-210 mg, 210-215 mg, 215-220 mg, 220-225 mg, 225-230 mg, 230-235 mg, 235-240 mg, 240-245 mg, 245-250 mg, 250-255 mg, 255-260 mg, 260-265 mg, 265-270 mg, or 270-275 mg of d9-caffeine, or a salt thereof Embodiment 98. The food product of Embodiment 96, wherein the food product is an energy bar, energy gel, pre-work out supplement or other performance enhancing supplements, tablet, or a powder, optionally wherein the tablet or powder are configured to be dissolved with a liquid to form a beverage.

Embodiment 99. The food product of Embodiment 98, wherein the energy bar further comprises one or more of sugar, cocoa butter, chocolate liquor, whole milk powder, soy lecithin, vanilla extract, caramel, peanuts, peanut butter, almonds, oats, molasses, cinnamon, salt, and soybean oil.

Embodiment 100. The food product of any one of Embodiments 96-99, wherein the percentage of the amount of d9-caffeine, or a pharmaceutically or nutraceutically acceptable salt thereof, relative to the total amount of caffeine present in the beverage ranges from about 10% to about 99%.

Embodiment 101. The food product of any one of Embodiments 96-99, wherein the percentage of the amount of d9-caffeine, or a pharmaceutically or nutraceutically acceptable salt thereof, relative to the total amount of caffeine present in the beverage ranges from about 10% to about 25%.

Embodiment 102. The food product of any one of Embodiments 96-99, wherein the percentage of the amount of d9-caffeine, or a pharmaceutically or nutraceutically acceptable salt thereof, relative to the total amount of caffeine present in the beverage ranges from about 25% to about 99%.

Embodiment 103. The food product of any one of Embodiments 96-99, wherein the percentage of the amount of d9-caffeine, or a pharmaceutically or nutraceutically acceptable salt thereof, relative to the total amount of caffeine present in the beverage ranges from about 25% to about 75%.

Embodiment 104. The food product of any one of Embodiments 96-99, wherein the percentage of the amount of d9-caffeine, or a pharmaceutically or nutraceutically acceptable salt thereof, relative to the total amount of caffeine present in the beverage ranges from about 30% to about 70%.

Embodiment 105. The food product of any one of Embodiments 96-99, wherein the percentage of the amount of d9-caffeine, or a pharmaceutically or nutraceutically acceptable salt thereof, relative to the total amount of caffeine present in the beverage ranges from about 25% to about 50%.

Embodiment 106. The food product of any one of Embodiments 96-99, wherein the percentage of the amount of d9-caffeine, or a pharmaceutically or nutraceutically acceptable salt thereof, relative to the total amount of caffeine present in the beverage ranges from about 40% to about 60%.

Embodiment 107. The food product of any one of Embodiments 96-99, wherein the percentage of the amount of d9-caffeine, or a pharmaceutically or nutraceutically acceptable salt thereof, relative to the total amount of caffeine present in the beverage ranges from about 50% to about 100%.

Embodiment 108. A nutritional supplement comprising d9-caffeine

Embodiment 109. The nutritional supplement of Embodiment 108, wherein the nutritional supplement comprises 10-15 mg, 15-20 mg, 20-25 mg, 25-30 mg, 30-35 mg, 35-40 mg, 40-45 mg, 45-50 mg, 50-55 mg, 55-60 mg, 60-65 mg, 65-70 mg, 70-75 mg, 75-80 mg, 80-85 mg, 85-90 mg, 90-95 mg, 95-100 mg, 100-105 mg, 105-110 mg, 110-115 mg, 115-120 mg, 120-125 mg, 125-130 mg, 130-135 mg, 135-140 mg, 140-145 mg, 145-150 mg, 150-155 mg, 155-160 mg, 160-165 mg, 165-170 mg, 170-175 mg, 175-180 mg, 180-185 mg, 185-190 mg, 190-195 mg, 195-200 mg, 200-205 mg, 205-210 mg, 210-215 mg, 215-220 mg, 220-225 mg, 225-230 mg, 230-235 mg, 235-240 mg, 240-245 mg, 245-250 mg, 250-255 mg, 255-260 mg, 260-265 mg, 265-270 mg, or 270-275 mg of d9-caffeine, or a salt thereof.

Embodiment 110. The nutritional supplement of Embodiment 108 or 109, wherein the nutritional supplement is a tablet, capsule, granule, powder, sachet, or chewable.

Embodiment 111. The nutritional supplement of any one of Embodiments 108-110, wherein the nutritional supplement is a composition that is mixed with water to form a beverage.

Embodiment 112. The nutritional supplement of any one of Embodiments 108-110, wherein the nutritional supplement is a composition that is added to a food product.

Embodiment 113. The nutritional supplement of any one of Embodiments 108-112, further comprising one or more of a flavoring, sweetener, or taste-masking agent.

Embodiment 114. The nutritional supplement of any one of Embodiments 108-113, wherein the percentage of the amount of d9-caffeine, or a pharmaceutically or nutraceutically acceptable salt thereof, relative to the total amount of caffeine present in the beverage ranges from about 10% to about 99%.

Embodiment 115. The nutritional supplement of any one of Embodiments 108-113, wherein the percentage of the amount of d9-caffeine, or a pharmaceutically or nutraceutically acceptable salt thereof, relative to the total amount of caffeine present in the beverage ranges from about 10% to about 25%.

Embodiment 116. The nutritional supplement of any one of Embodiments 108-113, wherein the percentage of the amount of d9-caffeine, or a pharmaceutically or nutraceutically acceptable salt thereof, relative to the total amount of caffeine present in the beverage ranges from about 25% to about 99%.

Embodiment 117. The nutritional supplement of any one of Embodiments 108-113, wherein the percentage of the amount of d9-caffeine, or a pharmaceutically or nutraceutically acceptable salt thereof, relative to the total amount of caffeine present in the beverage ranges from about 25% to about 75%.

Embodiment 118. The nutritional supplement of any one of Embodiments 108-113, wherein the percentage of the amount of d9-caffeine, or a pharmaceutically or nutraceutically acceptable salt thereof, relative to the total amount of caffeine present in the beverage ranges from about 30% to about 70%.

Embodiment 119. The nutritional supplement of any one of Embodiments 108-113, wherein the percentage of the amount of d9-caffeine, or a pharmaceutically or nutraceutically acceptable salt thereof, relative to the total amount of caffeine present in the beverage ranges from about 25% to about 50%.

Embodiment 120. The nutritional supplement of any one of Embodiments 108-113, wherein the percentage of the amount of d9-caffeine, or a pharmaceutically or nutraceutically acceptable salt thereof, relative to the total amount of caffeine present in the beverage ranges from about 40% to about 60%.

Embodiment 121. The nutritional supplement of any one of Embodiments 108-113, wherein the percentage of the amount of d9-caffeine, or a pharmaceutically or nutraceutically acceptable salt thereof, relative to the total amount of caffeine present in the beverage ranges from about 50% to about 99%.

Embodiment 122. A pharmaceutical composition comprising 10 mg to 250 mg of d9-caffeine, wherein the composition is effective at promoting alertness or wakefulness in a human subject when administered once daily to the subject.

Embodiment 123. The composition of Embodiment 122, wherein the composition is a pharmaceutical composition.

Embodiment 124. The composition of Embodiment 122, wherein the composition is suitable for oral administration.

Embodiment 125. The composition of Embodiment 122, wherein the composition is suitable for intravenous (IV) administration.

Embodiment 126. The composition of Embodiment 122, wherein the composition is a solid dose composition.

Embodiment 127. The composition of Embodiment 126, wherein the solid dose composition is a tablet, capsule, granule, powder, sachet, or chewable.

Embodiment 128. The composition of any one of Embodiments 122-125, further comprising a pharmaceutically acceptable carrier.

Embodiment 129. A nutraceutical composition comprising 10 mg to 250 mg of d9-caffeine, wherein the composition is effective at promoting alertness or wakefulness in a human subject when administered or consumed once daily to the subject.

Embodiment 130. The nutraceutical composition of Embodiment 129, wherein the nutraceutical composition is a solid dose composition comprising a tablet, capsule, granule, powder, sachet, or chewable.

Embodiment 131. A consumer product comprising 10 mg to 250 mg of d9-caffeine, wherein the product is effective at promoting alertness or wakefulness in a human subject when consumed once daily by the subject.

Embodiment 132. The product of Embodiment 131, wherein the product is a food product.

Embodiment 133. The product of Embodiment 131, wherein the product is a beverage.

Embodiment 134. The product of Embodiment 131, wherein the product is a nutritional supplement.

Embodiment 1A. A method for treating attention deficit hyperactivity disorder (ADHD) in a human subject in need thereof, the method comprising administering to the subject a pharmaceutical composition comprising d9-caffeine:

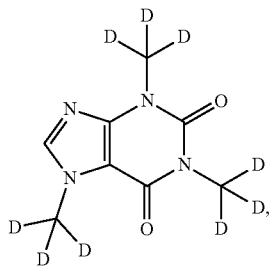

or a pharmaceutically acceptable salt thereof.

Embodiment 2A. The method of Embodiment 1A, wherein at least 90% of the total amount of caffeine in the composition is d9-caffeine.

Embodiment 3A. The method of Embodiment 1A or 2A, wherein at least 99% of the total amount of caffeine in the composition is d9-caffeine.

Embodiment 4A. The method of any one of Embodiments 1A-3A, wherein the composition comprises a pharmaceutically acceptable salt of d9-caffeine.

Embodiment 5A. The method of Embodiment 4A, wherein the pharmaceutically acceptable salt is a citrate salt.

Embodiment 6A. The method of any one of Embodiments 1A-5A, wherein the pharmaceutical composition comprises about 1 mg/ml to about 100 mg/ml of d9-caffeine, or a pharmaceutically acceptable salt thereof.

Embodiment 7A. The method of any one of Embodiments 1A-5A, wherein the pharmaceutical composition comprises about 1 mg to about 1000 mg of d9-caffeine, or a pharmaceutically acceptable salt thereof.

Embodiment 8A. The method of Embodiment 7A, wherein the pharmaceutical composition comprises about 1 mg to about 300 mg of d9-caffeine, or a pharmaceutically acceptable salt thereof.

Embodiment 9A. The method of any one of Embodiments 1A-8A, wherein the pharmaceutical composition is administered orally, parenterally, topically, by inhalation, or buccally.

Embodiment 10A. The method of Embodiment 9A, wherein the pharmaceutical composition is administered orally.

Embodiment 11A. The method of any one of Embodiments 1A-10A, wherein d9-caffeine, or pharmaceutically acceptable salt thereof, or pharmaceutical composition thereof, is administered once daily.

Embodiment 12A. The method of any one of Embodiments 1A-10A, wherein d9-caffeine, or pharmaceutically acceptable salt thereof, or pharmaceutical composition thereof, is administered two or more times daily.

Embodiment 13A. The method of any one of Embodiments 1A-12A, wherein the plasma $AUC_{0-\infty}$ of d9 caffeine in the subject is more than 300 h*ng/mL/mg following oral administration of a single dose of the composition.

Embodiment 14A. The method of any one of Embodiments 1A-13A, wherein the plasma half-life of d9 caffeine is longer than 6 hours following oral administration of a single dose of the composition.

Embodiment 15A. The method of any one of Embodiments 1A-14A, wherein the time of last measurable concentration of d9 caffeine in the subject is more than 36 hours following oral administration of a single dose of the composition.

Embodiment 16A. The method of any one of Embodiments 1A-15A, wherein the time of maximum concentration ($T_{max}$) of d9-caffeine in the central nervous system (CNS) of the subject after administration of the pharmaceutical composition is longer than that of non-isotopically enriched caffeine at an equivalent dose.

Embodiment 17A. The method of Embodiment 16A, wherein the time of maximum concentration ($T_{max}$) of d9-caffeine in the central nervous system (CNS) of the subject after administration of the pharmaceutical composition is at least 5%, 10%, 25%, 50%, 100%, 200%, 300%, or 400% longer than that of non-isotopically enriched caffeine at an equivalent dose.

Embodiment 18A. The method of any one of Embodiments 1A-17A, wherein one or more side effects are reduced relative to the administration of non-isotopically enriched caffeine at an equivalent dose.

Embodiment 19A. The method of Embodiment 18A, wherein the side effect is anxiety, insomnia, delirium, gastrointestinal issues, rhabdomyolysis, addiction, hypertension, rapid heart rate, atrial fibrillation, fatigue, irritability, nervousness, restlessness, nausea, or muscle tremors.

Embodiment 20A. The method of Embodiment 18A, wherein the side effect is caused by a caffeine metabolite.

Embodiment 21A. The method of Embodiment 20A, wherein the caffeine metabolite is theophylline or theobromine.

Embodiment 22A. The method of any one of Embodiments 1A-21A, wherein the human subject is a child or an adult.

Embodiment 23A. The method of any one of Embodiments 1A-22A, further comprising administering one or more additional therapeutic agents selected from stimulant or non-stimulant pharmaceutical therapies approved for the treatment of ADHD.

Embodiment 24A. The method of Embodiment 23A, wherein the stimulant is methylphenidate, dexmethylphenidate, serdexmethylphenidate, amphetamine, dextroamphetamine, lisdexamfetamine, methamphetamine, or a pharmaceutically acceptable salt thereof; or any combination thereof Embodiment 25A. The method of Embodiment 23A, wherein the non-stimulant pharmaceutical is atomoxetine, clonidine, guanfacine, bupropion, desipramine, imipramine, nortriptyline, venlafaxine, viloxazine, or buspirone.

Embodiment 26A. The method of any one of Embodiments 23A-25A, wherein d9-caffeine is administered before, after, simultaneously with the one or more additional therapeutic agents.

Embodiment 27A. The method of any one of Embodiments 1A-26A, wherein the subject is concurrently receiving another pharmaceutical therapy.

Embodiment 28A. The method of any one of Embodiments 1A-26A, wherein the subject is not receiving another pharmaceutical therapy.

Embodiment 29A. The method of any one of Embodiments 1A-28A, wherein the subject's ADHD is refractory to previous pharmaceutical therapies.

Embodiment 30A. The method of any one of Embodiments 1A-29A, wherein the subject has been diagnosed with hyperactive-type ADHD.

Embodiment 31A. The method of any one of Embodiments 1A-29A, wherein the subject has been diagnosed with inattentive-type ADHD.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising," "including," and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A method for treating attention deficit hyperactivity disorder (ADHD) in a human subject in need thereof, the method comprising administering to the subject a once daily loading dose of a first pharmaceutical composition comprising d9-caffeine:

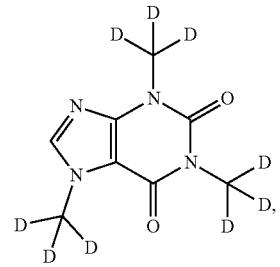

or a pharmaceutically acceptable salt thereof, wherein the method further comprises subsequently administering to the subject a once daily maintenance dose of a second pharmaceutical composition comprising d9-caffeine, or a pharmaceutically acceptable salt thereof, wherein the loading dose comprises a greater amount of d9-caffeine, or a pharmaceutically acceptable salt thereof, than the maintenance dose.

2. The method of claim 1, wherein at least 90% of the total amount of caffeine in the first and/or second pharmaceutical composition is d9-caffeine.

3. The method of claim 2, wherein at least 99% of the total amount of caffeine in the first and/or second pharmaceutical composition is d9-caffeine.

4. The method of claim 1, wherein the first and/or second pharmaceutical composition comprises a pharmaceutically acceptable salt of d9-caffeine.

5. The method of claim 4, wherein the pharmaceutically acceptable salt is a citrate salt.

6. The method of claim 1, wherein the first and/or second pharmaceutical composition comprises about 1 mg/ml to about 100 mg/ml of d9-caffeine, or a pharmaceutically acceptable salt thereof.

7. The method of claim 1, wherein the first and/or second pharmaceutical composition comprises about 1 mg to about 1000 mg of d9-caffeine, or a pharmaceutically acceptable salt thereof.

8. The method of claim 7, wherein the first and/or second pharmaceutical composition comprises about 1 mg to about 300 mg of d9-caffeine, or a pharmaceutically acceptable salt thereof.

9. The method of claim 1, wherein the first and/or second pharmaceutical composition is administered orally, parenterally, topically, by inhalation, or buccally.

10. The method of claim 9, wherein the first and/or second pharmaceutical composition is administered orally.

11. The method of claim 1, wherein the plasma $AUC_{0-\infty}$ of d9-caffeine in the subject is more than 300 h*ng/mL/mg following oral administration of a single loading dose of the first pharmaceutical composition.

12. The method of claim 1, wherein the plasma half-life of d9-caffeine is longer than 6 hours following oral administration of a single loading dose of the first pharmaceutical composition.

13. The method of claim 1, wherein the time of last measurable concentration of d9-caffeine in the subject is more than 36 hours following oral administration of a single loading dose of the first pharmaceutical composition.

14. The method of claim 1, wherein the time of maximum concentration ($T_{max}$) of d9-caffeine in the central nervous system (CNS) of the subject after administration of the first pharmaceutical composition is longer than that of non-isotopically enriched caffeine at an equivalent dose.

15. The method of claim 14, wherein the time of maximum concentration ($T_{max}$) of d9-caffeine in the central nervous system (CNS) of the subject after administration of the first pharmaceutical composition is at least 5%, 10%, 25%, 50%, 100%, 200%, 300%, or 400% longer than that of non-isotopically enriched caffeine at an equivalent dose.

16. The method of claim 1, wherein one or more side effects are reduced relative to the administration of non-isotopically enriched caffeine at an equivalent dose.

17. The method of claim 16, wherein the side effect is anxiety, insomnia, delirium, gastrointestinal issues, rhabdomyolysis, addiction, hypertension, rapid heart rate, atrial fibrillation, fatigue, irritability, nervousness, restlessness, nausea, or muscle tremors.

18. The method of claim 16, wherein the side effect is caused by a caffeine metabolite.

19. The method of claim 18, wherein the caffeine metabolite is theophylline or theobromine.

20. The method of claim 1, wherein the human subject is a child or an adult.

21. The method of claim 1, further comprising administering one or more additional therapeutic agents selected from stimulant and non-stimulant pharmaceutical therapies approved for the treatment of ADHD.

22. The method of claim 21, wherein the stimulant pharmaceutical therapy is methylphenidate, dexmethylphenidate, serdexmethylphenidate, amphetamine, dextroamphetamine, lisdexamfetamine, methamphetamine, or a pharmaceutically acceptable salt thereof; or any combination thereof.

23. The method of claim 21, wherein the non-stimulant pharmaceutical therapy is atomoxetine, clonidine, guanfacine, bupropion, desipramine, imipramine, nortriptyline, venlafaxine, viloxazine, or buspirone.

24. The method of claim 21, wherein the first and/or second pharmaceutical composition comprising d9-caffeine is administered before, after, simultaneously with the one or more additional therapeutic agents.

25. The method of claim 1, wherein the subject is concurrently receiving another pharmaceutical therapy.

26. The method of claim 1, wherein the subject's ADHD is refractory to previous pharmaceutical therapies.

27. The method of claim 1, wherein the subject has been diagnosed with hyperactive-type ADHD or with inattentive-type ADHD.

28. The method of claim 8, wherein the first and/or second pharmaceutical composition comprises about 1 mg to about 250 mg of d9-caffeine, or a pharmaceutically acceptable salt thereof.

29. The method of claim 28, wherein the first and/or second pharmaceutical composition comprises about 50 mg of d9-caffeine, or a pharmaceutically acceptable salt thereof.

* * * * *